United States Patent [19]

Makino et al.

[11] Patent Number: 5,152,824
[45] Date of Patent: Oct. 6, 1992

[54] SULFAMIDOSULFONAMIDE DERIVATIVES AND HERBICIDES

[75] Inventors: Kenzi Makino; Katsushi Morimoto; Shigeaki Akiyama; Hideaki Suzuki; Takeshi Nagaoka, all of Funabashi; Koichi Suzuki, Shiraoka; Tsutomu Nawamaki, Shiraoka; Shigeomi Watanabe, Shiraoka, all of Japan

[73] Assignee: Nissan Chemical Industries Ltd., Tokyo, Japan

[21] Appl. No.: 665,557

[22] Filed: Mar. 6, 1991

[30] Foreign Application Priority Data

| Mar. 6, 1990 | [JP] | Japan | 2-54455 |
| Mar. 6, 1990 | [JP] | Japan | 2-54456 |
| Jun. 12, 1990 | [JP] | Japan | 2-153345 |
| Nov. 6, 1990 | [JP] | Japan | 2-300127 |
| Dec. 19, 1990 | [JP] | Japan | 2-403735 |

[51] Int. Cl.⁵ .................. A01N 43/02; A01N 43/48; A01N 43/64; C07D 285/16
[52] U.S. Cl. ....................... 71/91; 71/92; 544/8; 544/60; 544/140; 546/211; 546/279; 548/127; 548/365.7; 548/379.4
[58] Field of Search .................... 544/8, 60, 140; 548/375, 378, 127; 546/211, 279; 71/92, 91

[56] References Cited

U.S. PATENT DOCUMENTS 4,629,495 12/1986 Hatton et al. .................. 71/92

FOREIGN PATENT DOCUMENTS 37482 10/1981 European Pat. Off.

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

A sulfamidosulfonamide derivative of the formula (1) and an agriculturally suitable salt thereof:

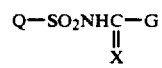

wherein Q is

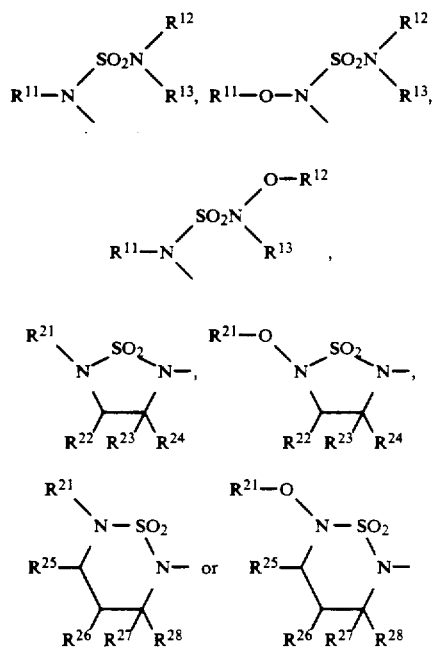

X is an oxygen atom or a sulfur atom; and G is

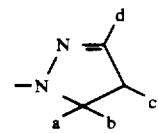

which are useful as herbicide.

7 Claims, No Drawings

SULFAMIDOSULFONAMIDE DERIVATIVES AND HERBICIDES

TECHNICAL FIELD

The present invention relates to novel sulfamidosulfonamide derivatives and agriculturally suitable salts thereof, and herbicides containing them as active ingredients.

BACKGROUND TECHNIQUE

It is indispensable to use herbicides to protect important crop plants such as rice, wheat, corn, soybean, cotton and sugar beet from weeds and thereby to increase the harvest. Especially in recent years, a selective herbicide is desired which is capable of selectively killing weeds without showing any phytotoxicity against crop plants when applied to the foliages of crop plants and weeds simultaneously in a field where such useful crop plants and weeds are coexistent. Further, with a view to avoiding environmental pollution and reducing the costs for transportation and application, researches and developments have been conducted for many years for compounds having high herbicidal effects at low doses. Some of the compounds having such properties are presently used as selective herbicides. However, there still exists a need for better compounds having such properties.

As the prior art showing a chemical structure similar to that of the compounds of the present invention, Japanese Unexamined Patent Publication No. 45473/1990 discloses substituted sulfonyldiamides, and Japanese Unexamined Patent Publication No. 122671/1988 discloses 1-carbamoyl-2-pyrazolines. However, sulfamidosulfonamide derivatives having a pyrazoline structure like the compounds of the present invention have not been known at all, and they are novel compounds.

DISCLOSURE OF THE INVENTION

The present inventors have conducted extensive researches over years to develop selective herbicides for important crop plants and have studied herbicidal properties of many compounds with an aim to find out compounds having higher herbicidal activities as well as selectivity. As a result, it has been found that sulfamidosulfonamide derivatives of the following formula (1) and agriculturally suitable salts thereof (hereinafter referred to as the compounds of the present invention) exhibit remarkably strong herbicidal activities against many weeds in soil treatment or in foliage treatment and at the same time have a high level of safety for important crop plants such as wheat, corn, cotton, soybean, sugar beet and rice. The present invention has been accomplished on the basis of this discovery. On the other hand, since the compounds of the present invention show high herbicidal activities at a very low dose as compared with conventional herbicides, they are also useful as herbicides for orchards or for non-agricultural fields.

Namely, the present invention provides a sulfamidosulfonamide derivative of the formula (1) and an agriculturally suitable salt thereof:

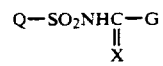

wherein Q is

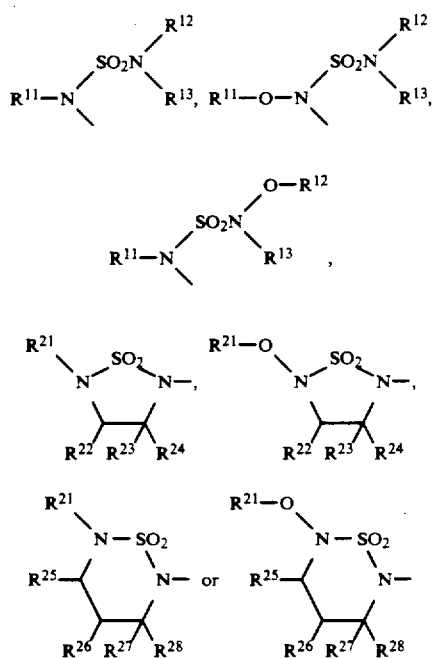

wherein $R^{11}$ is a hydrogen atom, a $C_{1-6}$ alkyl group, a $C_{3-7}$ cycloalkyl group, a $C_{1-6}$ alkyl group substituted by a $C_{3-7}$ cycloalkyl group, a $C_{2-6}$ alkenyl group, a $C_{1-6}$ alkynyl group, a $C_{1-6}$ alkyl group substituted by a $C_{1-6}$ alkoxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ mono- or poly-halogenoalkyl group, a $C_{1-6}$ alkyl group substituted by a cyano group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a nitro group, a $C_{1-6}$ alkyl group, a $C_{1-6}$ alkoxy group and a $C_{1-6}$ alkoxycarbonyl group);

$R^{12}$ is a hydrogen atom, a $C_{1-6}$ alkyl group, a $C_{2-6}$ alkenyl group, a $C_{2-6}$ alkynyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group and a $C_{1-6}$ alkoxycarbonyl group);

$R^{13}$ is a hydrogen atom, a $C_{1-6}$ alkyl group, a $C_{2-6}$ alkenyl group, a $C_{1-6}$ alkynyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);

or, $R^{12}$ and $R^{13}$ form, together with the nitrogen atom to which they are bonded, a saturated 5-7 membered heterocyclic group;

or, $R^{12}$ and $R^{13}$ form, together with the oxygen atom and the nitrogen atom to which they are bonded, a saturated 5-7 membered heterocyclic group;

$R^{21}$ is a hydrogen atom, a $C_{1-6}$ alkyl group, a $C_{2-6}$ alkenyl group, a $C_{2-6}$ alkynyl group, a $C_{1-6}$ alkyl group substituted by a $C_{1-6}$ alkoxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ mono- or poly-halogenoalkyl group, a $C_{1-6}$ alkyl group substituted by a cyano group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);

$R^{22}$ is a hydrogen atom or a $C_{1-6}$ alkyl group;

$R^{23}$ is a hydrogen atom or a $C_{1-6}$ alkyl group;

$R^{24}$ is a hydrogen atom, a $C_{1-6}$ alkyl group, a $C_{2-6}$ alkenyl group, a $C_{2-6}$ alkynyl group, a halogen atom, a $C_{1-6}$ mono- or poly-halogenoalkyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkyl group substituted by a cyano group, a $C_{1-6}$ alkoxycarbonyl group, a $C_{1-6}$ alkyl group substituted by a $C_{1-6}$ alkoxycarbonyl group, a $C_{1-6}$ alkylcarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);

$R^{25}$ is a hydrogen atom or a $C_{1-6}$ alkyl group;

$R^{26}$ is a hydrogen atom or a $C_{1-6}$ alkyl group;

$R^{27}$ is a hydrogen atom or a $C_{1-6}$ alkyl group;

$R^{28}$ is a hydrogen atom, a halogen atom, a $C_{1-6}$ alkyl group, a $C_{2-6}$ alkenyl group, a $C_{2-6}$ alkynyl group, a $C_{1-6}$ mono- or poly-halogenoalkyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkyl group substituted by a cyano group, a $C_{1-6}$ alkoxycarbonyl group, a $C_{1-6}$ alkylcarbonyl group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);

X is an oxygen atom or a sulfur atom;

G is

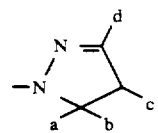

wherein each of a, b, c and d, which are independent from one another, is a hydrogen atom, a $C_{1-6}$ alkyl group, a $C_{2-6}$ alkenyl group, a $C_{2-6}$ alkynyl group, a $C_{1-6}$ alkyl group mono- or poly-substituted by a halogen atom, a $C_{1-6}$ alkoxy group, a $C_{1-6}$ alkyl group substituted by a $C_{1-6}$ alkoxy group, a $C_{1-6}$ alkoxycarbonyl group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkylthio group, a $C_{1-6}$ alkylcarbonyl group, a $C_{3-7}$ cycloalkyl group, a $C_{3-7}$ cycloalkenyl group, a cyano group, a nitro group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group), a 5- or 6-membered heterocyclic group (provided that such a heterocyclic group contains from 1 to 3 hetero atoms selected from the group consisting of nitrogen atoms, oxygen atoms and sulfur atoms in the ring, or contains a sulfonyl group, and such a heterocyclic group may be substituted by one or more substituents selected from the group consisting of a $C_{1-6}$ alkyl group, a $C_{1-6}$ alkoxy group, a halogen atom, a trifluoromethyl group, a nitro group and a $C_{1-6}$ alkoxycarbonyl group), a naphthyl group, a benzene-condensed heterocyclic group (provided that such a benzene-condensed heterocyclic group contains 1 or 2 hetero atoms selected from the group consisting of nitrogen atoms, oxygen atoms and sulfur atoms, and such a benzene-condensed heterocyclic group may be substituted by one or more substituents selected from the group consisting of a $C_{1-6}$ alkyl group, a $C_{1-6}$ alkoxy group, a halogen atom, a trifluoromethyl group, a nitro group and a $C_{1-6}$ alkoxycarbonyl group).

The present invention also provides a selective herbicide containing one or more compounds of the present invention as active ingredients.

Further, the present invention provides a herbicidal composition comprising a herbicidally effective amount of one or more compounds of the present invention and an agricultural adjuvant.

Now, the present invention will be described in detail with reference to the preferred embodiments.

The compounds of the formula (1) of the present invention can easily be prepared by any one of the following reaction schemes 1 to 5.

Reaction scheme 1

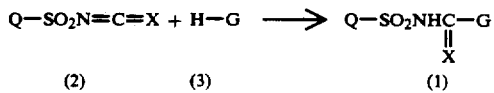

In the above formulas, Q, G and X are as defined above.

Namely, the reaction of a sulfamidosulfonyliso(thio)-cyanate derivative (2) with a pyrazoline derivative (3), is conducted by using the sulfamidosulfonyliso(thio)-cyanate derivative (2) in an amount of from 0.5 to 3.0 mols per mol of the pyrazoline derivative (3). Preferably the amount is within a range of from 0.8 to 1.2 mols.

The reaction temperature can be selected optionally within a range of from −50° C. to 200° C. However, the temperature is preferably within a range of from −20° C. to 50° C.

This reaction usually proceeds readily to present the compound (1) of the present invention. If the reaction tends to hardly proceed, a suitable base, for example, an organic base such as triethylamine, triethylenediamine, pyridine or 1,8-diazabicyclo[5.4.0]-7-undecene (DBU), a metal alkoxide such as sodium methoxide or sodium ethoxide, a metal hydride such as sodium hydride, an alkyl metal such as n-butyl lithium, or an inorganic base such as potassium carbonate, potassium hydroxide or sodium hydroxide, may be added to facilitate the reaction. As the base, it is particularly preferred to employ an organic base or an inorganic base.

As a solvent suitable for this reaction, a solvent inert to this reaction, for example, an aromatic hydrocarbon such as benzene, toluene or xylene, a halogenated hydrocarbon such as dichloromethane, chloroform, carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

After completion of the reaction, usual posttreatment is conducted to obtain the compound (1) of the present invention. The structure of the compound of the present invention was determined by e.g. IR, NMR or MASS.

Reaction scheme 2

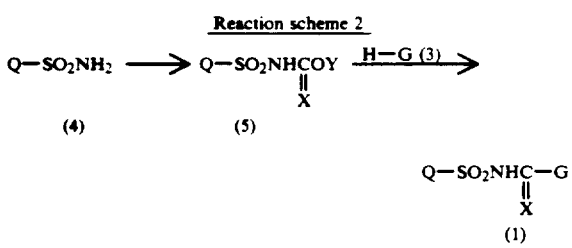

In the above formulas, Q, G and X are as defined above, and Y is a $C_{1-6}$ alkyl group, a phenyl group or a benzyl group (provided that such an alkyl group, a phenyl group or a benzyl group may be substituted by one or more substituents selected from the group consisting of a $C_{1-6}$ alkyl group, $C_{1-6}$ alkoxy group and a halogen atom).

Namely, the reaction of a sulfamidosulfonamide derivative (4) with chloro(thio)formic acid ester or thio)carbonic acid diester is conducted by using the chloro(thio)formic acid ester or the (thio)carbonic acid diester in an amount of from 0.5 to 3.0 mols per mol of the sulfamidosulfonamide derivative (4). The amount is preferably within a range of from 0.8 to 1.2 mols.

The reaction temperature can be selected optionally within a range of from −50° C. to 200° C. However, it is preferably within a range of from −20° C. to 100° C.

This reaction is conducted by using various bases. The base is used in an amount of from 0.5 to 5.0 mols per mol of the sulfamidosulfonamide derivative (4). As a suitable base, an organic base such as triethylamine, triethylenediamine, pyridine, 1,8-diazabicyclo[5.4.0]-7-undecene (DBU), a metal alkoxide such as sodium methoxide or sodium ethoxide, a metal hydride such as sodium hydride, an alkyl metal such as n-butyl lithium, or an inorganic base such as potassium carbonate, potassium hydroxide or sodium hydroxide, may, for example, be used. It is particularly preferred to employ an organic base or an inorganic base.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

After completion of the reaction, usual posttreatment is conducted to obtain an N-sulfamidosulfonyl(thio)carbamate derivative (5).

Then, the reaction of the N-sulfamidosulfonyl(thio)-carbamate derivative (5) with a pyrazoline derivative (3) is conducted by using the pyrazoline derivative (3) in an amount of from 0.5 to 10.0 mols per mol of the N-sulfamidosulfonyl(thio)carbamate derivative (5). The amount is preferably within a range of from 0.5 to 3.0 mols.

The reaction temperature can be selected optionally within a range of from 0° C. to 250° C. However, it is preferably within a range of from 50° C. to 150° C.

This reaction usually proceeds readily to present the compound (1) of the present invention. However, if the reaction tends to hardly proceed, a suitable base, for example, an organic base such as triethylamine, triethylenediamine, pyridine or 1,8-diazabicyclo[5.4.0]-7-undecene (DBU), a metal alkoxide such as sodium methoxide or sodium ethoxide, a metal hydride such as sodium hydride, an alkyl metal such as n-butyl lithium, or an inorganic base such as potassium carbonate, potassium hydroxide or sodium hydroxide, may be added to facilitate the reaction. As the base, it is particularly preferred to employ an organic base or an inorganic base.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

After completion of the reaction, usual posttreatment is conducted to obtain the compound (1) of the present invention. The structure of the compound of the present invention was determined by e.g. IR, NMR or MASS.

Reaction scheme 3

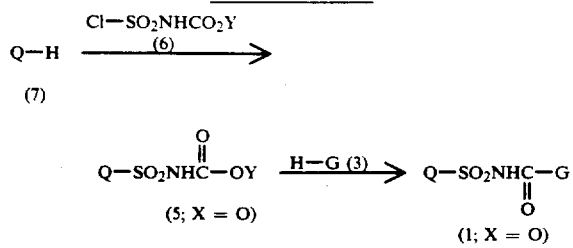

In the above formulas, Q, G and Y are as defined above.

Namely, the reaction of a sulfamide (7) with an N-chlorosulfonylcarbamate derivative (6) is conducted by using the N-chlorosulfonylcarbamate derivative (6) in an amount of from 0.5 to 3.0 mols per mol of the sulfamide (7) The amount is preferably within a range of from 0.9 to 1.2 mols.

The reaction temperature may be selected optionally within a range of from −50° C. to 100° C. However, it is preferably within a range of from −20° C. to 30° C.

This reaction can be conducted by using various bases. The base is used in an amount of from 0.5 to 4.0 mols per mol of the sulfamide (7). As a suitable base, a metal hydride such as sodium hydride, a metal alkoxide such as sodium methoxide or sodium ethoxide, an alkyl metal such as n-butyl lithium, an organic base such as triethylamine, triethylenediamine, pyridine or 1,8-diazabicyclo[5.4.0]-7-undecene (DBU), or an inorganic base such as potassium carbonate, potassium hydroxide or sodium hydroxide, may be employed. It is particularly preferred to employ a metal hydride, an organic base or an inorganic base.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture. It is particularly preferred to employ an ether or an amide.

After completion of the reaction, usual posttreatment is conducted to obtain an N-sulfamidosulfonylcarbamate derivative (5; X=0).

Then, the reaction of the N-sulfamidosulfonylcarbamate derivative (5; X=0) with a pyrazoline derivative (3) is conducted by using the pyrazoline derivative (3) in an amount of from 0.5 to 10.0 mols per mol of the N-sulfamidosulfonylcarbamate derivative (5; X=0). The amount is preferably within a range of from 0.5 to 3.0 mols.

The reaction temperature can be selected optionally within a range of from 0° C. to 250° C. However, it is preferably within a range of from 50° C. to 150° C.

This reaction usually proceeds readily to present the compound (1) of the present invention. However, if the reaction tends to hardly proceed, a suitable base, for example, an organic base such as triethylamine, triethylenediamine, pyridine or 1,8-diazabicyclo[5.4.0]-7-undecene (DBU), a metal alkoxide such as sodium methoxide or sodium ethoxide, metal hydride such as sodium hydride, an alkyl metal such as n-butyl lithium, or an inorganic base such as potassium carbonate, potassium hydroxide or sodium hydroxide, may be added to facilitate the reaction. As the base, it is particularly preferred to employ an organic base or an inorganic base.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

After completion of the reaction, usual posttreatment is conducted to obtain the compound (1; X=0) of the present invention. The structure of the compound of the present invention was determined by e.g. IR, NMR or MASS.

Reaction scheme 4

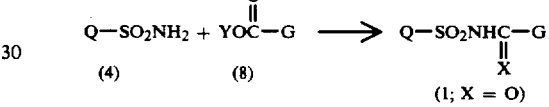

In the above formulas, Q, G and Y are as defined above.

Namely, the reaction of a sulfamidosulfonamide derivative (4) with a pyrazolinylformic acid ester (8) is conducted by using the pyrazolinylformic acid ester (8) in an amount of from 0.5 to 3.0 mols per mol of the sulfamidosulfonamide derivative (4). The amount is preferably within a range of from 0.8 to 1.2 mols.

The reaction temperature can be selected optionally within a range of from −50° C. to 100° C.

This reaction can be conducted by using various bases. The base is used in an amount of from 0.5 to 4.0 mols per mol of the sulfamidosulfonamide derivative (4). As a suitable base, an organic base such as triethylamine, triethylenediamine, pyridine or 1,8-diazabicyclo[5.4.0]-7-undecene (DBU), an inorganic base such as potassium carbonate, potassium hydroxide or sodium hydroxide, an alkyl metal such as n-butyl lithium or trimethyl aluminum, a metal hydride such as sodium hydride, or a metal alkoxide such as sodium methoxide or sodium ethoxide, may be employed. It is particularly preferred to employ an organic base, an inorganic base or an alkyl metal.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

After completion of the reaction, usual posttreatment is conducted to obtain the compound (1; X=O) of the present invention. The structure of the compound of the present invention was determined by e.g. IR, NMR or MASS.

Reaction scheme 5

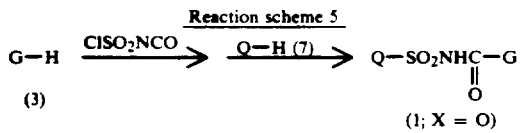

In the above formulas, Q and G are as defined above.

Namely, the reaction of a pyrazoline derivative (3) with a chlorosulfonyl isocyanate is conducted by using the chlorosulfonyl isocyanate in an amount of from 0.5 to 3.0 mols per mol of the pyrazoline derivative (3). The amount is preferably within a range of from 0.8 to 1.2 mols.

The reaction temperature can be selected optionally within a range of from −50° C. to 100° C. However, it is preferably within a range of from −30° C. to 50° C.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture.

This reaction usually proceeds readily without using a base.

Then, a suitable base is added to the reaction system of the pyrazoline derivative (3) and the chlorosulfonyl isocyanate, and a sulfamide derivative (7) is reacted to obtain a compound of the present invention (1; X=O). The base is used in an amount of from 0.5 to 4.0 mols, preferably from 0.8 to 2.2 mols, per mol of the pyrazoline derivative (3). Further, the sulfamide derivative (7) is used in an amount of from 0.5 to 2.0 mols, preferably from 0.8 to 1.2 mols, per mol of the pyrazoline derivative (3).

As a suitable base, an organic base such as triethylamine, triethylenediamine, pyridine or 1,8-diazabicyclo[5.4.0]-7-undecene (DBU), an inorganic base such as potassium carbonate, potassium hydroxide or sodium hydroxide, an alkyl metal such as n-butyl lithium, a metal hydride such as sodium hydride, or a metal alkoxide such as sodium methoxide or sodium ethoxide, may be employed. It is particularly preferred to employ an organic base, an inorganic base or a metal hydride.

The reaction temperature can be selected optionally within a range of from −50° C. to 150° C. However, it is preferably within a range of from −30° C. to 60° C.

After completion of the reaction, usual posttreatment is conducted to obtain the compound (1; X=O) of the present invention. The structure of the compound of the present invention was determined by e.g. IR, NMR or MASS.

The sulfamidosulfonyliso(thio)cyanate derivative (2) to be used in the Reaction scheme 1, can be prepared from the sulfamide derivative (7) or the sulfamidosulfonamide derivative (4) in accordance with the method disclosed in e.g. Japanese Unexamined Patent Publications No. 45473/1990, No. 151577/1989, No. 31775/1984, No. 148879/1983, No. 13266/1980 and No. 81320/1974.

Further, the sulfamidosulfonamide derivative (4) can be prepared from the sulfamide derivative (7) in accordance with the following Reaction schemes 6 and 7.

Reaction scheme 6

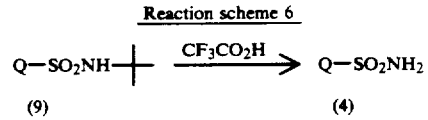

In the above formulas, Q is as defined above.

In the Reaction scheme 6, removal of the tert-butyl group is conducted by using trifluoroacetic acid.

The amount of trifluoroacetic acid can be selected optionally from an equimolar amount to excess amount. Further, trifluoroacetic acid may be used as a solvent without any problem.

The reaction temperature can be selected optionally within a range of from −50° C. to 80° C. It is preferably within a range of from −20° C. to 30° C.

In a case where a solvent is employed in this reaction, a solvent inert to the reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be used. These solvents may be used alone or in combination as a mixture.

Reaction scheme 7

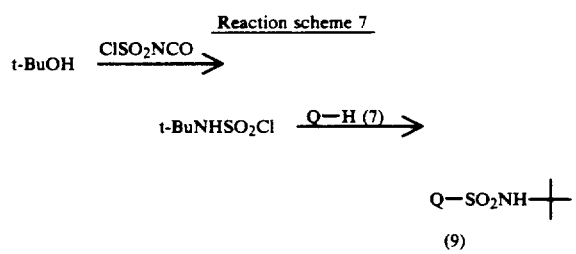

In the above formulas, Q is as defined above.

In the Reaction scheme 7, the reaction of t-butanol with chlorosulfonyl isocyanate can be conducted by a method per se known, such as the one disclosed in Japanese Unexamined Patent Publication No. 101323/1975.

The reaction of sulfamide (7) with tert-butyl sulfamoyl chloride is conducted by using tert-butyl sulfamoyl chloride in an amount of from 0.5 to 3.0 mols per mol of the sulfamide (7).

The reaction temperature can be selected optionally within a range of from −50° C. to 100° C. However, it is preferably within a range of from −20° C. to 30° C.

This reaction can be conducted by using various bases. The base is used in an amount of from 0.5 to 4.0 mols per mol of the sulfamide (7). The amount is preferably within a range of from 0.8 to 2.2 mols. As a suitable base, a metal hydride such as sodium hydride, a metal alkoxide such as sodium ethoxide, an alkyl metal such as n-butyl lithium, an organic base such as triethylamine, pyridine or 1,8-diazabicyclo[5.4.0]-7-undecene, or an inorganic base such as potassium hydroxide, sodium hydroxide or potassium carbonate, may be employed.

As a solvent suitable for this reaction, a solvent inert to this reaction, for example, an aromatic hydrocarbon such as benzene, toluene or xylene, a halogenated hydrocarbon such as dichloromethane, chloroform or carbon tetrachloride, an ether such as diethyl ether, isopropyl ether, dioxane or tetrahydrofuran, a nitrile such as acetonitrile or propionitrile, a hydrocarbon such as petroleum ether, petroleum benzin or n-hexane, a ketone such as acetone or methyl ethyl ketone, an ester such as ethyl acetate, or an amide such as dimethylformamide, dimethylacetamide or hexamethylphosphoric acid triamide, may be mentioned. These solvents may be used alone or in combination as a mixture. It is particularly preferred to employ an ether or an amide.

In the Reaction scheme 3, the N-chlorosulfonylcarbamate derivative (6) can be prepared by a method per se known in accordance with e.g. Chemishe Berichte, vol. 96, p. 56 (1963).

The sulfamide (7) to be used as the starting material for the above reactions, can readily be prepared in accordance with e.g. Synthetic organic Chemistry, Japan, vol. 27 (No. 10), p. 980 (1969); U.S. Pat. No. 2,624,729; Chemishe Berichte, vol. 111, p. 1915 (1978); Japanese Unexamined Patent Publications No. 208289/1983, No. 79894/1978; Indian Journal of Chemistry, Section B, vol. 21B, p. 941 (1982); Journal of the American Chemical Society, vol. 66, p. 1242 (1944); U.S. Pat. No. 2,826,594.

As typical examples, syntheses of 2,4-dimethyl-1,2,5-thiadiazolidine-1,1-dioxide, 2-methoxy-1,2,5-thiadiazolidine-1,1-dioxide, N,N-dimethyl-N'-ethylsulfamide, N,N-dimethyl-N'-methoxysulfamide and N-methyl-N-methoxy-N'-ethylsulfamide, will be described by Reaction schemes 8 to 12:

Reaction scheme 8

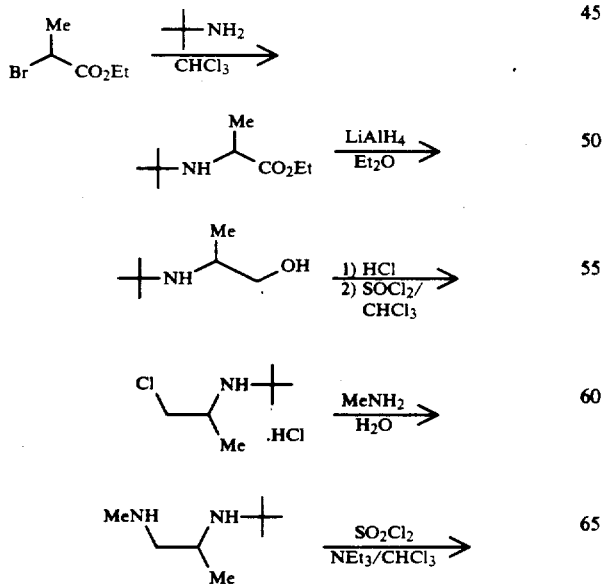

-continued
Reaction scheme 8

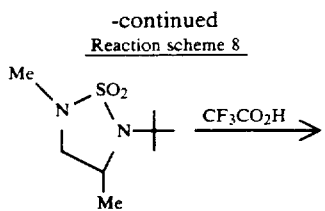

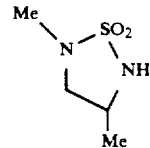

Reaction scheme 9

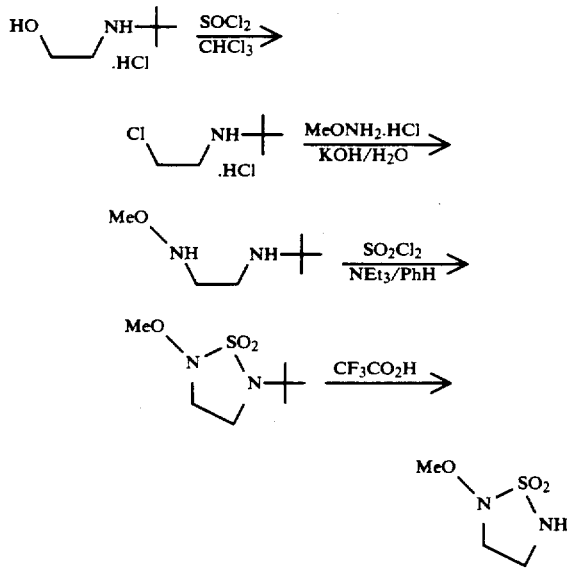

Reaction scheme 10

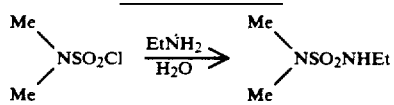

Reaction scheme 11

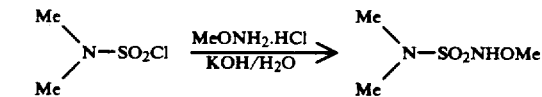

Reaction scheme 12

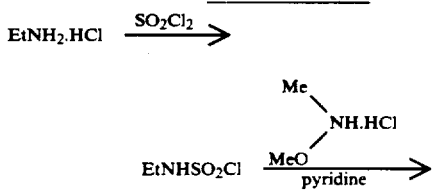

-continued
Reaction scheme 12

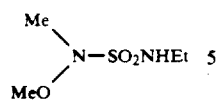

The pyrazoline derivative (3) to be used as a starting material in the above reactions can readily be prepared in accordance with e.g. Japanese Unexamined Patent Publication No. 122671/1988; U.S. Pat. No. 3,322,831; Journal of the American Chemical Society, vol. 80, p. 1926 (1958); Chemishe Berichte, vol. 35, p. 968 (1902); Shin Jikken Kagaku Koza, vol. 14, p. 1423. Typical Examples will be described by Reaction Schemes 13 to 21:

Reaction scheme 13

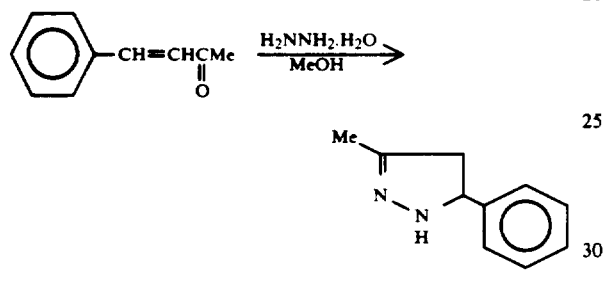

Reaction scheme 14

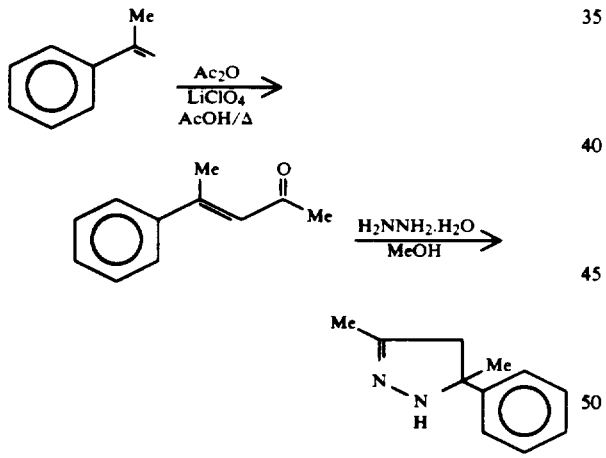

Reaction scheme 15

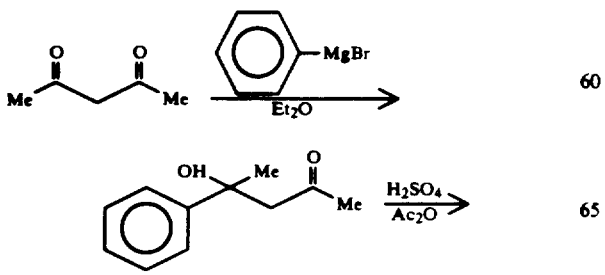

-continued
Reaction scheme 15

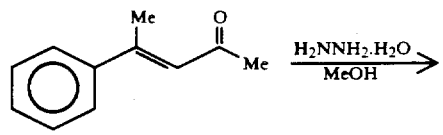

Reaction scheme 16

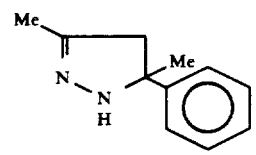

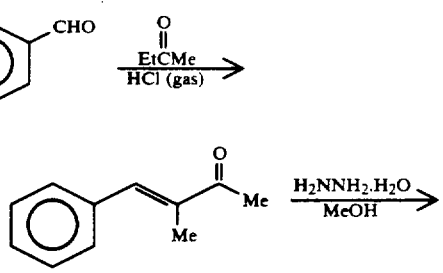

Reaction scheme 17

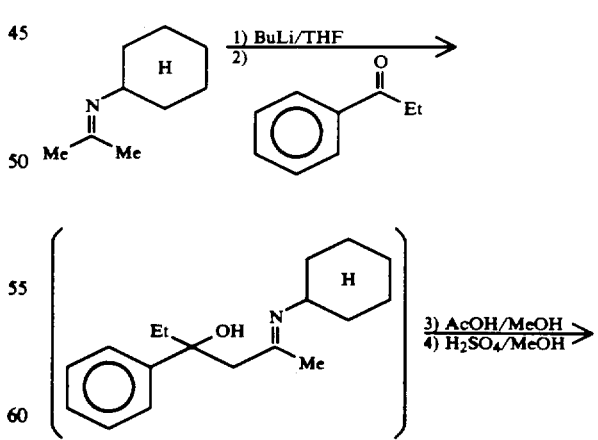

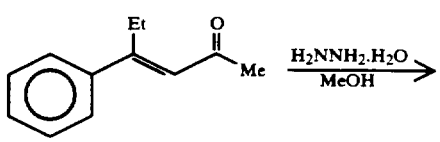

-continued
Reaction scheme 17

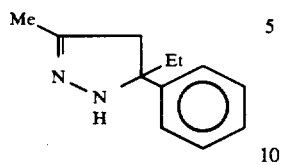

Reaction scheme 18

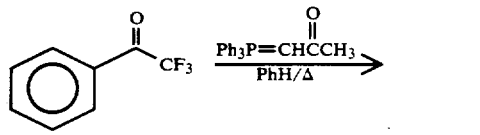

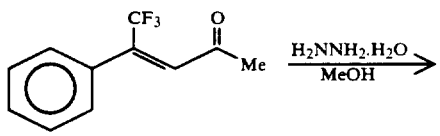

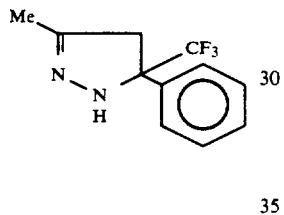

Reaction scheme 19

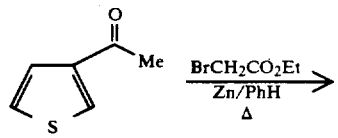

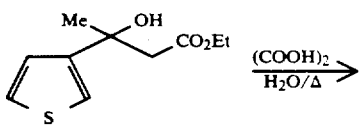

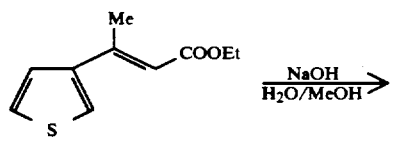

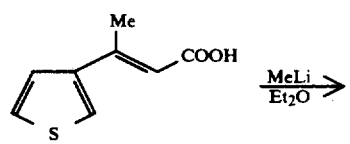

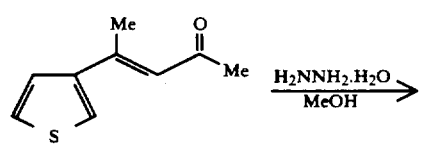

-continued
Reaction scheme 19

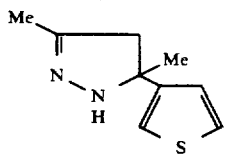

Reaction scheme 20

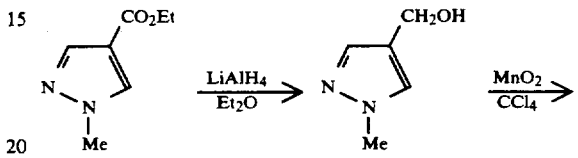

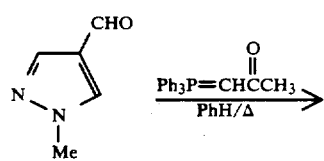

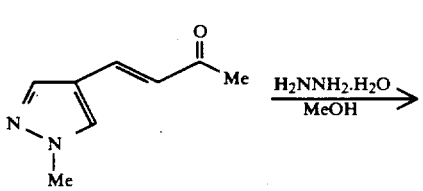

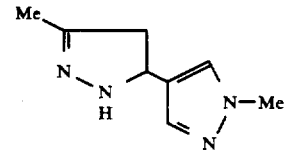

Reaction scheme 21

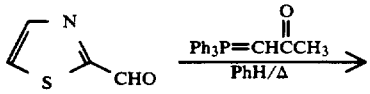

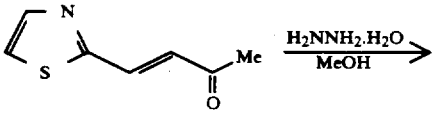

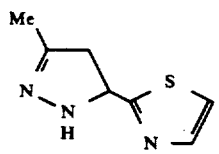

Now, preparation of the compounds of the present invention will be described in further detail with reference to Reference Examples and Examples. However, it should be understood that the present invention is by no means restricted by such specific Examples.

REFERENCE EXAMPLE 1

Preparation of phenyl N-[(N-dimethylsulfamoyl-N-methyl amino)sulfonyl]carbamate

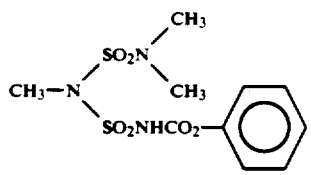

4.0 g (100 mmol) of 60% sodium hydride was washed with n-hexane and suspended in 100 ml of dry tetrahydrofuran (THF). Then, 6.9 g (50 mmol) of N,N,N'-trimethylsulfamide dissolved in 20 ml of dry THF was added thereto under cooling with ice, and the mixture was gradually heated and stirred at room temperature for 3 hours.

Then, 50 ml of a dry THF solution containing 13.0 g (55 mmol) of phenyl N-chlorosulfonylcarbamate was dropwise added thereto under cooling with ice, and the mixture was gradually heated to room temperature and then stirred at room temperature for 3 hours.

The reaction mixture was poured into 1000 ml of ice water containing 1.05 g of 35% hydrochloric acid and extracted with diethyl ether. The diethyl ether layer was washed sequentially with water and a saturated sodium chloride aqueous solution and then dried over anhydrous magnesium sulfate. Then, the solvent was distilled off under reduced pressure to obtain 16.0 g of phenyl N-[(N-dimethylsulfamoyl-N-methylamino)sulfonyl]carbamate as slightly yellow oil.

REFERENCE EXAMPLE 2

Preparation of phenyl N-[(N-dimethylsulfamoyl-N-methoxyamino)sulfonyl]-carbamate

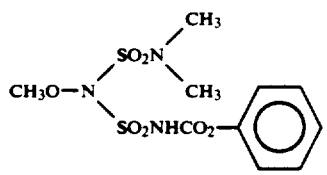

2.69 g (61.5 mmol) of 55% sodium hydride was washed with n-hexane and then suspended in 100 ml of dry THF. Then, 4.62 g (30 mmol) of N,N-dimethyl-N'-methoxysulfamide dissolved in 20 ml of THF was dropwise added thereto under cooling with ice. The mixture is heated to room temperature and then stirred at room temperature for one hour. Then, this reaction mixture was again cooled with ice, and 7.07 g (30 mmol) of phenyl N-chlorosulfonylcarbamate dissolved in 30 ml of dry THF was dropwise added thereto. The mixture was heated to room temperature and then stirred at room temperature for 30 minutes. The reaction mixture was poured into 500 ml of ice water containing 6.4 g of 35% hydrochloric acid and extracted three times with 80 ml of diethyl ether. The extract solution was washed three times with 100 ml of water and once with 100 ml of a saturated sodium chloride aqueous solution and then dried over anhydrous magnesium sulfate. Then, the solvent was distilled off under reduced pressure to obtain 10.1 g of phenyl N-[(N-dimethylsulfamoyl-N-methoxyamino)sulfonyl]carbamate as slightly yellow oil.

REFERENCE EXAMPLE 3

Preparation of phenyl N-[(N-(N-methyl-N-methoxyaminosulfonyl)-N-methylamino)sulfonyl]carbamate

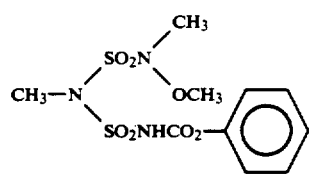

A mixture comprising 7 g (63 mmol) of methylsulfamic acid, 13.2 g (63 mmol) of phosphorus pentachloride and 100 ml of dry benzene, was refluxed for one hour. The reaction mixture was left to cool, and the solvent was distilled off under reduced pressure to obtain 7.63 g of methylsulfamoyl chloride.

5.75 g (58.9 mmol) of N,O-dimethylhydroxylamine hydrochloride was suspended in 300 ml of dichloromethane, and 11.9 g (118 mmol) of triethylamine was added thereto. Then, the mixture was cooled with ice, and a dichloromethane solution of 7.63 g of methylsulfamoyl chloride was dropwise added, and the mixture was stirred at room temperature for 3 hours. The solvent was distilled off under reduced pressure. To the residue, 200 ml of benzene was added, and insoluble substance was filtered off. Then, the solvent was distilled off again under reduced pressure. By the distillation under reduced pressure, 4.4 g of N,N'-dimethyl-N'-methoxysulfamide was obtained (boiling point: 85°-88° C./1.9 mmHg).

1.15 g (28.8 mmol) of 60% sodium hydride was washed with n-hexane, and dry THF was added, and the mixture was cooled with ice. To this mixture, a THF solution containing 2 g (13 mmol) of N,N'-dimethyl-N'-methoxysulfamide was dropwise added. After stirring the mixture for 10 minutes, a dry THF solution containing 3.21 g (13.6 mmol) of phenyl N-chlorosulfonylcarbamate was dropwise added thereto. The mixture was stirred at room temperature for 7 hours. The reaction mixture was poured into 500 ml of ice water containing 3.5 g of 35% hydrochloric acid and extracted three times with diethyl ether. The diethyl ether layer was washed sequentially with water and a saturated sodium chloride aqueous solution and dried over anhydrous sodium sulfate. The solvent was distilled off under reduced pressure to obtain 4.3 g of phenyl N-[(N-(N-methyl N-methoxyaminosulfonyl)-N-methylamino)-sulfonyl]carbamate as slightly yellow oil.

REFERENCE EXAMPLE 4

Preparation of phenyl N-(2-methyl-tetrahydro-1,2,6-thiadiazine-1,1-dioxide-6-sulfonyl)carbamate

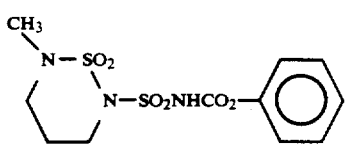

A mixture comprising 30 g (312 mmol) of sulfamide, 27.5 g (312 mmol) of N-methyl-1,3-propanediamine and 300 ml of dry pyridine was refluxed overnight at 130° C. The mixture was left to cool, and then pyridine was distilled off under reduced pressure. To the residue, 200 ml of chloroform was added and insoluble substance was filtered off. The solvent was distilled off under reduced pressure, and the residue was purified by silica gel column chromatography (CHCl3) and then subjected to distillation under reduced pressure to obtain 36.2 g of 2-methyl-tetrahydro-1,2,6-thiadiazine-1,1-dioxide (boiling point: 130°-133° C./0.23 mmHg).

Then, 5.87 g (147 mmol) of 60% sodium hydride was washed twice with 30 ml of n-hexane, and then 30 ml of dry THF was added thereto, and the mixture was cooled with ice. To this mixture, a dry THF solution containing 10.0 g (66.7 mmol) of 2-methyl-tetrahydro-1,2,6-thiadiazine-1,1-dioxide was dropwise added, and the mixture was stirred at room temperature for 2.5 hours. The solution was cooled again with ice, and a dry THF solution containing 16.5 g (70 mmol) of phenyl N-chlorosulfonylcarbamate, was dropwise added thereto. The mixture was stirred at room temperature for 2 hours, and then poured into 1500 ml of ice water containing 17.4 g of 35% hydrochloric acid and extracted twice with diethyl ether. The diethyl ether layer was washed twice with water and once with a saturated sodium chloride aqueous solution and dried over anhydrous sodium sulfate. The solvent was distilled off under reduced pressure to obtain 20.0 g of the desired phenyl N-(2-methyltetrahydro-1,2,6-thiadiazine-1,1-dioxide-6-sulfonyl)carbamate. Melting point: 144°-145° C.

The structures and physical properties or characteristics of the compounds prepared in the same manner as in the above Reference Examples 1 to 4 are shown below:

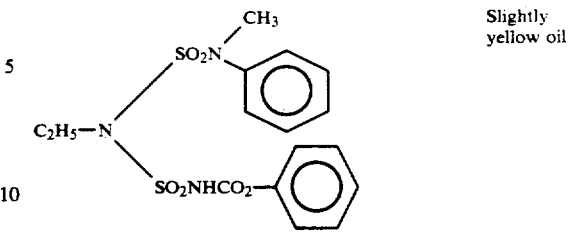
Slightly yellow oil

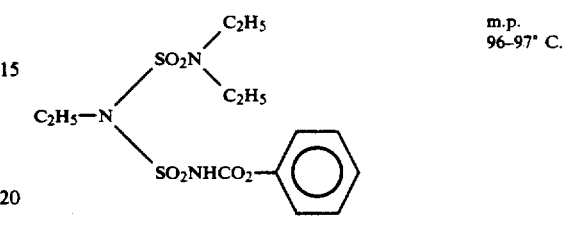
Slightly yellow oil

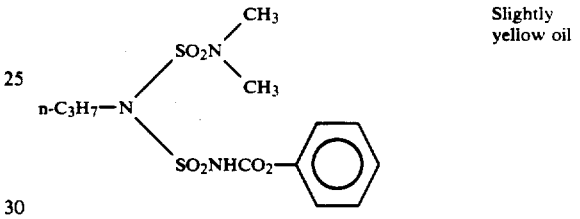
Slightly yellow oil

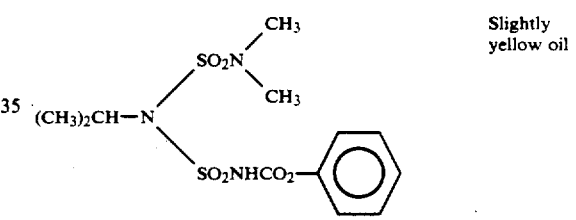
Slightly yellow oil

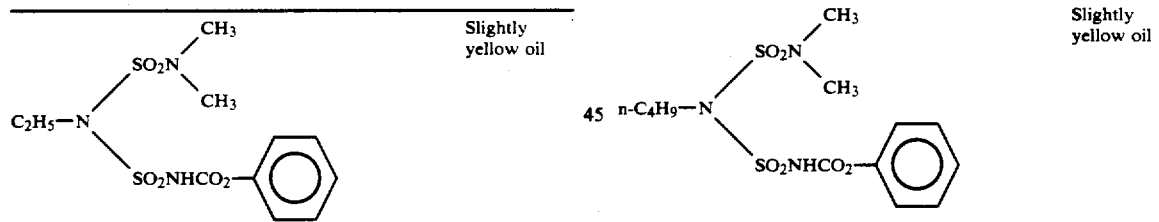
Slightly yellow oil m.p. 96–97° C.

Slightly yellow oil

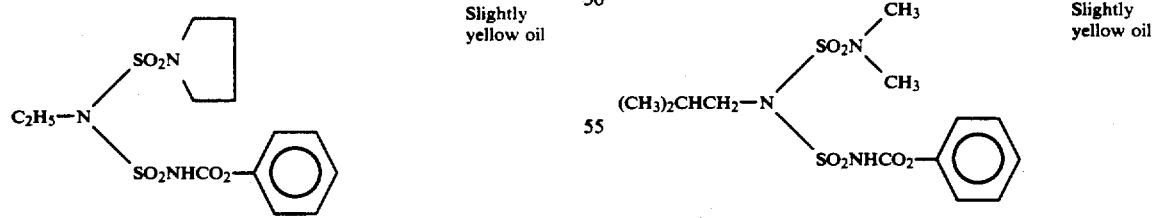
Slightly yellow oil

Slightly yellow oil

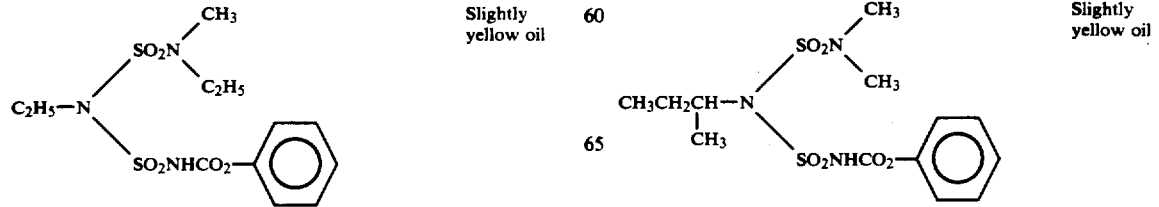
Slightly yellow oil

Slightly yellow oil

-continued
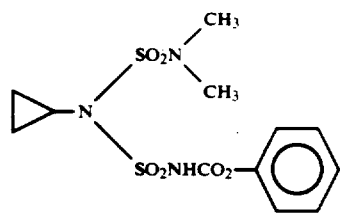 Slightly yellow oil
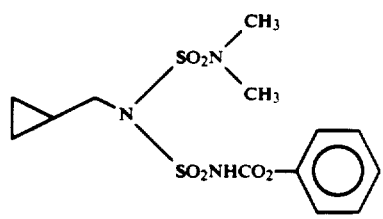 Slightly yellow oil
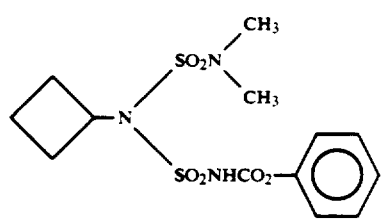 Slightly yellow oil
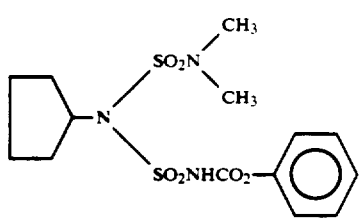 Slightly yellow oil
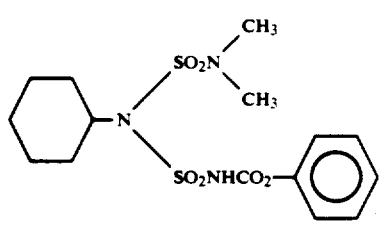 Slightly yellow oil
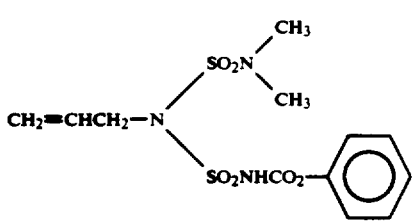 Slightly yellow oil
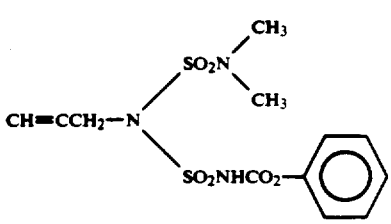 Slightly yellow oil
-continued
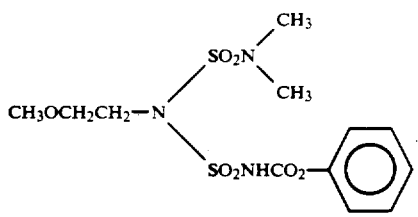 Slightly yellow oil
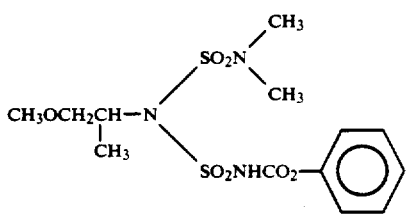 Slightly yellow oil
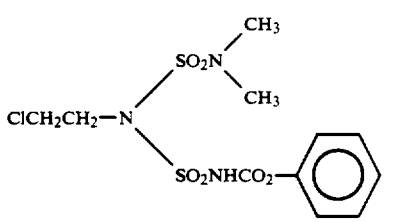 Slightly yellow oil
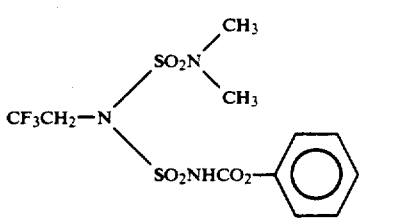 Slightly yellow oil
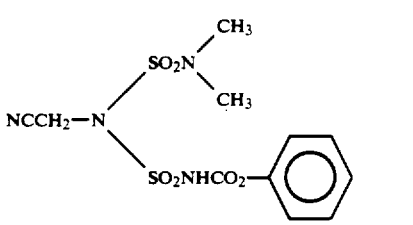 Slightly yellow oil
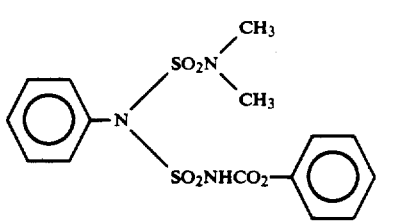 Slightly yellow oil
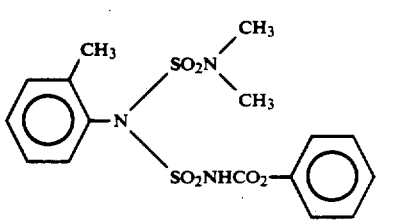 Slightly yellow oil

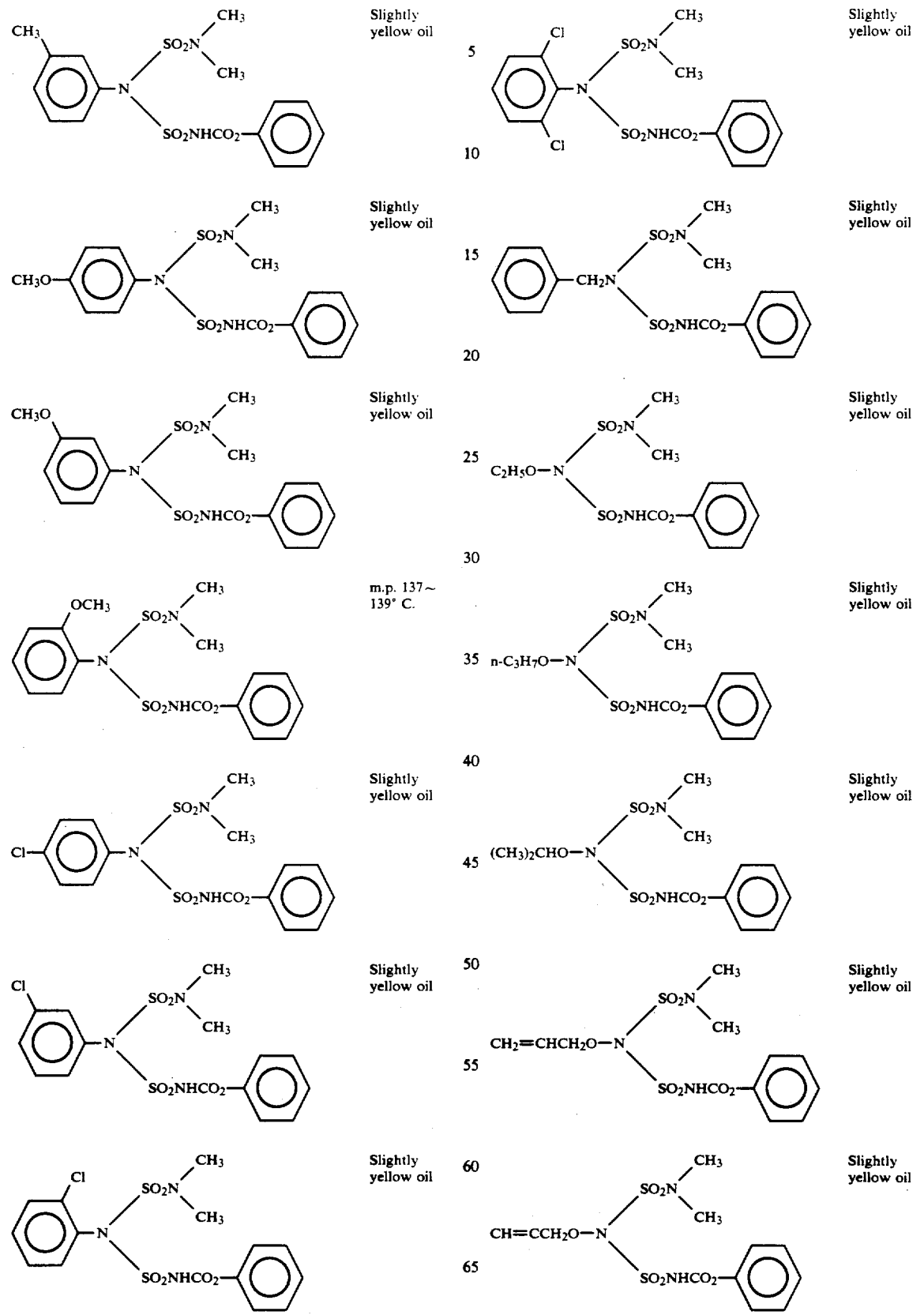

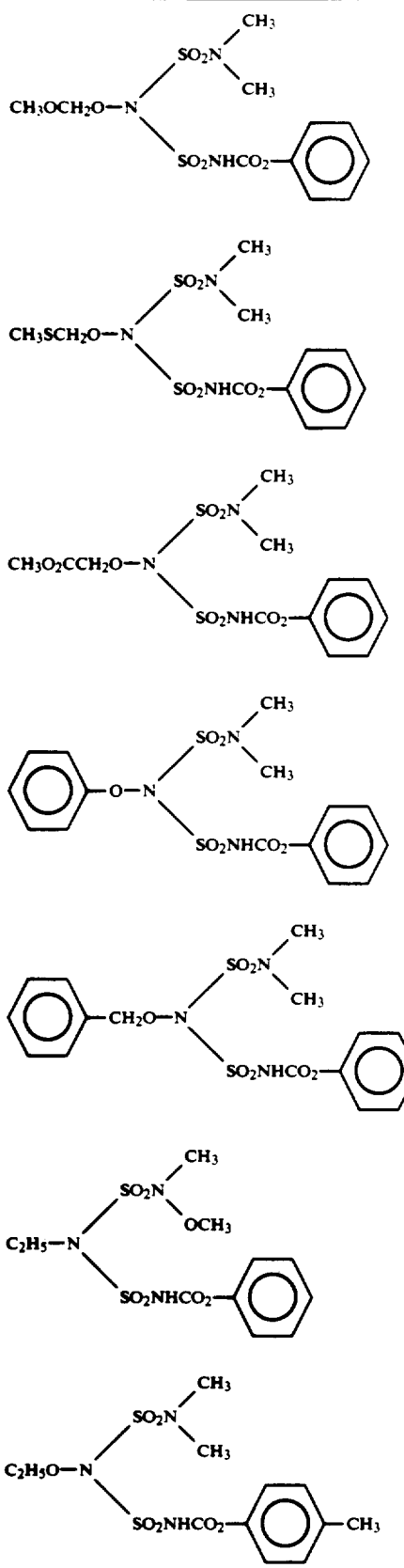
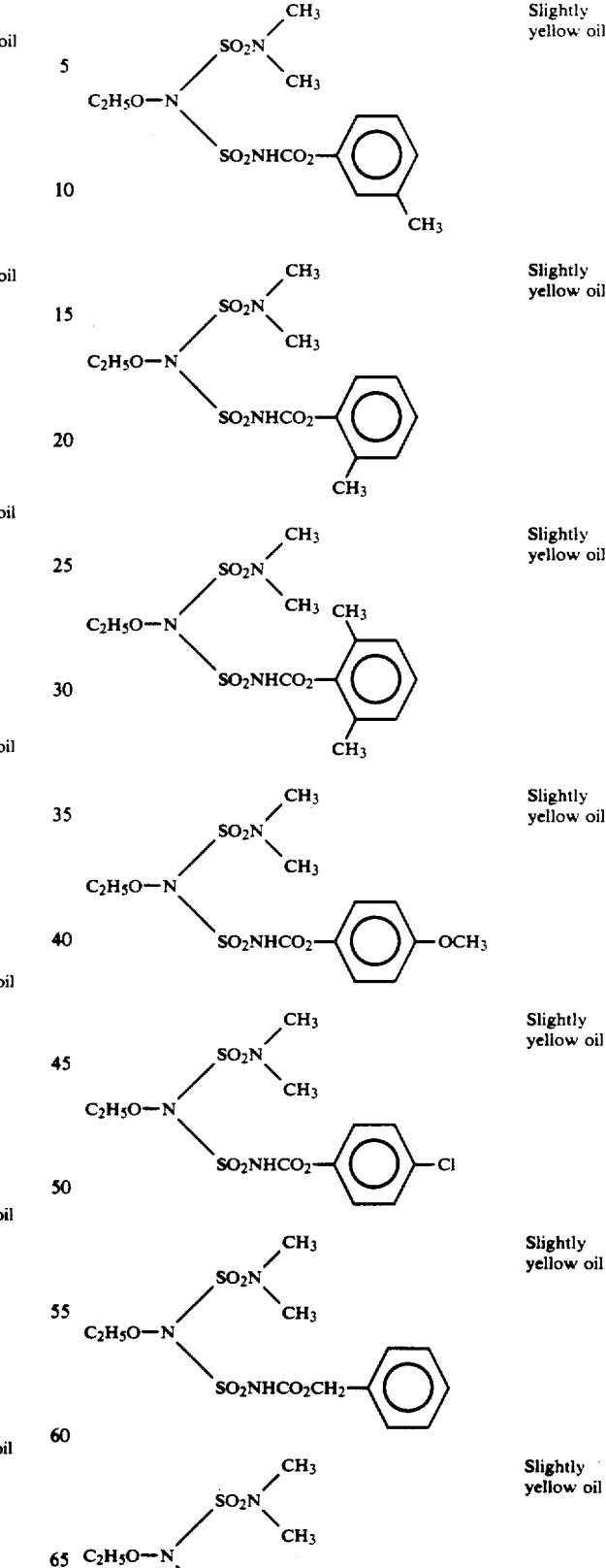

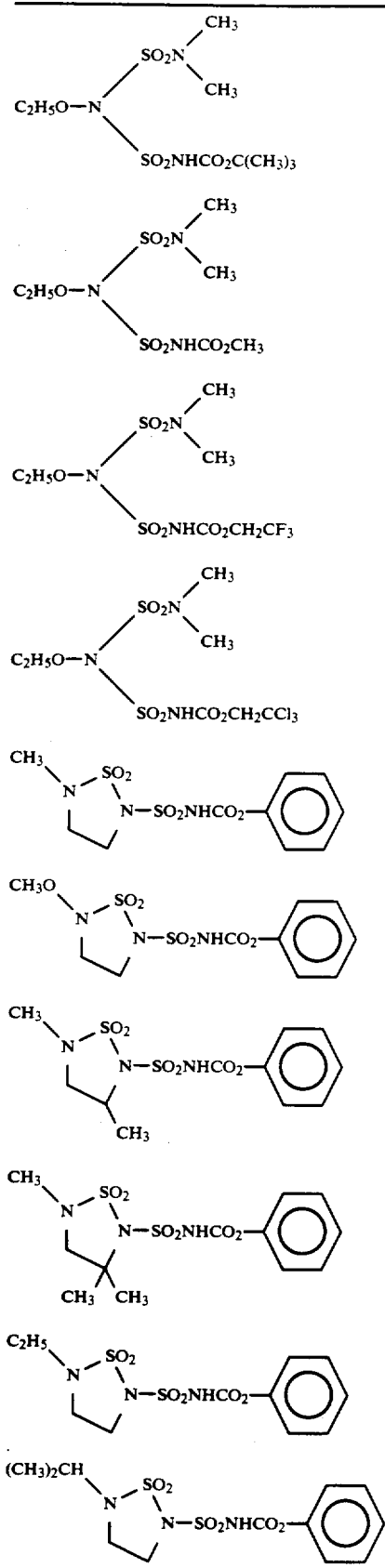
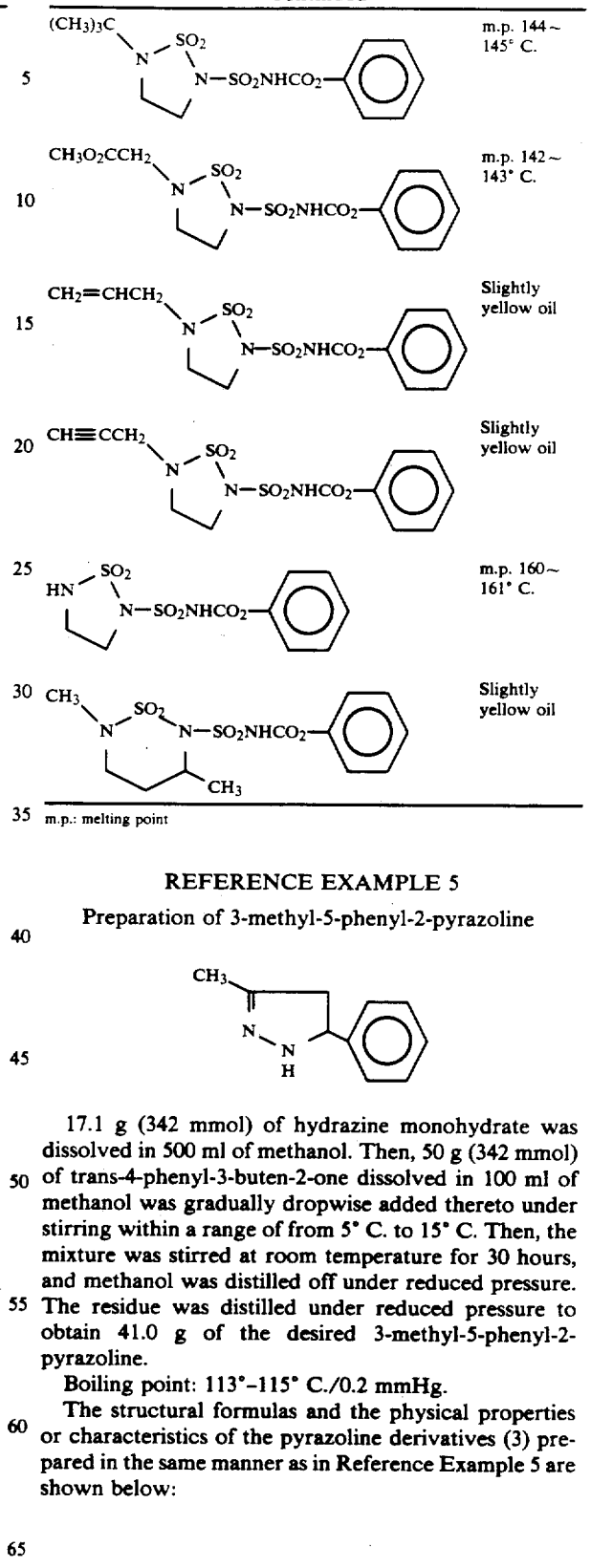

REFERENCE EXAMPLE 5

Preparation of 3-methyl-5-phenyl-2-pyrazoline

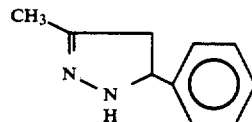

17.1 g (342 mmol) of hydrazine monohydrate was dissolved in 500 ml of methanol. Then, 50 g (342 mmol) of trans-4-phenyl-3-buten-2-one dissolved in 100 ml of methanol was gradually dropwise added thereto under stirring within a range of from 5° C. to 15° C. Then, the mixture was stirred at room temperature for 30 hours, and methanol was distilled off under reduced pressure. The residue was distilled under reduced pressure to obtain 41.0 g of the desired 3-methyl-5-phenyl-2-pyrazoline.

Boiling point: 113°–115° C./0.2 mmHg.

The structural formulas and the physical properties or characteristics of the pyrazoline derivatives (3) prepared in the same manner as in Reference Example 5 are shown below:

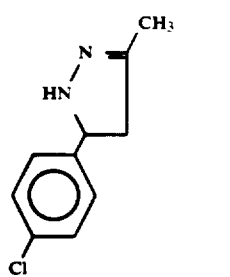 b.p. 127~132° C./2.8 mmHg
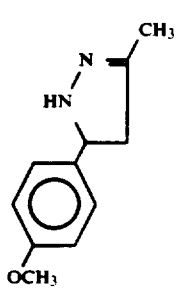 Oil
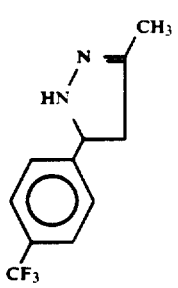 b.p. 103~107° C./0.09 mmHg
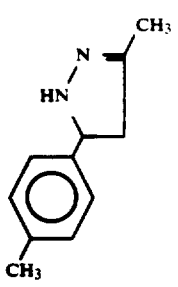 b.p. 124~134° C./0.3 mmHg
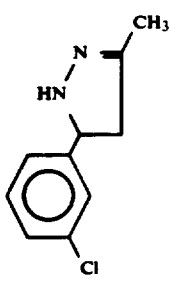 b.p. 124~127° C./0.3 mmHg
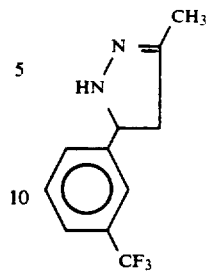 Oil
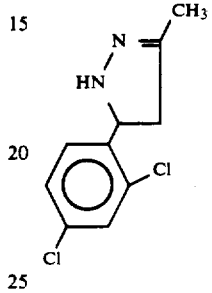 b.p. 144~146° C./2.5 mmHg
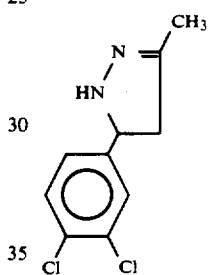 b.p. 150~154° C./1.7 mmHg
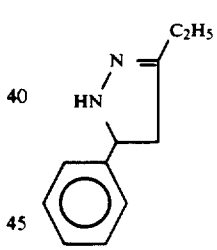 b.p. 110~117° C./3 mmHg
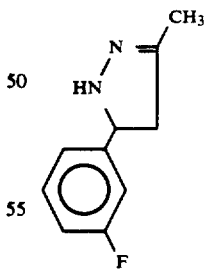 b.p. 111~113° C./0.3 mmHg
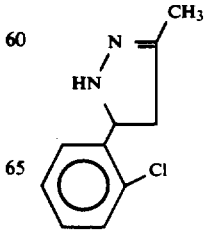 Oil -continued
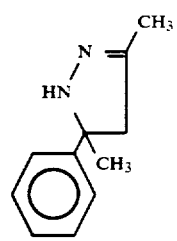 b.p. 102~107° C./0.08 mmHg
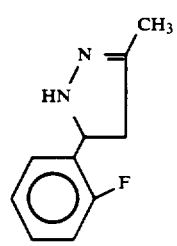 b.p. 97~105° C./0.17 mmHg
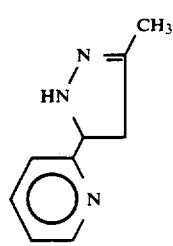 b.p. 108~115° C./0.07 mmHg
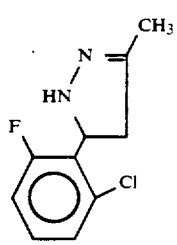 b.p. 133~134° C./0.8 mmHg
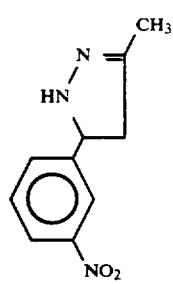 m.p. 83~85° C.
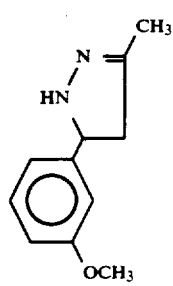 b.p. 128~132° C./0.25 mmHg
-continued
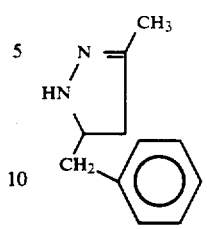 b.p. 108~118° C./0.8 mmHg
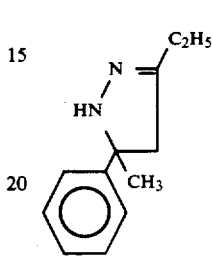 b.p. 104~105° C./0.4 mmHg
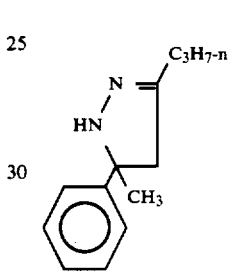 b.p. 114~115° C./0.25 mmHg
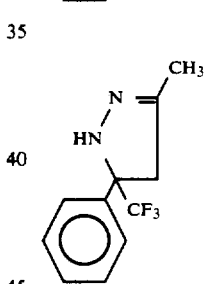 Oil
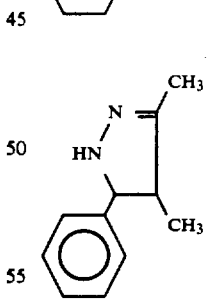 Oil
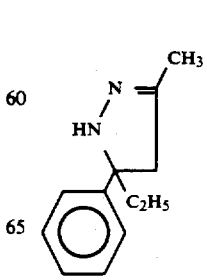 Oil -continued
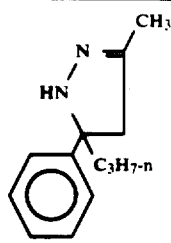 Oil
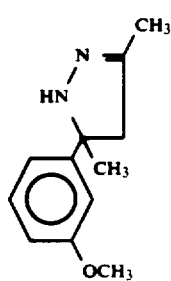 b.p. 118~120° C./0.4 mmHg
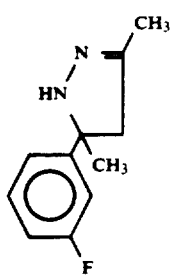 b.p. 103~105° C./0.5 mmHg
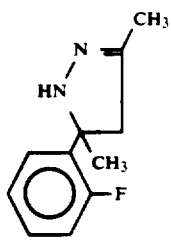 Oil
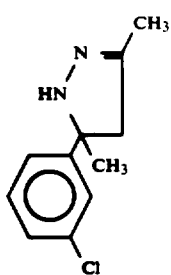 b.p. 101~103° C./0.4 mmHg
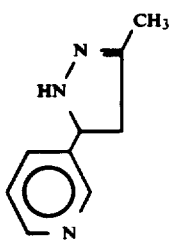 b.p. 118~120° C./0.2 mmHg
-continued
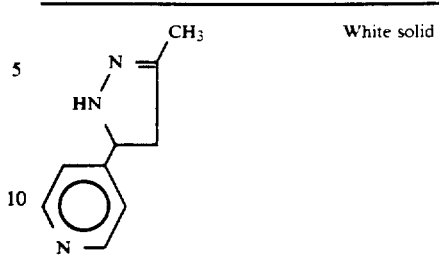 White solid
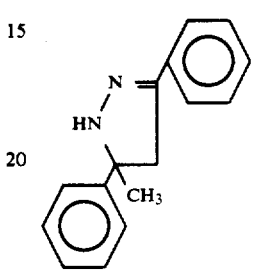 Oil
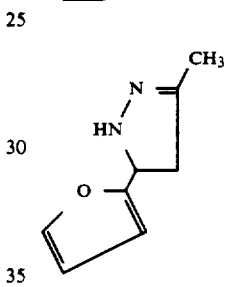 b.p. 98~100° C./0.2 mmHg
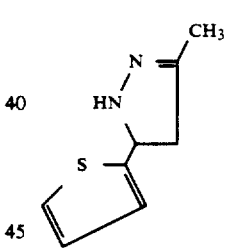 b.p. 108~110° C./1.0 mmHg
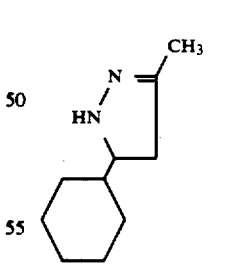 b.p. 83~87° C./0.35 mmHg
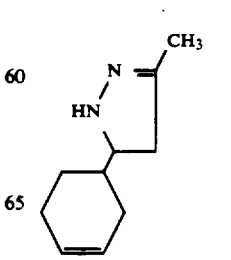 b.p. 90~94° C./0.45 mmHg -continued
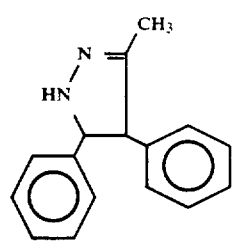 Oil
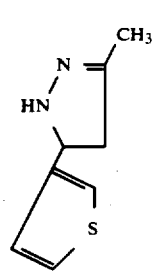 b.p. 106~108° C./0.4 mmHg
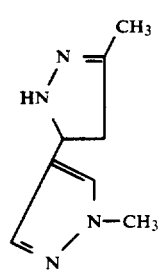 b.p. 126~128° C./0.6 mmHg
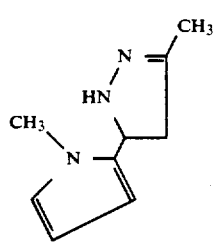 b.p. 111~113° C./0.4 mmHg
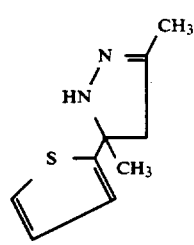 Oil
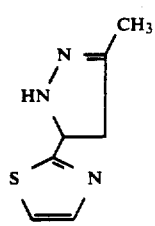 Oil
-continued
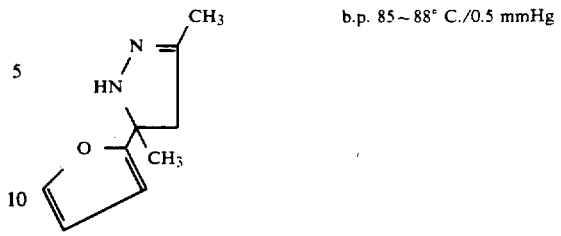 b.p. 85~88° C./0.5 mmHg
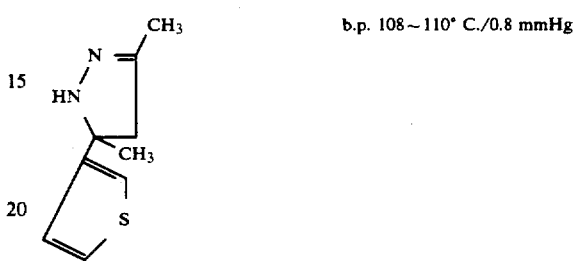 b.p. 108~110° C./0.8 mmHg
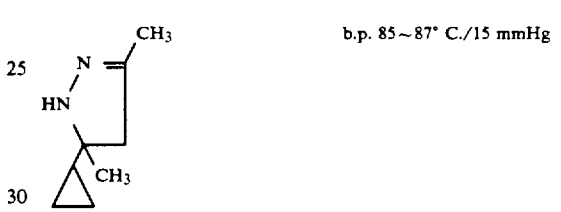 b.p. 85~87° C./15 mmHg
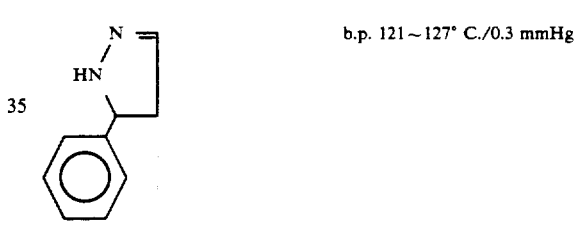 b.p. 121~127° C./0.3 mmHg
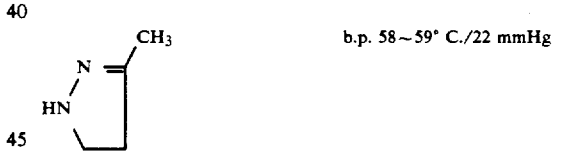 b.p. 58~59° C./22 mmHg
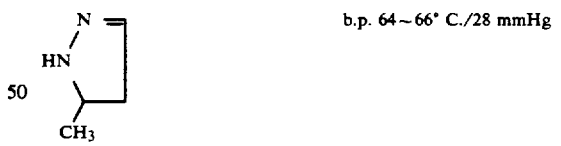 b.p. 64~66° C./28 mmHg
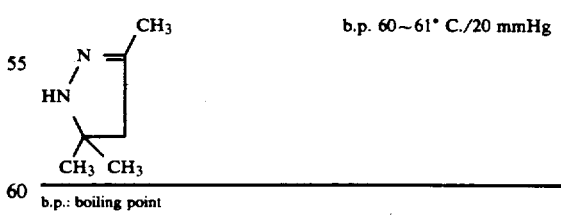 b.p. 60~61° C./20 mmHg
b.p.: boiling point

EXAMPLE 1

Preparation of 1-[(N-dimethylsulfamoyl-N-ethylamino)sulfonylcarbamoyl]-3-methyl-5-phenyl-2-pyrazoline

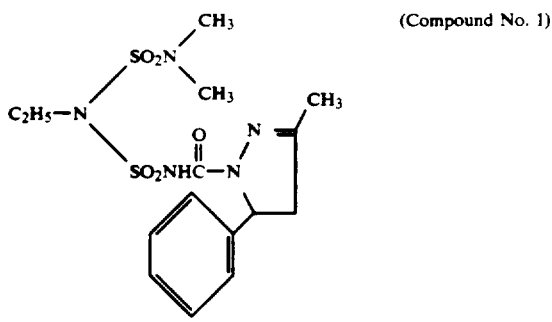

(Compound No. 1)

A mixture comprising 3.3 g (9.4 mmol) of phenyl N-(N-dimethylsulfamoyl-N-ethylamino)sulfonyl]carbamate, 3.76 g (23.5 mmol) of 3-methyl-5-phenyl-2-pyrazoline and 30 ml of dry benzene was refluxed for 5 minutes. The mixture was left to cool, and then 50 ml of benzene was added thereto. The benzene layer was washed twice with dilute hydrochloric acid and then twice with water. Then, it was dried over anhydrous sodium sulfate. Thereafter, the solvent was distilled off under reduced pressure. The obtained residue was purified by silica gel column chromatography ($CHCl_3$) and then washed sequentially with n-hexane and diethyl ether to obtain 2 g of the desired 1-[(N-dimethylsulfamoyl-N-ethylamino)sulfonylcarbamoyl]-3-methyl-5-phenyl-2-pyrazoline.

Melting point: 138°–139° C.

EXAMPLE 2

Preparation of 1-[(N-dimethylsulfamoyl-N-methylamino)sulfonylcarbamoyl]-3-methyl-5-(2-thienyl)-2-pyrazoline

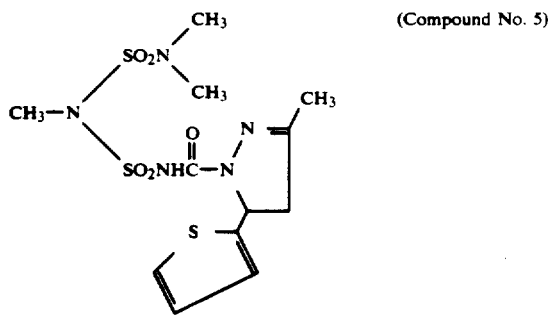

(Compound No. 5)

A mixture comprising 1.69 g (5.0 mmol) of phenyl N-[(N-dimethylsulfamoyl-N-methylamino)sulfonyl]carbamate, 0.58 g (3.5 mmol) of 3-methyl-5-(2-thienyl)-2-pyrazoline and 10 ml of dry benzene, was refluxed for 10 minutes. The mixture was left to cool, and then benzene was distilled off under reduced pressure. The obtained residue was washed with n-hexane. Then, the residue was stirred together with diethyl ether. The precipitated crystalline product was isolated by suction filtration and then washed with diethyl ether to obtain 1.1 g of the desired 1-[(N-dimethylsulfamoyl-N-methylamino)sulfonylcarbamoyl]-3-methyl-5-(2-thienyl)-2-pyrazoline.

Melting point: 112°–113° C.

EXAMPLE 3

Preparation of 1-[(N-dimethylsulfamoyl-N-methoxyamino)sulfonylcarbamoyl]-3-methyl-5-phenyl-2-pyrazoline

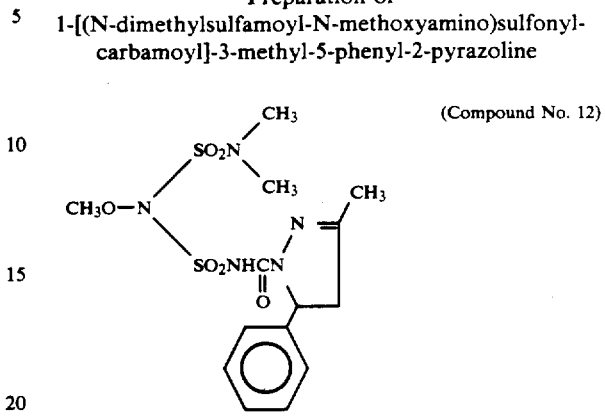

(Compound No. 12)

4.24 g (12 mmol) of phenyl N-[(N-dimethylsulfamoyl-N-methoxyamino)sulfonyl]carbamate was dissolved in 30 ml of dry benzene, and 1.6 g (10 mmol) of 3-methyl-5-phenyl-2-pyrazoline was added thereto. The mixture was refluxed for 5 minutes. The mixture was left to cool, and the solvent was distilled off under reduced pressure. The residue was purified by reverse phase column chromatography ($CH_3CN$: $H_2O$ = 7:3) to obtain 1.0 g of the desired 1-[(N-dimethylsulfamoyl-N-methoxyamino)sulfonylcarbamoyl]-3-methyl-5-phenyl-2-pyrazoline.

Melting point: 104°–105° C.

EXAMPLE 4

Preparation of 1-[(N-(N-methyl-N-methoxyaminosulfonyl)-N-methylamino)sulfonylcarbamoyl]-3-methyl-5-phenyl-2-pyrazoline

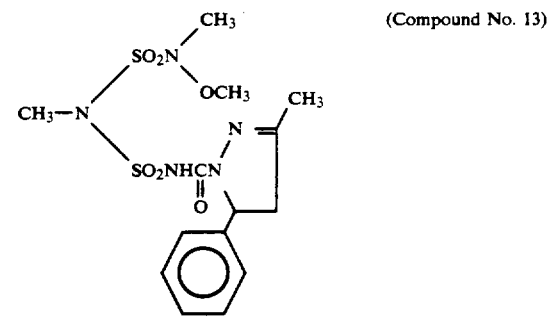

(Compound No. 13)

A mixture comprising 1 g (2.83 mmol) of phenyl N-[(N-(N-methyl-N-methoxyaminosulfonyl)-N-methylamino)sulfonyl]-carbamate, 0.45 g (2.81 mmol) of 3-methyl-5-phenyl-2-pyrazoline and 30 ml of dry benzene was heated at 80° C. for 5 minutes. The mixture was left to cool, and then the solvent was distilled off under reduced pressure. The residue was purified by reverse phase column chromatography ($CH_3CN$: $H_2O$ = 7:3) to obtain 0.5 g of the desired 1-[(N-(N-methyl-N-methoxyaminosulfonyl)-N-methyl-amino)sulfonylcarbamoyl]-3-methyl-5-phenyl-2-pyrazoline as glassy substance.

EXAMPLE 5

Preparation of 1-(2-methyl-tetrahydro-1,2,6-thiadiazine-1,1-dioxide-6-sulfonylcarbamoyl)-3-methyl-5-phenyl-2-pyrazoline

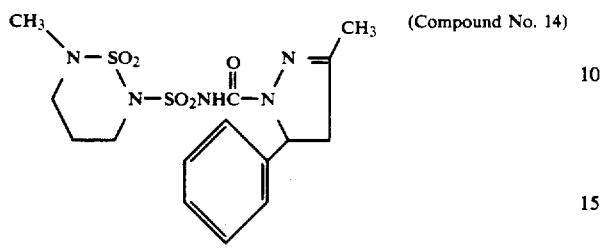
(Compound No. 14)

A mixture comprising 0.70 g (2 mmol) of phenyl N-(2-methyl-tetrahydro-1,2,6-thiadiazine-1,1-dioxide-6-sulfonyl)carbamate, 0.80 g (5 mmol) of 3-methyl-5-phenyl-2-pyrazoline and 30 ml of dry benzene, was refluxed for 5 minutes. The mixture was left to cool, and then 50 ml of benzene was added thereto. The benzene layer was washed three times with dilute hydrochloric acid and twice with water. Then, it was dried over anhydrous sodium sulfate, and then solvent was distilled off under reduced pressure. The obtained residue was washed sequentially with n-hexane and diethyl ether to obtain 0.7 g of the desired 1-(2-methyl-tetrahydro-1,2,6-thiadiazine-1,1- dioxide-6-sulfonylcarbamoyl)-3-methyl-5-phenyl-2-pyrazoline.

Melting point: 147°–148° C.

EXAMPLE 6

Preparation of 1-(2-methyl-tetrahydro-1,2,6-thiadiazine-1,1-dioxide-6-sulfonylcarbamoyl)-3,5-dimethyl-5-phenyl-2-pyrazoline

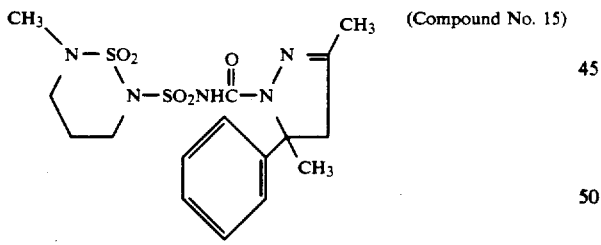
(Compound No. 15)

A mixture comprising 8 g (22.9 mmol) of phenyl N-(2-methyl-tetrahydro-1,2,6-thiadiazine-1,1-dioxide-6-sulfonyl)carbamate, 5.1 g (29.3 mmol) of 3,5-dimethyl-5-phenyl-2-pyrazoline and 200 ml of dry benzene, was heated at 80° C. for 5 minutes. The mixture was left to cool, and then solvent was distilled off under reduced pressure. The residue was washed with diethyl ether to obtain 6.2 g of the desired 1-(2-methyl-tetrahydro-1,2,6-thiadiazine-1,1-dioxide-6-sulfonylcarbamoyl)-3,5-dimethyl-5-phenyl-2-pyrazoline.

Melting point: 151°–154° C.

The structural formulas and the physical properties or characteristics of the compounds prepared in the same manner as in Examples 1 to 6 are shown below:

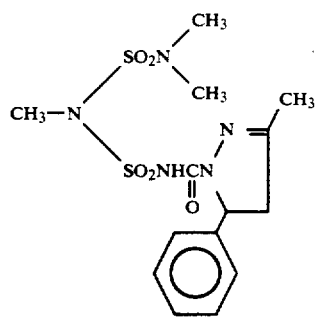
(Compound No. 2) m.p. 129–130° C.

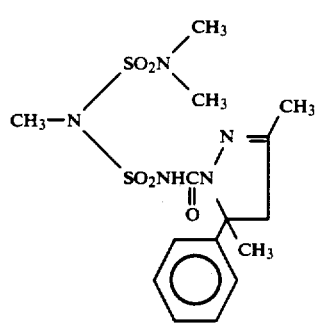
(Compound No. 3) m.p. 117–119° C.

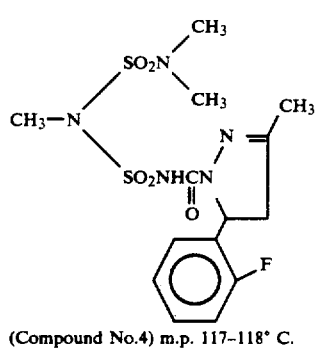
(Compound No.4) m.p. 117–118° C.

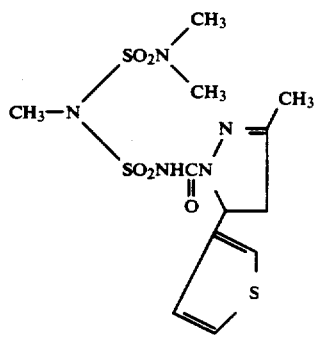
(Compound No. 6) m.p. 106–108° C.

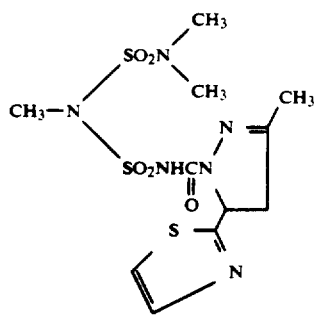
(Compound No. 7) m.p. 135-137° C.
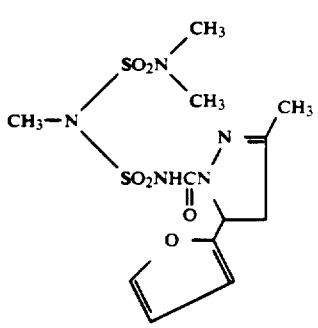
(Compound No. 8) m.p. 112-114° C.
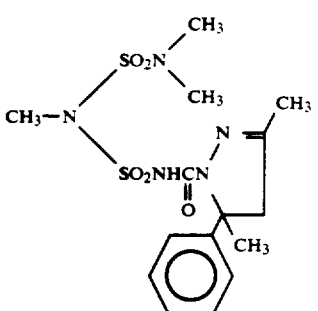
(Compound No. 9) m.p. 123-124° C.
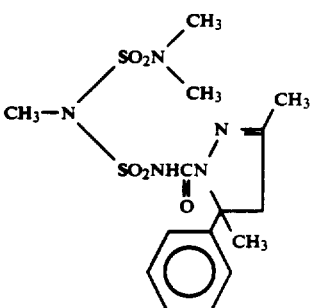
(Compound No. 10) m.p. 111-112° C.
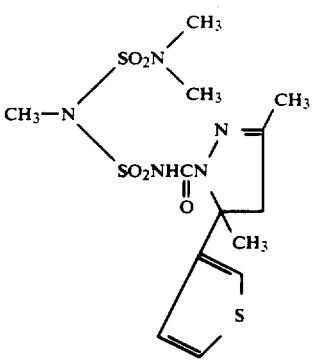
(Compound No. 11) m.p. 103-104° C.
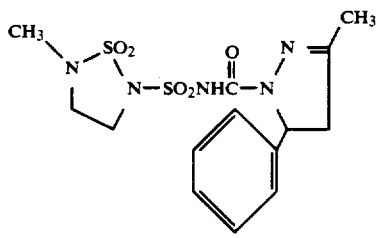
(Compound No. 16) m.p. 131-132° C.
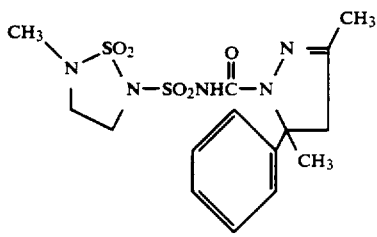
(Compound No. 17) m.p. 120-123° C.
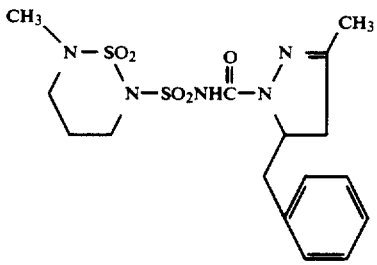
(Compound No. 18) m.p. 123-126° C.
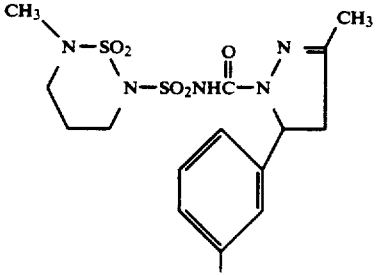
(Compound No. 19) m.p. 136-140° C.

-continued
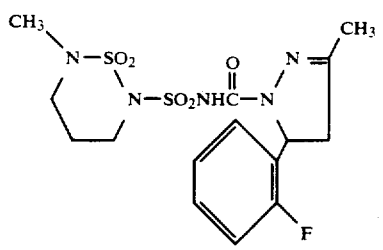
(Compound No. 20) m.p. 133-135° C.
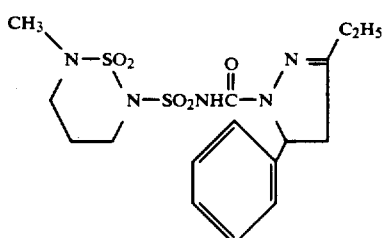
(Compound No. 21) m.p. 128-131° C.
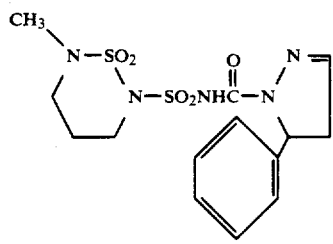
(Compound No. 22) m.p. 130-132° C.
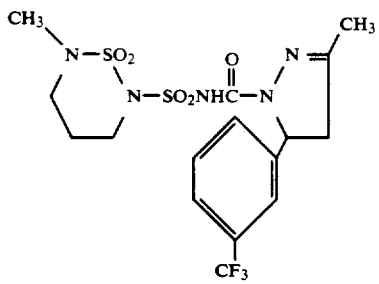
(Compound No. 23) m.p. 115-117° C.
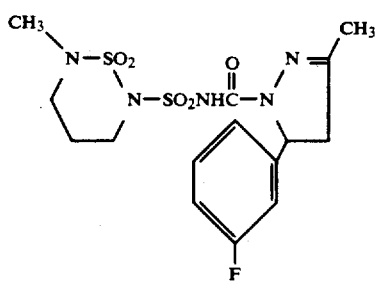
(Compound No. 24) m.p. 123-126° C.
-continued
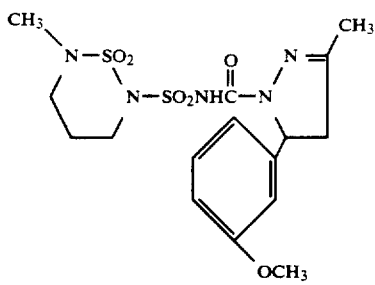
(Compound No. 25) m.p. 114-116° C.
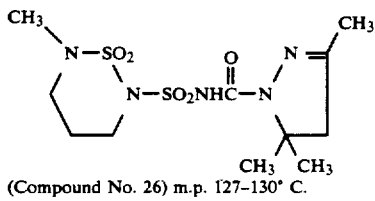
(Compound No. 26) m.p. 127-130° C.
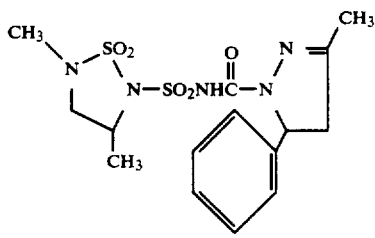
(Compound No. 27) (Glassy)
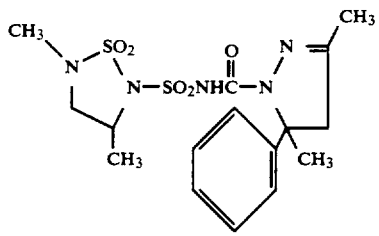
(Compound No. 28) (Glassy)
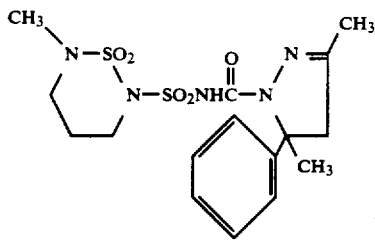
(Compound No. 29) (Glassy)
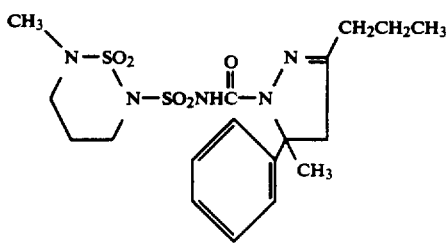
(Compound No. 30) m.p. 132-134° C.

-continued
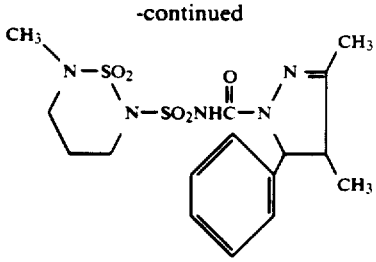
(Compound No. 31) m.p. 131–133° C.
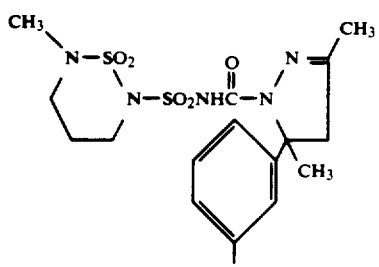
(Compound No. 32) m.p. 141–142° C.
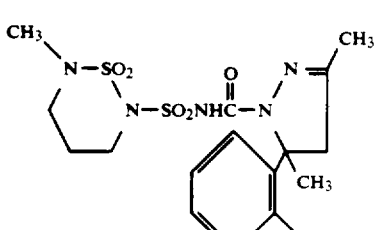
(Compound No. 33) m.p. 138–140° C.
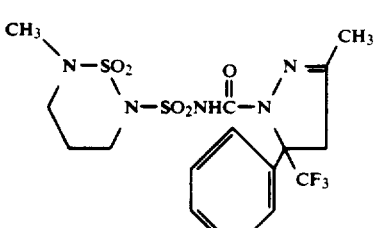
(Compound No. 34) m.p. 135–137° C.
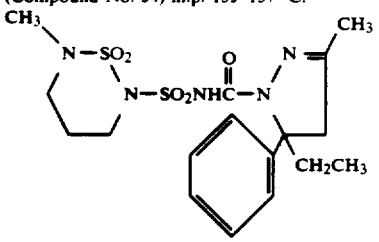
(Compound No. 35) m.p. 136–138° C.
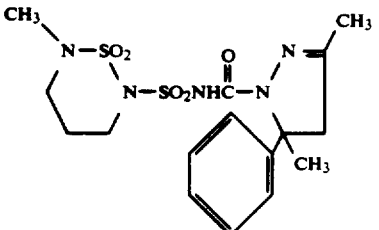
(Compound No. 36) m.p. 127–129° C.
-continued
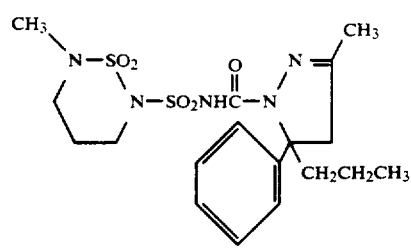
(Compound No. 37) m.p. 141–143° C.
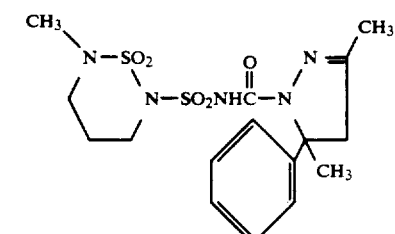
(Compound No. 38) m.p. 136–138° C.
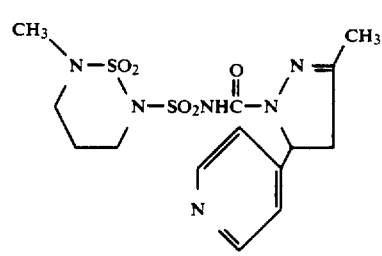
(Compound No. 39) m.p. 155–158° C.
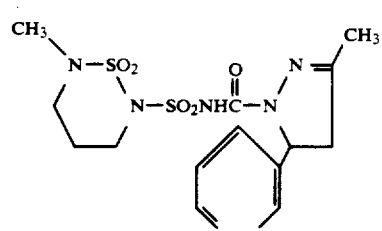
(Compound No. 40) m.p. 116–119° C.
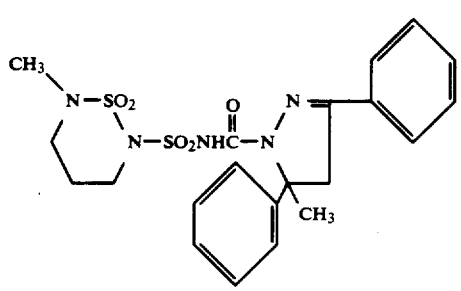
(Compound No. 41) m.p. 147–149° C.

-continued
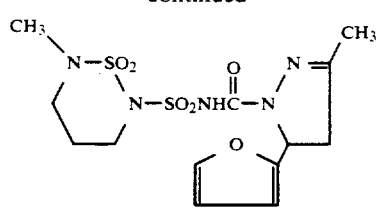
(Compound No. 42) m.p. 122-125° C.
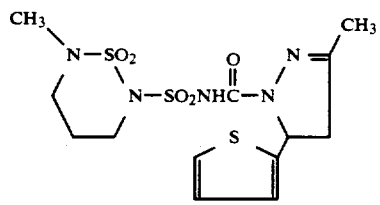
(Compound No. 43) (Glassy)
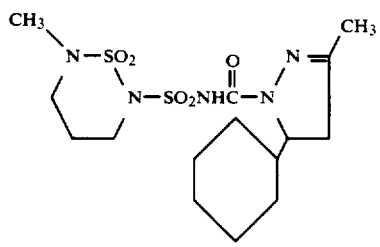
(Compound No. 44) (Glassy)
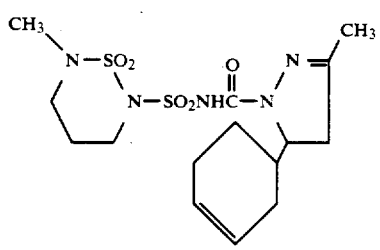
(Compound No. 45) (Glassy)
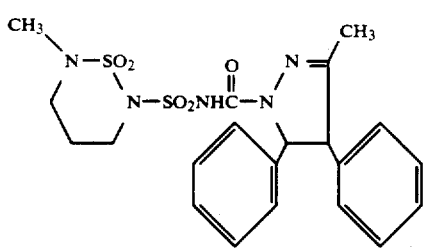
(Compound No. 46) m.p. 134-136° C.
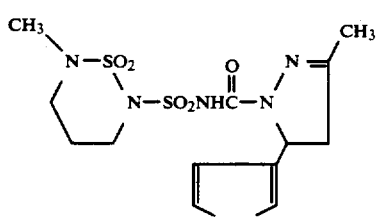
(Compound No. 47) m.p. 126-128° C.
-continued
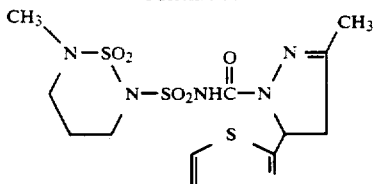
(Compound No. 48) m.p. 120-124° C.
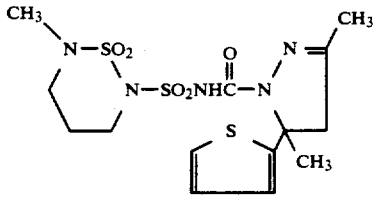
(Compound No. 49) m.p. 116-119° C.
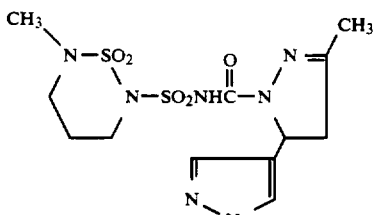
(Compound No. 50) m.p. 128-130° C.
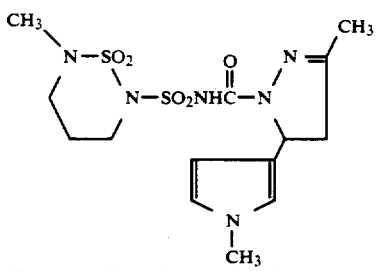
(Compound No. 51) m.p. 119-122° C.
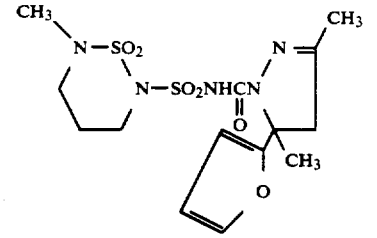
(Compound No. 52) (Glassy)
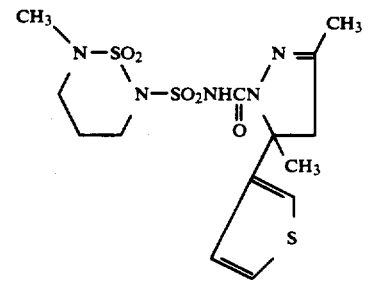
(Compound No. 53) m.p. 132-134° C.

-continued

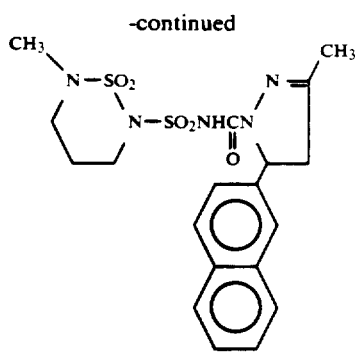

(Compound No. 54) m.p. 163-164° C.

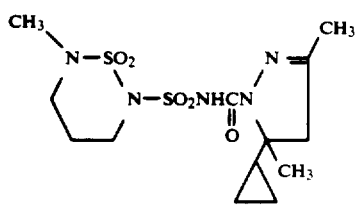

(Compound No. 55) (Glassy)

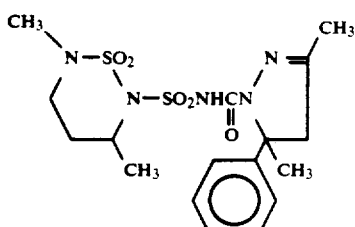

(Compound No. 56) m.p. 179-181° C.

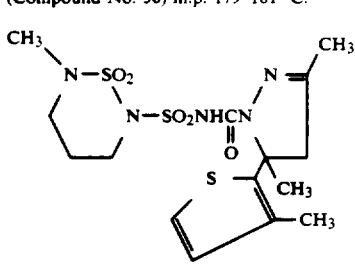

(Compound No. 57) m.p. 146-149° C.

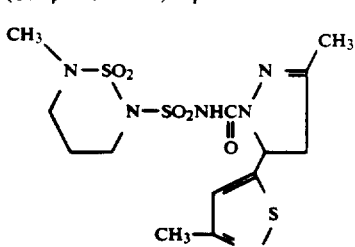

(Compound No. 58) m.p. 110-112° C.

Examples of compounds covered by the present invention including those prepared in the preceding Examples will be given in the following Tables 1 to 14 and Tables 1A to 14A. However, it should be understood that the compounds of the present invention are not limited to such specific Examples.

The symbols in the Tables have the following meanings.

Me: methyl group, Et: ethyl group, Pr-n: n-propyl group, Pr-i: isopropyl group, cyc-Pr: cyclopropyl group, Bu-n: n-butyl group, Bu-i: isobutyl group, Bu-sec: secondary butyl group, Bu-t: tert-butyl group, cyc-Bu: cyclobutyl group, Pen-n: n-pentyl group, cyc-Hex: cyclohexyl group, Ph: phenyl group, Gn is the same as the above G, and Ga, Gb and Gc have the following meanings.

Ga=G1–G643 (i.e. it means any one of G1 to G643.)

Gb=G1–G72 and G102–G136 (i.e. it means any one of G1 to G72 and G102 to G136.)

Gc=G1–G35 and G102–G136 (i.e. it means any one of G1 to G35 and G102 to G136.)

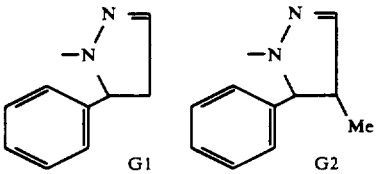

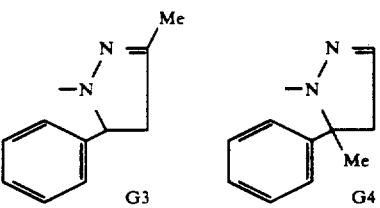

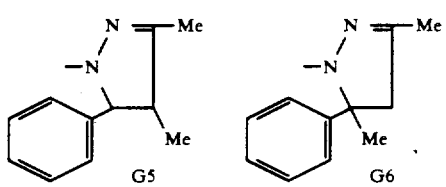

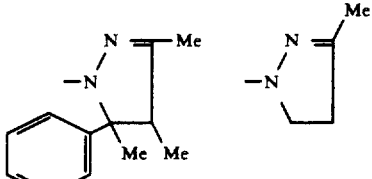

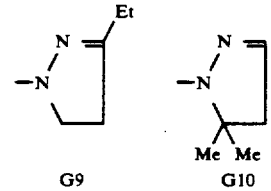

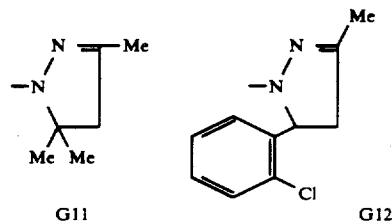

-continued
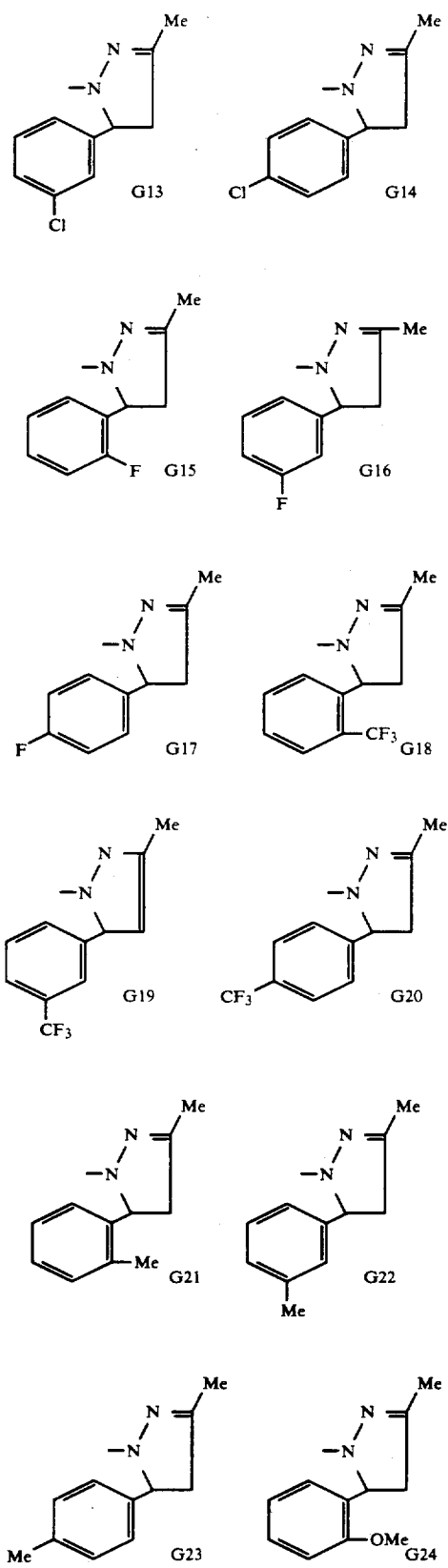
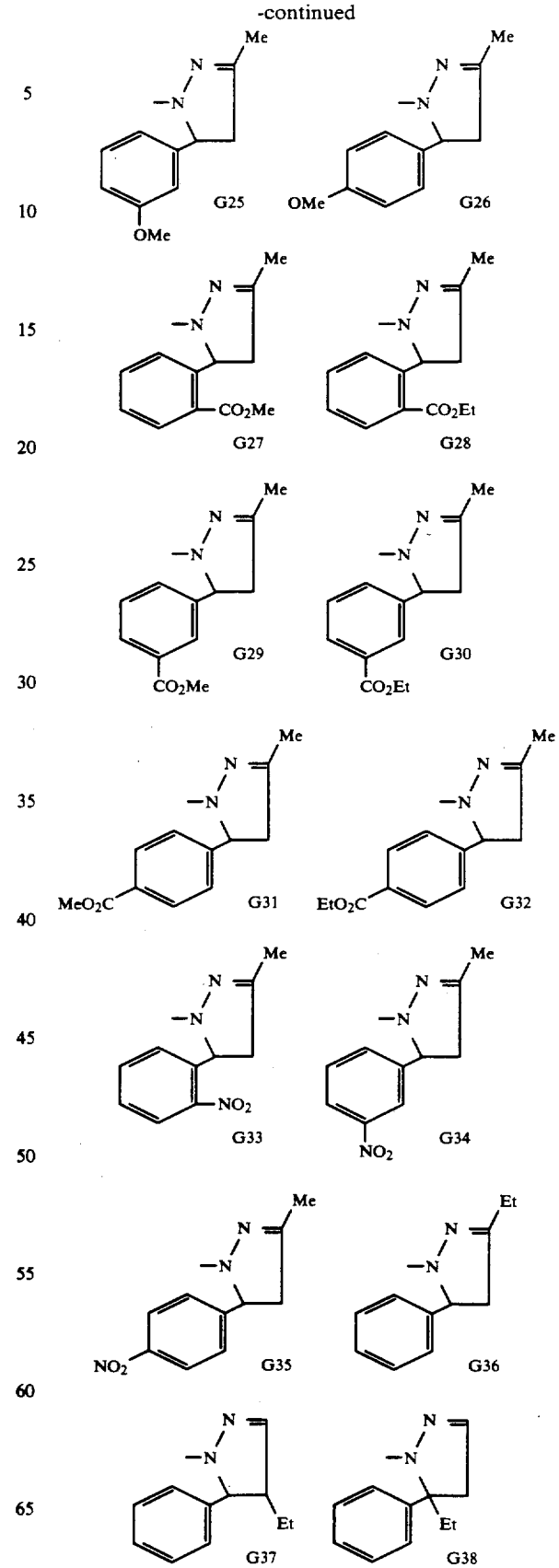

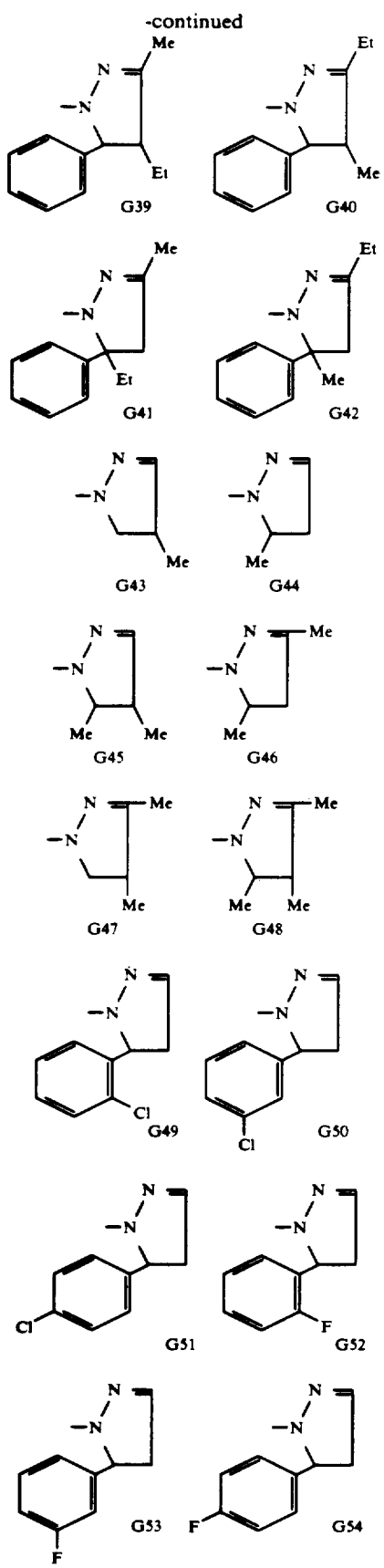
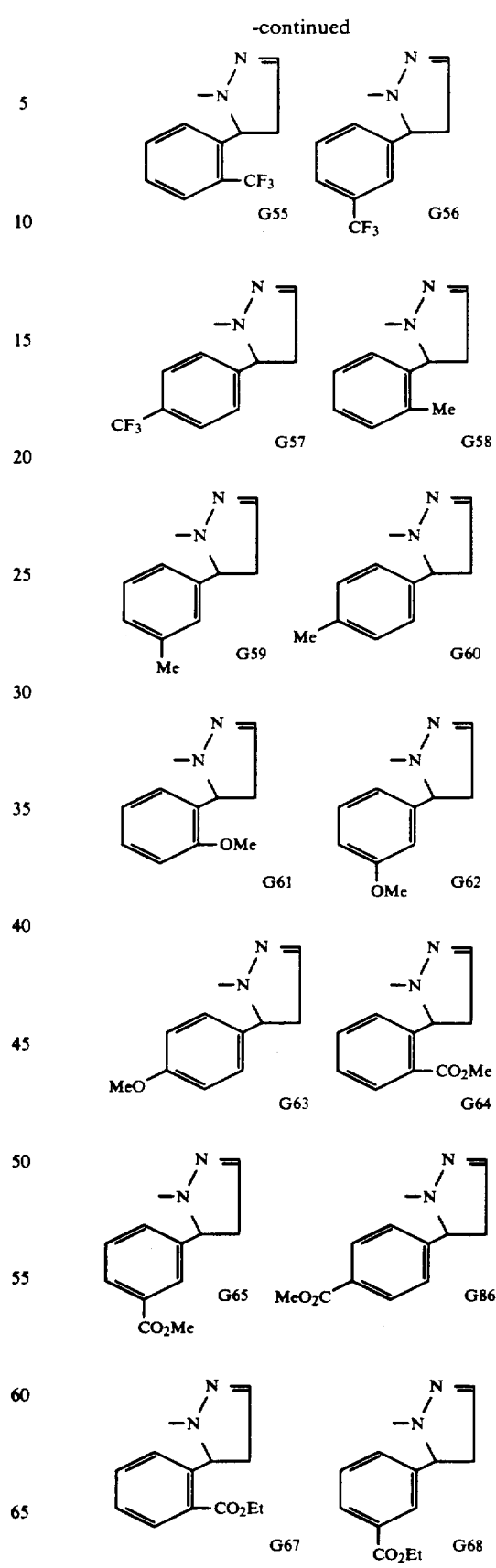

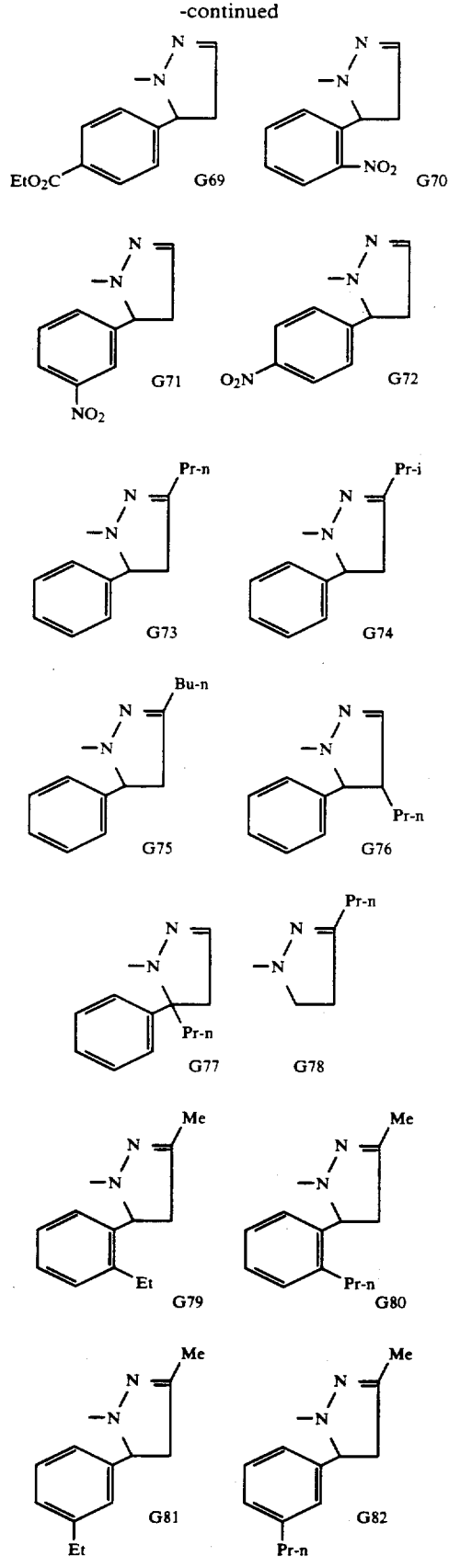

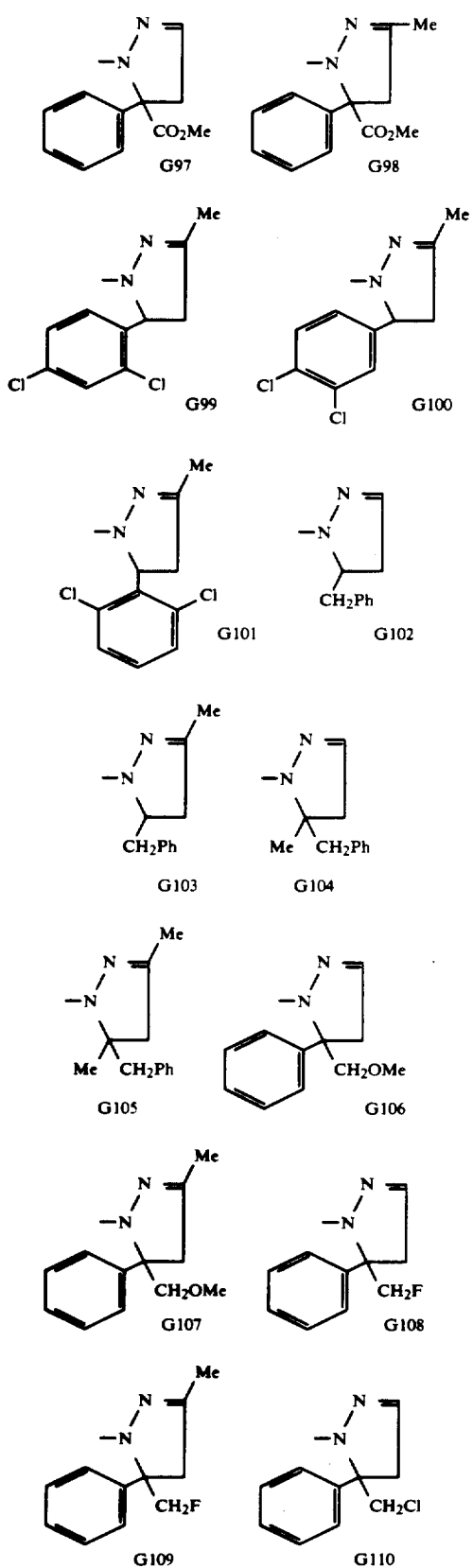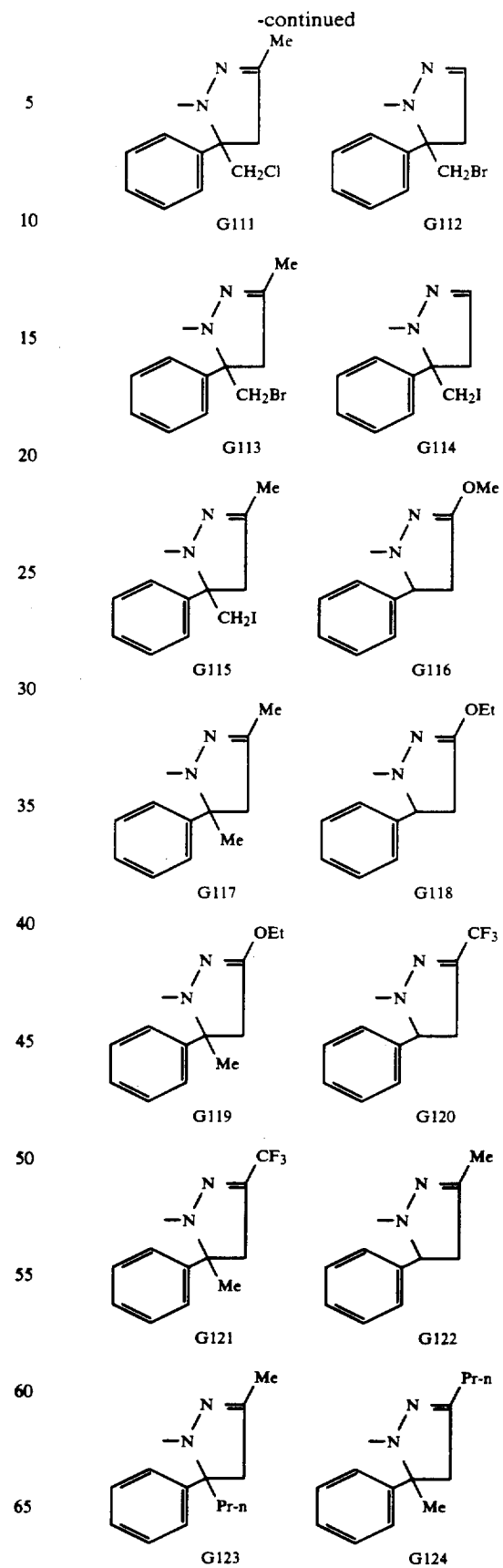

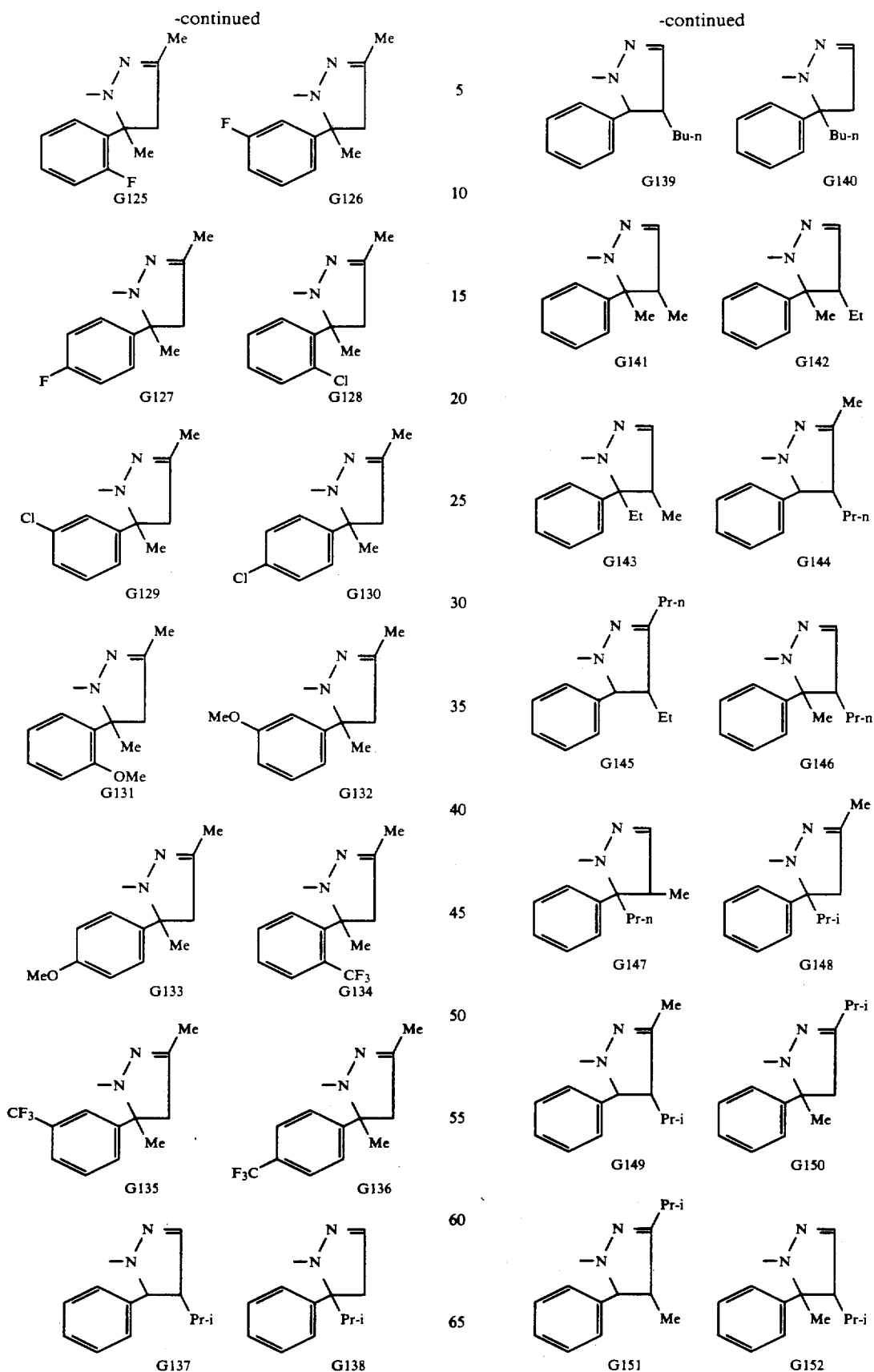

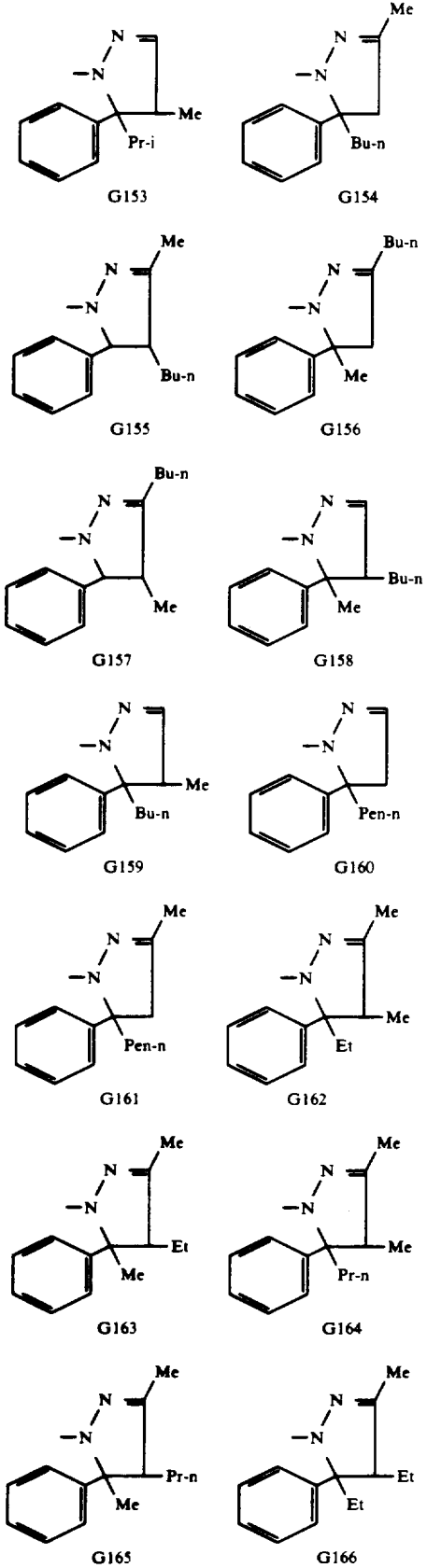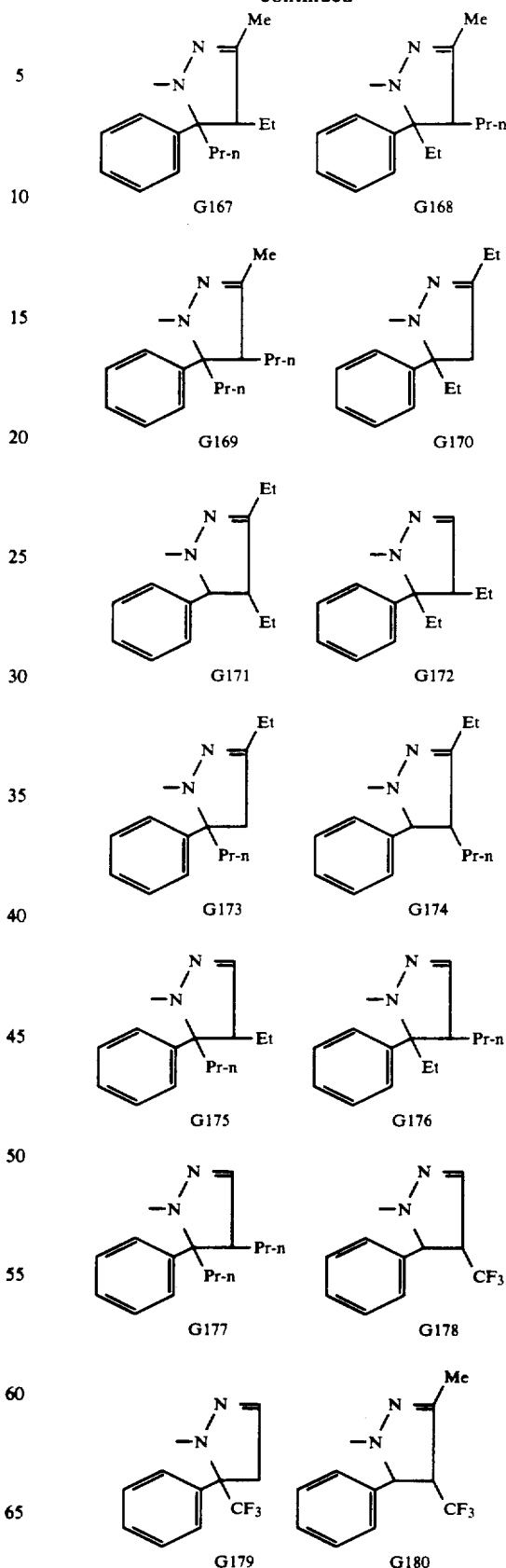

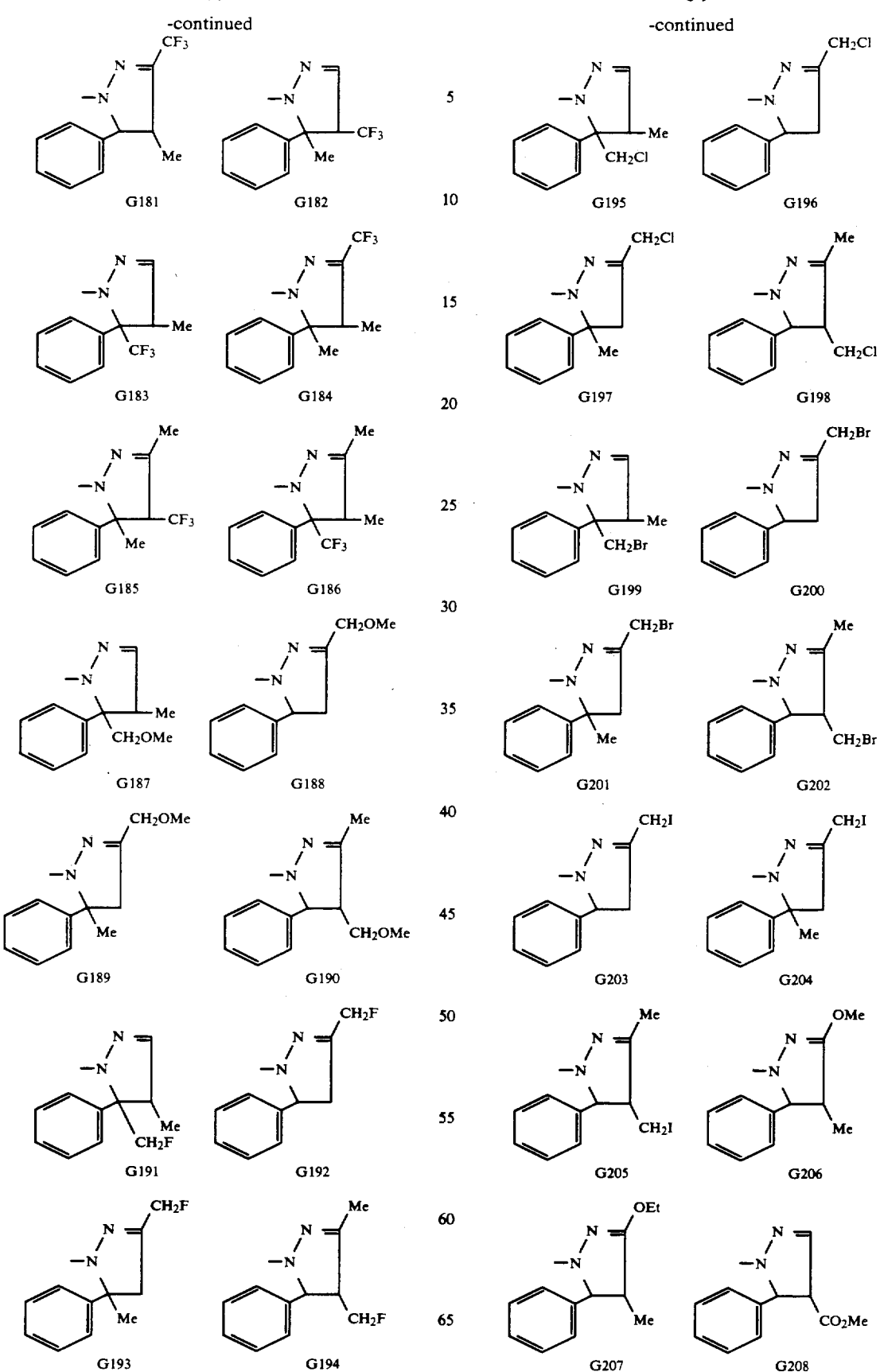

-continued
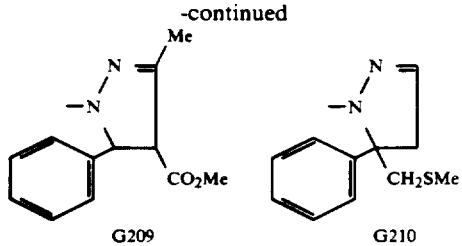
G209  G210
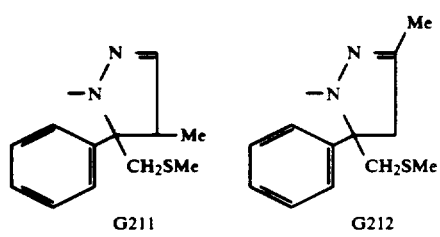
G211  G212
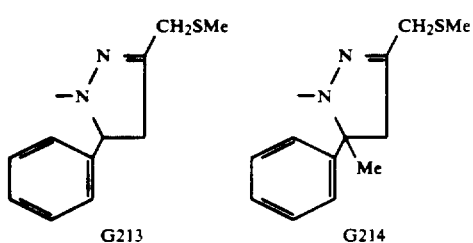
G213  G214
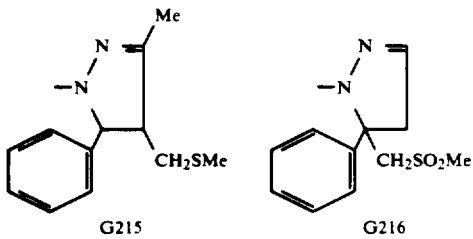
G215  G216
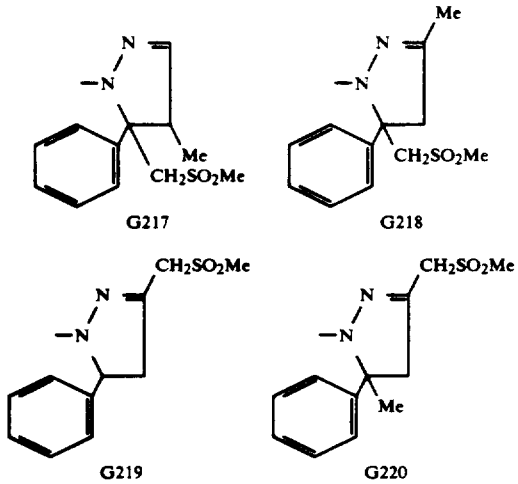
G217  G218
G219  G220
-continued
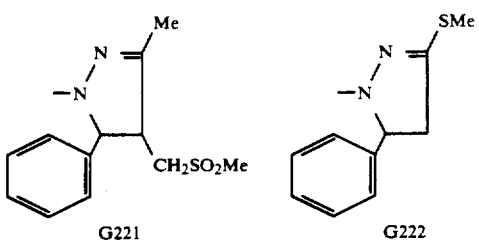
G221  G222
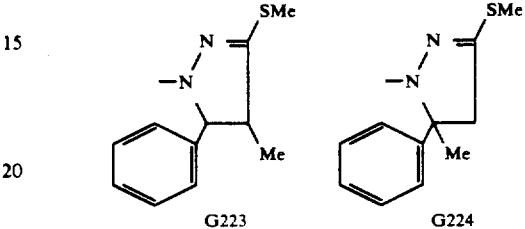
G223  G224
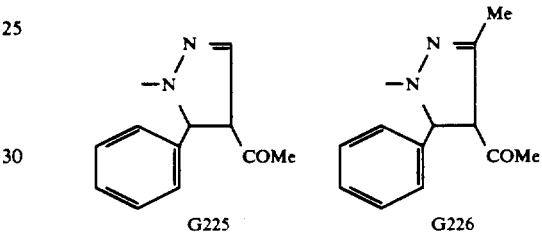
G225  G226
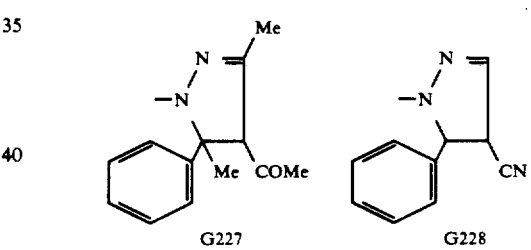
G227  G228
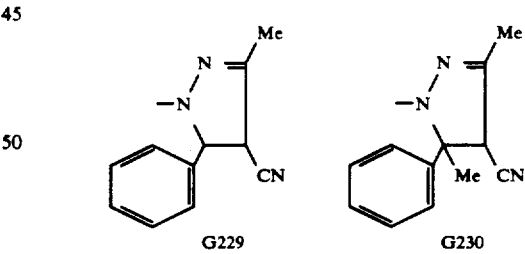
G229  G230
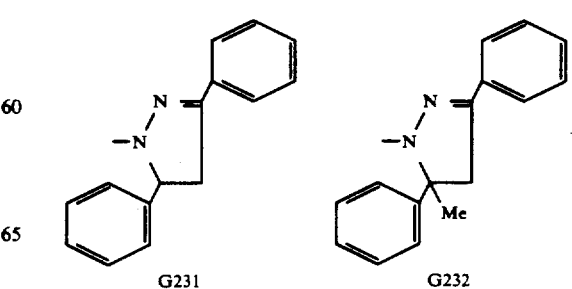
G231  G232

-continued
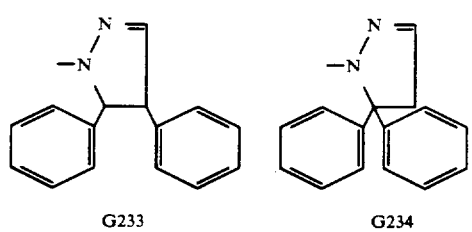
G233  G234
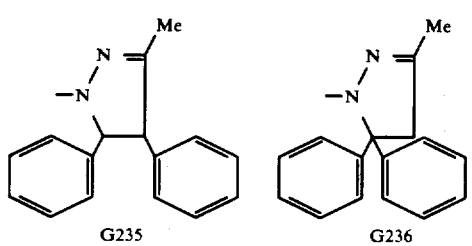
G235  G236
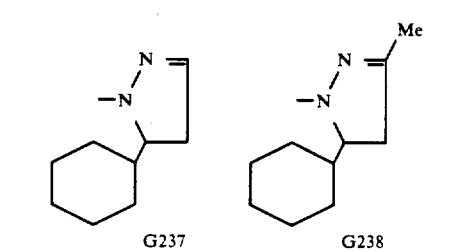
G237  G238
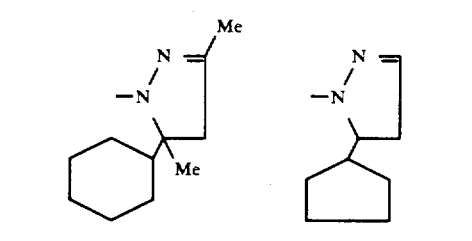
G239  G240
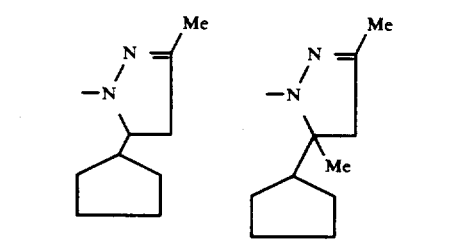
G241  G242
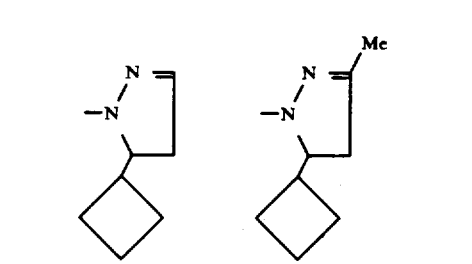
G243  G244
-continued
G245  G246
G247  G248
G249  G250
G251  G252
G253  G254
G255  G256

-continued
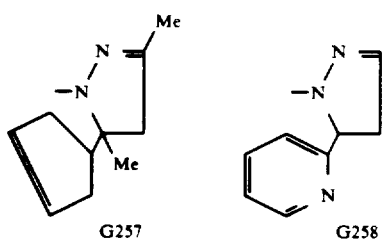
G257  G258
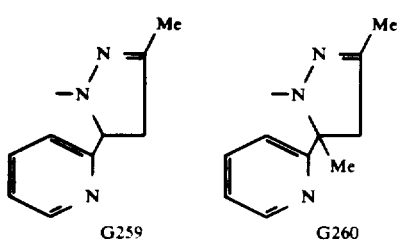
G259  G260
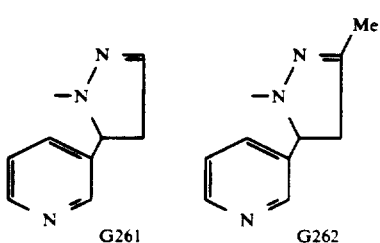
G261  G262
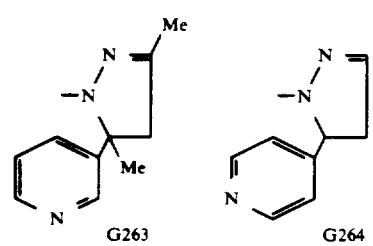
G263  G264
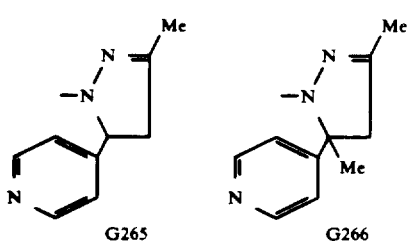
G265  G266
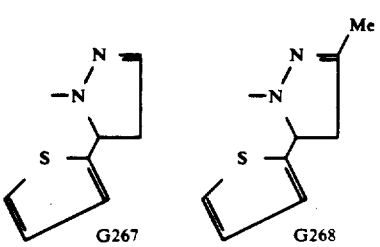
G267  G268
-continued
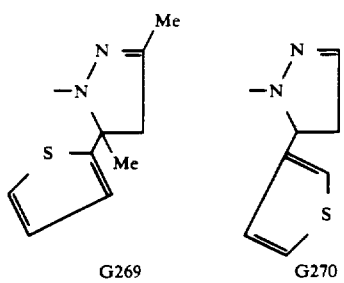
G269  G270
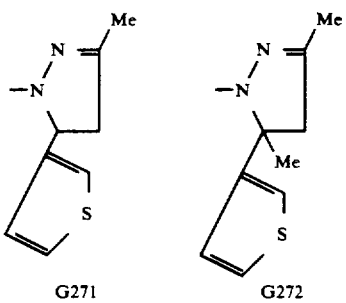
G271  G272
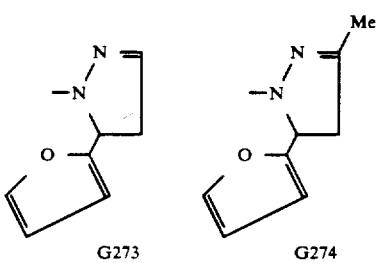
G273  G274
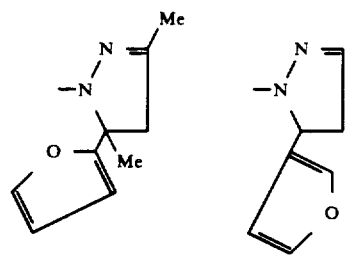
G275  G276
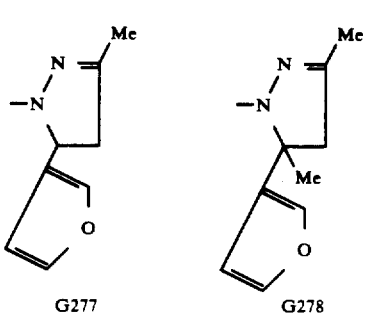
G277  G278

-continued
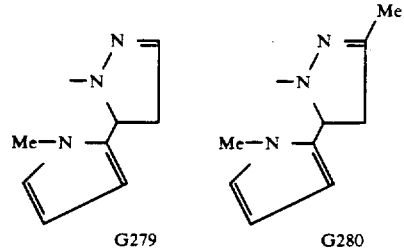
G279  G280
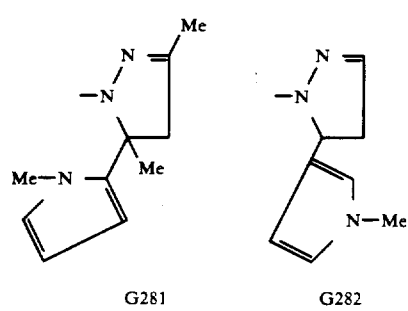
G281  G282
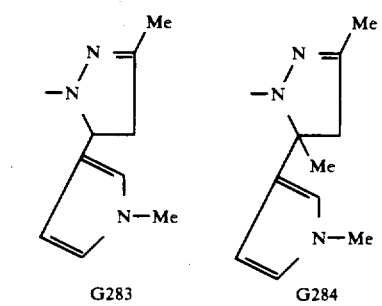
G283  G284
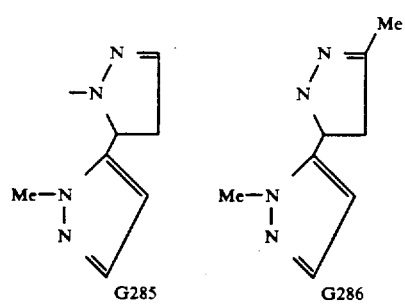
G285  G286
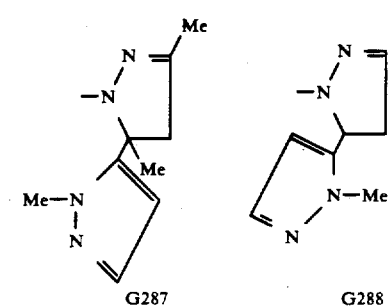
G287  G288
-continued
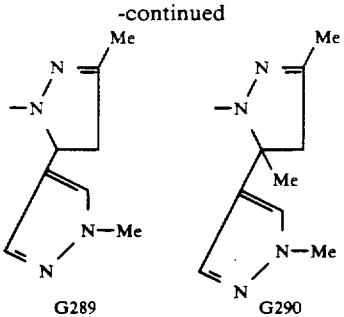
G289  G290
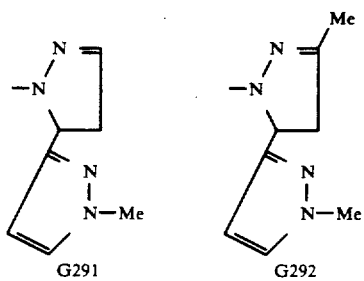
G291  G292
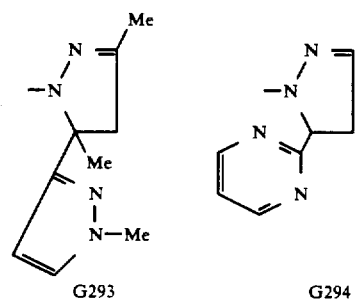
G293  G294
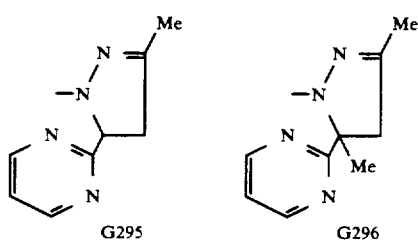
G295  G296
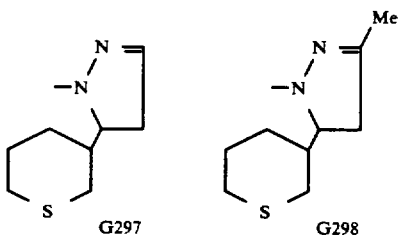
G297  G298
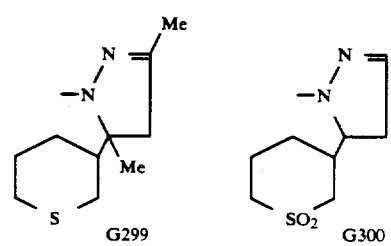
G299  G300

-continued
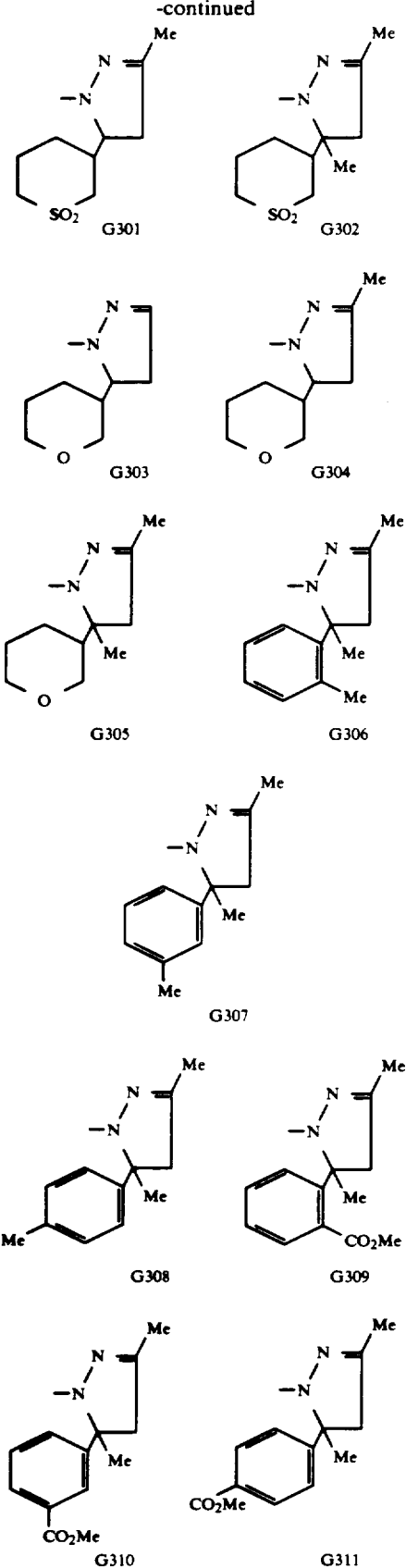
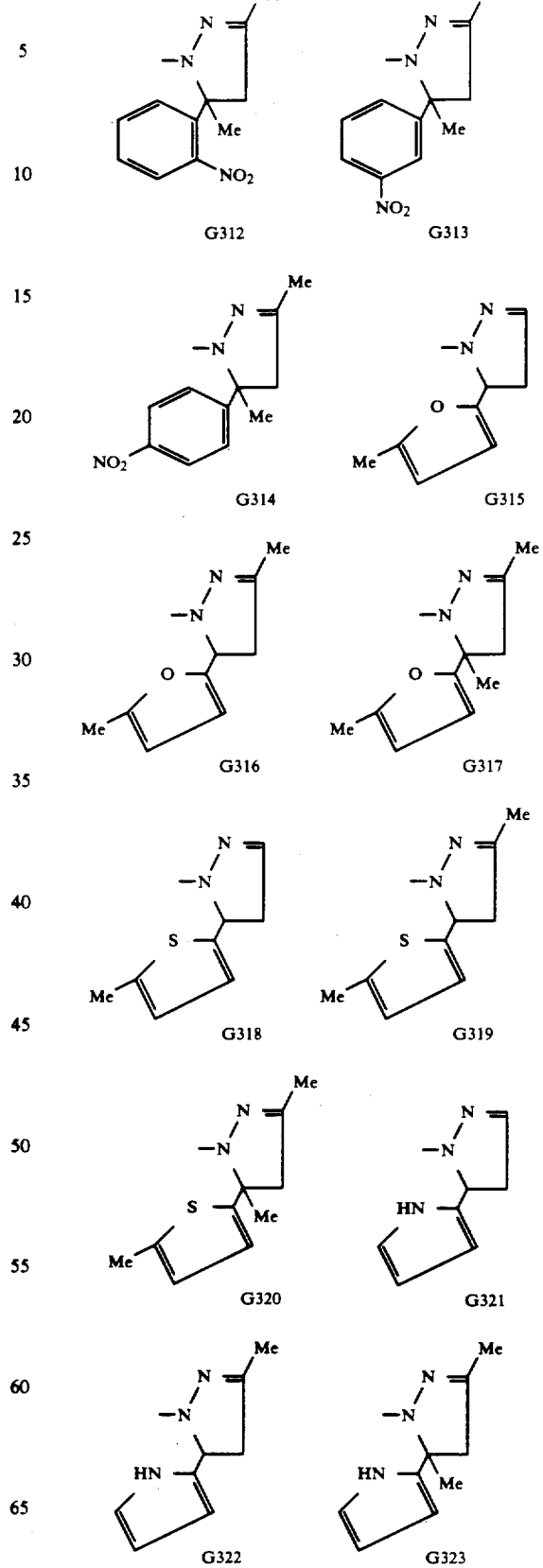

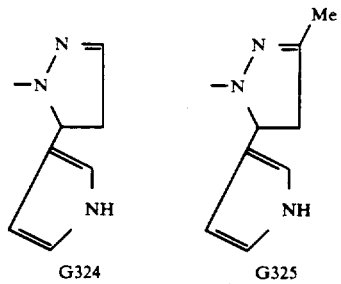
G324  G325
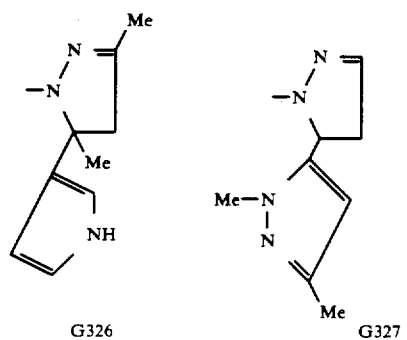
G326  G327
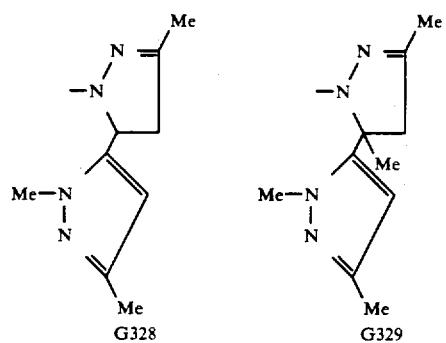
G328  G329
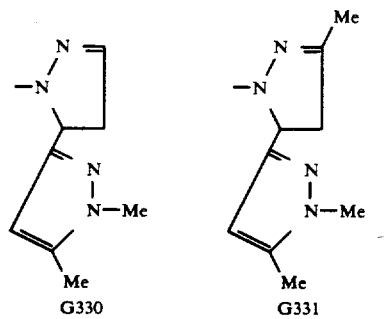
G330  G331
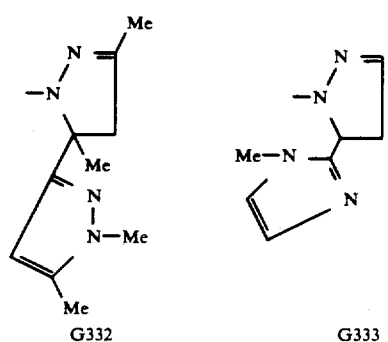
G332  G333
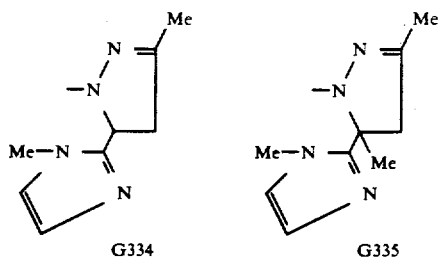
G334  G335
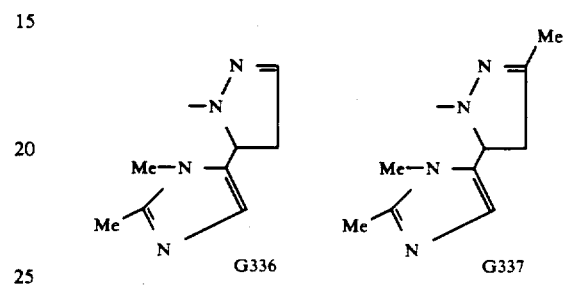
G336  G337
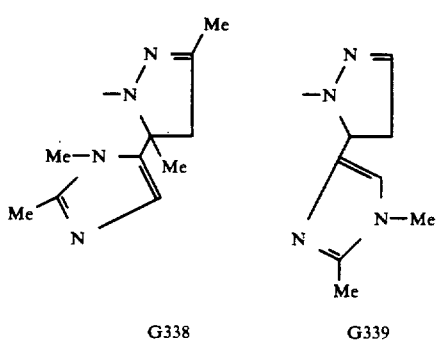
G338  G339
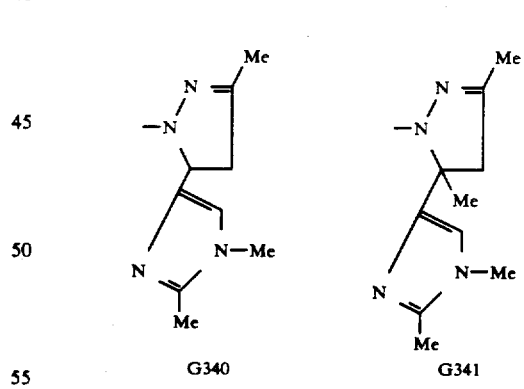
G340  G341
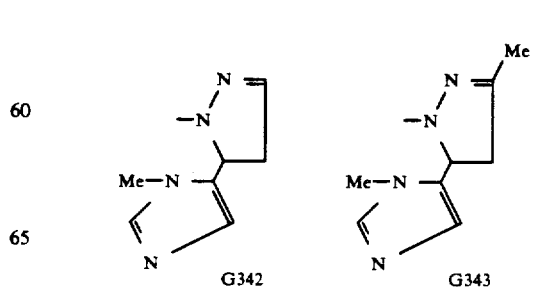
G342  G343

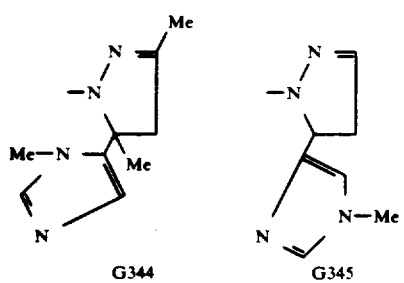
G344  G345
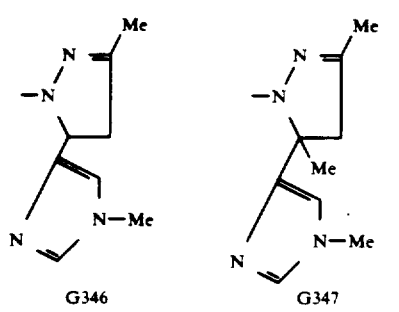
G346  G347
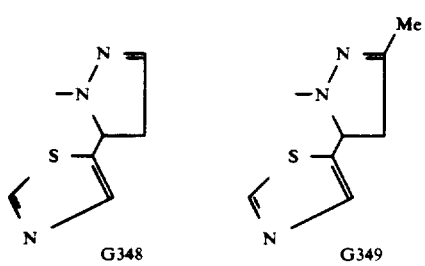
G348  G349
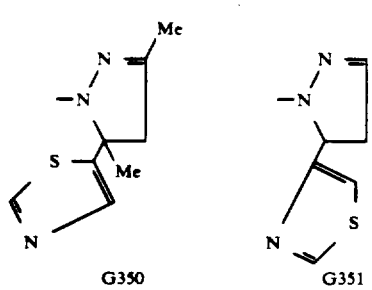
G350  G351
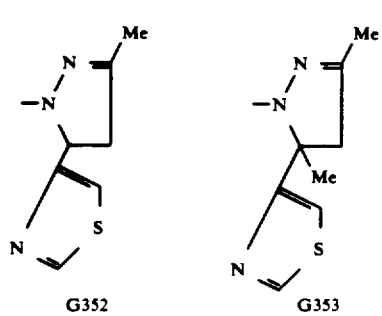
G352  G353
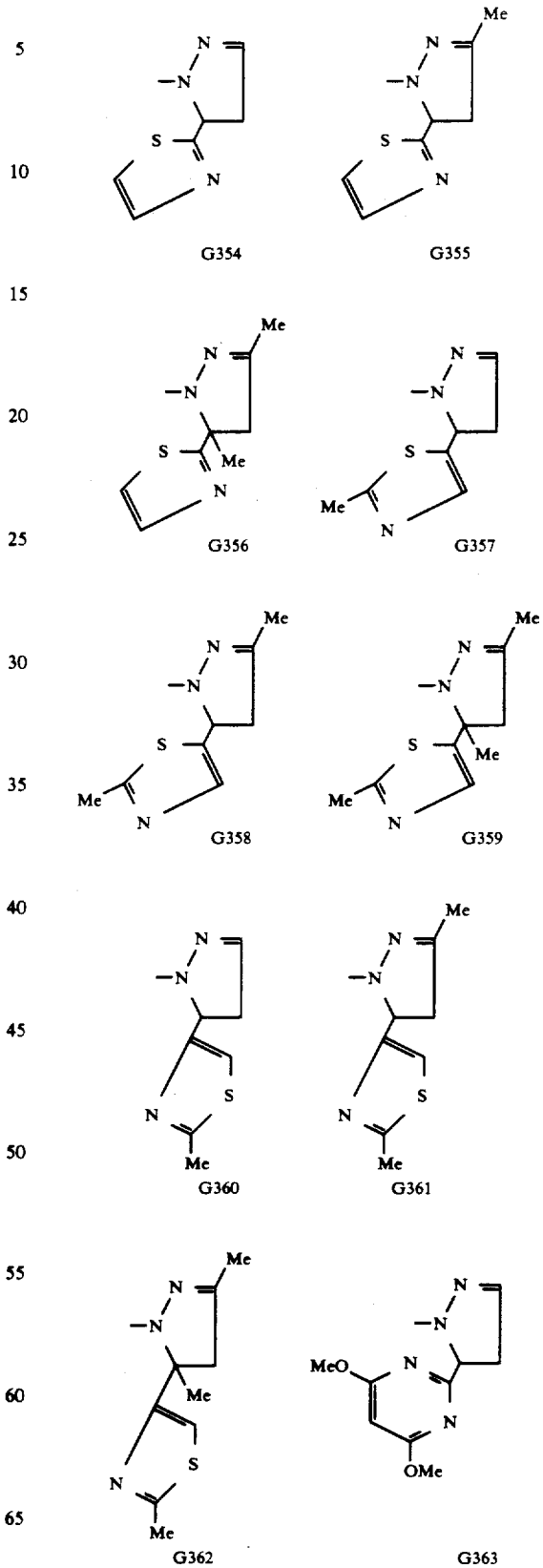
G354  G355
G356  G357
G358  G359
G360  G361
G362  G363

-continued
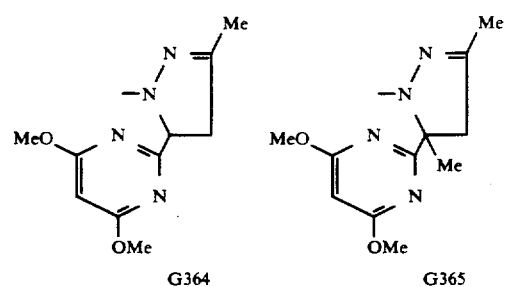
G364  G365
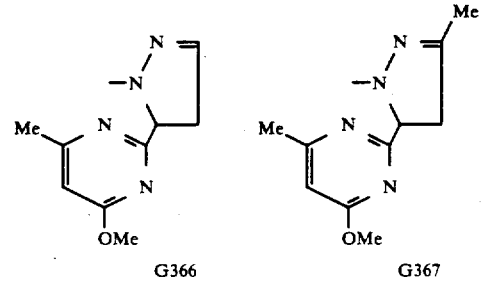
G366  G367
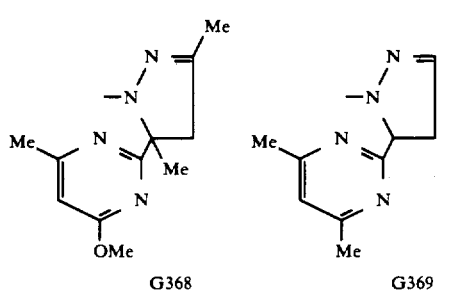
G368  G369
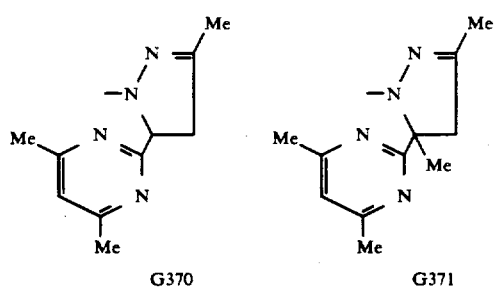
G370  G371
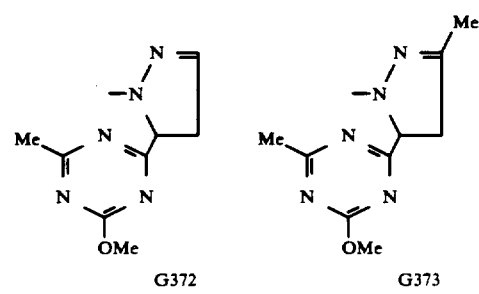
G372  G373
-continued
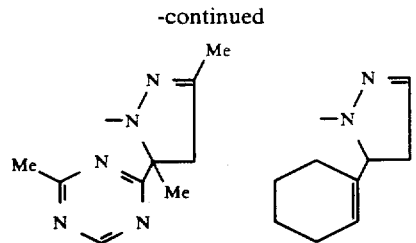
G374  G375
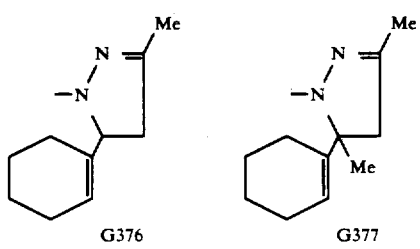
G376  G377
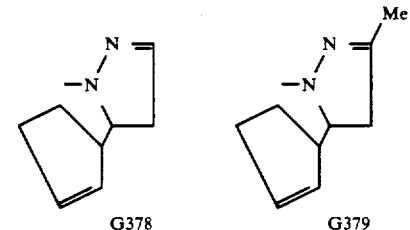
G378  G379
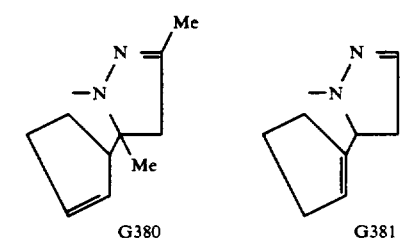
G380  G381
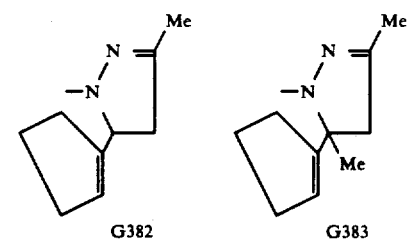
G382  G383
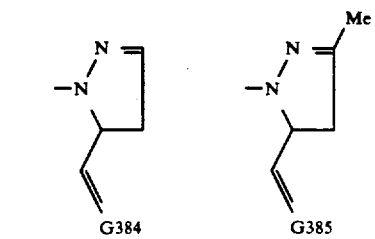
G384  G385

-continued
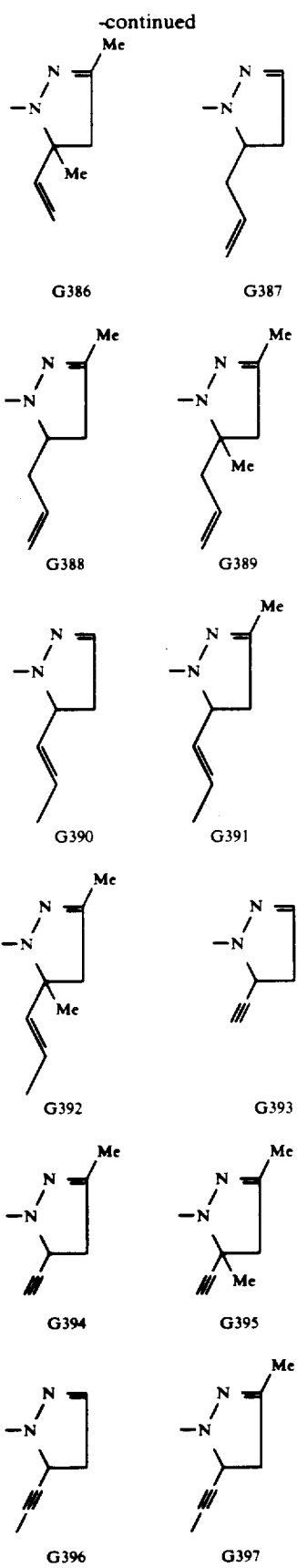
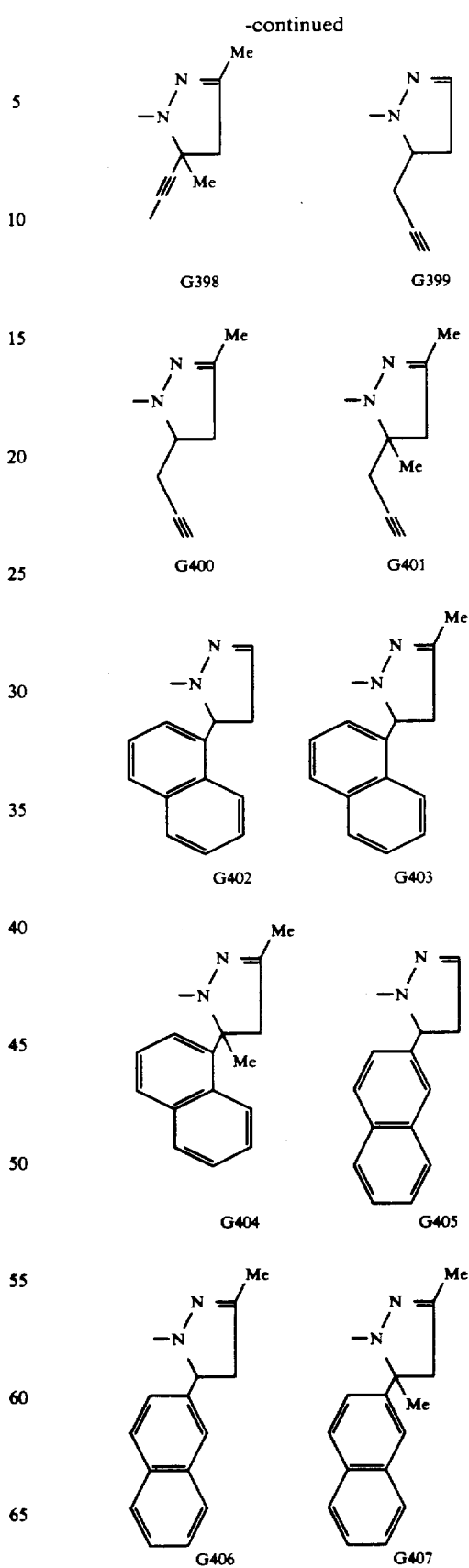

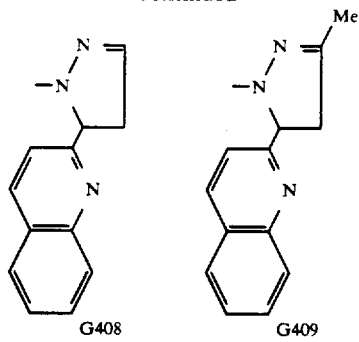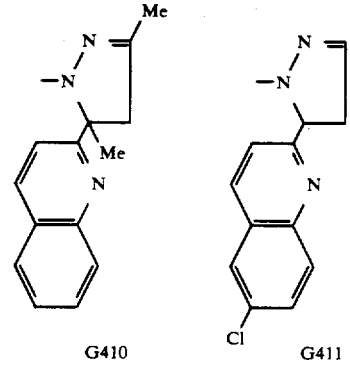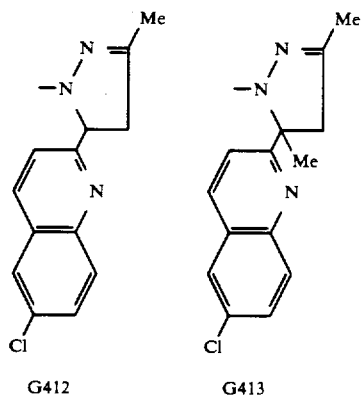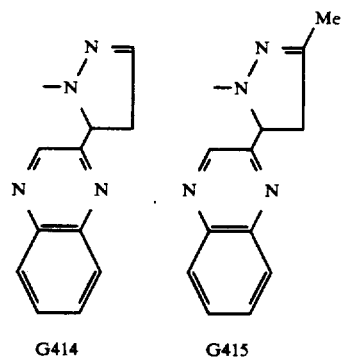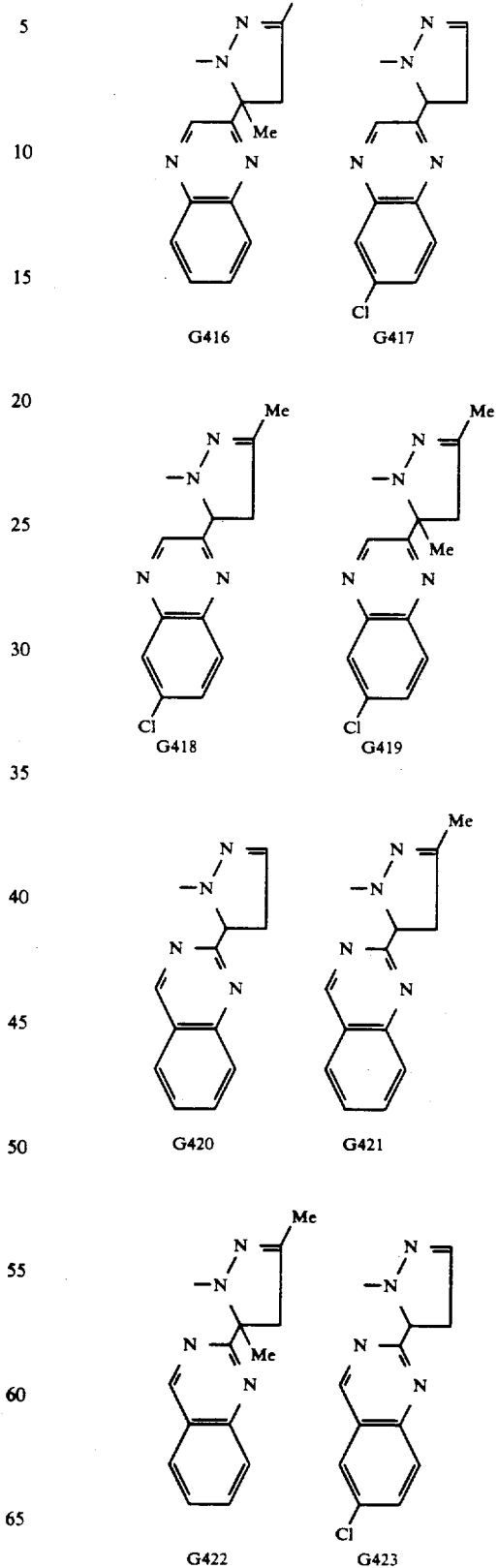

-continued
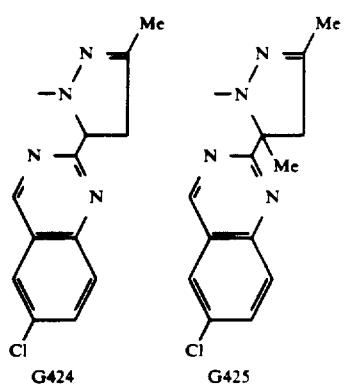
G424  G425
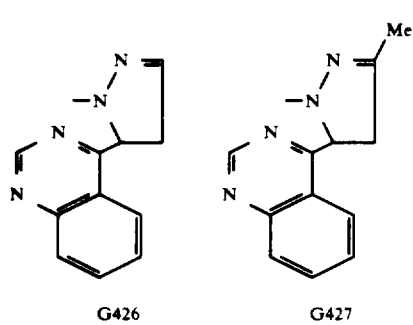
G426  G427
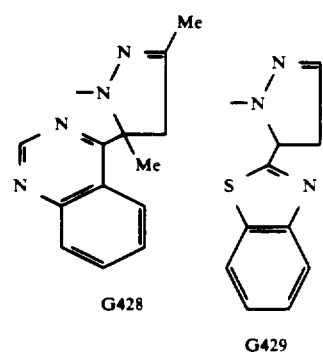
G428  G429
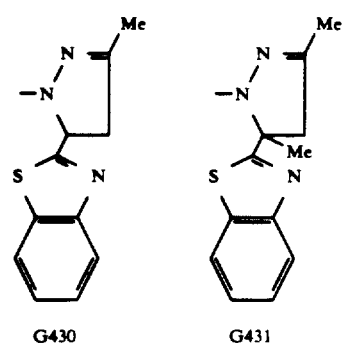
G430  G431
-continued
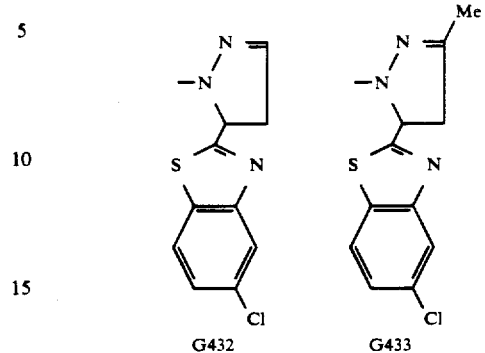
G432  G433
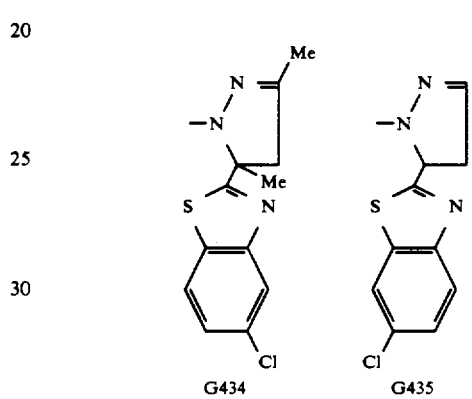
G434  G435
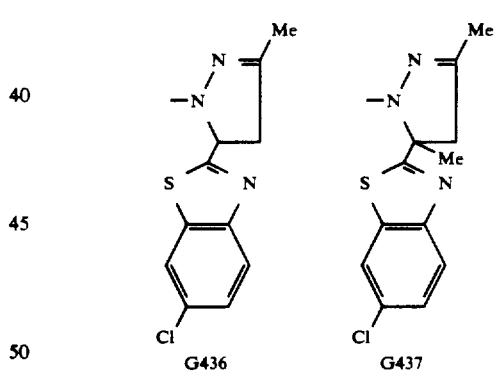
G436  G437
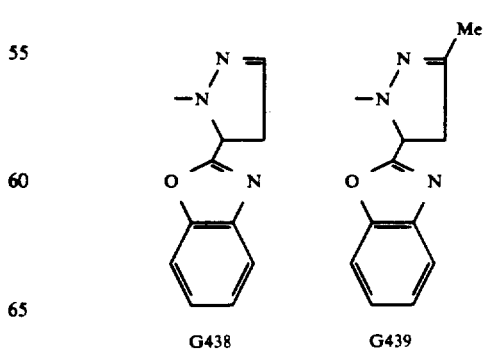
G438  G439

-continued
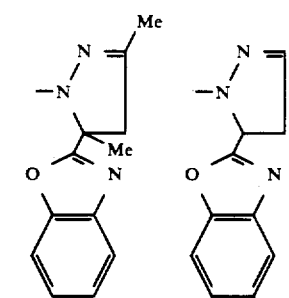
G440  G441
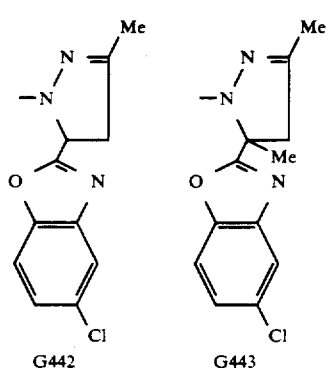
G442  G443
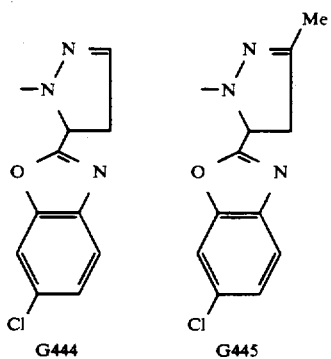
G444  G445
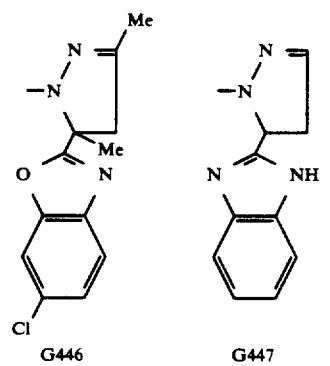
G446  G447
-continued
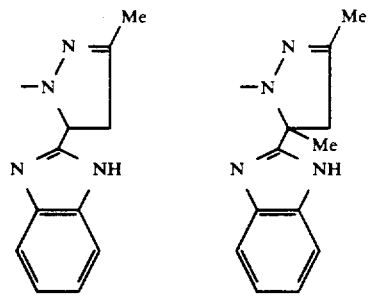
G448  G449
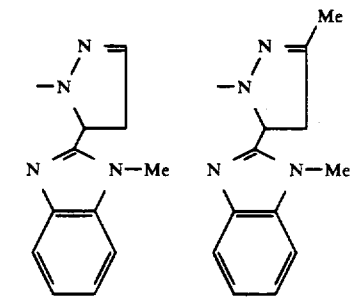
G450  G451
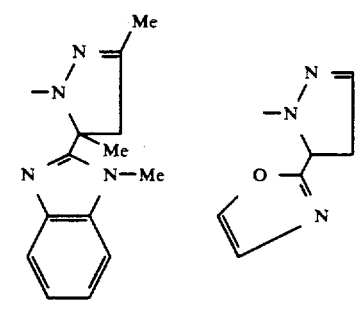
G452  G453
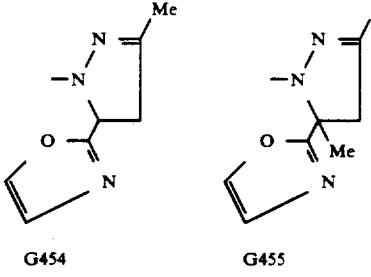
G454  G455
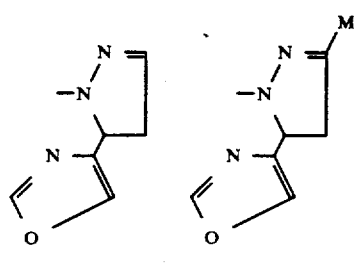
G456  G457

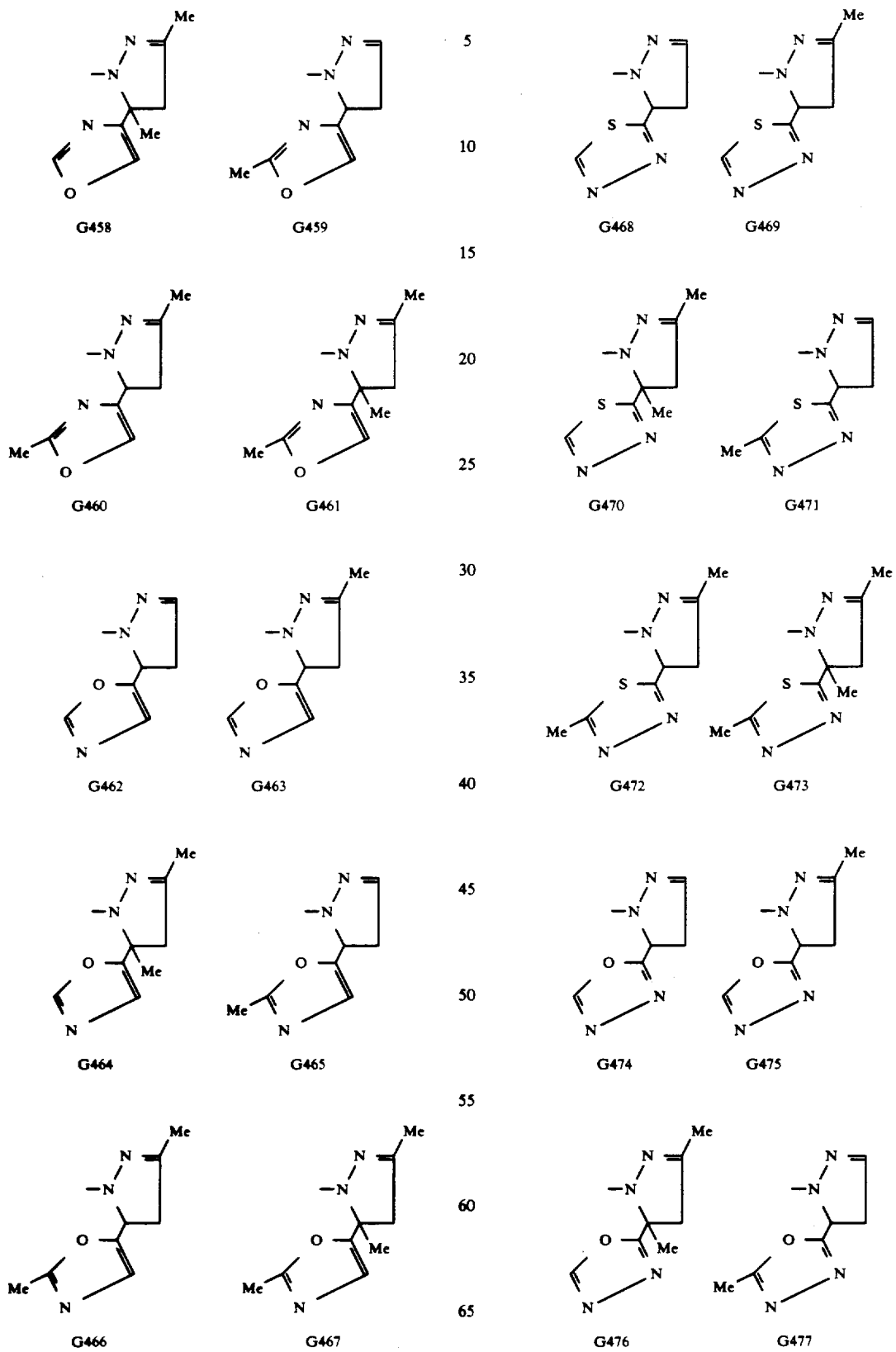

-continued
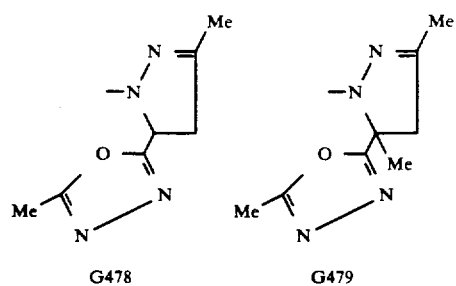
G478  G479
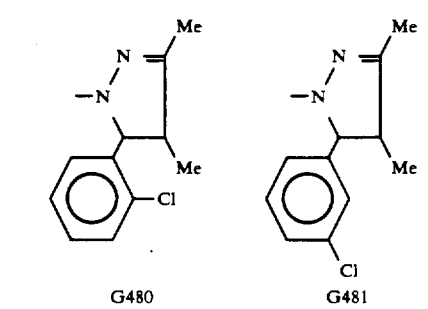
G480  G481
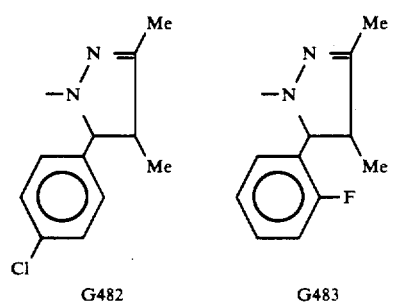
G482  G483
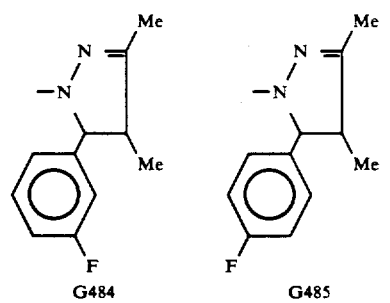
G484  G485
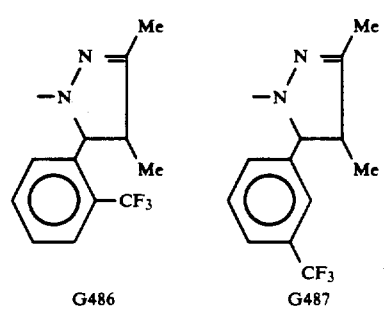
G486  G487
-continued
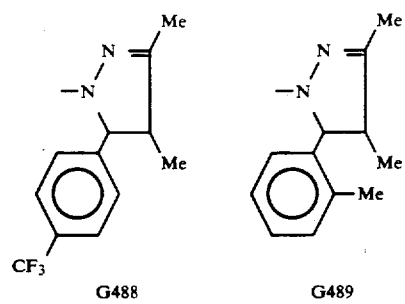
G488  G489
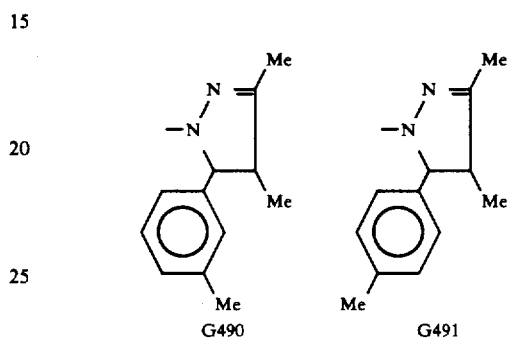
G490  G491
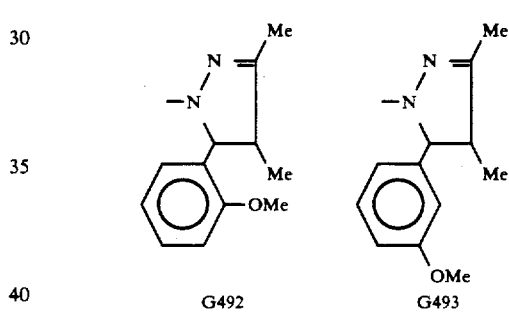
G492  G493
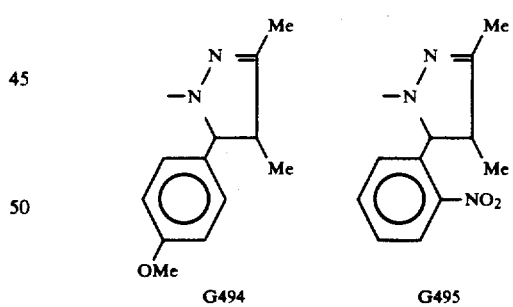
G494  G495
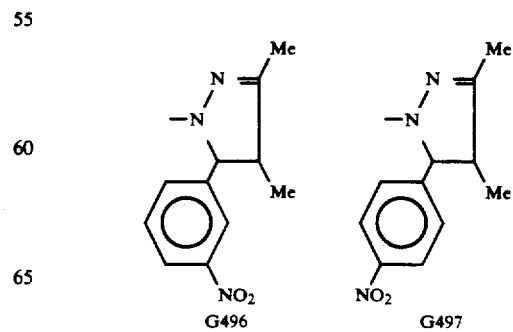
G496  G497

-continued
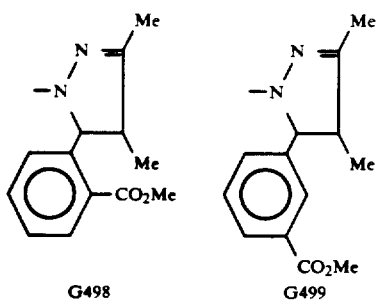
G498  G499
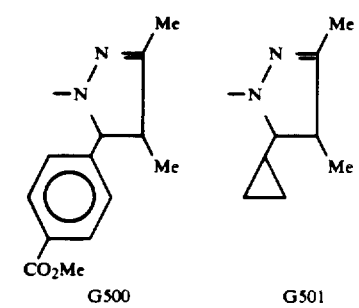
G500  G501
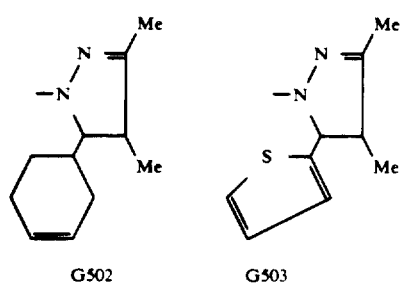
G502  G503
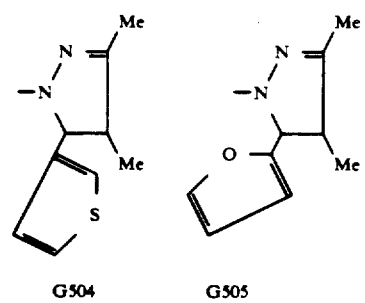
G504  G505
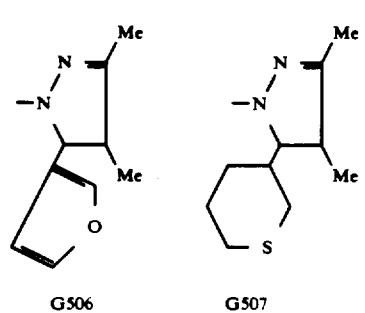
G506  G507
-continued
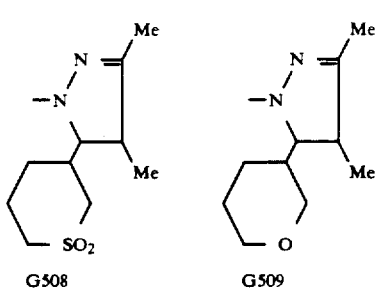
G508  G509
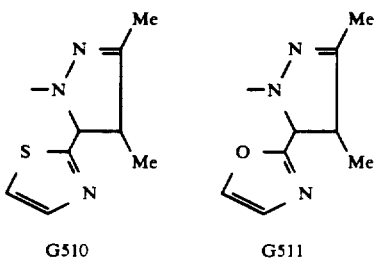
G510  G511
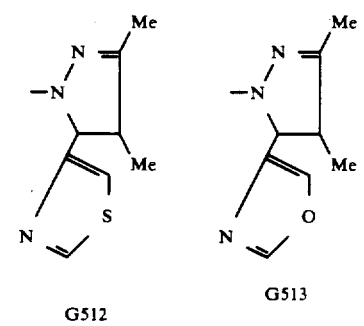
G512  G513
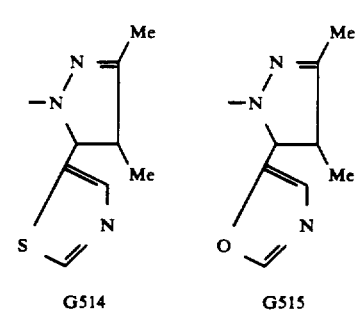
G514  G515
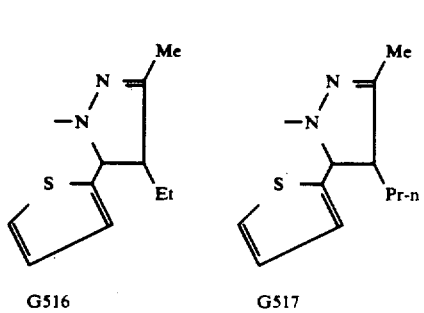
G516  G517

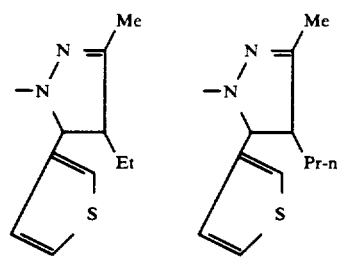
G518  G519
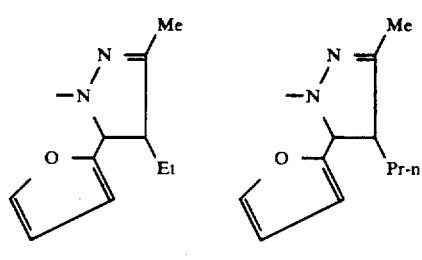
G520  G521
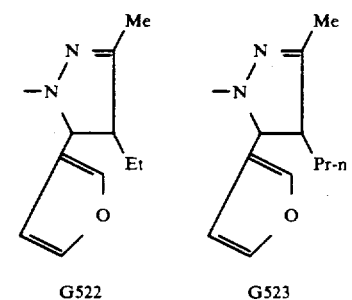
G522  G523
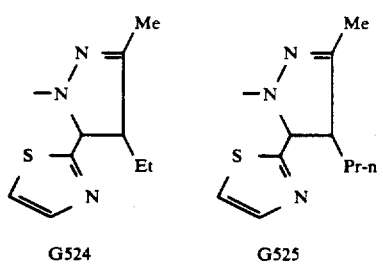
G524  G525
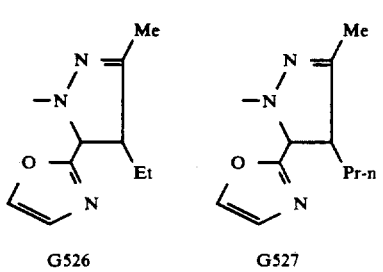
G526  G527
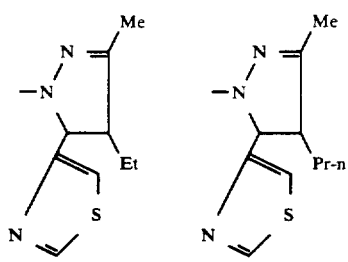
G528  G529
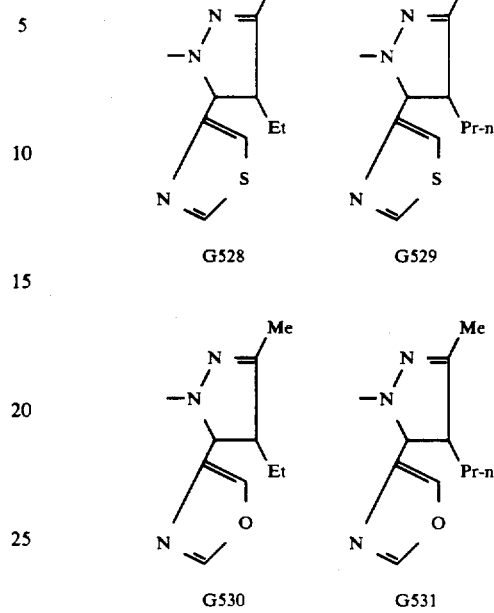
G530  G531
G532  G533
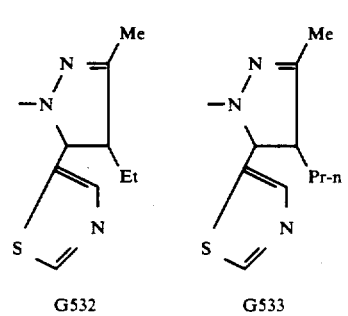
G534  G535
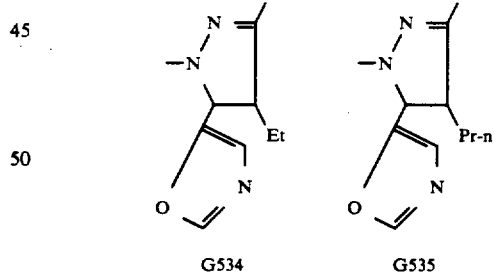
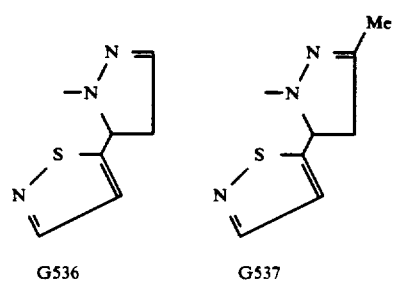
G536  G537

-continued
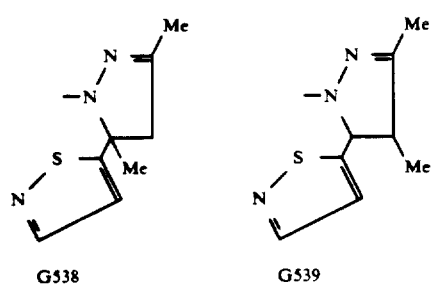
G538  G539
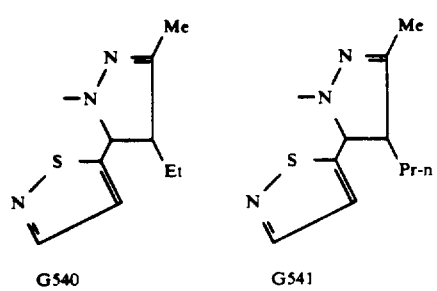
G540  G541
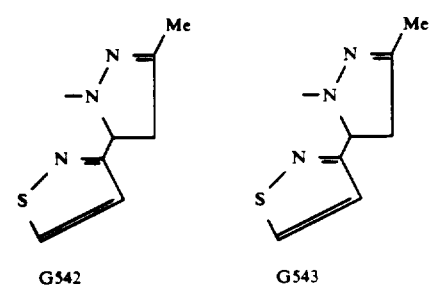
G542  G543
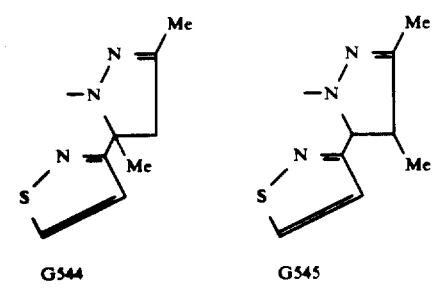
G544  G545
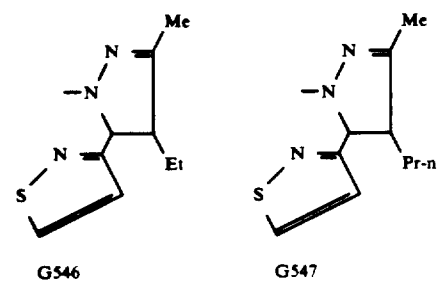
G546  G547
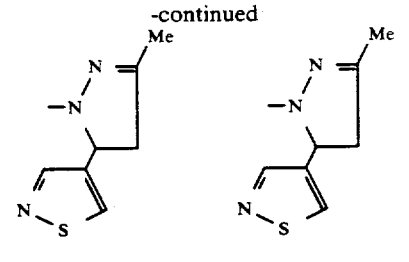
G548  G549
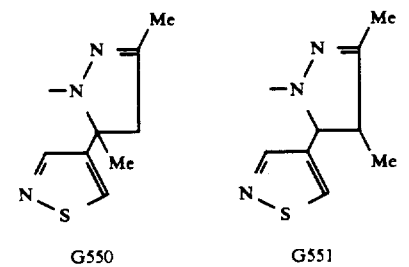
G550  G551
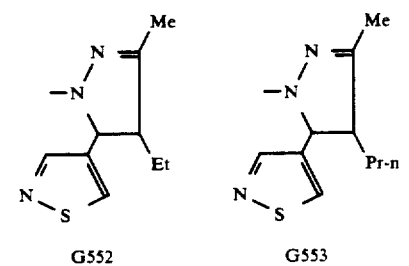
G552  G553
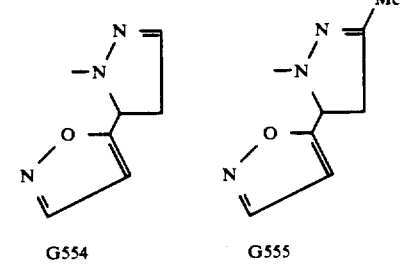
G554  G555
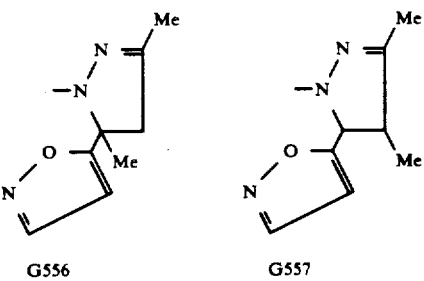
G556  G557
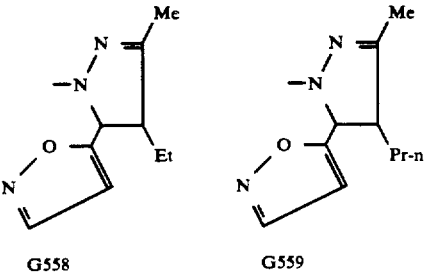
G558  G559

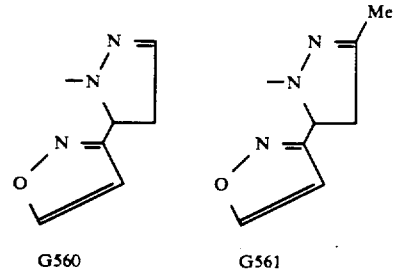
G560  G561
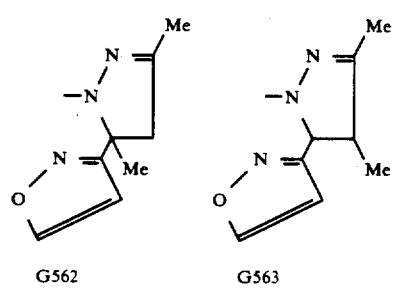
G562  G563
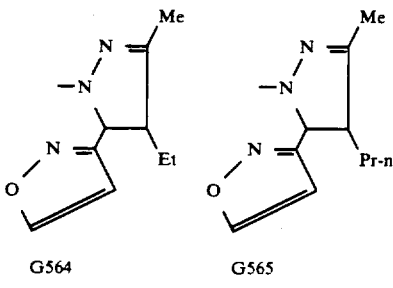
G564  G565
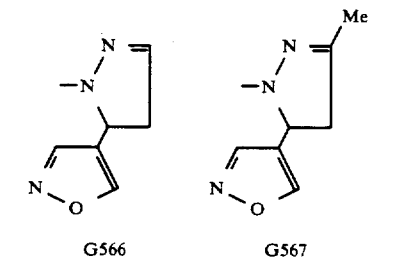
G566  G567
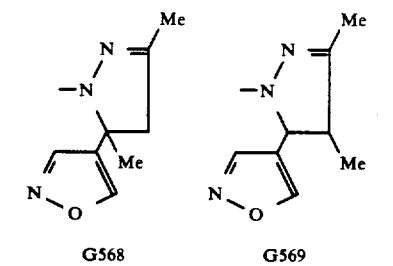
G568  G569
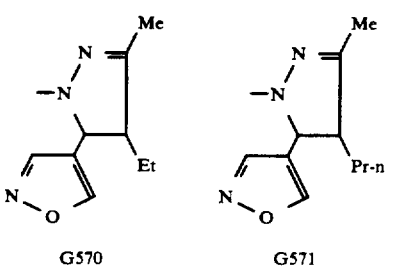
G570  G571
-continued
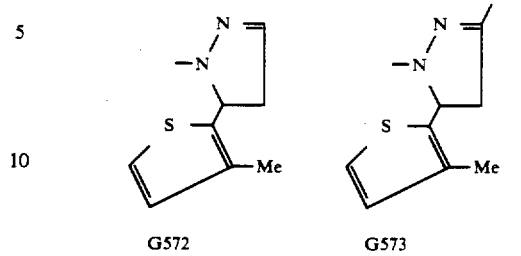
G572  G573
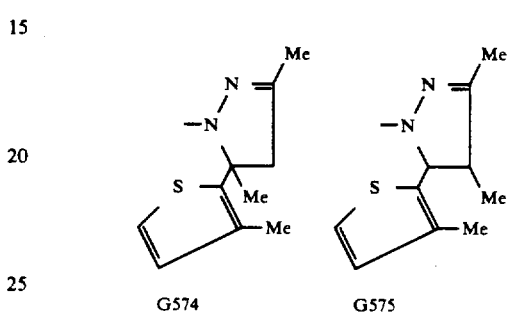
G574  G575
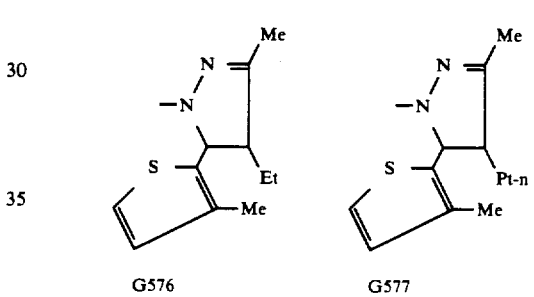
G576  G577
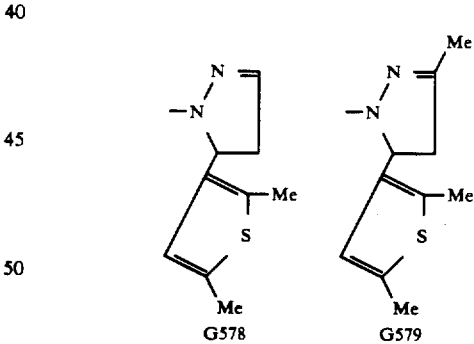
G578  G579
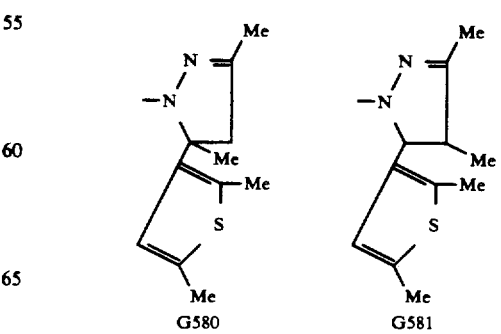
G580  G581

-continued
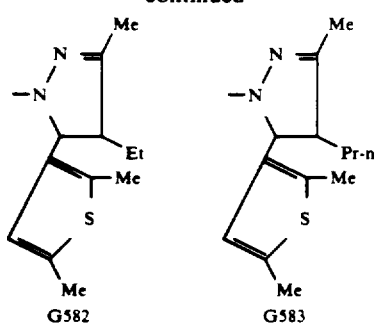
G582　　G583
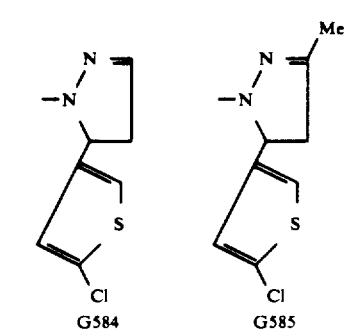
G584　　G585
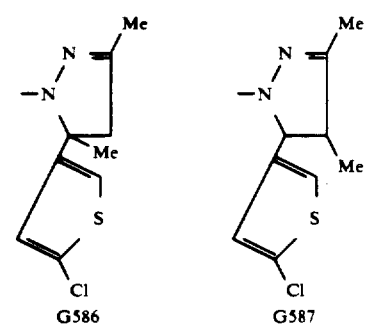
G586　　G587
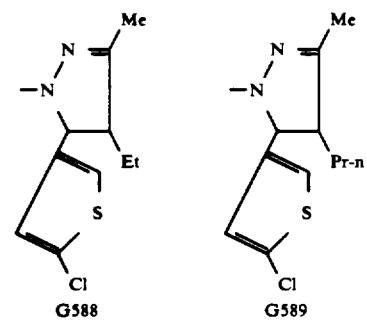
G588　　G589
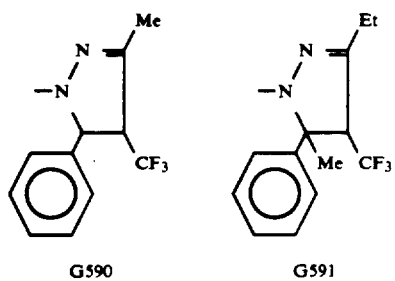
G590　　G591
-continued
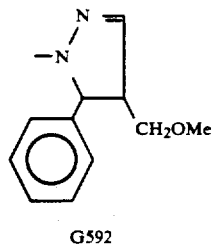
G592　　G593
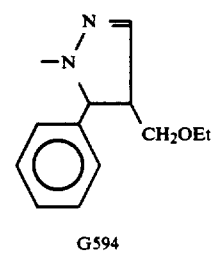
G594　　G595
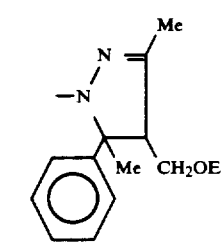
G596　　G597
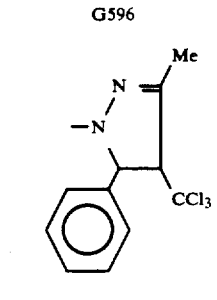
G598　　G599
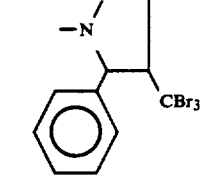
G600　　G601
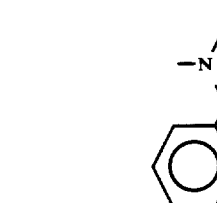
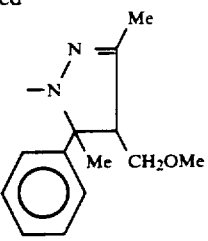
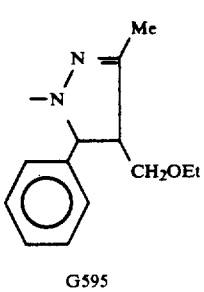
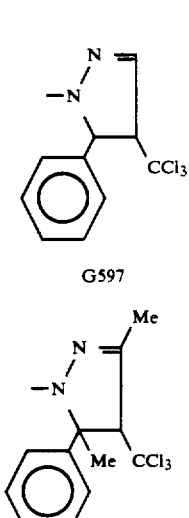
G602

-continued
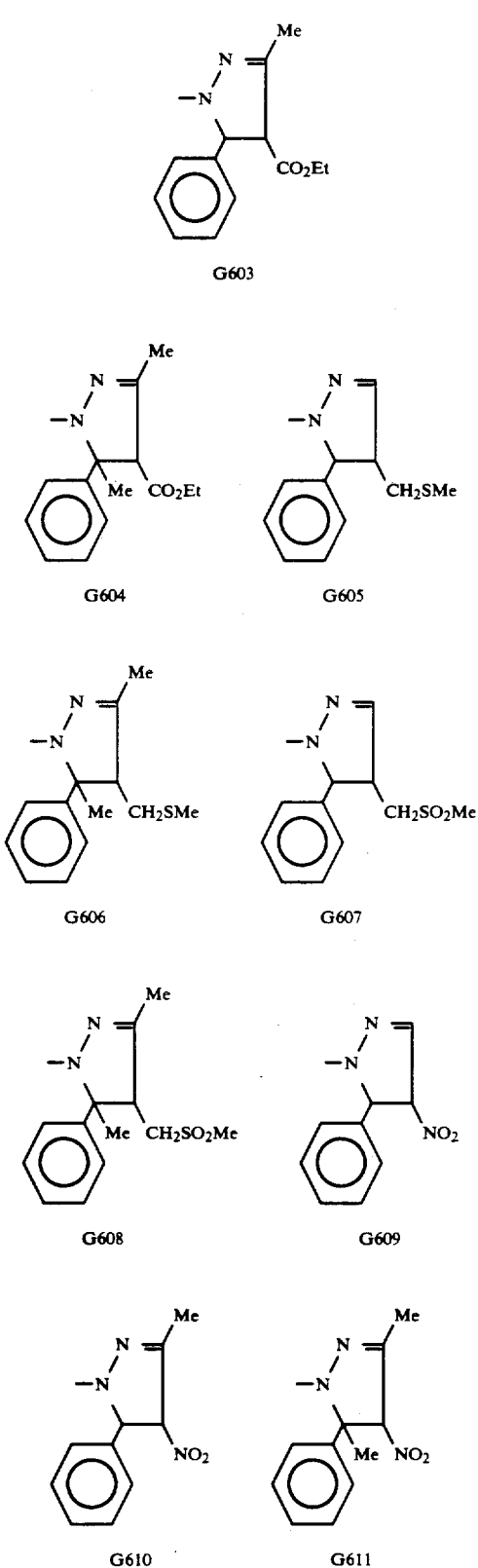
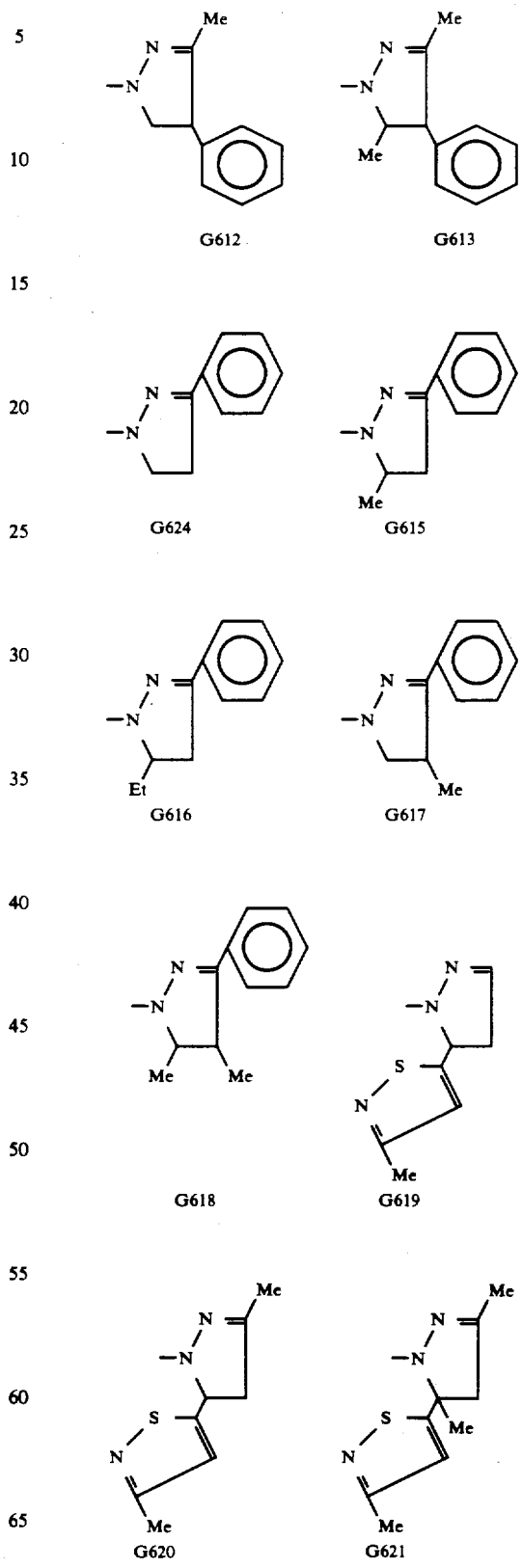

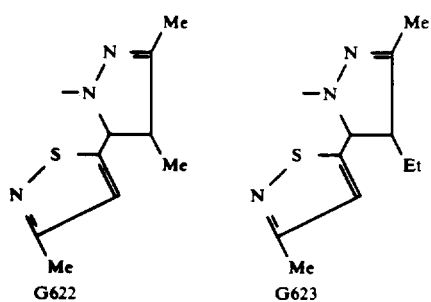
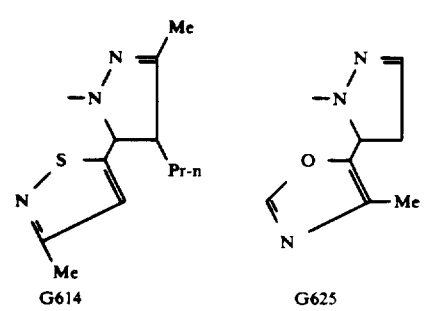
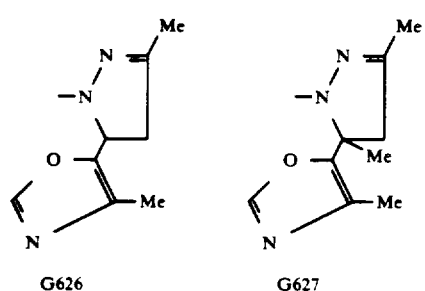
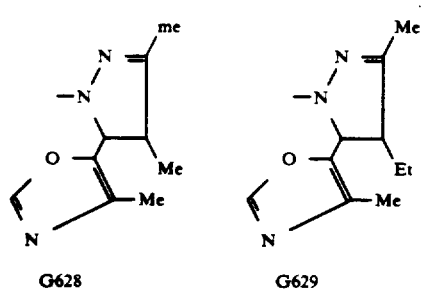
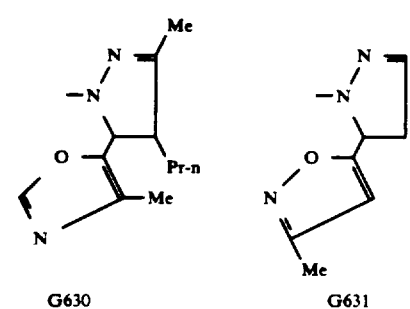
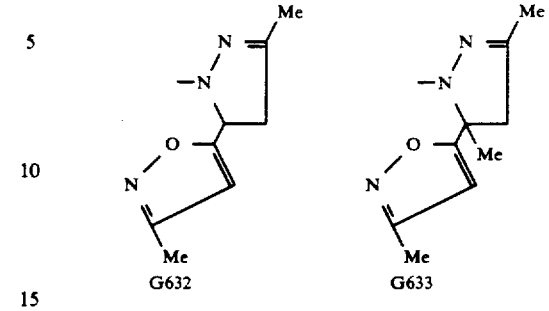
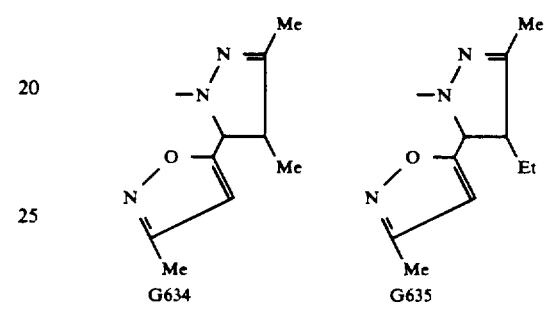
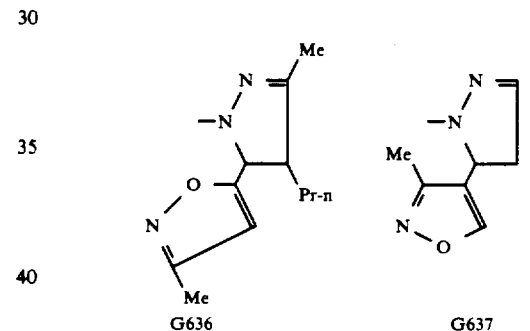
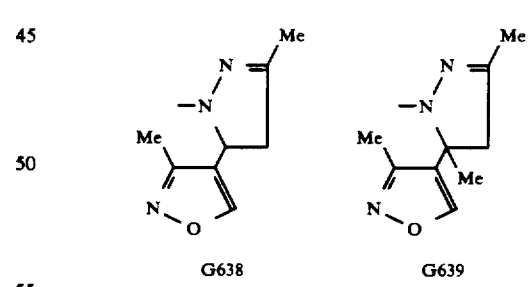
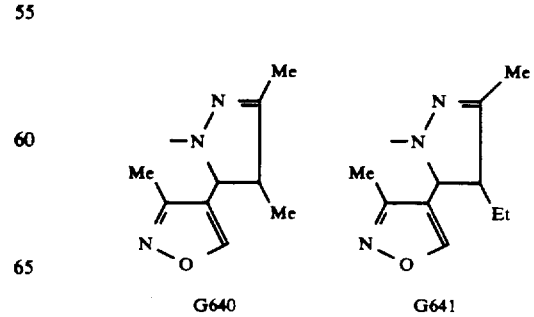

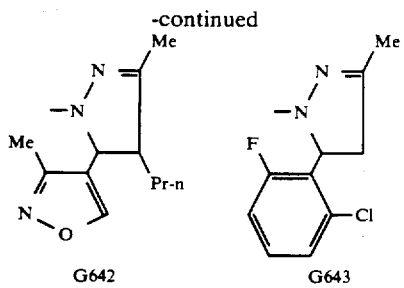

G642

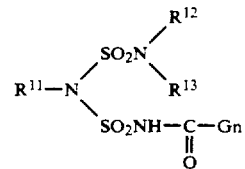

G643

TABLE 1

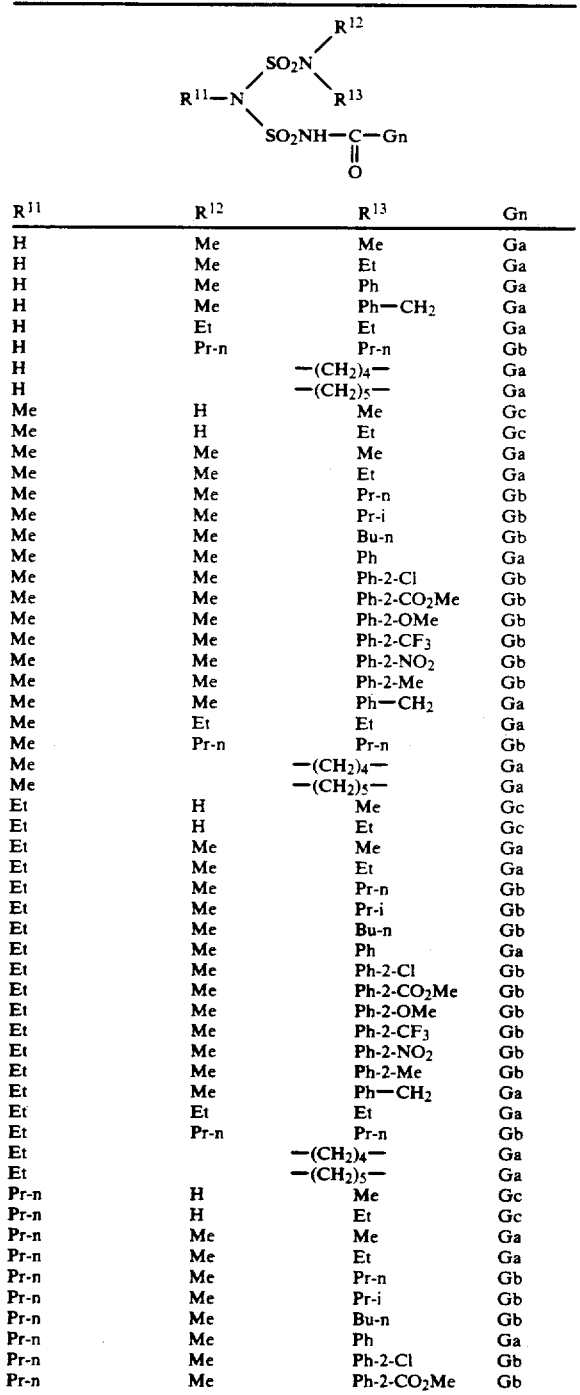

| R11 | R12 | R13 | Gn |
|---|---|---|---|
| H | Me | Me | Ga |
| H | Me | Et | Ga |
| H | Me | Ph | Ga |
| H | Me | Ph—CH2 | Ga |
| H | Et | Et | Ga |
| H | Pr-n | Pr-n | Gb |
| H | | —(CH2)4— | Ga |
| H | | —(CH2)5— | Ga |
| Me | H | Me | Gc |
| Me | H | Et | Gc |
| Me | Me | Me | Ga |
| Me | Me | Et | Ga |
| Me | Me | Pr-n | Gb |
| Me | Me | Pr-i | Gb |
| Me | Me | Bu-n | Gb |
| Me | Me | Ph | Ga |
| Me | Me | Ph-2-Cl | Gb |
| Me | Me | Ph-2-CO2Me | Gb |
| Me | Me | Ph-2-OMe | Gb |
| Me | Me | Ph-2-CF3 | Gb |
| Me | Me | Ph-2-NO2 | Gb |
| Me | Me | Ph-2-Me | Gb |
| Me | Me | Ph—CH2 | Ga |
| Me | Et | Et | Ga |
| Me | Pr-n | Pr-n | Gb |
| Me | | —(CH2)4— | Ga |
| Me | | —(CH2)5— | Ga |
| Et | H | Me | Gc |
| Et | H | Et | Gc |
| Et | Me | Me | Ga |
| Et | Me | Et | Ga |
| Et | Me | Pr-n | Gb |
| Et | Me | Pr-i | Gb |
| Et | Me | Bu-n | Gb |
| Et | Me | Ph | Ga |
| Et | Me | Ph-2-Cl | Gb |
| Et | Me | Ph-2-CO2Me | Gb |
| Et | Me | Ph-2-OMe | Gb |
| Et | Me | Ph-2-CF3 | Gb |
| Et | Me | Ph-2-NO2 | Gb |
| Et | Me | Ph-2-Me | Gb |
| Et | Me | Ph—CH2 | Ga |
| Et | Et | Et | Ga |
| Et | Pr-n | Pr-n | Gb |
| Et | | —(CH2)4— | Ga |
| Et | | —(CH2)5— | Ga |
| Pr-n | H | Me | Gc |
| Pr-n | H | Et | Gc |
| Pr-n | Me | Me | Ga |
| Pr-n | Me | Et | Ga |
| Pr-n | Me | Pr-n | Gb |
| Pr-n | Me | Pr-i | Gb |
| Pr-n | Me | Bu-n | Gb |
| Pr-n | Me | Ph | Ga |
| Pr-n | Me | Ph-2-Cl | Gb |
| Pr-n | Me | Ph-2-CO2Me | Gb |
| Pr-n | Me | Ph-2-OMe | Gb |
| Pr-n | Me | Ph-2-CF3 | Gb |
| Pr-n | Me | Ph-2-NO2 | Gb |
| Pr-n | Me | Ph-2-Me | Gb |
| Pr-n | Me | Ph—CH2 | Ga |
| Pr-n | Et | Et | Ga |
| Pr-n | Pr-n | Pr-n | Gb |
| Pr-n | | —(CH2)4— | Ga |
| Pr-n | | —(CH2)5— | Ga |
| Pr-i | H | Me | Gc |
| Pr-i | H | Et | Gc |
| Pr-i | Me | Me | Ga |
| Pr-i | Me | Et | Ga |
| Pr-i | Me | Pr-n | Gb |
| Pr-i | Me | Pr-i | Gb |
| Pr-i | Me | Bu-n | Gb |
| Pr-i | Me | Ph | Ga |
| Pr-i | Me | Ph-2-Cl | Gb |
| Pr-i | Me | Ph-2-CO2Me | Gb |
| Pr-i | Me | Ph-2-OMe | Gb |
| Pr-i | Me | Ph-2-CF3 | Gb |
| Pr-i | Me | Ph-2-NO2 | Gb |
| Pr-i | Me | Ph-2-Me | Gb |
| Pr-i | Me | Ph—CH2 | Ga |
| Pr-i | Et | Et | Ga |
| Pr-i | Pr-n | Pr-n | Gb |
| Pr-i | | —(CH2)4— | Ga |
| Pr-i | | —(CH2)5— | Ga |
| cyc-Pr | Me | Me | Ga |
| cyc-Pr | Me | Et | Ga |
| cyc-Pr | Me | Ph | Ga |
| cyc-Pr | Me | Ph—CH2 | Ga |
| cyc-Pr | Et | Et | Ga |
| cyc-Pr | Pr-n | Pr-n | Gb |
| cyc-Pr | | —(CH2)4— | Ga |
| cyc-Pr | | —(CH2)5— | Ga |
| cyc-Pr—CH2 | Me | Me | Ga |
| cyc-Pr—CH2 | Me | Et | Ga |
| cyc-Pr—CH2 | Me | Ph | Ga |
| cyc-Pr—CH2 | Me | Ph—CH2 | Ga |
| cyc-Pr—CH2 | Et | Et | Ga |
| cyc-Pr—CH2 | Pr-n | Pr-n | Gb |
| cyc-Pr—CH2 | | —(CH2)4— | Ga |
| cyc-Pr—CH2 | | —(CH2)5— | Ga |
| Bu-n | H | Me | Gc |
| Bu-n | H | Et | Gc |
| Bu-n | Me | Me | Ga |
| Bu-n | Me | Et | Ga |
| Bu-n | Me | Pr-n | Gb |
| Bu-n | Me | Pr-i | Gb |
| Bu-n | Me | Bu-n | Gb |
| Bu-n | Me | Ph | Ga |
| Bu-n | Me | Ph-2-Cl | Gb |
| Bu-n | Me | Ph-2-CO2Me | Gb |
| Bu-n | Me | Ph-2-OMe | Gb |
| Bu-n | Me | Ph-2-CF3 | Gb |
| Bu-n | Me | Ph-2-NO2 | Gb |
| Bu-n | Me | Ph-2-Me | Gb |
| Bu-n | Me | Ph—CH2 | Ga |
| Bu-n | Et | Et | Ga |
| Bu-n | Pr-n | Pr-n | Gb |
| Bu-n | | —(CH2)4— | Ga |
| Bu-n | | —(CH2)5— | Ga |
| Bu-sec | H | Me | Gc |
| Bu-sec | H | Et | Gc |
| Bu-sec | Me | Me | Ga |
| Bu-sec | Me | Et | Ga |
| Bu-sec | Me | Ph | Ga |
| Bu-sec | Me | Ph—CH2 | Ga |
| Bu-sec | Et | Et | Ga |
| Bu-sec | Pr-n | Pr-n | Gb |

TABLE 1-continued

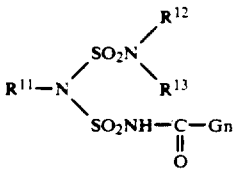

| R11 | R12 | R13 | Gn |
|---|---|---|---|
| Bu-sec | | —(CH2)4— | Ga |
| Bu-sec | | —(CH2)5— | Ga |
| Bu-t | H | Me | Gc |
| Bu-t | H | Et | Gc |
| Bu-t | Me | Me | Ga |
| Bu-t | Me | Et | Ga |
| Bu-t | Me | Ph | Ga |
| Bu-t | Me | Ph—CH2 | Ga |
| Bu-t | Et | Et | Ga |
| Bu-t | Pr-n | Pr-n | Gb |
| Bu-t | | —(CH2)4— | Ga |
| Bu-t | | —(CH2)5— | Ga |
| CH2=CHCH2 | H | Me | Gc |
| CH2=CHCH2 | H | Et | Gc |
| CH2=CHCH2 | Me | Me | Ga |
| CH2=CHCH2 | Me | Et | Ga |
| CH2=CHCH2 | Me | Pr-n | Gb |
| CH2=CHCH2 | Me | Pr-i | Gb |
| CH2=CHCH2 | Me | Bu-n | Gb |
| CH2=CHCH2 | Me | Ph | Ga |
| CH2=CHCH2 | Me | Ph-2-Cl | Gb |
| CH2=CHCH2 | Me | Ph-2-CO2Me | Gb |
| CH2=CHCH2 | Me | Ph-2-OMe | Gb |
| CH2=CHCH2 | Me | Ph-2-CF3 | Gb |
| CH2=CHCH2 | Me | Ph-2-NO2 | Gb |
| CH2=CHCH2 | Me | Ph-2-Me | Gb |
| CH2=CHCH2 | Me | Ph—CH2 | Ga |
| CH2=CHCH2 | Et | Et | Ga |
| CH2=CHCH2 | Pr-n | Pr-n | Gb |
| CH2=CHCH2 | | —(CH2)4— | Ga |
| CH2=CHCH2 | | —(CH2)5— | Ga |
| CH≡CCH2 | H | Me | Gc |
| CH≡CCH2 | H | Et | Gc |
| CH≡CCH2 | Me | Me | Ga |
| CH≡CCH2 | Me | Et | Ga |
| CH≡CCH2 | Me | Pr-n | Gb |
| CH≡CCH2 | Me | Pr-i | Gb |
| CH≡CCH2 | Me | Bu-n | Gb |
| CH≡CCH2 | Me | Ph | Ga |
| CH≡CCH2 | Me | Ph-2-Cl | Gb |
| CH≡CCH2 | Me | Ph-2-CO2Me | Gb |
| CH≡CCH2 | Me | Ph-2-OMe | Gb |
| CH≡CCH2 | Me | Ph-2-CF3 | Gb |
| CH≡CCH2 | Me | Ph-2-NO2 | Gb |
| CH≡CCH2 | Me | Ph-2-Me | Gb |
| CH≡CCH2 | Me | Ph—CH2 | Ga |
| CH≡CCH2 | Et | Et | Ga |
| CH≡CCH2 | Pr-n | Pr-n | Gb |
| CH≡CCH2 | | —(CH2)4— | Ga |
| CH≡CCH2 | | —(CH2)5— | Ga |
| MeOCH2 | Me | Me | Ga |
| MeOCH2 | Me | Et | Ga |
| MeOCH2 | Me | Ph | Ga |
| MeOCH2 | Me | Ph—CH2 | Ga |
| MeOCH2 | Et | Et | Ga |
| MeOCH2 | Pr-n | Pr-n | Gb |
| MeOCH2 | | —(CH2)4— | Ga |
| MeOCH2 | | —(CH2)5— | Ga |
| EtOCH2 | Me | Me | Ga |
| EtOCH2 | Me | Et | Ga |
| EtOCH2 | Me | Ph | Ga |
| EtOCH2 | Me | Ph—CH2 | Ga |
| EtOCH2 | Et | Et | Ga |
| EtOCH2 | Pr-n | Pr-n | Gb |
| EtOCH2 | | —(CH2)4— | Ga |
| EtOCH2 | | —(CH2)5— | Ga |
| MeOCH2CH2 | H | Me | Gc |
| MeOCH2CH2 | H | Et | Gc |
| MeOCH2CH2 | Me | Me | Ga |
| MeOCH2CH2 | Me | Et | Ga |
| MeOCH2CH2 | Me | Pr-n | Gb |
| MeOCH2CH2 | Me | Pr-i | Gb |
| MeOCH2CH2 | Me | Bu-n | Gb |
| MeOCH2CH2 | Me | Ph | Ga |
| MeOCH2CH2 | Me | Ph-2-Cl | Gb |
| MeOCH2CH2 | Me | Ph-2-CO2Me | Gb |
| MeOCH2CH2 | Me | Ph-2-OMe | Gb |
| MeOCH2CH2 | Me | Ph-2-CF3 | Gb |
| MeOCH2CH2 | Me | Ph-2-NO2 | Gb |
| MeOCH2CH2 | Me | Ph-2-Me | Gb |
| MeOCH2CH2 | Me | Ph—CH2 | Ga |
| MeOCH2CH2 | Et | Et | Ga |
| MeOCH2CH2 | Pr-n | Pr-n | Gb |
| MeOCH2CH2 | | —(CH2)4— | Ga |
| MeOCH2CH2 | | —(CH2)5— | Ga |
| EtOCH2CH2 | H | Me | Gc |
| EtOCH2CH2 | H | Et | Gc |
| EtOCH2CH2 | Me | Me | Ga |
| EtOCH2CH2 | Me | Et | Ga |
| EtOCH2CH2 | Me | Pr-n | Gb |
| EtOCH2CH2 | Me | Pr-i | Gb |
| EtOCH2CH2 | Me | Bu-n | Gb |
| EtOCH2CH2 | Me | Ph | Ga |
| EtOCH2CH2 | Me | Ph-2-Cl | Gb |
| EtOCH2CH2 | Me | Ph-2-CO2Me | Gb |
| EtOCH2CH2 | Me | Ph-2-OMe | Gb |
| EtOCH2CH2 | Me | Ph-2-CF3 | Gb |
| EtOCH2CH2 | Me | Ph-2-NO2 | Gb |
| EtOCH2CH2 | Me | Ph-2-Me | Gb |
| EtOCH2CH2 | Me | Ph—CH2 | Ga |
| EtOCH2CH2 | Et | Et | Ga |
| EtOCH2CH2 | Pr-n | Pr-n | Gb |
| EtOCH2CH2 | | —(CH2)4— | Ga |
| EtOCH2CH2 | | —(CH2)5— | Ga |
| MeOCH2(CH3)CH | H | Me | Gc |
| MeOCH2(CH3)CH | H | Et | Gc |
| MeOCH2(CH3)CH | Me | Me | Ga |
| MeOCH2(CH3)CH | Me | Et | Ga |
| MeOCH2(CH3)CH | Me | Pr-n | Gb |
| MeOCH2(CH3)CH | Me | Pr-i | Gb |
| MeOCH2(CH3)CH | Me | Bu-n | Gb |
| MeOCH2(CH3)CH | Me | Ph | Ga |
| MeOCH2(CH3)CH | Me | Ph-2-Cl | Gb |
| MeOCH2(CH3)CH | Me | Ph-2-CO2Me | Gb |
| MeOCH2(CH3)CH | Me | Ph-2-OMe | Gb |
| MeOCH2(CH3)CH | Me | Ph-2-CF3 | Gb |
| MeOCH2(CH3)CH | Me | Ph-2-NO2 | Gb |
| MeOCH2(CH3)CH | Me | Ph-2-Me | Gb |
| MeOCH2(CH3)CH | Me | Ph—CH2 | Ga |
| MeOCH2(CH3)CH | Et | Et | Ga |
| MeOCH2(CH3)CH | Pr-n | Pr-n | Gb |
| MeOCH2(CH3)CH | | —(CH2)4— | Ga |
| MeOCH2(CH3)CH | | —(CH2)5— | Ga |
| EtOCH2(CH3)CH | H | Me | Gc |
| EtOCH2(CH3)CH | H | Et | Gc |
| EtOCH2(CH3)CH | Me | Me | Ga |
| EtOCH2(CH3)CH | Me | Et | Ga |
| EtOCH2(CH3)CH | Me | Pr-n | Gb |
| EtOCH2(CH3)CH | Me | Pr-i | Gb |
| EtOCH2(CH3)CH | Me | Bu-n | Gb |
| EtOCH2(CH3)CH | Me | Ph | Ga |
| EtOCH2(CH3)CH | Me | Ph-2-Cl | Gb |
| EtOCH2(CH3)CH | Me | Ph-2-CO2Me | Gb |
| EtOCH2(CH3)CH | Me | Ph-2-OMe | Gb |
| EtOCH2(CH3)CH | Me | Ph-2-CF3 | Gb |
| EtOCH2(CH3)CH | Me | Ph-2-NO2 | Gb |
| EtOCH2(CH3)CH | Me | Ph-2-Me | Gb |
| EtOCH2(CH3)CH | Me | Ph—CH2 | Ga |
| EtOCH2(CH3)CH | Et | Et | Ga |
| EtOCH2(CH3)CH | Pr-n | Pr-n | Gb |
| EtOCH2(CH3)CH | | —(CH2)4— | Ga |
| EtOCH2(CH3)CH | | —(CH2)5— | Ga |

TABLE 1-continued

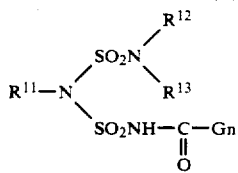

| R11 | R12 | R13 | Gn |
|---|---|---|---|
| CHF2OCH2 | H | Me | Gc |
| CHF2OCH2 | H | Et | Gc |
| CHF2OCH2 | Me | Me | Ga |
| CHF2OCH2 | Me | Et | Ga |
| CHF2OCH2 | Me | Pr-n | Gb |
| CHF2OCH2 | Me | Pr-i | Gb |
| CHF2OCH2 | Me | Bu-n | Gb |
| CHF2OCH2 | Me | Ph | Ga |
| CHF2OCH2 | Me | Ph-2-Cl | Gb |
| CHF2OCH2 | Me | Ph-2-CO2Me | Gb |
| CHF2OCH2 | Me | Ph-2-OMe | Gb |
| CHF2OCH2 | Me | Ph-2-CF3 | Gb |
| CHF2OCH2 | Me | Ph-2-NO2 | Gb |
| CHF2OCH2 | Me | Ph-2-Me | Gb |
| CHF2OCH2 | Me | Ph—CH2 | Ga |
| CHF2OCH2 | Et | Et | Ga |
| CHF2OCH2 | Pr-n | Pr-n | Gb |
| CHF2OCH2 | | —(CH2)4— | Ga |
| CHF2OCH2 | | —(CH2)5— | Ga |
| MeSCH2 | Me | Me | Ga |
| MeSCH2 | Me | Et | Ga |
| MeSCH2 | Me | Ph | Ga |
| MeSCH2 | Me | Ph—CH2 | Ga |
| MeSCH2 | Et | Et | Ga |
| MeSCH2 | Pr-n | Pr-n | Gb |
| MeSCH2 | | —(CH2)4— | Ga |
| MeSCH2 | | —(CH2)5— | Ga |
| EtSCH2 | Me | Me | Ga |
| EtSCH2 | Me | Et | Ga |
| EtSCH2 | Me | Ph | Ga |
| EtSCH2 | Me | Ph—CH2 | Ga |
| EtSCH2 | Et | Et | Ga |
| EtSCH2 | Pr-n | Pr-n | Gb |
| EtSCH2 | | —(CH2)4— | Ga |
| EtSCH2 | | —(CH2)5— | Ga |
| MeSCH2CH2 | H | Me | Gc |
| MeSCH2CH2 | H | Et | Gc |
| MeSCH2CH2 | Me | Me | Ga |
| MeSCH2CH2 | Me | Et | Ga |
| MeSCH2CH2 | Me | Pr-n | Gb |
| MeSCH2CH2 | Me | Pr-i | Gb |
| MeSCH2CH2 | Me | Bu-n | Gb |
| MeSCH2CH2 | Me | Ph | Ga |
| MeSCH2CH2 | Me | Ph-2-Cl | Gb |
| MeSCH2CH2 | Me | Ph-2-CO2Me | Gb |
| MeSCH2CH2 | Me | Ph-2-OMe | Gb |
| MeSCH2CH2 | Me | Ph-2-CF3 | Gb |
| MeSCH2CH2 | Me | Ph-2-NO2 | Gb |
| MeSCH2CH2 | Me | Ph-2-Me | Gb |
| MeSCH2CH2 | Me | Ph—CH2 | Ga |
| MeSCH2CH2 | Et | Et | Ga |
| MeSCH2CH2 | Pr-n | Pr-n | Gb |
| MeSCH2CH2 | | —(CH2)4— | Ga |
| MeSCH2CH2 | | —(CH2)5— | Ga |
| EtSCH2CH2 | H | Me | Gc |
| EtSCH2CH2 | H | Et | Gc |
| EtSCH2CH2 | Me | Me | Ga |
| EtSCH2CH2 | Me | Et | Ga |
| EtSCH2CH2 | Me | Pr-n | Gb |
| EtSCH2CH2 | Me | Pr-i | Gb |
| EtSCH2CH2 | Me | Bu-n | Gb |
| EtSCH2CH2 | Me | Ph | Ga |
| EtSCH2CH2 | Me | Ph-2-Cl | Gb |
| EtSCH2CH2 | Me | Ph-2-CO2Me | Gb |
| EtSCH2CH2 | Me | Ph-2-OMe | Gb |
| EtSCH2CH2 | Me | Ph-2-CF3 | Gb |
| EtSCH2CH2 | Me | Ph-2-NO2 | Gb |
| EtSCH2CH2 | Me | Ph-2-Me | Gb |
| EtSCH2CH2 | Me | Ph—CH2 | Ga |
| EtSCH2CH2 | Et | Et | Ga |
| EtSCH2CH2 | Pr-n | Pr-n | Gb |

TABLE 1-continued

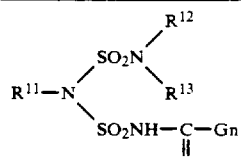

| R11 | R12 | R13 | Gn |
|---|---|---|---|
| EtSCH2CH2 | | —(CH2)4— | Ga |
| EtSCH2CH2 | | —(CH2)5— | Ga |
| MeSO2CH2 | Me | Me | Ga |
| MeSO2CH2 | Me | Et | Ga |
| MeSO2CH2 | Me | Ph | Ga |
| MeSO2CH2 | Me | Ph—CH2 | Ga |
| MeSO2CH2 | Et | Et | Ga |
| MeSO2CH2 | Pr-n | Pr-n | Gb |
| MeSO2CH2 | | —(CH2)4— | Ga |
| MeSO2CH2 | | —(CH2)5— | Ga |
| EtSO2CH2 | Me | Me | Ga |
| EtSO2CH2 | Me | Et | Ga |
| EtSO2CH2 | Me | Ph | Ga |
| EtSO2CH2 | Me | Ph—CH2 | Ga |
| EtSO2CH2 | Et | Et | Ga |
| EtSO2CH2 | Pr-n | Pr-n | Gb |
| EtSO2CH2 | | —(CH2)4— | Ga |
| EtSO2CH2 | | —(CH2)5— | Ga |
| MeSO2CH2CH2 | H | Me | Gc |
| MeSO2CH2CH2 | H | Et | Gc |
| MeSO2CH2CH2 | Me | Me | Ga |
| MeSO2CH2CH2 | Me | Et | Ga |
| MeSO2CH2CH2 | Me | Pr-n | Gb |
| MeSO2CH2CH2 | Me | Pr-i | Gb |
| MeSO2CH2CH2 | Me | Bu-n | Gb |
| MeSO2CH2CH2 | Me | Ph | Ga |
| MeSO2CH2CH2 | Me | Ph-2-Cl | Gb |
| MeSO2CH2CH2 | Me | Ph-2-CO2Me | Gb |
| MeSO2CH2CH2 | Me | Ph-2-OMe | Gb |
| MeSO2CH2CH2 | Me | Ph-2-CF3 | Gb |
| MeSO2CH2CH2 | Me | Ph-2-NO2 | Gb |
| MeSO2CH2CH2 | Me | Ph-2-Me | Gb |
| MeSO2CH2CH2 | Me | Ph—CH2 | Ga |
| MeSO2CH2CH2 | Et | Et | Ga |
| MeSO2CH2CH2 | Pr-n | Pr-n | Gb |
| MeSO2CH2CH2 | | —(CH2)4— | Ga |
| MeSO2CH2CH2 | | —(CH2)5— | Ga |
| EtSO2CH2CH2 | H | Me | Gc |
| EtSO2CH2CH2 | H | Et | Gc |
| EtSO2CH2CH2 | Me | Me | Ga |
| EtSO2CH2CH2 | Me | Et | Ga |
| EtSO2CH2CH2 | Me | Pr-n | Gb |
| EtSO2CH2CH2 | Me | Pr-i | Gb |
| EtSO2CH2CH2 | Me | Bu-n | Gb |
| EtSO2CH2CH2 | Me | Ph | Ga |
| EtSO2CH2CH2 | Me | Ph-2-Cl | Gb |
| EtSO2CH2CH2 | Me | Ph-2-CO2Me | Gb |
| EtSO2CH2CH2 | Me | Ph-2-OMe | Gb |
| EtSO2CH2CH2 | Me | Ph-2-CF3 | Gb |
| EtSO2CH2CH2 | Me | Ph-2-NO2 | Gb |
| EtSO2CH2CH2 | Me | Ph-2-Me | Gb |
| EtSO2CH2CH2 | Me | Ph—CH2 | Ga |
| EtSO2CH2CH2 | Et | Et | Ga |
| EtSO2CH2CH2 | Pr-n | Pr-n | Gb |
| EtSO2CH2CH2 | | —(CH2)4— | Ga |
| EtSO2CH2CH2 | | —(CH2)5— | Ga |
| FCH2 | Me | Me | Ga |
| FCH2 | Me | Et | Ga |
| FCH2 | Me | Ph | Ga |
| FCH2 | Me | Ph—CH2 | Ga |
| FCH2 | Et | Et | Ga |
| FCH2 | Pr-n | Pr-n | Gb |
| FCH2 | | —(CH2)4— | Ga |
| FCH2 | | —(CH2)5— | Ga |
| ClCH2 | Me | Me | Ga |
| ClCH2 | Me | Et | Ga |
| ClCH2 | Me | Ph | Ga |
| ClCH2 | Me | Ph—CH2 | Ga |
| ClCH2 | Et | Et | Ga |
| ClCH2 | Pr-n | Pr-n | Gb |
| ClCH2 | | —(CH2)4— | Ga |

TABLE 1-continued

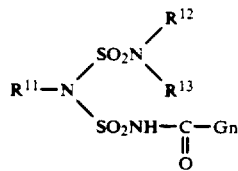

| R¹¹ | R¹² | R¹³ | Gn |
|---|---|---|---|
| ClCH₂ | | —(CH₂)₅— | Ga |
| BrCH₂ | Me | Me | Ga |
| BrCH₂ | Me | Et | Ga |
| BrCH₂ | Me | Ph | Ga |
| BrCH₂ | Me | Ph—CH₂ | Ga |
| BrCH₂ | Et | Et | Ga |
| BrCH₂ | Pr-n | Pr-n | Gb |
| BrCH₂ | | —(CH₂)₄— | Ga |
| BrCH₂ | | —(CH₂)₅— | Ga |
| ICH₂ | Me | Me | Ga |
| ICH₂ | Me | Et | Ga |
| ICH₂ | Me | Ph | Ga |
| ICH₂ | Me | Ph—CH₂ | Ga |
| ICH₂ | Et | Et | Ga |
| ICH₂ | Pr-n | Pr-n | Gb |
| ICH₂ | | —(CH₂)₄— | Ga |
| ICH₂ | | —(CH₂)₅— | Ga |
| FCH₂CH₂ | H | Me | Gc |
| FCH₂CH₂ | H | Et | Gc |
| FCH₂CH₂ | Me | Me | Ga |
| FCH₂CH₂ | Me | Et | Ga |
| FCH₂CH₂ | Me | Pr-n | Gb |
| FCH₂CH₂ | Me | Pr-i | Gb |
| FCH₂CH₂ | Me | Bu-n | Gb |
| FCH₂CH₂ | Me | Ph | Ga |
| FCH₂CH₂ | Me | Ph-2-Cl | Gb |
| FCH₂CH₂ | Me | Ph-2-CO₂Me | Gb |
| FCH₂CH₂ | Me | Ph-2-OMe | Gb |
| FCH₂CH₂ | Me | Ph-2-CF₃ | Gb |
| FCH₂CH₂ | Me | Ph-2-NO₂ | Gb |
| FCH₂CH₂ | Me | Ph-2-Me | Gb |
| FCH₂CH₂ | Me | Ph—CH₂ | Ga |
| FCH₂CH₂ | Et | Et | Ga |
| FCH₂CH₂ | Pr-n | Pr-n | Gb |
| FCH₂CH₂ | | —(CH₂)₄— | Ga |
| FCH₂CH₂ | | —(CH₂)₅— | Ga |
| ClCH₂CH₂ | H | Me | Gc |
| ClCH₂CH₂ | H | Et | Gc |
| ClCH₂CH₂ | Me | Me | Ga |
| ClCH₂CH₂ | Me | Et | Ga |
| ClCH₂CH₂ | Me | Pr-n | Gb |
| ClCH₂CH₂ | Me | Pr-i | Gb |
| ClCH₂CH₂ | Me | Bu-n | Gb |
| ClCH₂CH₂ | Me | Ph | Ga |
| ClCH₂CH₂ | Me | Ph-2-Cl | Gb |
| ClCH₂CH₂ | Me | Ph-2-CO₂Me | Gb |
| ClCH₂CH₂ | Me | Ph-2-OMe | Gb |
| ClCH₂CH₂ | Me | Ph-2-CF₃ | Gb |
| ClCH₂CH₂ | Me | Ph-2-NO₂ | Gb |
| ClCH₂CH₂ | Me | Ph-2-Me | Gb |
| ClCH₂CH₂ | Me | Ph—CH₂ | Ga |
| ClCH₂CH₂ | Et | Et | Ga |
| ClCH₂CH₂ | Pr-n | Pr-n | Gb |
| ClCH₂CH₂ | | —(CH₂)₄— | Ga |
| ClCH₂CH₂ | | —(CH₂)₅— | Ga |
| BrCH₂CH₂ | H | Me | Gc |
| BrCH₂CH₂ | H | Et | Gc |
| BrCH₂CH₂ | Me | Me | Ga |
| BrCH₂CH₂ | Me | Et | Ga |
| BrCH₂CH₂ | Me | Pr-n | Gb |
| BrCH₂CH₂ | Me | Pr-i | Gb |
| BrCH₂CH₂ | Me | Bu-n | Gb |
| BrCH₂CH₂ | Me | Ph | Ga |
| BrCH₂CH₂ | Me | Ph-2-Cl | Gb |
| BrCH₂CH₂ | Me | Ph-2-CO₂Me | Gb |
| BrCH₂CH₂ | Me | Ph-2-OMe | Gb |
| BrCH₂CH₂ | Me | Ph-2-CF₃ | Gb |
| BrCH₂CH₂ | Me | Ph-2-NO₂ | Gb |
| BrCH₂CH₂ | Me | Ph-2-Me | Gb |
| BrCH₂CH₂ | Me | Ph—CH₂ | Ga |
| BrCH₂CH₂ | Et | Et | Ga |

TABLE 1-continued

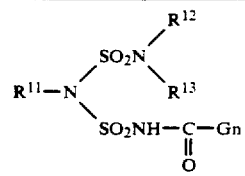

| R¹¹ | R¹² | R¹³ | Gn |
|---|---|---|---|
| BrCH₂CH₂ | Pr-n | Pr-n | Gb |
| BrCH₂CH₂ | | —(CH₂)₄— | Ga |
| BrCH₂CH₂ | | —(CH₂)₅— | Ga |
| ICH₂CH₂ | H | Me | Gc |
| ICH₂CH₂ | H | Et | Gc |
| ICH₂CH₂ | Me | Me | Ga |
| ICH₂CH₂ | Me | Et | Ga |
| ICH₂CH₂ | Me | Pr-n | Gb |
| ICH₂CH₂ | Me | Pr-i | Gb |
| ICH₂CH₂ | Me | Bu-n | Gb |
| ICH₂CH₂ | Me | Ph | Ga |
| ICH₂CH₂ | Me | Ph-2-Cl | Gb |
| ICH₂CH₂ | Me | Ph-2-CO₂Me | Gb |
| ICH₂CH₂ | Me | Ph-2-OMe | Gb |
| ICH₂CH₂ | Me | Ph-2-CF₃ | Gb |
| ICH₂CH₂ | Me | Ph-2-NO₂ | Gb |
| ICH₂CH₂ | Me | Ph-2-Me | Gb |
| ICH₂CH₂ | Me | Ph—CH₂ | Ga |
| ICH₂CH₂ | Et | Et | Ga |
| ICH₂CH₂ | Pr-n | Pr-n | Gb |
| ICH₂CH₂ | | —(CH₂)₄— | Ga |
| ICH₂CH₂ | | —(CH₂)₅— | Ga |
| FCH₂(CH₃)CH | Me | Me | Ga |
| FCH₂(CH₃)CH | Me | Et | Ga |
| FCH₂(CH₃)CH | Me | Ph | Ga |
| FCH₂(CH₃)CH | Me | Ph—CH₂ | Ga |
| FCH₂(CH₃)CH | Et | Et | Ga |
| FCH₂(CH₃)CH | Pr-n | Pr-n | Gb |
| FCH₂(CH₃)CH | | —(CH₂)₄— | Ga |
| FCH₂(CH₃)CH | | —(CH₂)₅— | Ga |
| ClCH₂(CH₃)CH | Me | Me | Ga |
| ClCH₂(CH₃)CH | Me | Et | Ga |
| ClCH₂(CH₃)CH | Me | Ph | Ga |
| ClCH₂(CH₃)CH | Me | Ph—CH₂ | Ga |
| ClCH₂(CH₃)CH | Et | Et | Ga |
| ClCH₂(CH₃)CH | Pr-n | Pr-n | Gb |
| ClCH₂(CH₃)CH | | —(CH₂)₄— | Ga |
| ClCH₂(CH₃)CH | | —(CH₂)₅— | Ga |
| BrCH₂(CH₃)CH | Me | Me | Ga |
| BrCH₂(CH₃)CH | Me | Et | Ga |
| BrCH₂(CH₃)CH | Me | Ph | Ga |
| BrCH₂(CH₃)CH | Me | Ph—CH₂ | Ga |
| BrCH₂(CH₃)CH | Et | Et | Ga |
| BrCH₂(CH₃)CH | Pr-n | Pr-n | Gb |
| BrCH₂(CH₃)CH | | —(CH₂)₄— | Ga |
| BrCH₂(CH₃)CH | | —(CH₂)₅— | Ga |
| ICH₂(CH₃)CH | Me | Me | Ga |
| ICH₂(CH₃)CH | Me | Et | Ga |
| ICH₂(CH₃)CH | Me | Ph | Ga |
| ICH₂(CH₃)CH | Me | Ph—CH₂ | Ga |
| ICH₂(CH₃)CH | Et | Et | Ga |
| ICH₂(CH₃)CH | Pr-n | Pr-n | Gb |
| ICH₂(CH₃)CH | | —(CH₂)₄— | Ga |
| ICH₂(CH₃)CH | | —(CH₂)₅— | Ga |
| CF₃CH₂ | H | Me | Gc |
| CF₃CH₂ | H | Et | Gc |
| CF₃CH₂ | Me | Me | Ga |
| CF₃CH₂ | Me | Et | Ga |
| CF₃CH₂ | Me | Pr-n | Gb |
| CF₃CH₂ | Me | Pr-i | Gb |
| CF₃CH₂ | Me | Bu-n | Gb |
| CF₃CH₂ | Me | Ph | Ga |
| CF₃CH₂ | Me | Ph-2-Cl | Gb |
| CF₃CH₂ | Me | Ph-2-CO₂Me | Gb |
| CF₃CH₂ | Me | Ph-2-OMe | Gb |
| CF₃CH₂ | Me | Ph-2-CF₃ | Gb |
| CF₃CH₂ | Me | Ph-2-NO₂ | Gb |
| CF₃CH₂ | Me | Ph-2-Me | Gb |
| CF₃CH₂ | Me | Ph—CH₂ | Ga |
| CF₃CH₂ | Et | Et | Ga |
| CF₃CH₂ | Pr-n | Pr-n | Gb |

TABLE 1-continued

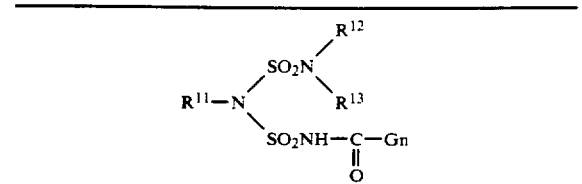

| R11 | R12 | R13 | Gn |
|---|---|---|---|
| CF3CH2 | | —(CH2)4— | Ga |
| CF3CH2 | | —(CH2)5— | Ga |
| NCCH2 | H | Me | Gc |
| NCCH2 | H | Et | Gc |
| NCCH2 | Me | Me | Ga |
| NCCH2 | Me | Et | Ga |
| NCCH2 | Me | Pr-n | Gb |
| NCCH2 | Me | Pr-i | Gb |
| NCCH2 | Me | Bu-n | Gb |
| NCCH2 | Me | Ph | Ga |
| NCCH2 | Me | Ph-2-Cl | Gb |
| NCCH2 | Me | Ph-2-CO2Me | Gb |
| NCCH2 | Me | Ph-2-OMe | Gb |
| NCCH2 | Me | Ph-2-CF3 | Gb |
| NCCH2 | Me | Ph-2-NO2 | Gb |
| NCCH2 | Me | Ph-2-Me | Gb |
| NCCH2 | Me | Ph—CH2 | Ga |
| NCCH2 | Et | Et | Ga |
| NCCH2 | Pr-n | Pr-n | Gb |
| NCCH2 | | —(CH2)4— | Ga |
| NCCH2 | | —(CH2)5— | Ga |
| NCCH2CH2 | H | Me | Gc |
| NCCH2CH2 | H | Et | Gc |
| NCCH2CH2 | Me | Me | Ga |
| NCCH2CH2 | Me | Et | Ga |
| NCCH2CH2 | Me | Pr-n | Gb |
| NCCH2CH2 | Me | Pr-i | Gb |
| NCCH2CH2 | Me | Bu-n | Gb |
| NCCH2CH2 | Me | Ph | Ga |
| NCCH2CH2 | Me | Ph-2-Cl | Gb |
| NCCH2CH2 | Me | Ph-2-CO2Me | Gb |
| NCCH2CH2 | Me | Ph-2-OMe | Gb |
| NCCH2CH2 | Me | Ph-2-CF3 | Gb |
| NCCH2CH2 | Me | Ph-2-NO2 | Gb |
| NCCH2CH2 | Me | Ph-2-Me | Gb |
| NCCH2CH2 | Me | Ph—CH2 | Ga |
| NCCH2CH2 | Et | Et | Ga |
| NCCH2CH2 | Pr-n | Pr-n | Gb |
| NCCH2CH2 | | —(CH2)4— | Ga |
| NCCH2CH2 | | —(CH2)5— | Ga |
| MeO2CCH2 | H | Me | Gc |
| MeO2CCH2 | H | Et | Gc |
| MeO2CCH2 | Me | Me | Ga |
| MeO2CCH2 | Me | Et | Ga |
| MeO2CCH2 | Me | Pr-n | Gb |
| MeO2CCH2 | Me | Pr-i | Gb |
| MeO2CCH2 | Me | Bu-n | Gb |
| MeO2CCH2 | Me | Ph | Ga |
| MeO2CCH2 | Me | Ph-2-Cl | Gb |
| MeO2CCH2 | Me | Ph-2-CO2Me | Gb |
| MeO2CCH2 | Me | Ph-2-OMe | Gb |
| MeO2CCH2 | Me | Ph-2-CF3 | Gb |
| MeO2CCH2 | Me | Ph-2-NO2 | Gb |
| MeO2CCH2 | Me | Ph-2-Me | Gb |
| MeO2CCH2 | Me | Ph—CH2 | Ga |
| MeO2CCH2 | Et | Et | Ga |
| MeO2CCH2 | Pr-n | Pr-n | Gb |
| MeO2CCH2 | | —(CH2)4— | Ga |
| MeO2CCH2 | | —(CH2)5— | Ga |
| EtO2CCH2 | H | Me | Gc |
| EtO2CCH2 | H | Et | Gc |
| EtO2CCH2 | Me | Me | Ga |
| EtO2CCH2 | Me | Et | Ga |
| EtO2CCH2 | Me | Pr-n | Gb |
| EtO2CCH2 | Me | Pr-i | Gb |
| EtO2CCH2 | Me | Bu-n | Gb |
| EtO2CCH2 | Me | Ph | Ga |
| EtO2CCH2 | Me | Ph-2-Cl | Gb |
| EtO2CCH2 | Me | Ph-2-CO2Me | Gb |
| EtO2CCH2 | Me | Ph-2-OMe | Gb |
| EtO2CCH2 | Me | Ph-2-CF3 | Gb |
| EtO2CCH2 | Me | Ph-2-NO2 | Gb |
| EtO2CCH2 | Me | Ph-2-Me | Gb |
| EtO2CCH2 | Me | Ph—CH2 | Ga |
| EtO2CCH2 | Et | Et | Ga |
| EtO2CCH2 | Pr-n | Pr-n | Gb |
| EtO2CCH2 | | —(CH2)4— | Ga |
| EtO2CCH2 | | —(CH2)5— | Ga |
| Pr-nO2CCH2 | Me | Me | Ga |
| Pr-nO2CCH2 | Me | Et | Ga |
| Pr-nO2CCH2 | Me | Ph | Ga |
| Pr-nO2CCH2 | Me | Ph—CH2 | Ga |
| Pr-nO2CCH2 | Et | Et | Ga |
| Pr-nO2CCH2 | Pr-n | Pr-n | Gb |
| Pr-nO2CCH2 | | —(CH2)4— | Ga |
| Pr-nO2CCH2 | | —(CH2)5— | Ga |
| MeO2CCH2CH2 | H | Me | Gc |
| MeO2CCH2CH2 | H | Et | Gc |
| MeO2CCH2CH2 | Me | Me | Ga |
| MeO2CCH2CH2 | Me | Et | Ga |
| MeO2CCH2CH2 | Me | Pr-n | Gb |
| MeO2CCH2CH2 | Me | Pr-i | Gb |
| MeO2CCH2CH2 | Me | Bu-n | Gb |
| MeO2CCH2CH2 | Me | Ph | Ga |
| MeO2CCH2CH2 | Me | Ph-2-Cl | Gb |
| MeO2CCH2CH2 | Me | Ph-2-CO2Me | Gb |
| MeO2CCH2CH2 | Me | Ph-2-OMe | Gb |
| MeO2CCH2CH2 | Me | Ph-2-CF3 | Gb |
| MeO2CCH2CH2 | Me | Ph-2-NO2 | Gb |
| MeO2CCH2CH2 | Me | Ph-2-Me | Gb |
| MeO2CCH2CH2 | Me | Ph—CH2 | Ga |
| MeO2CCH2CH2 | Et | Et | Ga |
| MeO2CCH2CH2 | Pr-n | Pr-n | Gb |
| MeO2CCH2CH2 | | —(CH2)4— | Ga |
| MeO2CCH2CH2 | | —(CH2)5— | Ga |
| EtO2CCH2CH2 | H | Me | Gc |
| EtO2CCH2CH2 | H | Et | Gc |
| EtO2CCH2CH2 | Me | Me | Ga |
| EtO2CCH2CH2 | Me | Et | Ga |
| EtO2CCH2CH2 | Me | Pr-n | Gb |
| EtO2CCH2CH2 | Me | Pr-i | Gb |
| EtO2CCH2CH2 | Me | Bu-n | Gb |
| EtO2CCH2CH2 | Me | Ph | Ga |
| EtO2CCH2CH2 | Me | Ph-2-Cl | Gb |
| EtO2CCH2CH2 | Me | Ph-2-CO2Me | Gb |
| EtO2CCH2CH2 | Me | Ph-2-OMe | Gb |
| EtO2CCH2CH2 | Me | Ph-2-CF3 | Gb |
| EtO2CCH2CH2 | Me | Ph-2-NO2 | Gb |
| EtO2CCH2CH2 | Me | Ph-2-Me | Gb |
| EtO2CCH2CH2 | Me | Ph—CH2 | Ga |
| EtO2CCH2CH2 | Et | Et | Ga |
| EtO2CCH2CH2 | Pr-n | Pr-n | Gb |
| EtO2CCH2CH2 | | —(CH2)4— | Ga |
| EtO2CCH2CH2 | | —(CH2)5— | Ga |
| Pr-nO2CCH2CH2 | Me | Me | Ga |
| Pr-nO2CCH2CH2 | Me | Et | Ga |
| Pr-nO2CCH2CH2 | Me | Ph | Ga |
| Pr-nO2CCH2CH2 | Me | Ph—CH2 | Ga |
| Pr-nO2CCH2CH2 | Et | Et | Ga |
| Pr-nO2CCH2CH2 | Pr-n | Pr-n | Gb |
| Pr-nO2CCH2CH2 | | —(CH2)4— | Ga |
| Pr-nO2CCH2CH2 | | —(CH2)5— | Ga |
| MeCOCH2 | Me | Me | Ga |
| MeCOCH2 | Me | Et | Ga |
| MeCOCH2 | Me | Ph | Ga |
| MeCOCH2 | Me | Ph—CH2 | Ga |
| MeCOCH2 | Et | Et | Ga |
| MeCOCH2 | Pr-n | Pr-n | Gb |
| MeCOCH2 | | —(CH2)4— | Ga |
| MeCOCH2 | | —(CH2)5— | Ga |
| EtCOCH2 | Me | Me | Ga |
| EtCOCH2 | Me | Et | Ga |

TABLE 1-continued $$R^{11}-N\begin{matrix}SO_2N\begin{matrix}R^{12}\\R^{13}\end{matrix}\\SO_2NH-\underset{\underset{O}{\|}}{C}-Gn\end{matrix}$$

| $R^{11}$ | $R^{12}$ | $R^{13}$ | Gn |
|---|---|---|---|
| EtCOCH$_2$ | Me | Ph | Ga |
| EtCOCH$_2$ | Me | Ph—CH$_2$ | Ga |
| EtCOCH$_2$ | Et | Et | Ga |
| EtCOCH$_2$ | Pr-n | Pr-n | Gb |
| EtCOCH$_2$ | —(CH$_2$)$_4$— | | Ga |
| EtCOCH$_2$ | —(CH$_2$)$_5$— | | Ga |
| PhCH$_2$ | H | Me | Gc |
| PhCH$_2$ | H | Et | Gc |
| PhCH$_2$ | Me | Me | Ga |
| PhCH$_2$ | Me | Et | Ga |
| PhCH$_2$ | Me | Pr-n | Gb |
| PhCH$_2$ | Me | Pr-i | Gb |
| PhCH$_2$ | Me | Bu-n | Gb |
| PhCH$_2$ | Me | Ph | Ga |
| PhCH$_2$ | Me | Ph-2-Cl | Gb |
| PhCH$_2$ | Me | Ph-2-CO$_2$Me | Gb |
| PhCH$_2$ | Me | Ph-2-OMe | Gb |
| PhCH$_2$ | Me | Ph-2-CF$_3$ | Gb |
| PhCH$_2$ | Me | Ph-2-NO$_2$ | Gb |
| PhCH$_2$ | Me | Ph-2-Me | Gb |
| PhCH$_2$ | Me | Ph—CH$_2$ | Ga |
| PhCH$_2$ | Et | Et | Ga |
| PhCH$_2$ | Pr-n | Pr-n | Gb |
| PhCH$_2$ | —(CH$_2$)$_4$— | | Ga |
| PhCH$_2$ | —(CH$_2$)$_5$— | | Ga |
| Ph | Me | Me | Ga |
| Ph | Me | Et | Ga |
| Ph | —(CH$_2$)$_4$— | | Ga |
| Ph | —(CH$_2$)$_5$— | | Ga |
| Me | CH$_2$=CHCH$_2$ | Me | Ga |
| Et | CH$_2$=CHCH$_2$ | Me | Ga |
| Me | CH≡CCH$_2$ | Me | Ga |
| Et | CH≡CCH$_2$ | Me | Ga |
| Me | CH$_2$=CHCH$_2$ | CH$_2$=CHCH$_2$ | Ga |
| Et | CH$_2$=CHCH$_2$ | CH$_2$=CHCH$_2$ | Ga |
| Me | CH≡CCH$_2$ | CH≡CCH$_2$ | Ga |
| Et | CH≡CCH$_2$ | CH≡CCH$_2$ | Ga |
| Me | H | H | Gb |
| Et | H | H | Gb |
| Bu-i | Me | Me | Gb |
| cyc-Bu | Me | Me | Gb |
| cyc-Pen | Me | Me | Gc |
| cyc-Hex | Me | Me | Gc |
| Ph-2-Me | Me | Me | Gb |
| Ph-3-Me | Me | Me | Gb |
| Ph-4-OMe | Me | Me | Gb |
| Ph-3-OMe | Me | Me | Gb |
| Ph-2-OMe | Me | Me | Gb |
| Ph-4-Cl | Me | Me | Gb |
| Ph-3-Cl | Me | Me | Gb |
| Ph-2-Cl | Me | Me | Gb |
| Ph-2,6-Cl$_2$ | Me | Me | Gb |

TABLE 2

$$R^{11}-O-N\begin{matrix}SO_2N\begin{matrix}R^{12}\\R^{13}\end{matrix}\\SO_2NH-\underset{\underset{O}{\|}}{C}-Gn\end{matrix}$$

| $R^{11}$ | $R^{12}$ | $R^{13}$ | Gn |
|---|---|---|---|
| Me | H | Me | Gc |
| Me | H | Et | Gc |
| Me | Me | Me | Ga |
| Me | Me | Et | Ga |
| Me | Me | Pr-n | Gb |
| Me | Me | Pr-i | Gb |
| Me | Me | Bu-n | Gb |
| Me | Me | Ph | Ga |
| Me | Me | Ph-2-Cl | Gb |
| Me | Me | Ph-2-CO$_2$Me | Gb |
| Me | Me | Ph-2-OMe | Gb |
| Me | Me | Ph-2-CF$_3$ | Gb |
| Me | Me | Ph-2-NO$_2$ | Gb |
| Me | Me | Ph-2-Me | Gb |
| Me | Me | Ph—CH$_2$ | Ga |
| Me | Et | Et | Ga |
| Me | Pr-n | Pr-n | Gb |
| Me | —(CH$_2$)$_4$— | | Ga |
| Me | —(CH$_2$)$_5$— | | Ga |
| Et | H | Me | Gc |
| Et | H | Et | Gc |
| Et | Me | Me | Ga |
| Et | Me | Et | Ga |
| Et | Me | Pr-n | Gb |
| Et | Me | Pr-i | Gb |
| Et | Me | Bu-n | Gb |
| Et | Me | Ph | Ga |
| Et | Me | Ph-2-Cl | Gb |
| Et | Me | Ph-2-CO$_2$Me | Gb |
| Et | Me | Ph-2-OMe | Gb |
| Et | Me | Ph-2-CF$_3$ | Gb |
| Et | Me | Ph-2-NO$_2$ | Gb |
| Et | Me | Ph-2-Me | Gb |
| Et | Me | Ph—CH$_2$ | Ga |
| Et | Et | Et | Ga |
| Et | Pr-n | Pr-n | Gb |
| Et | —(CH$_2$)$_4$— | | Ga |
| Et | —(CH$_2$)$_5$— | | Ga |
| Pr-n | H | Me | Gc |
| Pr-n | H | Et | Gc |
| Pr-n | Me | Me | Ga |
| Pr-n | Me | Et | Ga |
| Pr-n | Me | Ph | Ga |
| Pr-n | Me | Ph—CH$_2$ | Ga |
| Pr-n | Et | Et | Ga |
| Pr-n | Pr-n | Pr-n | Gb |
| Pr-n | —(CH$_2$)$_4$— | | Ga |
| Pr-n | —(CH$_2$)$_5$— | | Ga |
| CH$_2$=CHCH$_2$ | H | Me | Gc |
| CH$_2$=CHCH$_2$ | H | Et | Gc |
| CH$_2$=CHCH$_2$ | Me | Me | Ga |
| CH$_2$=CHCH$_2$ | Me | Et | Ga |
| CH$_2$=CHCH$_2$ | Me | Pr-n | Gb |
| CH$_2$=CHCH$_2$ | Me | Pr-i | Gb |
| CH$_2$=CHCH$_2$ | Me | Bu-n | Gb |
| CH$_2$=CHCH$_2$ | Me | Ph | Ga |
| CH$_2$=CHCH$_2$ | Me | Ph-2-Cl | Gb |
| CH$_2$=CHCH$_2$ | Me | Ph-2-CO$_2$Me | Gb |
| CH$_2$=CHCH$_2$ | Me | Ph-2-OMe | Gb |
| CH$_2$=CHCH$_2$ | Me | Ph-2-CF$_3$ | Gb |
| CH$_2$=CHCH$_2$ | Me | Ph-2-NO$_2$ | Gb |
| CH$_2$=CHCH$_2$ | Me | Ph-2-Me | Gb |
| CH$_2$=CHCH$_2$ | Me | Ph—CH$_2$ | Ga |
| CH$_2$=CHCH$_2$ | Et | Et | Ga |
| CH$_2$=CHCH$_2$ | Pr-n | pr-n | Gb |
| CH$_2$=CHCH$_2$ | —(CH$_2$)$_4$— | | Ga |
| CH$_2$=CHCH$_2$ | —(CH$_2$)$_5$— | | Ga |
| Ph | Me | Me | Ga |
| Ph | Me | Et | Ga |
| Ph | —(CH$_2$)$_4$— | | Ga |
| Ph | —(CH$_2$)$_5$— | | Ga |
| CH≡CCH$_2$ | Me | Me | Ga |
| MeOCH$_2$ | Me | Me | Ga |
| MeSCH$_2$ | Me | Me | Ga |
| MeO$_2$CCH$_2$ | Me | Me | Ga |

TABLE 2-continued

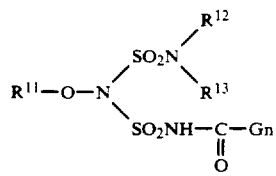

| R[11] | R[12] | R[13] | Gn |
|---|---|---|---|
| Pr-i | Me | Me | Gb |
| PhCH$_2$ | Me | Me | Gc |

TABLE 3

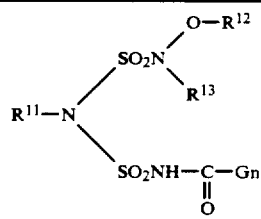

| R[11] | R[12] | R[13] | Gn |
|---|---|---|---|
| H | Me | Me | Ga |
| Me | Me | Me | Ga |
| Et | Me | Me | Ga |
| Pr-n | Me | Me | Gb |
| Pr-i | Me | Me | Gb |
| cyc-Pr | Me | Me | Gb |
| cyc-Pr—CH$_2$ | Me | Me | Gb |
| Bu-n | Me | Me | Gb |
| Bu-sec | Me | Me | Gb |
| Bu-t | Me | Me | Gb |
| CH$_2$=CHCH$_2$ | Me | Me | Ga |
| CH≡CCH$_2$ | Me | Me | Ga |
| MeOCH$_2$ | Me | Me | Ga |
| EtOCH$_2$ | Me | Me | Gb |
| MeOCH$_2$CH$_2$ | Me | Me | Ga |
| EtOCH$_2$CH$_2$ | Me | Me | Gb |
| MeOCH$_2$(CH$_3$)CH | Me | Me | Gb |
| EtOCH$_2$(CH$_3$)CH | Me | Me | Gb |
| CHF$_2$OCH$_2$ | Me | Me | Ga |
| MeSCH$_2$ | Me | Me | Ga |
| EtSCH$_2$ | Me | Me | Gb |
| MeSCH$_2$CH$_2$ | Me | Me | Ga |
| EtSCH$_2$CH$_2$ | Me | Me | Gb |
| MeSO$_2$CH$_2$ | Me | Me | Ga |
| EtSO$_2$CH$_2$ | Me | Me | Gb |
| MeSO$_2$CH$_2$CH$_2$ | Me | Me | Ga |
| EtSO$_2$CH$_2$CH$_2$ | Me | Me | Gb |
| FCH$_2$ | Me | Me | Ga |
| ClCH$_2$ | Me | Me | Ga |
| BrCH$_2$ | Me | Me | Ga |
| ICH$_2$ | Me | Me | Ga |
| FCH$_2$CH$_2$ | Me | Me | Ga |
| ClCH$_2$CH$_2$ | Me | Me | Ga |
| BrCH$_2$CH$_2$ | Me | Me | Ga |
| ICH$_2$CH$_2$ | Me | Me | Ga |
| FCH$_2$(CH$_3$)CH | Me | Me | Gb |
| ClCH$_2$(CH$_3$)CH | Me | Me | Gb |
| BrCH$_2$(CH$_3$)CH | Me | Me | Gb |
| ICH$_2$(CH$_3$)CH | Me | Me | Gb |
| CF$_3$CH$_2$ | Me | Me | Ga |
| NCCH$_2$ | Me | Me | Ga |
| NCCH$_2$CH$_2$ | Me | Me | Ga |
| MeO$_2$CCH$_2$ | Me | Me | Ga |
| EtO$_2$CCH$_2$ | Me | Me | Gb |
| Pr-nO$_2$CCH$_2$ | Me | Me | Gc |
| MeO$_2$CCH$_2$CH$_2$ | Me | Me | Ga |
| EtO$_2$CCH$_2$CH$_2$ | Me | Me | Gb |
| Pr-nO$_2$CCH$_2$CH$_2$ | Me | Me | Gc |
| MeCOCH$_2$ | Me | Me | Ga |
| PhCH$_2$ | Me | Me | Ga |
| Ph | Me | Me | Ga |
| H | Me | Et | Ga |

TABLE 3-continued

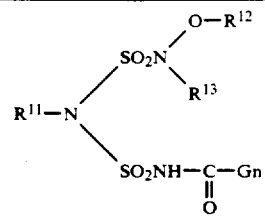

| R[11] | R[12] | R[13] | Gn |
|---|---|---|---|
| Me | Me | Et | Ga |
| Et | Me | Et | Ga |
| Pr-n | Me | Et | Gb |
| Pr-i | Me | Et | Gb |
| cyc-Pr | Me | Et | Gb |
| cyc-Pr—CH$_2$ | Me | Et | Gb |
| Bu-n | Me | Et | Gb |
| Bu-sec | Me | Et | Ga |
| Bu-t | Me | Et | Ga |
| CH$_2$=CHCH$_2$ | Me | Et | Ga |
| CH≡CCH$_2$ | Me | Et | Gb |
| MeOCH$_2$ | Me | Et | Ga |
| EtOCH$_2$ | Me | Et | Ga |
| MeOCH$_2$CH$_2$ | Me | Et | Gb |
| EtOCH$_2$CH$_2$ | Me | Et | Gb |
| MeOCH$_2$(CH$_3$)CH | Me | Et | Gb |
| EtOCH$_2$(CH$_3$)CH | Me | Et | Gb |
| CHF$_2$OCH$_2$ | Me | Et | Gb |
| MeSCH$_2$ | Me | Et | Ga |
| EtSCH$_2$ | Me | Et | Ga |
| MeSCH$_2$CH$_2$ | Me | Et | Gb |
| EtSCH$_2$CH$_2$ | Me | Et | Ga |
| MeSO$_2$CH$_2$ | Me | Et | Gb |
| EtSO$_2$CH$_2$ | Me | Et | Ga |
| MeSO$_2$CH$_2$CH$_2$ | Me | Et | Gb |
| EtSO$_2$CH$_2$CH$_2$ | Me | Et | Gb |
| FCH$_2$ | Me | Et | Ga |
| ClCH$_2$ | Me | Et | Ga |
| BrCH$_2$ | Me | Et | Ga |
| ICH$_2$ | Me | Et | Ga |
| FCH$_2$CH$_2$ | Me | Et | Ga |
| ClCH$_2$CH$_2$ | Me | Et | Ga |
| BrCH$_2$CH$_2$ | Me | Et | Ga |
| ICH$_2$CH$_2$ | Me | Et | Ga |
| FCH$_2$(CH$_3$)CH | Me | Et | Gb |
| ClCH$_2$(CH$_3$)CH | Me | Et | Gb |
| BrCH$_2$(CH$_3$)CH | Me | Et | Gb |
| ICH$_2$(CH$_3$)CH | Me | Et | Gb |
| CF$_3$CH$_2$ | Me | Et | Ga |
| NCCH$_2$ | Me | Et | Ga |
| NCCH$_2$CH$_2$ | Me | Et | Ga |
| MeO$_2$CCH$_2$ | Me | Et | Ga |
| EtO$_2$CCH$_2$ | Me | Et | Gb |
| Pr-nO$_2$CCH$_2$ | Me | Et | Gc |
| MeO$_2$CCH$_2$CH$_2$ | Me | Et | Ga |
| EtO$_2$CCH$_2$CH$_2$ | Me | Et | Gb |
| Pr-nO$_2$CCH$_2$CH$_2$ | Me | Et | Gc |
| MeCOCH$_2$ | Me | Et | Ga |
| PhCH$_2$ | Me | Et | Ga |
| Ph | Me | Et | Ga |
| H | Me | Pr-n | Ga |
| Me | Me | Pr-n | Ga |
| Et | Me | Pr-n | Ga |
| Pr-n | Me | Pr-n | Gb |
| Pr-i | Me | Pr-n | Gb |
| cyc-Pr | Me | Pr-n | Gb |
| CH$_2$=CHCH$_2$ | Me | Pr-n | Ga |
| CH≡CCH$_2$ | Me | Pr-n | Ga |
| MeOCH$_2$ | Me | Pr-n | Ga |
| MeOCH$_2$CH$_2$ | Me | Pr-n | Ga |
| CHF$_2$OCH$_2$ | Me | Pr-n | Ga |
| MeSCH$_2$ | Me | Pr-n | Ga |
| MeSCH$_2$CH$_2$ | Me | Pr-n | Ga |
| MeSO$_2$CH$_2$ | Me | Pr-n | Ga |
| MeSO$_2$CH$_2$CH$_2$ | Me | Pr-n | Ga |
| FCH$_2$ | Me | Pr-n | Ga |
| ClCH$_2$ | Me | Pr-n | Ga |
| BrCH$_2$ | Me | Pr-n | Ga |
| ICH$_2$ | Me | Pr-n | Ga |

TABLE 3-continued

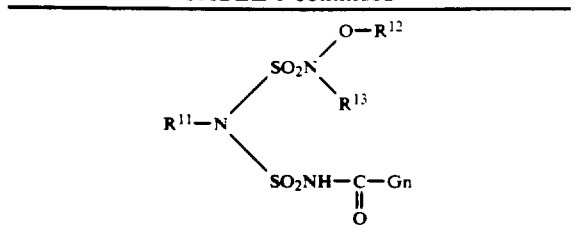

| R11 | R12 | R13 | Gn |
|---|---|---|---|
| FCH2CH2 | Me | Pr-n | Ga |
| ClCH2CH2 | Me | Pr-n | Ga |
| BrCH2CH2 | Me | Pr-n | Ga |
| ICH2CH2 | Me | Pr-n | Ga |
| CF3CH2 | Me | Pr-n | Ga |
| NCCH2 | Me | Pr-n | Ga |
| NCCH2CH2 | Me | Pr-n | Ga |
| MeO2CCH2 | Me | Pr-n | Ga |
| MeCOCH2 | Me | Pr-n | Ga |
| PhCH2 | Me | Pr-n | Ga |
| Ph | Me | Pr-n | Ga |
| H | Et | Me | Ga |
| Me | Et | Me | Ga |
| Et | Et | Me | Ga |
| Pr-n | Et | Me | Gb |
| Pr-i | Et | Me | Gb |
| cyc-Pr | Et | Me | Gb |
| cyc-Pr—CH2 | Et | Me | Gb |
| Bu-n | Et | Me | Gb |
| Bu-sec | Et | Me | Gb |
| Bu-t | Et | Me | Gb |
| CH2=CHCH2 | Et | Me | Ga |
| CH≡CCH2 | Et | Me | Ga |
| MeOCH2 | Et | Me | Ga |
| EtOCH2 | Et | Me | Gb |
| MeOCH2CH2 | Et | Me | Ga |
| EtOCH2CH2 | Et | Me | Gb |
| MeOCH2(CH3)CH | Et | Me | Gb |
| EtOCH2(CH3)CH | Et | Me | Gb |
| CHF2OCH2 | Et | Me | Ga |
| MeSCH2 | Et | Me | Ga |
| EtSCH2 | Et | Me | Gb |
| MeSCH2CH2 | Et | Me | Ga |
| EtSCH2CH2 | Et | Me | Gb |
| MeSO2CH2 | Et | Me | Ga |
| EtSO2CH2 | Et | Me | Gb |
| MeSO2CH2CH2 | Et | Me | Ga |
| EtSO2CH2CH2 | Et | Me | Ga |
| FCH2 | Et | Me | Ga |
| ClCH2 | Et | Me | Ga |
| BrCH2 | Et | Me | Ga |
| ICH2 | Et | Me | Ga |
| FCH2CH2 | Et | Me | Ga |
| ClCH2CH2 | Et | Me | Ga |
| BrCH2CH2 | Et | Me | Ga |
| ICH2CH2 | Et | Me | Ga |
| FCH2(CH3)CH | Et | Me | Gb |
| ClCH2(CH3)CH | Et | Me | Gb |
| BrCH2(CH3)CH | Et | Me | Gb |
| ICH2(CH3)CH | Et | Me | Gb |
| CF3CH2 | Et | Me | Ga |
| NCCH2 | Et | Me | Ga |
| NCCH2CH2 | Et | Me | Ga |
| MeO2CCH2 | Et | Me | Ga |
| EtO2CCH2 | Et | Me | Gb |
| Pr-nO2CCH2 | Et | Me | Gc |
| MeO2CCH2CH2 | Et | Me | Ga |
| EtO2CCH2CH2 | Et | Me | Gb |
| Pr-nO2CCH2CH2 | Et | Me | Gc |
| MeCOCH2 | Et | Me | Ga |
| PhCH2 | Et | Me | Ga |
| Ph | Et | Me | Ga |
| H | Pr-n | Me | Ga |
| Me | Pr-n | Me | Ga |
| Et | Pr-n | Me | Ga |
| Pr-n | Pr-n | Me | Gb |
| Pr-i | Pr-n | Me | Gb |
| cyc-Pr | Pr-n | Me | Gb |
| CH2=CHCH2 | Pr-n | Me | Ga |

| R11 | R12 | R13 | Gn |
|---|---|---|---|
| CH≡CCH2 | Pr-n | Me | Ga |
| MeOCH2 | Pr-n | Me | Ga |
| MeSCH2 | Pr-n | Me | Ga |
| MeSCH2CH2 | Pr-n | Me | Ga |
| MeSO2CH2 | Pr-n | Me | Ga |
| MeSO2CH2CH2 | Pr-n | Me | Ga |
| FCH2 | Pr-n | Me | Ga |
| ClCH2 | Pr-n | Me | Ga |
| BrCH2 | Pr-n | Me | Ga |
| ICH2 | Pr-n | Me | Ga |
| FCH2CH2 | Pr-n | Me | Ga |
| ClCH2CH2 | Pr-n | Me | Ga |
| BrCH2CH2 | Pr-n | Me | Ga |
| ICH2CH2 | Pr-n | Me | Ga |
| CF3CH2 | Pr-n | Me | Ga |
| NCCH2 | Pr-n | Me | Ga |
| NCCH2CH2 | Pr-n | Me | Ga |
| MeO2CCH2 | Pr-n | Me | Ga |
| MeCOCH2 | Pr-n | Me | Ga |
| PhCH2 | Pr-n | Me | Ga |
| Ph | Pr-n | Me | Ga |
| H | Et | Et | Ga |
| Me | Et | Et | Ga |
| Et | Et | Et | Ga |
| Pr-n | Et | Et | Gb |
| Pr-i | Et | Et | Gb |
| cyc-Pr | Et | Et | Gb |
| CH2=CHCH2 | Et | Et | Ga |
| CH≡CCH2 | Et | Et | Ga |
| MeOCH2 | Et | Et | Ga |
| MeOCH2CH2 | Et | Et | Ga |
| MeSCH2 | Et | Et | Ga |
| MeSCH2CH2 | Et | Et | Ga |
| MeSO2CH2 | Et | Et | Ga |
| MeSO2CH2CH2 | Et | Et | Ga |
| FCH2 | Et | Et | Ga |
| ClCH2 | Et | Et | Ga |
| BrCH2 | Et | Et | Ga |
| ICH2 | Et | Et | Ga |
| FCH2CH2 | Et | Et | Ga |
| ClCH2CH2 | Et | Et | Ga |
| BrCH2CH2 | Et | Et | Ga |
| ICH2CH2 | Et | Et | Ga |
| CF3CH2 | Et | Et | Ga |
| NCCH2 | Et | Et | Ga |
| NCCH2CH2 | Et | Et | Ga |
| MeO2CCH2 | Et | Et | Ga |
| MeO2CCH2CH2 | Et | Et | Ga |
| MeCOCH2 | Et | Et | Ga |
| PhCH2 | Et | Et | Ga |
| Ph | Et | Et | Ga |
| H | CH2=CHCH2 | Me | Ga |
| Me | CH2=CHCH2 | Me | Ga |
| Et | CH2=CHCH2 | Me | Ga |
| Pr-n | CH2=CHCH2 | Me | Gb |
| Pr-i | CH2=CHCH2 | Me | Gb |
| cyc-Pr | CH2=CHCH2 | Me | Gb |
| cyc-Pr—CH2 | CH2=CHCH2 | Me | Gb |
| Bu-n | CH2=CHCH2 | Me | Gb |
| Bu-sec | CH2=CHCH2 | Me | Gb |
| Bu-t | CH2=CHCH2 | Me | Gb |
| CH2=CHCH2 | CH2=CHCH2 | Me | Ga |
| CH≡CCH2 | CH2=CHCH2 | Me | Ga |
| MeOCH2 | CH2=CHCH2 | Me | Ga |
| EtOCH2 | CH2=CHCH2 | Me | Gb |
| MeOCH2CH2 | CH2=CHCH2 | Me | Ga |
| EtOCH2CH2 | CH2=CHCH2 | Me | Gb |
| MeOCH2(CH3)CH | CH2=CHCH2 | Me | Gb |
| EtOCH2(CH3)CH | CH2=CHCH2 | Me | Gb |

TABLE 3-continued

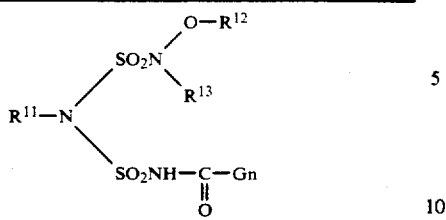

| R11 | R12 | R13 | Gn |
|---|---|---|---|
| CHF2OCH2 | CH2=CHCH2 | Me | Ga |
| MeSCH2 | CH2=CHCH2 | Me | Ga |
| EtSCH2 | CH2=CHCH2 | Me | Gb |
| MeSCH2CH2 | CH2=CHCH2 | Me | Ga |
| EtSCH2CH2 | CH2=CHCH2 | Me | Gb |
| MeSO2CH2 | CH2=CHCH2 | Me | Ga |
| EtSO2CH2 | CH2=CHCH2 | Me | Gb |
| MeSO2CH2CH2 | CH2=CHCH2 | Me | Ga |
| EtSO2CH2CH2 | CH2=CHCH2 | Me | Gb |
| FCH2 | CH2=CHCH2 | Me | Ga |
| ClCH2 | CH2=CHCH2 | Me | Ga |
| BrCH2 | CH2=CHCH2 | Me | Ga |
| ICH2 | CH2=CHCH2 | Me | Ga |
| FCH2CH2 | CH2=CHCH2 | Me | Ga |
| ClCH2CH2 | CH2=CHCH2 | Me | Ga |
| BrCH2CH2 | CH2=CHCH2 | Me | Ga |
| ICH2CH2 | CH2=CHCH2 | Me | Ga |
| FCH2(CH3)CH | CH2=CHCH2 | Me | Gb |
| ClCH2(CH3)CH | CH2=CHCH2 | Me | Gb |
| BrCH2(CH3)CH | CH2=CHCH2 | Me | Gb |
| ICH2(CH3)CH | CH2=CHCH2 | Me | Gb |
| CF3CH2 | CH2=CHCH2 | Me | Ga |
| NCCH2 | CH2=CHCH2 | Me | Ga |
| NCCH2CH2 | CH2=CHCH2 | Me | Ga |
| MeO2CCH2 | CH2=CHCH2 | Me | Ga |
| EtO2CCH2 | CH2=CHCH2 | Me | Gb |
| Pr-nO2CCH2 | CH2=CHCH2 | Me | Gc |
| MeO2CCH2CH2 | CH2=CHCH2 | Me | Ga |
| EtO2CCH2CH2 | CH2=CHCH2 | Me | Gb |
| Pr-nO2CCH2CH2 | CH2=CHCH2 | Me | Gc |
| MeCOCH2 | CH2=CHCH2 | Me | Ga |
| PhCH2 | CH2=CHCH2 | Me | Ga |
| Ph | CH2=CHCH2 | Me | Ga |
| H | CH2=CHCH2 | Et | Ga |
| Me | CH2=CHCH2 | Et | Ga |
| Et | CH2=CHCH2 | Et | Ga |
| Pr-n | CH2=CHCH2 | Et | Gb |
| Pr-i | CH2=CHCH2 | Et | Gb |
| cyc-Pr | CH2=CHCH2 | Et | Gb |
| cyc-Pr—CH2 | CH2=CHCH2 | Et | Gb |
| Bu-n | CH2=CHCH2 | Et | Gb |
| Bu-sec | CH2=CHCH2 | Et | Gb |
| Bu-t | CH2=CHCH2 | Et | Gb |
| CH2=CHCH2 | CH2=CHCH2 | Et | Ga |
| CH≡CCH2 | CH2=CHCH2 | Et | Ga |
| MeOCH2 | CH2=CHCH2 | Et | Ga |
| EtOCH2 | CH2=CHCH2 | Et | Gb |
| MeOCH2CH2 | CH2=CHCH2 | Et | Ga |
| EtOCH2CH2 | CH2=CHCH2 | Et | Gb |
| MeOCH2(CH3)CH | CH2=CHCH2 | Et | Gb |
| EtOCH2(CH3)CH | CH2=CHCH2 | Et | Gb |
| CHF2OCH2 | CH2=CHCH2 | Et | Ga |
| MeSCH2 | CH2=CHCH2 | Et | Ga |
| EtSCH2 | CH2=CHCH2 | Et | Gb |
| MeSCH2CH2 | CH2=CHCH2 | Et | Ga |
| EtSCH2CH2 | CH2=CHCH2 | Et | Gb |
| MeSO2CH2 | CH2=CHCH2 | Et | Ga |
| EtSO2CH2 | CH2=CHCH2 | Et | Gb |
| MeSO2CH2CH2 | CH2=CHCH2 | Et | Ga |
| EtSO2CH2CH2 | CH2=CHCH2 | Et | Gb |
| FCH2 | CH2=CHCH2 | Et | Ga |
| ClCH2 | CH2=CHCH2 | Et | Ga |
| BrCH2 | CH2=CHCH2 | Et | Ga |
| ICH2 | CH2=CHCH2 | Et | Ga |
| FCH2CH2 | CH2=CHCH2 | Et | Ga |
| ClCH2CH2 | CH2=CHCH2 | Et | Ga |
| BrCH2CH2 | CH2=CHCH2 | Et | Ga |
| ICH2CH2 | CH2=CHCH2 | Et | Ga |
| FCH2(CH3)CH | CH2=CHCH2 | Et | Gb |

TABLE 3-continued

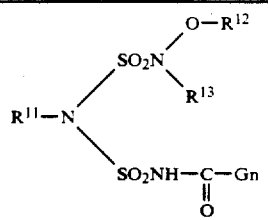

| R11 | R12 | R13 | Gn |
|---|---|---|---|
| ClCH2(CH3)CH | CH2=CHCH2 | Et | Gb |
| BrCH2(CH3)CH | CH2=CHCH2 | Et | Gb |
| ICH2(CH3)CH | CH2=CHCH2 | Et | Gb |
| CF3CH2 | CH2=CHCH2 | Et | Ga |
| NCCH2 | CH2=CHCH2 | Et | Ga |
| NCCH2CH2 | CH2=CHCH2 | Et | Ga |
| MeO2CCH2 | CH2=CHCH2 | Et | Ga |
| EtO2CCH2 | CH2=CHCH2 | Et | Gb |
| Pr-nO2CCH2 | CH2=CHCH2 | Et | Gc |
| MeO2CCH2CH2 | CH2=CHCH2 | Et | Ga |
| EtO2CCH2CH2 | CH2=CHCH2 | Et | Gb |
| Pr-nO2CCH2CH2 | CH2=CHCH2 | Et | Gc |
| MeCOCH2 | CH2=CHCH2 | Et | Ga |
| PhCH2 | CH2=CHCH2 | Et | Ga |
| Ph | CH2=CHCH2 | Et | Ga |
| H | Ph | Me | Ga |
| Me | Ph | Me | Ga |
| Et | Ph | Me | Ga |
| Pr-n | Ph | Me | Gb |
| Pr-i | Ph | Me | Gb |
| cyc-Pr | Ph | Me | Gb |
| cyc-Pr—CH2 | Ph | Me | Gb |
| Bu-n | Ph | Me | Gb |
| Bu-sec | Ph | Me | Gb |
| Bu-t | Ph | Me | Gb |
| CH2=CHCH2 | Ph | Me | Ga |
| CH≡CCH2 | Ph | Me | Ga |
| MeOCH2 | Ph | Me | Ga |
| EtOCH2 | Ph | Me | Gb |
| MeOCH2CH2 | Ph | Me | Ga |
| EtOCH2CH2 | Ph | Me | Gb |
| MeOCH2(CH3)CH | Ph | Me | Gb |
| EtOCH2(CH3)CH | Ph | Me | Gb |
| CHF2OCH2 | Ph | Me | Ga |
| MeSCH2 | Ph | Me | Ga |
| EtSCH2 | Ph | Me | Gb |
| MeSCH2CH2 | Ph | Me | Ga |
| EtSCH2CH2 | Ph | Me | Gb |
| MeSO2CH2 | Ph | Me | Ga |
| EtSO2CH2 | Ph | Me | Gb |
| MeSO2CH2CH2 | Ph | Me | Gb |
| EtSO2CH2CH2 | Ph | Me | Gb |
| FCH2 | Ph | Me | Ga |
| ClCH2 | Ph | Me | Ga |
| BrCH2 | Ph | Me | Ga |
| ICH2 | Ph | Me | Ga |
| FCH2CH2 | Ph | Me | Ga |
| ClCH2CH2 | Ph | Me | Ga |
| BrCH2CH2 | Ph | Me | Ga |
| ICH2CH2 | Ph | Me | Ga |
| FCH2(CH3)CH | Ph | Me | Gb |
| ClCH2(CH3)CH | Ph | Me | Gb |
| BrCH2(CH3)CH | Ph | Me | Gb |
| ICH2(CH3)CH | Ph | Me | Gb |
| CF3CH2 | Ph | Me | Ga |
| NCCH2 | Ph | Me | Ga |
| NCCH2CH2 | Ph | Me | Ga |
| MeO2CCH2 | Ph | Me | Ga |
| EtO2CCH2 | Ph | Me | Gb |
| Pr-nO2CCH2 | Ph | Me | Gc |
| MeO2CCH2CH2 | Ph | Me | Ga |
| EtO2CCH2CH2 | Ph | Me | Gb |
| Pr-nO2CCH2CH2 | Ph | Me | Gc |
| MeCOCH2 | Ph | Me | Ga |
| PhCH2 | Ph | Me | Ga |
| Ph | Ph | Me | Ga |
| H | Ph | Et | Ga |
| Me | Ph | Et | Ga |
| Et | Ph | Et | Ga |

TABLE 3-continued

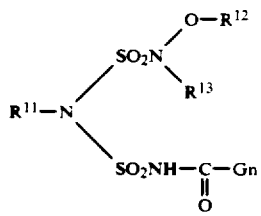

| $R^{11}$ | $R^{12}$ | $R^{13}$ | Gn |
|---|---|---|---|
| Pr-n | Ph | Et | Gb |
| Pr-i | Ph | Et | Gb |
| cyc-Pr | Ph | Et | Gb |
| cyc-Pr—CH$_2$ | Ph | Et | Gb |
| Bu-n | Ph | Et | Gb |
| Bu-sec | Ph | Et | Gb |
| Bu-t | Ph | Et | Gb |
| CH$_2$=CHCH$_2$ | Ph | Et | Ga |
| CH≡CCH$_2$ | Ph | Et | Ga |
| MeOCH$_2$ | Ph | Et | Ga |
| EtOCH$_2$ | Ph | Et | Gb |
| MeOCH$_2$CH$_2$ | Ph | Et | Ga |
| EtOCH$_2$CH$_2$ | Ph | Et | Gb |
| MeOCH$_2$(CH$_3$)CH | Ph | Et | Gb |
| EtOCH$_2$(CH$_3$)CH | Ph | Et | Gb |
| CHF$_2$OCH$_2$ | Ph | Et | Ga |
| MeSCH$_2$ | Ph | Et | Ga |
| EtSCH$_2$ | Ph | Et | Gb |
| MeSCH$_2$CH$_2$ | Ph | Et | Ga |
| EtSCH$_2$CH$_2$ | Ph | Et | Gb |
| MeSO$_2$CH$_2$ | Ph | Et | Ga |
| EtSO$_2$CH$_2$ | Ph | Et | Gb |
| MeSO$_2$CH$_2$CH$_2$ | Ph | Et | Ga |
| EtSO$_2$CH$_2$CH$_2$ | Ph | Et | Gb |
| FCH$_2$ | Ph | Et | Ga |
| ClCH$_2$ | Ph | Et | Ga |
| BrCH$_2$ | Ph | Et | Ga |
| ICH$_2$ | Ph | Et | Ga |
| FCH$_2$CH$_2$ | Ph | Et | Ga |
| ClCH$_2$CH$_2$ | Ph | Et | Ga |
| BrCH$_2$CH$_2$ | Ph | Et | Ga |
| ICH$_2$CH$_2$ | Ph | Et | Ga |
| FCH$_2$(CH$_3$)CH | Ph | Et | Gb |
| ClCH$_2$(CH$_3$)CH | Ph | Et | Gb |
| BrCH$_2$(CH$_3$)CH | Ph | Et | Gb |
| ICH$_2$(CH$_3$)CH | Ph | Et | Gb |
| CF$_3$CF$_2$ | Ph | Et | Ga |
| NCCH$_2$ | Ph | Et | Ga |
| NCCH$_2$CH$_2$ | Ph | Et | Ga |
| MeO$_2$CCH$_2$ | Ph | Et | Ga |
| EtO$_2$CCH$_2$ | Ph | Et | Gb |
| Pr-nO$_2$CCH$_2$ | Ph | Et | Gc |
| MeO$_2$CCH$_2$CH$_2$ | Ph | Et | Ga |
| EtO$_2$CCH$_2$CH$_2$ | Ph | Et | Gb |
| Pr-nO$_2$CCH$_2$CH$_2$ | Ph | Et | Gc |
| MeCOCH$_2$ | Ph | Et | Ga |
| PhCH$_2$ | Ph | Et | Ga |
| Ph | Ph | Et | Ga |
| H | | —(CH$_2$)$_3$— | Ga |
| Me | | —(CH$_2$)$_3$— | Ga |
| Et | | —(CH$_2$)$_3$— | Ga |
| Pr-n | | —(CH$_2$)$_3$— | Gb |
| Pr-i | | —(CH$_2$)$_3$— | Gb |
| cyc-Pr | | —(CH$_2$)$_3$— | Gb |
| cyc-Pr—CH$_2$ | | —(CH$_2$)$_3$— | Gb |
| Bu-n | | —(CH$_2$)$_3$— | Gb |
| Bu-sec | | —(CH$_2$)$_3$— | Gb |
| Bu-t | | —(CH$_2$)$_3$— | Gb |
| CH$_2$=CHCH$_2$ | | —(CH$_2$)$_3$— | Ga |
| CH≡CCH$_2$ | | —(CH$_2$)$_3$— | Ga |
| MeOCH$_2$ | | —(CH$_2$)$_3$— | Ga |
| EtOCH$_2$ | | —(CH$_2$)$_3$— | Gb |
| MeOCH$_2$CH$_2$ | | —(CH$_2$)$_3$— | Ga |
| EtOCH$_2$CH$_2$ | | —(CH$_2$)$_3$— | Gb |
| MeOCH$_2$(CH$_3$)CH | | —(CH$_2$)$_3$— | Gb |
| EtOCH$_2$(CH$_3$)CH | | —(CH$_2$)$_3$— | Gb |
| CHF$_2$OCH$_2$ | | —(CH$_2$)$_3$— | Ga |
| MeSCH$_2$ | | —(CH$_2$)$_3$— | Ga |
| EtSCH$_2$ | | —(CH$_2$)$_3$— | Gb |

TABLE 3-continued

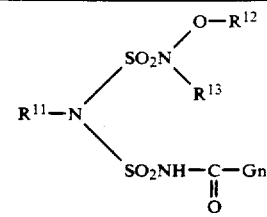

| $R^{11}$ | $R^{12}$ | $R^{13}$ | Gn |
|---|---|---|---|
| MeSCH$_2$CH$_2$ | | —(CH$_2$)$_3$— | Ga |
| EtSCH$_2$CH$_2$ | | —(CH$_2$)$_3$— | Gb |
| MeSO$_2$CH$_2$ | | —(CH$_2$)$_3$— | Ga |
| EtSO$_2$CH$_2$ | | —(CH$_2$)$_3$— | Gb |
| MeSO$_2$CH$_2$CH$_2$ | | —(CH$_2$)$_3$— | Ga |
| EtSO$_2$CH$_2$CH$_2$ | | —(CH$_2$)$_3$— | Gb |
| FCH$_2$ | | —(CH$_2$)$_3$— | Ga |
| ClCH$_2$ | | —(CH$_2$)$_3$— | Ga |
| BrCH$_2$ | | —(CH$_2$)$_3$— | Ga |
| ICH$_2$ | | —(CH$_2$)$_3$— | Ga |
| FCH$_2$CH$_2$ | | —(CH$_2$)$_3$— | Ga |
| ClCH$_2$CH$_2$ | | —(CH$_2$)$_3$— | Ga |
| BrCH$_2$CH$_2$ | | —(CH$_2$)$_3$— | Ga |
| ICH$_2$CH$_2$ | | —(CH$_2$)$_3$— | Ga |
| FCH$_2$(CH$_3$)CH | | —(CH$_2$)$_3$— | Gb |
| ClCH$_2$(CH$_3$)CH | | —(CH$_2$)$_3$— | Gb |
| BrCH$_2$(CH$_3$)CH | | —(CH$_2$)$_3$— | Gb |
| ICH$_2$(CH$_3$)CH | | —(CH$_2$)$_3$— | Gb |
| CF$_3$CH$_2$ | | —(CH$_2$)$_3$— | Ga |
| NCCH$_2$ | | —(CH$_2$)$_3$— | Ga |
| NCCH$_2$CH$_2$ | | —(CH$_2$)$_3$— | Ga |
| MeO$_2$CCH$_2$ | | —(CH$_2$)$_3$— | Ga |
| EtO$_2$CCH$_2$ | | —(CH$_2$)$_3$— | Gb |
| Pr-nO$_2$CCH$_2$ | | —(CH$_2$)$_3$— | Gc |
| MeO$_2$CCH$_2$CH$_2$ | | —(CH$_2$)$_3$— | Ga |
| EtO$_2$CCH$_2$CH$_2$ | | —(CH$_2$)$_3$— | Gb |
| Pr-nO$_2$CCH$_2$CH$_2$ | | —(CH$_2$)$_3$— | Gc |
| MeCOCH$_2$ | | —(CH$_2$)$_3$— | Ga |
| PhCH$_2$ | | —(CH$_2$)$_3$— | Ga |
| Ph | | —(CH$_2$)$_3$— | Ga |
| H | | —(CH$_2$)$_4$— | Ga |
| Me | | —(CH$_2$)$_4$— | Ga |
| Et | | —(CH$_2$)$_4$— | Ga |
| Pr-n | | —(CH$_2$)$_4$— | Gb |
| Pr-i | | —(CH$_2$)$_4$— | Gb |
| cyc-Pr | | —(CH$_2$)$_4$— | Gb |
| cyc-Pr—CH$_2$ | | —(CH$_2$)$_4$— | Gb |
| Bu-n | | —(CH$_2$)$_4$— | Gb |
| Bu-sec | | —(CH$_2$)$_4$— | Gb |
| Bu-t | | —(CH$_2$)$_4$— | Gb |
| CH$_2$=CHCH$_2$ | | —(CH$_2$)$_4$— | Ga |
| CH≡CCH$_2$ | | —(CH$_2$)$_4$— | Ga |
| MeOCH$_2$ | | —(CH$_2$)$_4$— | Ga |
| EtOCH$_2$ | | —(CH$_2$)$_4$— | Gb |
| MeOCH$_2$CH$_2$ | | —(CH$_2$)$_4$— | Ga |
| EtOCH$_2$CH$_2$ | | —(CH$_2$)$_4$— | Gb |
| MeOCH$_2$(CH$_3$)CH | | —(CH$_2$)$_4$— | Gb |
| EtOCH$_2$(CH$_3$)CH | | —(CH$_2$)$_4$— | Gb |
| CHF$_2$OCH$_2$ | | —(CH$_2$)$_4$— | Ga |
| MeSCH$_2$ | | —(CH$_2$)$_4$— | Ga |
| EtSCH$_2$ | | —(CH$_2$)$_4$— | Gb |
| MeSCH$_2$CH$_2$ | | —(CH$_2$)$_4$— | Ga |
| EtSCH$_2$CH$_2$ | | —(CH$_2$)$_4$— | Gb |
| MeSO$_2$CH$_2$ | | —(CH$_2$)$_4$— | Ga |
| EtSO$_2$CH$_2$ | | —(CH$_2$)$_4$— | Gb |
| MeSO$_2$CH$_2$CH$_2$ | | —(CH$_2$)$_4$— | Ga |
| EtSO$_2$CH$_2$CH$_2$ | | —(CH$_2$)$_4$— | Gb |
| FCH$_2$ | | —(CH$_2$)$_4$— | Ga |
| ClCH$_2$ | | —(CH$_2$)$_4$— | Ga |
| BrCH$_2$ | | —(CH$_2$)$_4$— | Ga |
| ICH$_2$ | | —(CH$_2$)$_4$— | Ga |
| FCH$_2$CH$_2$ | | —(CH$_2$)$_4$— | Ga |
| ClCH$_2$CH$_2$ | | —(CH$_2$)$_4$— | Ga |
| BrCH$_2$CH$_2$ | | —(CH$_2$)$_4$— | Ga |
| ICH$_2$CH$_2$ | | —(CH$_2$)$_4$— | Ga |
| FCH$_2$(CH$_3$)CH | | —(CH$_2$)$_4$— | Gb |
| ClCH$_2$(CH$_3$)CH | | —(CH$_2$)$_4$— | Gb |
| BrCH$_2$(CH$_3$)CH | | —(CH$_2$)$_4$— | Gb |
| ICH$_2$(CH$_3$)CH | | —(CH$_2$)$_4$— | Gb |

TABLE 3-continued $$R^{11}-N \begin{matrix} SO_2N \begin{matrix} O-R^{12} \\ R^{13} \end{matrix} \\ SO_2NH-\underset{\underset{O}{\|}}{C}-Gn \end{matrix}$$

| $R^{11}$ | $R^{12}$ | $R^{13}$ | Gn |
|---|---|---|---|
| CF$_3$CH$_2$ | —(CH$_2$)$_4$— | | Ga |
| NCCH$_2$ | —(CH$_2$)$_4$— | | Ga |
| NCCH$_2$CH$_2$ | —(CH$_2$)$_4$— | | Ga |
| MeO$_2$CCH$_2$ | —(CH$_2$)$_4$— | | Ga |
| EtO$_2$CCH$_2$ | —(CH$_2$)$_4$— | | Gb |
| Pr-nO$_2$CCH$_2$ | —(CH$_2$)$_4$— | | Gc |
| MeO$_2$CCH$_2$CH$_2$ | —(CH$_2$)$_4$— | | Ga |
| EtO$_2$CCH$_2$CH$_2$ | —(CH$_2$)$_4$— | | Gb |
| Pr-nO$_2$CCH$_2$CH$_2$ | —(CH$_2$)$_4$— | | Gc |
| MeCOCH$_2$ | —(CH$_2$)$_4$— | | Ga |
| PhCH$_2$ | —(CH$_2$)$_4$— | | Ga |
| Ph | —(CH$_2$)$_4$— | | Ga |

TABLE 4

$$R^{11}-N \begin{matrix} SO_2N \begin{matrix} R^{12} \\ R^{13} \end{matrix} \\ SO_2NH-\underset{\underset{S}{\|}}{C}-Gn \end{matrix}$$

| $R^{11}$ | $R^{12}$ | $R^{13}$ | Gn |
|---|---|---|---|
| Me | Me | Me | Gb |
| Me | Me | Et | Gc |
| Me | Et | Et | Gb |
| Me | Me | Ph | Gc |
| Me | —(CH$_2$)$_4$— | | Gb |
| Me | —(CH$_2$)$_5$— | | Gb |
| Et | Me | Me | Gb |
| Et | Me | Et | Gc |
| Et | Et | Et | Gb |
| Et | Me | Ph | Gc |
| Et | —(CH$_2$)$_4$— | | Gb |
| Et | —(CH$_2$)$_5$— | | Gb |
| Pr-n | Me | Me | Gb |
| Pr-n | Me | Et | Gc |
| Pr-n | Et | Et | Gb |
| Pr-n | Me | Ph | Gc |
| Pr-n | —(CH$_2$)$_4$— | | Gb |
| Pr-n | —(CH$_2$)$_5$— | | Gb |
| CH$_2$=CHCH$_2$ | Me | Me | Gb |
| CH$_2$=CHCH$_2$ | Me | Et | Gc |
| CH$_2$=CHCH$_2$ | Et | Et | Gb |
| CH$_2$=CHCH$_2$ | Me | Ph | Gc |
| CH$_2$=CHCH$_2$ | —(CH$_2$)$_4$— | | Gb |
| CH$_2$=CHCH$_2$ | —(CH$_2$)$_5$— | | Gb |
| CH≡CCH$_2$ | Me | Me | Gb |
| CH≡CCH$_2$ | Me | Et | Gc |
| CH≡CCH$_2$ | Et | Et | Gb |
| CH≡CCH$_2$ | Me | Ph | Gc |
| CH≡CCH$_2$ | —(CH$_2$)$_4$— | | Gb |
| CH≡CCH$_2$ | —(CH$_2$)$_5$— | | Gb |
| MeOCH$_2$CH$_2$ | Me | Me | Gb |
| MeOCH$_2$CH$_2$ | Me | Et | Gc |
| MeOCH$_2$CH$_2$ | Et | Et | Gb |
| MeOCH$_2$CH$_2$ | Me | Ph | Gc |
| MeOCH$_2$CH$_2$ | —(CH$_2$)$_4$— | | Gb |
| MeOCH$_2$CH$_2$ | —(CH$_2$)$_5$— | | Gb |
| ClCH$_2$CH$_2$ | Me | Me | Gb |
| ClCH$_2$CH$_2$ | Me | Et | Gc |
| ClCH$_2$CH$_2$ | Et | Et | Gb |
| ClCH$_2$CH$_2$ | Me | Ph | Gc |
| ClCH$_2$CH$_2$ | —(CH$_2$)$_4$— | | Gb |
| ClCH$_2$CH$_2$ | —(CH$_2$)$_5$— | | Gb |

TABLE 4-continued $$R^{11}-N \begin{matrix} SO_2N \begin{matrix} R^{12} \\ R^{13} \end{matrix} \\ SO_2NH-\underset{\underset{S}{\|}}{C}-Gn \end{matrix}$$

| $R^{11}$ | $R^{12}$ | $R^{13}$ | Gn |
|---|---|---|---|
| CF$_3$CH$_2$ | Me | Me | Gb |
| CF$_3$CH$_2$ | Me | Et | Gc |
| CF$_3$CH$_2$ | Et | Et | Gb |
| CF$_3$CH$_2$ | Me | Ph | Gc |
| CF$_3$CH$_2$ | —(CH$_2$)$_4$— | | Gb |
| CF$_3$CH$_2$ | —(CH$_2$)$_5$— | | Gb |
| NCCH$_2$ | Me | Me | Gb |
| NCCH$_2$ | Me | Et | Gc |
| NCCH$_2$ | Et | Et | Gb |
| NCCH$_2$ | Me | Ph | Gc |
| NCCH$_2$ | —(CH$_2$)$_4$— | | Gb |
| NCCH$_2$ | —(CH$_2$)$_5$— | | Gb |
| MeO$_2$CCH$_2$ | Me | Me | Gb |
| MeO$_2$CCH$_2$ | Me | Et | Gc |
| MeO$_2$CCH$_2$ | Et | Et | Gb |
| MeO$_2$CCH$_2$ | Me | Ph | Gc |
| MeO$_2$CCH$_2$ | —(CH$_2$)$_4$— | | Gb |
| MeO$_2$CCH$_2$ | —(CH$_2$)$_5$— | | Gb |
| PhCH$_2$ | Me | Me | Gb |
| PhCH$_2$ | Me | Et | Gc |
| PhCH$_2$ | Et | Et | Gb |
| PhCH$_2$ | Me | Ph | Gc |
| PhCH$_2$ | —(CH$_2$)$_4$— | | Gb |
| PhCH$_2$ | —(CH$_2$)$_5$— | | Gb |

TABLE 5

$$R^{11}-O-N \begin{matrix} SO_2N \begin{matrix} R^{12} \\ R^{13} \end{matrix} \\ SO_2NH-\underset{\underset{S}{\|}}{C}-Gn \end{matrix}$$

| $R^{11}$ | $R^{12}$ | $R^{13}$ | Gn |
|---|---|---|---|
| Me | Me | Me | Gb |
| Me | Me | Et | Gc |
| Me | Et | Et | Gb |
| Me | Me | Ph | Gc |
| Me | —(CH$_2$)$_4$— | | Gb |
| Me | —(CH$_2$)$_5$— | | Gb |
| Et | Me | Me | Gb |
| Et | Me | Et | Gc |
| Et | Et | Et | Gb |
| Et | Me | Ph | Gc |
| Et | —(CH$_2$)$_4$— | | Gb |
| Et | —(CH$_2$)$_5$— | | Gb |
| Pr-n | Me | Me | Gb |
| Pr-n | Me | Et | Gc |
| Pr-n | Et | Et | Gb |
| Pr-n | Me | Ph | Gc |
| Pr-n | —(CH$_2$)$_4$— | | Gb |
| Pr-n | —(CH$_2$)$_5$— | | Gb |
| CH$_2$=CHCH$_2$ | Me | Me | Gb |
| CH$_2$=CHCH$_2$ | Me | Et | Gc |
| CH$_2$=CHCH$_2$ | Et | Et | Gb |
| CH$_2$=CHCH$_2$ | Me | Ph | Gc |
| CH$_2$=CHCH$_2$ | —(CH$_2$)$_4$— | | Gb |
| CH$_2$=CHCH$_2$ | —(CH$_2$)$_5$— | | Gb |

TABLE 6

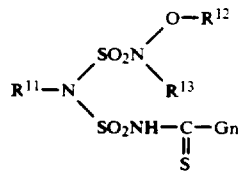

| R[11] | R[12] | R[13] | Gn |
|---|---|---|---|
| Me | Me | Me | Gb |
| Et | Me | Me | Gb |
| cyc-Pr | Me | Me | Gb |
| $CH_2=CHCH_2$ | Me | Me | Gc |
| $CH\equiv CCH_2$ | Me | Me | Gc |
| $MeOCH_2$ | Me | Me | Gc |
| $MeOCH_2CH_2$ | Me | Me | Gc |
| $MeSCH_2$ | Me | Me | Gc |
| $MeSO_2CH_2$ | Me | Me | Gc |
| $ClCH_2CH_2$ | Me | Me | Gc |
| $CF_3CH_2$ | Me | Me | Gc |
| $NCCH_2CH_2$ | Me | Me | Gc |
| $MeO_2CCH_2$ | Me | Me | Gc |
| $MeCOCH_2$ | Me | Me | Gc |
| $PhCH_2$ | Me | Me | Gc |
| Ph | Me | Me | Gc |
| Me | Me | Et | Gb |
| Me | Me | Pr-n | Gb |
| Me | Et | Me | Gb |
| Me | Pr-n | Me | Gb |
| Me | Et | Et | Gb |
| Me | $CH_2=CHCH_2$ | Me | Gb |
| Me | $CH_2=CHCH_2$ | Et | Gb |
| Me | Ph | Me | Gb |
| Me | Ph | Et | Gb |
| Me | $-(CH_2)_3-$ | | Gb |
| Me | $-(CH_2)_4-$ | | Gb |

TABLE 7

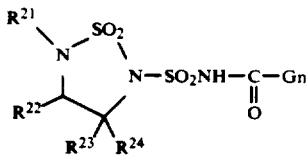

| R[21] | R[22] | R[23] | R[24] | Gn |
|---|---|---|---|---|
| H | H | H | H | Ga |
| H | H | H | Me | Ga |
| H | H | H | Et | Gb |
| H | Me | H | H | Ga |
| H | Et | H | H | Gb |
| H | Me | H | Me | Gb |
| H | Me | H | Et | Gb |
| H | H | Me | Me | Ga |
| H | H | Me | Et | Gb |
| H | H | H | $CF_3$ | Ga |
| H | H | H | $CH_2F$ | Ga |
| H | H | H | $CH_2Cl$ | Ga |
| H | H | H | $CH_2Br$ | Gb |
| H | H | H | $CH_2I$ | Gb |
| H | H | H | $CH_2OMe$ | Ga |
| H | H | H | $CH_2OEt$ | Ga |
| H | H | H | $CH_2OCH_2CH=CH_2$ | Ga |
| H | H | H | $CH_2OCH_2C\equiv CH$ | Ga |
| H | H | H | $CH_2OCHF_2$ | Ga |
| H | H | H | $CH_2OCF_3$ | Ga |
| H | H | H | $CH_2SMe$ | Ga |
| H | H | H | $CH_2SEt$ | Ga |
| H | H | H | $CH_2SO_2Me$ | Ga |
| H | H | H | $CH_2SO_2Et$ | Ga |
| H | H | H | $CH_2CF_3$ | Ga |
| H | H | H | $CH_2CN$ | Ga |
| H | H | H | $CO_2Me$ | Ga |
| H | H | H | $CO_2Et$ | Ga |
| H | H | H | $CH_2CO_2Me$ | Ga |
| H | H | H | $CH_2CO_2Et$ | Ga |

TABLE 7-continued

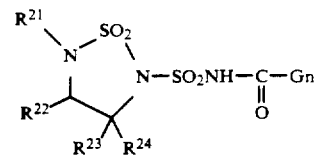

| R[21] | R[22] | R[23] | R[24] | Gn |
|---|---|---|---|---|
| H | H | H | COMe | Ga |
| H | H | H | COEt | Ga |
| H | H | H | $CH_2COMe$ | Ga |
| H | H | H | $CH_2COEt$ | Ga |
| Me | H | H | H | Ga |
| Me | H | H | Me | Ga |
| Me | H | H | Et | Gb |
| Me | H | H | Pr-n | Gb |
| Me | H | H | Pr-i | Gb |
| Me | H | H | Bu-n | Gc |
| Me | Me | H | H | Ga |
| Me | Et | H | H | Gb |
| Me | Me | H | Me | Gb |
| Me | Me | H | Et | Gb |
| Me | H | Me | Me | Ga |
| Me | H | Me | Et | Gb |
| Me | H | H | F | Ga |
| Me | H | H | Cl | Ga |
| Me | H | H | Br | Gb |
| Me | H | H | I | Gb |
| Me | H | H | $CF_3$ | Ga |
| Me | H | H | $CH_2F$ | Ga |
| Me | H | H | $CH_2Cl$ | Ga |
| Me | H | H | $CH_2Br$ | Gb |
| Me | H | H | $CH_2I$ | Gb |
| Me | H | H | $CH_2CH_2F$ | Ga |
| Me | H | H | $CH_2CH_2Cl$ | Ga |
| Me | H | H | $CH_2CH_2Br$ | Gb |
| Me | H | H | $CH_2CH_2I$ | Gb |
| Me | H | H | $CH(CH_3)CH_2F$ | Ga |
| Me | H | H | $CH(CH_3)CH_2Cl$ | Ga |
| Me | H | H | $CH(CH_3)CH_2Br$ | Gb |
| Me | H | H | $CH(CH_3CH_2I$ | Gb |
| Me | H | H | $CH_2OMe$ | Ga |
| Me | H | H | $CH_2OEt$ | Ga |
| Me | H | H | $CH_2CH_2OMe$ | Ga |
| Me | H | H | $CH_2CH_2OEt$ | Ga |
| Me | H | H | $CH(CH_3)CH_2OMe$ | Gb |
| Me | H | H | $CH(CH_3)CH_2OEt$ | Gb |
| Me | H | H | $CH_2OCH_2CH=CH_2$ | Ga |
| Me | H | H | $CH_2OCH_2C\equiv CH$ | Ga |
| Me | H | H | $CH_2OCHF_2$ | Ga |
| Me | H | H | $CH_2OCF_3$ | Ga |
| Me | H | H | $CH_2SMe$ | Ga |
| Me | H | H | $CH_2SEt$ | Ga |
| Me | H | H | $CH_2SO_2Me$ | Ga |
| Me | H | H | $CH_2SO_2Et$ | Ga |
| Me | H | H | $CH_2CF_3$ | Ga |
| Me | H | H | $CH_2CN$ | Ga |
| Me | H | H | $CO_2Me$ | Ga |
| Me | H | H | $CO_2Et$ | Ga |
| Me | H | H | $CO_2Pr-n$ | Gb |
| Me | H | H | $CH_2CO_2Me$ | Ga |
| Me | H | H | $CH_2CO_2Et$ | Ga |
| Me | H | H | $CH_2CO_2Pr-n$ | Gb |
| Me | H | H | COMe | Ga |
| Me | H | H | COEt | Ga |
| Me | H | H | COPr-n | Gb |
| Me | H | H | $CH_2COMe$ | Ga |
| Me | H | H | $CH_2COEt$ | Ga |
| Et | H | H | H | Ga |
| Et | H | H | Me | Ga |
| Et | H | H | Et | Gb |
| Et | H | H | Pr-n | Gb |
| Et | H | H | Pr-i | Gb |
| Et | H | H | Bu-n | Gc |
| Et | Me | H | H | Ga |
| Et | Et | H | H | Gb |
| Et | Me | H | Me | Gb |
| Et | Me | H | Et | Gb |
| Et | H | Me | Me | Ga |
| Et | H | Me | Et | Gb |

TABLE 7-continued

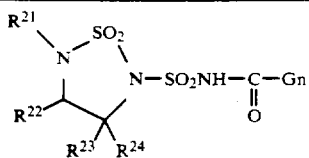

| R²¹ | R²² | R²³ | R²⁴ | Gn |
|---|---|---|---|---|
| Et | H | H | F | Ga |
| Et | H | H | Cl | Ga |
| Et | H | H | Br | Gb |
| Et | H | H | I | Gb |
| Et | H | H | CF₃ | Ga |
| Et | H | H | CH₂F | Ga |
| Et | H | H | CH₂Cl | Ga |
| Et | H | H | CH₂Br | Gb |
| Et | H | H | CH₂I | Gb |
| Et | H | H | CH₂CH₂F | Ga |
| Et | H | H | CH₂CH₂Cl | Ga |
| Et | H | H | CH₂CH₂Br | Gb |
| Et | H | H | CH₂CH₂I | Gb |
| Et | H | H | CH(CH₃)CH₂F | Ga |
| Et | H | H | CH(CH₃)CH₂Cl | Ga |
| Et | H | H | CH(CH₃)CH₂Br | Gb |
| Et | H | H | CH(CH₃)CH₂I | Gb |
| Et | H | H | CH₂OMe | Ga |
| Et | H | H | CH₂OEt | Ga |
| Et | H | H | CH₂CH₂OMe | Ga |
| Et | H | H | CH₂CH₂OEt | Ga |
| Et | H | H | CH(CH₃)CH₂OMe | Gb |
| Et | H | H | CH(CH₃)CH₂OEt | Gb |
| Et | H | H | CH₂OCH₂CH=CH₂ | Ga |
| Et | H | H | CH₂OCH₂C≡CH | Ga |
| Et | H | H | CH₂OCHF₂ | Ga |
| Et | H | H | CH₂OCF₃ | Ga |
| Et | H | H | CH₂SMe | Ga |
| Et | H | H | CH₂SEt | Ga |
| Et | H | H | CH₂SO₂Me | Ga |
| Et | H | H | CH₂SO₂Et | Ga |
| Et | H | H | CH₂CF₃ | Ga |
| Et | H | H | CH₂CN | Ga |
| Et | H | H | CO₂Me | Ga |
| Et | H | H | CO₂Et | Ga |
| Et | H | H | CO₂Pr-n | Gb |
| Et | H | H | CH₂CO₂Me | Ga |
| Et | H | H | CH₂CO₂Et | Ga |
| Et | H | H | CH₂CO₂Pr-n | Gb |
| Et | H | H | COMe | Ga |
| Et | H | H | COEt | Ga |
| Et | H | H | COPr-n | Gb |
| Et | H | H | CH₂COMe | Ga |
| Et | H | H | CH₂COEt | Ga |
| Pr-n | H | H | H | Ga |
| Pr-n | H | H | Me | Ga |
| Pr-n | H | H | Et | Gb |
| Pr-n | Me | H | H | Ga |
| Pr-n | Et | H | H | Gb |
| Pr-n | Me | H | Me | Gb |
| Pr-n | Me | H | Et | Gb |
| Pr-n | H | Me | Me | Ga |
| Pr-n | H | Me | Et | Gb |
| Pr-n | H | H | CF₃ | Ga |
| Pr-n | H | H | CH₂F | Ga |
| Pr-n | H | H | CH₂Cl | Ga |
| Pr-n | H | H | CH₂Br | Gb |
| Pr-n | H | H | CH₂I | Gb |
| Pr-n | H | H | CH₂OMe | Ga |
| Pr-n | H | H | CH₂OEt | Ga |
| Pr-n | H | H | CH₂OCH₂CH=CH₂ | Ga |
| Pr-n | H | H | CH₂OCH₂C≡CH | Ga |
| Pr-n | H | H | CH₂OCHF₂ | Ga |
| Pr-n | H | H | CH₂OCF₃ | Ga |
| Pr-n | H | H | CH₂SMe | Ga |
| Pr-n | H | H | CH₂SEt | Ga |
| Pr-n | H | H | CH₂SO₂Me | Ga |
| Pr-n | H | H | CH₂SO₂Et | Ga |
| Pr-n | H | H | CH₂CF₃ | Ga |
| Pr-n | H | H | CH₂CN | Ga |
| Pr-n | H | H | CO₂Me | Ga |
| Pr-n | H | H | CO₂Et | Ga |

TABLE 7-continued

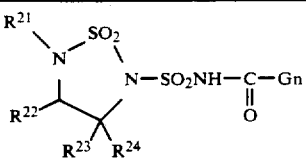

| R²¹ | R²² | R²³ | R²⁴ | Gn |
|---|---|---|---|---|
| Pr-n | H | H | CH₂CO₂Me | Ga |
| Pr-n | H | H | CH₂CO₂Et | Ga |
| Pr-n | H | H | COMe | Ga |
| Pr-n | H | H | COEt | Ga |
| Pr-n | H | H | CH₂COMe | Ga |
| Pr-n | H | H | CH₂COEt | Ga |
| Pr-i | H | H | H | Ga |
| Pr-i | H | H | Me | Ga |
| Pr-i | H | H | Et | Gb |
| Pr-i | Me | H | H | Gb |
| Pr-i | Et | H | H | Gb |
| Pr-i | Me | H | Me | Gb |
| Pr-i | Me | H | Et | Gb |
| Pr-i | H | Me | Me | Ga |
| Pr-i | H | Me | Et | Gb |
| Pr-i | H | H | CF₃ | Ga |
| Pr-i | H | H | CH₂F | Ga |
| Pr-i | H | H | CH₂Cl | Ga |
| Pr-i | H | H | CH₂Br | Gb |
| Pr-i | H | H | CH₂I | Gb |
| Pr-i | H | H | CH₂OMe | Ga |
| Pr-i | H | H | CH₂OEt | Ga |
| Pr-i | H | H | CH₂OCH₂CH=CH₂ | Ga |
| Pr-i | H | H | CH₂OCH₂C≡CH | Ga |
| Pr-i | H | H | CH₂OCHF₂ | Ga |
| Pr-i | H | H | CH₂OCF₃ | Ga |
| Pr-i | H | H | CH₂SMe | Ga |
| Pr-i | H | H | CH₂SEt | Ga |
| Pr-i | H | H | CH₂SO₂Me | Ga |
| Pr-i | H | H | CH₂SO₂Et | Ga |
| Pr-i | H | H | CH₂CF₃ | Ga |
| Pr-i | H | H | CH₂CN | Ga |
| Pr-i | H | H | CO₂Me | Ga |
| Pr-i | H | H | CO₂Et | Ga |
| Pr-i | H | H | CH₂CO₂Me | Ga |
| Pr-i | H | H | CH₂CO₂Et | Ga |
| Pr-i | H | H | COMe | Ga |
| Pr-i | H | H | COEt | Ga |
| Pr-i | H | H | CH₂COMe | Ga |
| Pr-i | H | H | CH₂COEt | Ga |
| Bu-n | H | H | H | Ga |
| Bu-n | H | H | Me | Ga |
| Bu-n | Me | H | H | Ga |
| Bu-n | Me | H | Me | Gb |
| Bu-n | H | Me | Me | Ga |
| Bu-n | H | H | CF₃ | Ga |
| Bu-n | H | H | CH₂F | Ga |
| Bu-n | H | H | CH₂Cl | Ga |
| Bu-n | H | H | CH₂Br | Gb |
| Bu-n | H | H | CH₂I | Gb |
| Bu-n | H | H | CH₂OMe | Ga |
| Bu-n | H | H | CH₂OCH₂CH=CH₂ | Ga |
| Bu-n | H | H | CH₂OCH₂C≡CH | Ga |
| Bu-n | H | H | CH₂OCHF₂ | Ga |
| Bu-n | H | H | CH₂OCF₃ | Ga |
| Bu-n | H | H | CH₂SMe | Ga |
| Bu-n | H | H | CH₂SO₂Me | Ga |
| Bu-n | H | H | CH₂CF₃ | Ga |
| Bu-n | H | H | CH₂CN | Ga |
| Bu-n | H | H | CO₂Me | Ga |
| Bu-n | H | H | CH₂CO₂Me | Ga |
| Bu-n | H | H | COMe | Ga |
| Bu-n | H | H | CH₂COMe | Ga |
| CH₂CH=CH₂ | H | H | H | Ga |
| CH₂CH=CH₂ | H | H | Me | Gb |
| CH₂CH=CH₂ | H | H | Et | Gb |
| CH₂CH=CH₂ | Me | H | H | Ga |
| CH₂CH=CH₂ | Et | H | H | Gb |
| CH₂CH=CH₂ | Me | H | Me | Gb |
| CH₂CH=CH₂ | Me | H | Et | Gb |
| CH₂CH=CH₂ | H | Me | Me | Ga |
| CH₂CH=CH₂ | H | Me | Et | Gb |

TABLE 7-continued

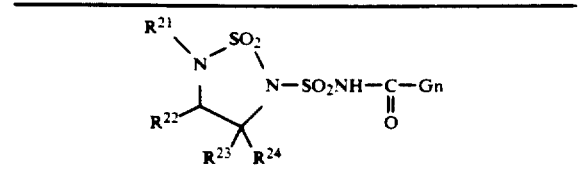

| R21 | R22 | R23 | R24 | Gn |
|---|---|---|---|---|
| CH2CH=CH2 | H | H | CF3 | Ga |
| CH2CH=CH2 | H | H | CH2F | Ga |
| CH2CH=CH2 | H | H | CH2Cl | Ga |
| CH2CH=CH2 | H | H | CH2Br | Gb |
| CH2CH=CH2 | H | H | CH2I | Gb |
| CH2CH=CH2 | H | H | CH2OMe | Ga |
| CH2CH=CH2 | H | H | CH2OEt | Ga |
| CH2CH=CH2 | H | H | CH2OCH2CH=CH2 | Ga |
| CH2CH=CH2 | H | H | CH2OCH2C≡CH | Ga |
| CH2CH=CH2 | H | H | CH2OCHF2 | Ga |
| CH2CH=CH2 | H | H | CH2OCF3 | Ga |
| CH2CH=CH2 | H | H | CH2SMe | Ga |
| CH2CH=CH2 | H | H | CH2SEt | Ga |
| CH2CH=CH2 | H | H | CH2SO2Me | Ga |
| CH2CH=CH2 | H | H | CH2SO2Et | Ga |
| CH2CH=CH2 | H | H | CH2CF3 | Ga |
| CH2CH=CH2 | H | H | CH2CN | Ga |
| CH2CH=CH2 | H | H | CO2Me | Ga |
| CH2CH=CH2 | H | H | CO2Et | Ga |
| CH2CH=CH2 | H | H | CH2CO2Me | Ga |
| CH2CH=CH2 | H | H | CH2CO2Et | Ga |
| CH2CH=CH2 | H | H | COMe | Ga |
| CH2CH=CH2 | H | H | COEt | Ga |
| CH2CH=CH2 | H | H | CH2COMe | Ga |
| CH2CH=CH2 | H | H | CH2COEt | Ga |
| CH2C≡CH | H | H | H | Ga |
| CH2C≡CH | H | H | Me | Gb |
| CH2C≡CH | H | H | Et | Gb |
| CH2C≡CH | Me | H | H | Ga |
| CH2C≡CH | Et | H | H | Gb |
| CH2C≡CH | Me | H | Me | Gb |
| CH2C≡CH | Me | H | Et | Gb |
| CH2C≡CH | H | Me | Me | Ga |
| CH2C≡CH | H | H | F | Ga |
| CH2C≡CH | H | Me | Et | Gb |
| CH2C≡CH | H | H | CF3 | Ga |
| CH2C≡CH | H | H | CH2F | Ga |
| CH2C≡CH | H | H | CH2Cl | Ga |
| CH2C≡CH | H | H | CH2Br | Gb |
| CH2C≡CH | H | H | CH2I | Gb |
| CH2C≡CH | H | H | CH2OMe | Ga |
| CH2C≡CH | H | H | CH2OEt | Ga |
| CH2C≡CH | H | H | CH2OCH2CH=CH2 | Ga |
| CH2C≡CH | H | H | CH2OCH2C≡CH | Ga |
| CH2C≡CH | H | H | CH2OCHF2 | Ga |
| CH2C≡CH | H | H | CH2OCF3 | Ga |
| CH2C≡CH | H | H | CH2SMe | Ga |
| CH2C≡CH | H | H | CH2SEt | Ga |
| CH2C≡CH | H | H | CH2SO2Me | Ga |
| CH2C≡CH | H | H | CH2SO2Et | Ga |
| CH2C≡CH | H | H | CH2CF3 | Ga |
| CH2C≡CH | H | H | CH2CN | Ga |
| CH2C≡CH | H | H | CO2Me | Ga |
| CH2C≡CH | H | H | CO2Et | Ga |
| CH2C≡CH | H | H | CH2CO2Me | Ga |
| CH2C≡CH | H | H | CH2CO2Et | Ga |
| CH2C≡CH | H | H | COMe | Ga |
| CH2C≡CH | H | H | COEt | Ga |
| CH2C≡CH | H | H | CH2COMe | Ga |
| CH2C≡CH | H | H | CH2COEt | Ga |
| CH2OMe | H | H | H | Ga |
| CH2OMe | H | H | Me | Gb |
| CH2OMe | H | H | Et | Gb |
| CH2OMe | H | H | Pr-n | Gb |
| CH2OMe | H | H | Pr-i | Gb |
| CH2OMe | H | H | Bu-n | Gc |
| CH2OMe | Me | H | H | Ga |
| CH2OMe | Et | H | H | Gb |
| CH2OMe | Me | H | Me | Gb |
| CH2OMe | Me | H | Et | Gb |
| CH2OMe | H | Me | Me | Ga |
| CH2OMe | H | Me | Et | Gb |
| CH2OMe | H | H | F | Ga |
| CH2OMe | H | H | Cl | Ga |
| CH2OMe | H | H | Br | Gb |
| CH2OMe | H | H | I | Gb |
| CH2OMe | H | H | CF3 | Ga |
| CH2OMe | H | H | CH2F | Ga |
| CH2OMe | H | H | CH2Cl | Ga |
| CH2OMe | H | H | CH2Br | Gb |
| CH2OMe | H | H | CH2I | Gb |
| CH2OMe | H | H | CH2CH2F | Ga |
| CH2OMe | H | H | CH2CH2Cl | Ga |
| CH2OMe | H | H | CH2CH2Br | Gb |
| CH2OMe | H | H | CH2CH2I | Gb |
| CH2OMe | H | H | CH(CH3)CH2F | Ga |
| CH2OMe | H | H | CH(CH3)CH2Cl | Ga |
| CH2OMe | H | H | CH(CH3)CH2Br | Gb |
| CH2OMe | H | H | CH(CH3)CH2I | Gb |
| CH2OMe | H | H | CH2OMe | Ga |
| CH2OMe | H | H | CH2OEt | Ga |
| CH2OMe | H | H | CH2CH2OMe | Ga |
| CH2OMe | H | H | CH2CH2OEt | Ga |
| CH2OMe | H | H | CH(CH3)CH2OMe | Gb |
| CH2OMe | H | H | CH(CH3)CH2OEt | Gb |
| CH2OMe | H | H | CH2OCH2CH=CH2 | Ga |
| CH2OMe | H | H | CH2OCH2C≡CH | Ga |
| CH2OMe | H | H | CH2OCHF2 | Ga |
| CH2OMe | H | H | CH2OCF3 | Ga |
| CH2OMe | H | H | CH2SMe | Ga |
| CH2OMe | H | H | CH2SEt | Ga |
| CH2OMe | H | H | CH2SO2Me | Ga |
| CH2OMe | H | H | CH2SO2Et | Ga |
| CH2OMe | H | H | CH2CF3 | Ga |
| CH2OMe | H | H | CH2CN | Ga |
| CH2OMe | H | H | CO2Me | Ga |
| CH2OMe | H | H | CO2Et | Ga |
| CH2OMe | H | H | CO2Pr-n | Gb |
| CH2OMe | H | H | CH2CO2Me | Ga |
| CH2OMe | H | H | CH2CO2Et | Ga |
| CH2OMe | H | H | CH2CO2Pr-n | Gb |
| CH2OMe | H | H | COMe | Ga |
| CH2OMe | H | H | COEt | Ga |
| CH2OMe | H | H | COPr-n | Gb |
| CH2OMe | H | H | CH2COMe | Ga |
| CH2OMe | H | H | CH2COEt | Ga |
| CH2OEt | H | H | H | Ga |
| CH2OEt | H | H | Me | Gb |
| CH2OEt | H | H | Et | Gb |
| CH2OEt | Me | H | H | Ga |
| CH2OEt | Et | H | H | Gb |
| CH2OEt | Me | H | Me | Gb |
| CH2OEt | Me | H | Et | Gb |
| CH2OEt | H | Me | Me | Ga |
| CH2OEt | H | Me | Et | Gb |
| CH2OEt | H | H | CF3 | Ga |
| CH2OEt | H | H | CH2F | Ga |
| CH2OEt | H | H | CH2Cl | Ga |
| CH2OEt | H | H | CH2Br | Gb |
| CH2OEt | H | H | CH2I | Gb |
| CH2OEt | H | H | CH2OMe | Ga |
| CH2OEt | H | H | CH2OEt | Ga |
| CH2OEt | H | H | CH2OCH2CH=CH2 | Ga |
| CH2OEt | H | H | CH2OCH2C≡CH | Ga |
| CH2OEt | H | H | CH2OCHF2 | Ga |
| CH2OEt | H | H | CH2OCF3 | Ga |
| CH2OEt | H | H | CH2SMe | Ga |
| CH2OEt | H | H | CH2SEt | Ga |
| CH2OEt | H | H | CH2SO2Me | Ga |
| CH2OEt | H | H | CH2SO2Et | Ga |
| CH2OEt | H | H | CH2CF3 | Ga |
| CH2OEt | H | H | CH2CN | Ga |
| CH2OEt | H | H | CO2Me | Ga |
| CH2OEt | H | H | CO2Et | Ga |

TABLE 7-continued

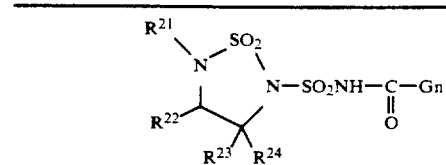

| R21 | R22 | R23 | R24 | Gn |
|---|---|---|---|---|
| CH2OEt | H | H | CH2CO2Me | Ga |
| CH2OEt | H | H | CH2CO2Et | Ga |
| CH2OEt | H | H | COMe | Ga |
| CH2OEt | H | H | COEt | Ga |
| CH2OEt | H | H | CH2COMe | Ga |
| CH2OEt | H | H | CH2COEt | Ga |
| CH2CH2OMe | H | H | H | Ga |
| CH2CH2OMe | H | H | Me | Gb |
| CH2CH2OMe | H | H | Et | Gb |
| CH2CH2OMe | Me | H | H | Ga |
| CH2CH2OMe | Et | H | H | Gb |
| CH2CH2OMe | Me | H | Me | Gb |
| CH2CH2OMe | Me | H | Et | Gb |
| CH2CH2OMe | H | Me | Me | Ga |
| CH2CH2OMe | H | Me | Et | Gb |
| CH2CH2OMe | H | H | CF3 | Ga |
| CH2CH2OMe | H | H | CH2F | Ga |
| CH2CH2OMe | H | H | CH2Cl | Ga |
| CH2CH2OMe | H | H | CH2Cl | Ga |
| CH2CH2OMe | H | H | CH2Br | Gb |
| CH2CH2OMe | H | H | CH2I | Gb |
| CH2CH2OMe | H | H | CH2OMe | Ga |
| CH2CH2OMe | H | H | CH2OEt | Ga |
| CH2CH2OMe | H | H | CH2OCH2CH=CH2 | Ga |
| CH2CH2OMe | H | H | CH2OCH2C≡CH | Ga |
| CH2CH2OMe | H | H | CH2OCHF2 | Ga |
| CH2CH2OMe | H | H | CH2OCF3 | Ga |
| CH2CH2OMe | H | H | CH2SMe | Ga |
| CH2CH2OMe | H | H | CH2SEt | Ga |
| CH2CH2OMe | H | H | CH2SO2Me | Ga |
| CH2CH2OMe | H | H | CH2SO2Et | Ga |
| CH2CH2OMe | H | H | CH2CF3 | Ga |
| CH2CH2OMe | H | H | CH2CN | Ga |
| CH2CH2OMe | H | H | CO2Me | Ga |
| CH2CH2OMe | H | H | CO2Et | Ga |
| CH2CH2OMe | H | H | CH2CO2Me | Ga |
| CH2CH2OMe | H | H | CH2CO2Et | Ga |
| CH2CH2OMe | H | H | COMe | Ga |
| CH2CH2OMe | H | H | COEt | Ga |
| CH2CH2OMe | H | H | CH2COMe | Ga |
| CH2CH2OMe | H | H | CH2COEt | Ga |
| CH2CH2OEt | H | H | H | Ga |
| CH2CH2OEt | H | H | Me | Gb |
| CH2CH2OEt | Me | H | H | Ga |
| CH2CH2OEt | Me | H | Me | Gb |
| CH2CH2OEt | H | Me | Me | Ga |
| CH2CH2OEt | H | H | CF3 | Ga |
| CH2CH2OEt | H | H | CH2F | Ga |
| CH2CH2OEt | H | H | CH2Cl | Ga |
| CH2CH2OEt | H | H | CH2Br | Gb |
| CH2CH2OEt | H | H | CH2I | Gb |
| CH2CH2OEt | H | H | CH2OMe | Ga |
| CH2CH2OEt | H | H | CH2OCH2CH=CH2 | Ga |
| CH2CH2OEt | H | H | CH2OCH2C≡CH | Ga |
| CH2CH2OEt | H | H | CH2OCHF2 | Ga |
| CH2CH2OEt | H | H | CH2OCF3 | Ga |
| CH2CH2OEt | H | H | CH2SMe | Ga |
| CH2CH2OEt | H | H | CH2SO2Me | Ga |
| CH2CH2OEt | H | H | CH2CF3 | Ga |
| CH2CH2OEt | H | H | CH2CN | Ga |
| CH2CH2OEt | H | H | CO2Me | Ga |
| CH2CH2OEt | H | H | CH2CO2Me | Ga |
| CH2CH2OEt | H | H | COMe | Ga |
| CH2CH2OEt | H | H | CH2COMe | Ga |
| CH(CH3)CH2OMe | H | H | H | Ga |
| CH(CH3)CH2OMe | H | H | Me | Gb |
| CH(CH3)CH2OMe | H | H | Et | Gb |
| CH(CH3)CH2OMe | Me | H | H | Ga |
| CH(CH3)CH2OMe | Et | H | H | Gb |
| CH(CH3)CH2OMe | Me | H | Me | Gb |
| CH(CH3)CH2OMe | Me | H | Et | Gb |
| CH(CH3)CH2OMe | H | Me | Me | Ga |
| CH(CH3)CH2OMe | H | Me | Et | Gb |
| CH(CH3)CH2OMe | H | H | CF3 | Ga |
| CH(CH3)CH2OMe | H | H | CH2F | Ga |
| CH(CH3)CH2OMe | H | H | CH2Cl | Ga |
| CH(CH3)CH2OMe | H | H | CH2Br | Gb |
| CH(CH3)CH2OMe | H | H | CH2I | Gb |
| CH(CH3)CH2OMe | H | H | CH2OMe | Ga |
| CH(CH3)CH2OMe | H | H | CH2OEt | Ga |
| CH(CH3)CH2OMe | H | H | CH2OCH2CH=CH2 | Ga |
| CH(CH3)CH2OMe | H | H | CH2OCH2C≡CH | Ga |
| CH(CH3)CH2OMe | H | H | CH2OCHF2 | Ga |
| CH(CH3)CH2OMe | H | H | CH2OCF3 | Ga |
| CH(CH3)CH2OMe | H | H | CH2SMe | Ga |
| CH(CH3)CH2OMe | H | H | CH2SEt | Ga |
| CH(CH3)CH2OMe | H | H | CH2SO2Me | Ga |
| CH(CH3)CH2OMe | H | H | CH2SO2Et | Ga |
| CH(CH3)CH2OMe | H | H | CH2CF3 | Ga |
| CH(CH3)CH2OMe | H | H | CH2CN | Ga |
| CH(CH3)CH2OMe | H | H | CO2Me | Ga |
| CH(CH3)CH2OMe | H | H | CO2Et | Ga |
| CH(CH3)CH2OMe | H | H | CH2CO2Me | Ga |
| CH(CH3)CH2OMe | H | H | CH2CO2Et | Ga |
| CH(CH3)CH2OMe | H | H | COMe | Ga |
| CH(CH3)CH2OMe | H | H | COEt | Ga |
| CH(CH3)CH2OMe | H | H | CH2COMe | Ga |
| CH(CH3)CH2OMe | H | H | CH2COEt | Ga |
| CH(CH3)CH2OEt | H | H | H | Ga |
| CH(CH3)CH2OEt | H | H | Me | Gb |
| CH(CH3)CH2OEt | Me | H | H | Ga |
| CH(CH3)CH2OEt | Me | H | Me | Gb |
| CH(CH3)CH2OEt | H | Me | Me | Ga |
| CH(CH3)CH2OEt | H | H | CF3 | Ga |
| CH(CH3)CH2OEt | H | H | CH2F | Ga |
| CH(CH3)CH2OEt | H | H | CH2Cl | Ga |
| CH(CH3)CH2OEt | H | H | CH2Br | Gb |
| CH(CH3)CH2OEt | H | H | CH2I | Gb |
| CH(CH3)CH2OEt | H | H | CH2OMe | Ga |
| CH(CH3)CH2OEt | H | H | CH2OCH2CH=CH2 | Ga |
| CH(CH3)CH2OEt | H | H | CH2OCH2C≡CH | Ga |
| CH(CH3)CH2OEt | H | H | CH2OCHF2 | Ga |
| CH(CH3)CH2OEt | H | H | CH2OCF3 | Ga |
| CH(CH3)CH2OEt | H | H | CH2SMe | Ga |
| CH(CH3)CH2OEt | H | H | CH2SO2Me | Ga |
| CH(CH3)CH2OEt | H | H | CH2CF3 | Ga |
| CH(CH3)CH2OEt | H | H | CH2CN | Ga |
| CH(CH3)CH2OEt | H | H | CO2Me | Ga |
| CH(CH3)CH2OEt | H | H | CH2CO2Me | Ga |
| CH(CH3)CH2OEt | H | H | COMe | Ga |
| CH(CH3)CH2OEt | H | H | CH2COMe | Ga |
| CH2OCHF2 | H | H | H | Ga |
| CH2OCHF2 | H | H | Me | Gb |
| CH2OCHF2 | H | H | Et | Gb |
| CH2OCHF2 | H | H | Pr-n | Gb |
| CH2OCHF2 | H | H | Pr-i | Gb |
| CH2OCHF2 | H | H | Bu-n | Gc |
| CH2OCHF2 | Me | H | H | Ga |
| CH2OCHF2 | Et | H | H | Gb |
| CH2OCHF2 | Me | H | Me | Gb |
| CH2OCHF2 | Me | H | Et | Gb |
| CH2OCHF2 | H | Me | Me | Ga |
| CH2OCHF2 | H | Me | Et | Gb |
| CH2OCHF2 | H | H | F | Ga |
| CH2OCHF2 | H | H | Cl | Ga |
| CH2OCHF2 | H | H | Br | Gb |
| CH2OCHF2 | H | H | I | Gb |
| CH2OCHF2 | H | H | CF3 | Ga |
| CH2OCHF2 | H | H | CH2F | Ga |
| CH2OCHF2 | H | H | CH2Cl | Ga |
| CH2OCHF2 | H | H | CH2Br | Gb |
| CH2OCHF2 | H | H | CH2I | Gb |
| CH2OCHF2 | H | H | CH2CH2F | Ga |
| CH2OCHF2 | H | H | CH2CH2Cl | Ga |

TABLE 7-continued

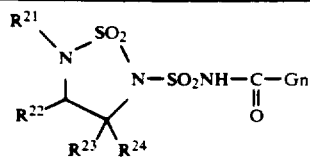

| R21 | R22 | R23 | R24 | Gn |
|---|---|---|---|---|
| CH2OCHF2 | H | H | CH2CH2Br | Gb |
| CH2OCHF2 | H | H | CH2CH2I | Gb |
| CH2OCHF2 | H | H | CH(CH3)CH2F | Ga |
| CH2OCHF2 | H | H | CH(CH3)CH2Cl | Ga |
| CH2OCHF2 | H | H | CH(CH3)CH2Br | Gb |
| CH2OCHF2 | H | H | CH(CH3)CH2I | Gb |
| CH2OCHF2 | H | H | CH2OMe | Ga |
| CH2OCHF2 | H | H | CH2OEt | Ga |
| CH2OCHF2 | H | H | CH2CH2OMe | Ga |
| CH2OCHF2 | H | H | CH2CH2OEt | Ga |
| CH2OCHF2 | H | H | CH(CH3)CH2OMe | Gb |
| CH2OCHF2 | H | H | CH(CH3)CH2OEt | Gb |
| CH2OCHF2 | H | H | CH2OCH2CH=CH2 | Ga |
| CH2OCHF2 | H | H | CH2OCH2C≡CH | Ga |
| CH2OCHF2 | H | H | CH2OCHF2 | Ga |
| CH2OCHF2 | H | H | CH2OCF3 | Ga |
| CH2OCHF2 | H | H | CH2SMe | Ga |
| CH2OCHF2 | H | H | CH2SEt | Ga |
| CH2OCHF2 | H | H | CH2SO2Me | Ga |
| CH2OCHF2 | H | H | CH2SO2Et | Ga |
| CH2OCHF2 | H | H | CH2CF3 | Ga |
| CH2OCHF2 | H | H | CH2CN | Ga |
| CH2OCHF2 | H | H | CO2Me | Ga |
| CH2OCHF2 | H | H | CO2Et | Ga |
| CH2OCHF2 | H | H | CO2Pr-n | Gb |
| CH2OCHF2 | H | H | CH2CO2Me | Ga |
| CH2OCHF2 | H | H | CH2CO2Et | Ga |
| CH2OCHF2 | H | H | CH2CO2Pr-n | Gb |
| CH2OCHF2 | H | H | COMe | Ga |
| CH2OCHF2 | H | H | COEt | Gb |
| CH2OCHF2 | H | H | COPr-n | Gb |
| CH2OCHF2 | H | H | CH2COMe | Ga |
| CH2OCHF2 | H | H | CH2COEt | Ga |
| CH2SMe | H | H | H | Ga |
| CH2SMe | H | H | Me | Gb |
| CH2SMe | H | H | Et | Gb |
| CH2SMe | H | H | Pr-n | Gb |
| CH2SMe | H | H | Pr-i | Gb |
| CH2SMe | H | H | Bu-n | Gc |
| CH2SMe | Me | H | H | Ga |
| CH2SMe | Et | H | H | Gb |
| CH2SMe | Me | H | Me | Gb |
| CH2SMe | Me | H | Et | Gb |
| CH2SMe | H | Me | Me | Ga |
| CH2SMe | H | Me | Et | Gb |
| CH2SMe | H | H | F | Ga |
| CH2SMe | H | H | Cl | Ga |
| CH2SMe | H | H | Br | Gb |
| CH2SMe | H | H | I | Gb |
| CH2SMe | H | H | CF3 | Ga |
| CH2SMe | H | H | CH2F | Ga |
| CH2SMe | H | H | CH2Cl | Ga |
| CH2SMe | H | H | CH2Br | Gb |
| CH2SMe | H | H | CH2I | Gb |
| CH2SMe | H | H | CH2CH2F | Ga |
| CH2SMe | H | H | CH2CH2Cl | Ga |
| CH2SMe | H | H | CH2CH2Br | Gb |
| CH2SMe | H | H | CH2CH2I | Gb |
| CH2SMe | H | H | CH(CH3)CH2F | Ga |
| CH2SMe | H | H | CH(CH3)CH2Cl | Ga |
| CH2SMe | H | H | CH(CH3)CH2Br | Gb |
| CH2SMe | H | H | CH(CH3)CH2I | Gb |
| CH2SMe | H | H | CH2OMe | Ga |
| CH2SMe | H | H | CH2OEt | Ga |
| CH2SMe | H | H | CH2CH2OMe | Ga |
| CH2SMe | H | H | CH2CH2OEt | Ga |
| CH2SMe | H | H | CH(CH3)CH2OMe | Gb |
| CH2SMe | H | H | CH(CH3)CH2OEt | Gb |
| CH2SMe | H | H | CH2OCH2CH=CH2 | Ga |
| CH2SMe | H | H | CH2OCH2C≡CH | Ga |
| CH2SMe | H | H | CH2OCHF2 | Ga |
| CH2SMe | H | H | CH2OCF3 | Ga |

TABLE 7-continued

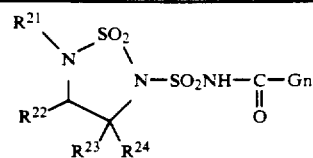

| R21 | R22 | R23 | R24 | Gn |
|---|---|---|---|---|
| CH2SMe | H | H | CH2SMe | Ga |
| CH2SMe | H | H | CH2SEt | Ga |
| CH2SMe | H | H | CH2SO2Me | Ga |
| CH2SMe | H | H | CH2SO2Et | Ga |
| CH2SMe | H | H | CH2CF3 | Ga |
| CH2SMe | H | H | CH2CN | Ga |
| CH2SMe | H | H | CO2Me | Ga |
| CH2SMe | H | H | CO2Et | Ga |
| CH2SMe | H | H | CO2Pr-n | Gb |
| CH2SMe | H | H | CH2CO2Me | Ga |
| CH2SMe | H | H | CH2CO2Et | Ga |
| CH2SMe | H | H | CH2CO2Pr-n | Gb |
| CH2SMe | H | H | COMe | Ga |
| CH2SMe | H | H | COEt | Ga |
| CH2SMe | H | H | COPr-n | Gb |
| CH2SMe | H | H | CH2COMe | Ga |
| CH2SMe | H | H | CH2COEt | Ga |
| CH2SEt | H | H | H | Ga |
| CH2SEt | H | H | Me | Gb |
| CH2SEt | H | H | Et | Gb |
| CH2SEt | Me | H | H | Ga |
| CH2SEt | Et | H | H | Gb |
| CH2SEt | Me | H | Me | Gb |
| CH2SEt | Me | H | Et | Gb |
| CH2SEt | H | Me | Me | Ga |
| CH2SEt | H | Me | Et | Gb |
| CH2SEt | H | H | CF3 | Ga |
| CH2SEt | H | H | CH2F | Ga |
| CH2SEt | H | H | CH2Cl | Ga |
| CH2SEt | H | H | CH2Br | Gb |
| CH2SEt | H | H | CH2I | Gb |
| CH2SEt | H | H | CH2OMe | Ga |
| CH2SEt | H | H | CH2OEt | Ga |
| CH2SEt | H | H | CH2OCH2CH=CH2 | Ga |
| CH2SEt | H | H | CH2OCH2C≡CH | Ga |
| CH2SEt | H | H | CH2OCHF2 | Ga |
| CH2SEt | H | H | CH2OCF3 | Ga |
| CH2SEt | H | H | CH2SMe | Ga |
| CH2SEt | H | H | CH2SEt | Ga |
| CH2SEt | H | H | CH2SO2Me | Ga |
| CH2SEt | H | H | CH2SO2Et | Ga |
| CH2SEt | H | H | CH2CF3 | Ga |
| CH2SEt | H | H | CH2CN | Ga |
| CH2SEt | H | H | CO2Me | Ga |
| CH2SEt | H | H | CO2Et | Ga |
| CH2SEt | H | H | CH2CO2Me | Ga |
| CH2SEt | H | H | CH2CO2Et | Ga |
| CH2SEt | H | H | COMe | Ga |
| CH2SEt | H | H | COEt | Ga |
| CH2SEt | H | H | CH2COMe | Ga |
| CH2SEt | H | H | CH2COEt | Ga |
| CH2SO2Me | H | H | H | Ga |
| CH2SO2Me | H | H | Me | Gb |
| CH2SO2Me | H | H | Et | Gb |
| CH2SO2Me | H | H | Pr-n | Gb |
| CH2SO2Me | H | H | Pr-i | Gb |
| CH2SO2Me | H | H | Bu-n | Gc |
| CH2SO2Me | Me | H | H | Ga |
| CH2SO2Me | Et | H | H | Gb |
| CH2SO2Me | Me | H | Me | Gb |
| CH2SO2Me | Me | H | Et | Gb |
| CH2SO2Me | H | Me | Me | Ga |
| CH2SO2Me | H | Me | Et | Gb |
| CH2SO2Me | H | H | F | Ga |
| CH2SO2Me | H | H | Cl | Ga |
| CH2SO2Me | H | H | Br | Gb |
| CH2SO2Me | H | H | I | Gb |
| CH2SO2Me | H | H | CF3 | Ga |
| CH2SO2Me | H | H | CH2F | Ga |
| CH2SO2Me | H | H | CH2Cl | Ga |

TABLE 7-continued

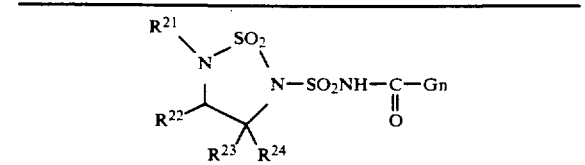

| R²¹ | R²² | R²³ | R²⁴ | Gn |
|---|---|---|---|---|
| CH₂SO₂Me | H | H | CH₂Br | Gb |
| CH₂SO₂Me | H | H | CH₂I | Gb |
| CH₂SO₂Me | H | H | CH₂CH₂F | Ga |
| CH₂SO₂Me | H | H | CH₂CH₂Cl | Ga |
| CH₂SO₂Me | H | H | CH₂CH₂Br | Gb |
| CH₂SO₂Me | H | H | CH₂CH₂I | Gb |
| CH₂SO₂Me | H | H | CH(CH₃)CH₂F | Ga |
| CH₂SO₂Me | H | H | CH(CH₃)CH₂Cl | Ga |
| CH₂SO₂Me | H | H | CH(CH₃)CH₂Br | Gb |
| CH₂SO₂Me | H | H | CH(CH₃)CH₂I | Gb |
| CH₂SO₂Me | H | H | CH₂OMe | Ga |
| CH₂SO₂Me | H | H | CH₂OEt | Ga |
| CH₂SO₂Me | H | H | CH₂CH₂OMe | Ga |
| CH₂SO₂Me | H | H | CH₂CH₂OEt | Ga |
| CH₂SO₂Me | H | H | CH(CH₃)CH₂OMe | Gb |
| CH₂SO₂Me | H | H | CH(CH₃)CH₂OEt | Gb |
| CH₂SO₂Me | H | H | CH₂OCH₂CH=CH₂ | Ga |
| CH₂SO₂Me | H | H | CH₂OCH₂C≡CH | Ga |
| CH₂SO₂Me | H | H | CH₂OCHF₂ | Ga |
| CH₂SO₂Me | H | H | CH₂OCF₃ | Ga |
| CH₂SO₂Me | H | H | CH₂SMe | Ga |
| CH₂SO₂Me | H | H | CH₂SEt | Ga |
| CH₂SO₂Me | H | H | CH₂SO₂Me | Ga |
| CH₂SO₂Me | H | H | CH₂SO₂Et | Ga |
| CH₂SO₂Me | H | H | CH₂CF₃ | Ga |
| CH₂SO₂Me | H | H | CH₂CN | Ga |
| CH₂SO₂Me | H | H | CO₂Me | Ga |
| CH₂SO₂Me | H | H | CO₂Et | Ga |
| CH₂SO₂Me | H | H | CO₂Pr-n | Gb |
| CH₂SO₂Me | H | H | CH₂CO₂Me | Ga |
| CH₂SO₂Me | H | H | CH₂CO₂Et | Ga |
| CH₂SO₂Me | H | H | CH₂CO₂Pr-n | Gb |
| CH₂SO₂Me | H | H | COMe | Ga |
| CH₂SO₂Me | H | H | COEt | Ga |
| CH₂SO₂Me | H | H | COPr-n | Gb |
| CH₂SO₂Me | H | H | CH₂COMe | Ga |
| CH₂SO₂Me | H | H | CH₂COEt | Ga |
| CH₂SO₂Et | H | H | H | Ga |
| CH₂SO₂Et | H | H | Me | Gb |
| CH₂SO₂Et | H | H | Et | Gb |
| CH₂SO₂Et | Me | H | H | Ga |
| CH₂SO₂Et | Et | H | H | Gb |
| CH₂SO₂Et | Me | H | Me | Gb |
| CH₂SO₂Et | Me | H | Et | Gb |
| CH₂SO₂Et | H | Me | Me | Ga |
| CH₂SO₂Et | H | Me | Et | Gb |
| CH₂SO₂Et | H | H | CF₃ | Ga |
| CH₂SO₂Et | H | H | CH₂F | Ga |
| CH₂SO₂Et | H | H | CH₂Cl | Ga |
| CH₂SO₂Et | H | H | CH₂Br | Gb |
| CH₂SO₂Et | H | H | CH₂I | Gb |
| CH₂SO₂Et | H | H | CH₂OMe | Ga |
| CH₂SO₂Et | H | H | CH₂OEt | Ga |
| CH₂SO₂Et | H | H | CH₂OCH₂CH=CH₂ | Ga |
| CH₂SO₂Et | H | H | CH₂OCH₂C≡CH | Ga |
| CH₂SO₂Et | H | H | CH₂OCHF₂ | Ga |
| CH₂SO₂Et | H | H | CH₂OCF₃ | Ga |
| CH₂SO₂Et | H | H | CH₂SMe | Ga |
| CH₂SO₂Et | H | H | CH₂SEt | Ga |
| CH₂SO₂Et | H | H | CH₂SO₂Me | Ga |
| CH₂SO₂Et | H | H | CH₂SO₂Et | Ga |
| CH₂SO₂Et | H | H | CH₂CF₃ | Ga |
| CH₂SO₂Et | H | H | CH₂CN | Ga |
| CH₂SO₂Et | H | H | CO₂Me | Ga |
| CH₂SO₂Et | H | H | CO₂Et | Ga |
| CH₂SO₂Et | H | H | CH₂CO₂Me | Ga |
| CH₂SO₂Et | H | H | CH₂CO₂Et | Ga |
| CH₂SO₂Et | H | H | COMe | Ga |
| CH₂SO₂Et | H | H | COEt | Ga |
| CH₂SO₂Et | H | H | CH₂COMe | Ga |
| CH₂SO₂Et | H | H | CH₂COEt | Ga |
| CH₂F | H | H | H | Ga |
| CH₂F | H | H | Me | Gb |
| CH₂F | H | H | Et | Gb |
| CH₂F | H | H | Pr-n | Gb |
| CH₂F | H | H | Pr-i | Gb |
| CH₂F | H | H | Bu-n | Gc |
| CH₂F | Me | H | H | Ga |
| CH₂F | Et | H | H | Gb |
| CH₂F | Me | H | Me | Gb |
| CH₂F | Me | H | Et | Gb |
| CH₂F | H | Me | Me | Ga |
| CH₂F | H | Me | Et | Gb |
| CH₂F | H | H | F | Ga |
| CH₂F | H | H | Cl | Ga |
| CH₂F | H | H | Br | Gb |
| CH₂F | H | H | I | Gb |
| CH₂F | H | H | CF₃ | Ga |
| CH₂F | H | H | CH₂F | Ga |
| CH₂F | H | H | CH₂Cl | Ga |
| CH₂F | H | H | CH₂Br | Gb |
| CH₂F | H | H | CH₂I | Gb |
| CH₂F | H | H | CH₂CH₂F | Ga |
| CH₂F | H | H | CH₂CH₂Cl | Ga |
| CH₂F | H | H | CH₂CH₂Br | Gb |
| CH₂F | H | H | CH₂CH₂I | Gb |
| CH₂F | H | H | CH(CH₃)CH₂F | Ga |
| CH₂F | H | H | CH(CH₃)CH₂Cl | Ga |
| CH₂F | H | H | CH(CH₃)CH₂Br | Gb |
| CH₂F | H | H | CH(CH₃)CH₂I | Gb |
| CH₂F | H | H | CH₂OMe | Ga |
| CH₂F | H | H | CH₂OEt | Ga |
| CH₂F | H | H | CH₂CH₂OMe | Ga |
| CH₂F | H | H | CH₂CH₂OEt | Ga |
| CH₂F | H | H | CH(CH₃)CH₂OMe | Gb |
| CH₂F | H | H | CH(CH₃)CH₂OEt | Gb |
| CH₂F | H | H | CH₂OCH₂CH=CH₂ | Ga |
| CH₂F | H | H | CH₂OCH₂C≡CH | Ga |
| CH₂F | H | H | CH₂OCHF₂ | Ga |
| CH₂F | H | H | CH₂OCF₃ | Ga |
| CH₂F | H | H | CH₂SMe | Ga |
| CH₂F | H | H | CH₂SEt | Ga |
| CH₂F | H | H | CH₂SO₂Me | Ga |
| CH₂F | H | H | CH₂SO₂Et | Ga |
| CH₂F | H | H | CH₂CF₃ | Ga |
| CH₂F | H | H | CH₂CN | Ga |
| CH₂F | H | H | CO₂Me | Ga |
| CH₂F | H | H | CO₂Et | Ga |
| CH₂F | H | H | CO₂Pr-n | Gb |
| CH₂F | H | H | CH₂CO₂Me | Ga |
| CH₂F | H | H | CH₂CO₂Et | Ga |
| CH₂F | H | H | CH₂CO₂Pr-n | Gb |
| CH₂F | H | H | COMe | Ga |
| CH₂F | H | H | COEt | Ga |
| CH₂F | H | H | COPr-n | Gb |
| CH₂F | H | H | CH₂COMe | Ga |
| CH₂F | H | H | CH₂COEt | Ga |
| CH₂Cl | H | H | H | Ga |
| CH₂Cl | H | H | Me | Gb |
| CH₂Cl | H | H | Et | Gb |
| CH₂Cl | H | H | Pr-n | Gb |
| CH₂Cl | H | H | Pr-i | Gb |
| CH₂Cl | H | H | Bu-n | Gc |
| CH₂Cl | Me | H | H | Ga |
| CH₂Cl | Et | H | H | Gb |
| CH₂Cl | Me | H | Me | Gb |
| CH₂Cl | Me | H | Et | Gb |
| CH₂Cl | H | Me | Me | Ga |
| CH₂Cl | H | Me | Et | Gb |
| CH₂Cl | H | H | F | Ga |
| CH₂Cl | H | H | Cl | Ga |
| CH₂Cl | H | H | Br | Gb |
| CH₂Cl | H | H | I | Gb |
| CH₂Cl | H | H | CF₃ | Ga |

TABLE 7-continued

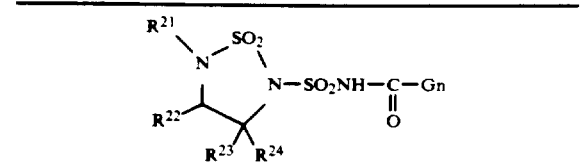

| R21 | R22 | R23 | R24 | Gn |
|---|---|---|---|---|
| CH2Cl | H | H | CH2F | Ga |
| CH2Cl | H | H | CH2Cl | Ga |
| CH2Cl | H | H | CH2Br | Gb |
| CH2Cl | H | H | CH2I | Gb |
| CH2Cl | H | H | CH2CH2F | Ga |
| CH2Cl | H | H | CH2CH2Cl | Ga |
| CH2Cl | H | H | CH2CH2Br | Gb |
| CH2Cl | H | H | CH2CH2I | Gb |
| CH2Cl | H | H | CH(CH3)CH2F | Ga |
| CH2Cl | H | H | CH(CH3)CH2Cl | Ga |
| CH2Cl | H | H | CH(CH3)CH2Br | Gb |
| CH2Cl | H | H | CH(CH3)CH2I | Gb |
| CH2Cl | H | H | CH2OMe | Ga |
| CH2Cl | H | H | CH2OEt | Ga |
| CH2Cl | H | H | CH2CH2OMe | Ga |
| CH2Cl | H | H | CH2CH2OEt | Ga |
| CH2Cl | H | H | CH(CH3)CH2OMe | Gb |
| CH2Cl | H | H | CH(CH3)CH2OEt | Gb |
| CH2Cl | H | H | CH2OCH2CH=CH2 | Ga |
| CH2Cl | H | H | CH2OCH2C≡CH | Ga |
| CH2Cl | H | H | CH2OCHF2 | Ga |
| CH2Cl | H | H | CH2OCF3 | Ga |
| CH2Cl | H | H | CH2SMe | Ga |
| CH2Cl | H | H | CH2SEt | Ga |
| CH2Cl | H | H | CH2SO2Me | Ga |
| CH2Cl | H | H | CH2SO2Et | Ga |
| CH2Cl | H | H | CH2CF3 | Ga |
| CH2Cl | H | H | CH2CN | Ga |
| CH2Cl | H | H | CO2Me | Ga |
| CH2Cl | H | H | CO2Et | Ga |
| CH2Cl | H | H | CO2Pr-n | Gb |
| CH2Cl | H | H | CH2CO2Me | Ga |
| CH2Cl | H | H | CH2CO2Et | Ga |
| CH2Cl | H | H | CH2CO2Pr-n | Gb |
| CH2Cl | H | H | COMe | Ga |
| CH2Cl | H | H | COEt | Ga |
| CH2Cl | H | H | COPr-n | Gb |
| CH2Cl | H | H | CH2COMe | Ga |
| CH2Cl | H | H | CH2COEt | Ga |
| CH2Br | H | H | H | Ga |
| CH2Br | H | H | Me | Gb |
| CH2Br | H | H | Et | Gb |
| CH2Br | Me | H | H | Ga |
| CH2Br | Et | H | H | Gb |
| CH2Br | Me | H | Me | Gb |
| CH2Br | Me | H | Et | Gb |
| CH2Br | H | Me | Me | Ga |
| CH2Br | H | Me | Et | Gb |
| CH2Br | H | H | CF3 | Ga |
| CH2Br | H | H | CH2F | Ga |
| CH2Br | H | H | CH2Cl | Ga |
| CH2Br | H | H | CH2Br | Gb |
| CH2Br | H | H | CH2I | Gb |
| CH2Br | H | H | CH2OMe | Ga |
| CH2Br | H | H | CH2OEt | Ga |
| CH2Br | H | H | CH2OCH2CH=CH2 | Ga |
| CH2Br | H | H | CH2OCH2C≡CH | Ga |
| CH2Br | H | H | CH2OCHF2 | Ga |
| CH2Br | H | H | CH2OCF3 | Ga |
| CH2Br | H | H | CH2SMe | Ga |
| CH2Br | H | H | CH2SEt | Ga |
| CH2Br | H | H | CH2SO2Me | Ga |
| CH2Br | H | H | CH2SO2Et | Ga |
| CH2Br | H | H | CH2CF3 | Ga |
| CH2Br | H | H | CH2CN | Ga |
| CH2Br | H | H | CO2Me | Ga |
| CH2Br | H | H | CO2Et | Ga |
| CH2Br | H | H | CH2CO2Me | Ga |
| CH2Br | H | H | CH2CO2Et | Ga |
| CH2Br | H | H | COMe | Ga |
| CH2Br | H | H | COEt | Ga |
| CH2Br | H | H | CH2COMe | Ga |

TABLE 7-continued

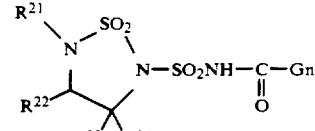

| R21 | R22 | R23 | R24 | Gn |
|---|---|---|---|---|
| CH2Br | H | H | CH2COEt | Ga |
| CH2I | H | H | H | Ga |
| CH2I | H | H | Me | Gb |
| CH2I | H | H | Et | Gb |
| CH2I | Me | H | H | Ga |
| CH2I | Et | H | H | Gb |
| CH2I | Me | H | Me | Gb |
| CH2I | Me | H | Et | Gb |
| CH2I | H | Me | Me | Ga |
| CH2I | H | Me | Et | Gb |
| CH2I | H | H | CF3 | Ga |
| CH2I | H | H | CH2F | Ga |
| CH2I | H | H | CH2Cl | Ga |
| CH2I | H | H | CH2Br | Gb |
| CH2I | H | H | CH2I | Gb |
| CH2I | H | H | CH2OMe | Ga |
| CH2I | H | H | CH2OEt | Ga |
| CH2I | H | H | CH2OCH2CH=CH2 | Ga |
| CH2I | H | H | CH2OCH2C≡CH | Ga |
| CH2I | H | H | CH2OCHF2 | Ga |
| CH2I | H | H | CH2OCF3 | Ga |
| CH2I | H | H | CH2SMe | Ga |
| CH2I | H | H | CH2SEt | Ga |
| CH2I | H | H | CH2SO2Me | Ga |
| CH2I | H | H | CH2SO2Et | Ga |
| CH2I | H | H | CH2CF3 | Ga |
| CH2I | H | H | CH2CN | Ga |
| CH2I | H | H | CO2Me | Ga |
| CH2I | H | H | CO2Et | Ga |
| CH2I | H | H | CH2CO2Me | Ga |
| CH2I | H | H | CH2CO2Et | Ga |
| CH2I | H | H | COMe | Ga |
| CH2I | H | H | COEt | Ga |
| CH2I | H | H | CH2COMe | Ga |
| CH2I | H | H | CH2COEt | Ga |
| CH2CH2F | H | H | H | Ga |
| CH2CH2F | H | H | Me | Gb |
| CH2CH2F | H | H | Et | Gb |
| CH2CH2F | Me | H | H | Ga |
| CH2CH2F | Et | H | H | Gb |
| CH2CH2F | Me | H | Me | Gb |
| CH2CH2F | Me | H | Et | Gb |
| CH2CH2F | H | Me | Me | Ga |
| CH2CH2F | H | Me | Et | Gb |
| CH2CH2F | H | H | CF3 | Ga |
| CH2CH2F | H | H | CH2F | Ga |
| CH2CH2F | H | H | CH2Cl | Ga |
| CH2CH2F | H | H | CH2Br | Gb |
| CH2CH2F | H | H | CH2I | Gb |
| CH2CH2F | H | H | CH2OMe | Ga |
| CH2CH2F | H | H | CH2OEt | Ga |
| CH2CH2F | H | H | CH2OCH2CH=CH2 | Ga |
| CH2CH2F | H | H | CH2OCH2C≡CH | Ga |
| CH2CH2F | H | H | CH2OCHF2 | Ga |
| CH2CH2F | H | H | CH2OCF3 | Ga |
| CH2CH2F | H | H | CH2SMe | Ga |
| CH2CH2F | H | H | CH2SEt | Ga |
| CH2CH2F | H | H | CH2SO2Me | Ga |
| CH2CH2F | H | H | CH2SO2Et | Ga |
| CH2CH2F | H | H | CH2CF3 | Ga |
| CH2CH2F | H | H | CH2CN | Ga |
| CH2CH2F | H | H | CO2Me | Ga |
| CH2CH2F | H | H | CO2Et | Ga |
| CH2CH2F | H | H | CH2CO2Me | Ga |
| CH2CH2F | H | H | CH2CO2Et | Ga |
| CH2CH2F | H | H | COMe | Ga |
| CH2CH2F | H | H | COEt | Ga |
| CH2CH2F | H | H | CH2COMe | Ga |
| CH2CH2F | H | H | CH2COEt | Ga |
| CH2CH2Cl | H | H | H | Ga |
| CH2CH2Cl | H | H | Me | Gb |
| CH2CH2Cl | H | H | Et | Gb |

TABLE 7-continued

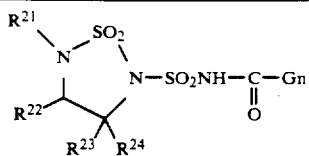

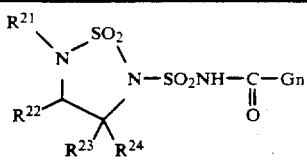

| R21 | R22 | R23 | R24 | Gn |
|---|---|---|---|---|
| CH2CH2Cl | Me | H | H | Ga |
| CH2CH2Cl | Et | H | H | Gb |
| CH2CH2Cl | Me | H | Me | Gb |
| CH2CH2Cl | Me | H | Et | Gb |
| CH2CH2Cl | H | Me | Me | Ga |
| CH2CH2Cl | H | Me | Et | Gb |
| CH2CH2Cl | H | H | CF3 | Ga |
| CH2CH2Cl | H | H | CH2F | Ga |
| CH2CH2Cl | H | H | CH2Cl | Ga |
| CH2CH2Cl | H | H | CH2Br | Gb |
| CH2CH2Cl | H | H | CH2I | Gb |
| CH2CH2Cl | H | H | CH2OMe | Ga |
| CH2CH2Cl | H | H | CH2OEt | Ga |
| CH2CH2Cl | H | H | CH2OCH2CH=CH2 | Ga |
| CH2CH2Cl | H | H | CH2OCH2C≡CH | Ga |
| CH2CH2Cl | H | H | CH2OCHF2 | Ga |
| CH2CH2Cl | H | H | CH2OCF3 | Ga |
| CH2CH2Cl | H | H | CH2SMe | Ga |
| CH2CH2Cl | H | H | CH2SEt | Ga |
| CH2CH2Cl | H | H | CH2SO2Me | Ga |
| CH2CH2Cl | H | H | CH2SO2Et | Ga |
| CH2CH2Cl | H | H | CH2CF3 | Ga |
| CH2CH2Cl | H | H | CH2CN | Ga |
| CH2CH2Cl | H | H | CO2Me | Ga |
| CH2CH2Cl | H | H | CO2Et | Ga |
| CH2CH2Cl | H | H | CH2CO2Me | Ga |
| CH2CH2Cl | H | H | CH2CO2Et | Ga |
| CH2CH2Cl | H | H | COMe | Ga |
| CH2CH2Cl | H | H | COEt | Ga |
| CH2CH2Cl | H | H | CH2COMe | Ga |
| CH2CH2Cl | H | H | CH2COEt | Ga |
| CH2CH2Br | H | H | H | Ga |
| CH2CH2Br | H | H | Me | Gb |
| CH2CH2Br | Me | H | H | Ga |
| CH2CH2Br | Me | H | Me | Gb |
| CH2CH2Br | H | Me | Me | Ga |
| CH2CH2Br | H | H | CF3 | Ga |
| CH2CH2Br | H | H | CH2F | Ga |
| CH2CH2Br | H | H | CH2Cl | Ga |
| CH2CH2Br | H | H | CH2Br | Gb |
| CH2CH2Br | H | H | CH2I | Gb |
| CH2CH2Br | H | H | CH2OMe | Ga |
| CH2CH2Br | H | H | CH2OCH2CH=CH2 | Ga |
| CH2CH2Br | H | H | CH2OCH2C≡CH | Ga |
| CH2CH2Br | H | H | CH2OCHF2 | Ga |
| CH2CH2Br | H | H | CH2OCF3 | Ga |
| CH2CH2Br | H | H | CH2SMe | Ga |
| CH2CH2Br | H | H | CH2SO2Me | Ga |
| CH2CH2Br | H | H | CH2CF3 | Ga |
| CH2CH2Br | H | H | CH2CN | Ga |
| CH2CH2Br | H | H | CO2Me | Ga |
| CH2CH2Br | H | H | CH2CO2Me | Ga |
| CH2CH2Br | H | H | COMe | Ga |
| CH2CH2Br | H | H | CH2COMe | Ga |
| CH2CH2I | H | H | H | Ga |
| CH2CH2I | H | H | Me | Gb |
| CH2CH2I | Me | H | H | Ga |
| CH2CH2I | Me | H | Me | Gb |
| CH2CH2I | H | Me | Me | Ga |
| CH2CH2I | H | H | CF3 | Ga |
| CH2CH2I | H | H | CH2F | Ga |
| CH2CH2I | H | H | CH2Cl | Ga |
| CH2CH2I | H | H | CH2Br | Gb |
| CH2CH2I | H | H | CH2I | Gb |
| CH2CH2I | H | H | CH2OMe | Ga |
| CH2CH2I | H | H | CH2OCH2CH=CH2 | Ga |
| CH2CH2I | H | H | CH2OCH2C≡CH | Ga |
| CH2CH2I | H | H | CH2OCHF2 | Ga |
| CH2CH2I | H | H | CH2OCF3 | Ga |
| CH2CH2I | H | H | CH2SMe | Ga |
| CH2CH2I | H | H | CH2SO2Me | Ga |
| CH2CH2I | H | H | CH2CF3 | Ga |
| CH2CH2I | H | H | CH2CN | Ga |
| CH2CH2I | H | H | CO2Me | Ga |
| CH2CH2I | H | H | CH2CO2Me | Ga |
| CH2CH2I | H | H | COMe | Ga |
| CH2CH2I | H | H | CH2COMe | Ga |
| CH(CH3)CH2F | H | H | H | Ga |
| CH(CH3)CH2F | H | H | Me | Gb |
| CH(CH3)CH2F | H | H | Et | Gb |
| CH(CH3)CH2F | Me | H | H | Ga |
| CH(CH3)CH2F | Et | H | H | Gb |
| CH(CH3)CH2F | Me | H | Me | Gb |
| CH(CH3)CH2F | Me | H | Et | Gb |
| CH(CH3)CH2F | H | Me | Me | Ga |
| CH(CH3)CH2F | H | Me | Et | Gb |
| CH(CH3)CH2F | H | H | CF3 | Ga |
| CH(CH3)CH2F | H | H | CH2F | Ga |
| CH(CH3)CH2F | H | H | CH2Cl | Ga |
| CH(CH3)CH2F | H | H | CH2Br | Gb |
| CH(CH3)CH2F | H | H | CH2I | Gb |
| CH(CH3)CH2F | H | H | CH2OMe | Ga |
| CH(CH3)CH2F | H | H | CH2OEt | Ga |
| CH(CH3)CH2F | H | H | CH2OCH2CH=CH2 | Ga |
| CH(CH3)CH2F | H | H | CH2OCH2C≡CH | Ga |
| CH(CH3)CH2F | H | H | CH2OCHF2 | Ga |
| CH(CH3)CH2F | H | H | CH2OCF3 | Ga |
| CH(CH3)CH2F | H | H | CH2SMe | Ga |
| CH(CH3)CH2F | H | H | CH2SEt | Ga |
| CH(CH3)CH2F | H | H | CH2SO2Me | Ga |
| CH(CH3)CH2F | H | H | CH2SO2Et | Ga |
| CH(CH3)CH2F | H | H | CH2CF3 | Ga |
| CH(CH3)CH2F | H | H | CH2CN | Ga |
| CH(CH3)CH2F | H | H | CO2Me | Ga |
| CH(CH3)CH2F | H | H | CO2Et | Ga |
| CH(CH3)CH2F | H | H | CH2CO2Me | Ga |
| CH(CH3)CH2F | H | H | CH2CO2Et | Ga |
| CH(CH3)CH2F | H | H | COMe | Ga |
| CH(CH3)CH2F | H | H | COEt | Ga |
| CH(CH3)CH2F | H | H | CH2COMe | Ga |
| CH(CH3)CH2F | H | H | CH2COEt | Ga |
| CH(CH3)CH2Cl | H | H | H | Ga |
| CH(CH3)CH2Cl | H | H | Me | Gb |
| CH(CH3)CH2Cl | H | H | Et | Gb |
| CH(CH3)CH2Cl | Me | H | H | Ga |
| CH(CH3)CH2Cl | Et | H | H | Gb |
| CH(CH3)CH2Cl | Me | H | Me | Gb |
| CH(CH3)CH2Cl | Me | H | Et | Gb |
| CH(CH3)CH2Cl | H | Me | Me | Ga |
| CH(CH3)CH2Cl | H | Me | Et | Gb |
| CH(CH3)CH2Cl | H | H | CF3 | Ga |
| CH(CH3)CH2Cl | H | H | CH2F | Ga |
| CH(CH3)CH2Cl | H | H | CH2Cl | Ga |
| CH(CH3)CH2Cl | H | H | CH2Br | Gb |
| CH(CH3)CH2Cl | H | H | CH2I | Gb |
| CH(CH3)CH2Cl | H | H | CH2OMe | Ga |
| CH(CH3)CH2Cl | H | H | CH2OEt | Ga |
| CH(CH3)CH2Cl | H | H | CH2OCH2CH=CH2 | Ga |
| CH(CH3)CH2Cl | H | H | CH2OCH2C≡CH | Ga |
| CH(CH3)CH2Cl | H | H | CH2OCHF2 | Ga |
| CH(CH3)CH2Cl | H | H | CH2OCF3 | Ga |
| CH(CH3)CH2Cl | H | H | CH2SMe | Ga |
| CH(CH3)CH2Cl | H | H | CH2SEt | Ga |
| CH(CH3)CH2Cl | H | H | CH2SO2Me | Ga |
| CH(CH3)CH2Cl | H | H | CH2SO2Et | Ga |
| CH(CH3)CH2Cl | H | H | CH2CF3 | Ga |
| CH(CH3)CH2Cl | H | H | CH2CN | Ga |
| CH(CH3)CH2Cl | H | H | CO2Me | Ga |
| CH(CH3)CH2Cl | H | H | CO2Et | Ga |
| CH(CH3)CH2Cl | H | H | CH2CO2Me | Ga |
| CH(CH3)CH2Cl | H | H | CH2CO2Et | Ga |
| CH(CH3)CH2Cl | H | H | COMe | Ga |
| CH(CH3)CH2Cl | H | H | COEt | Ga |
| CH(CH3)CH2Cl | H | H | CH2COMe | Ga |

TABLE 7-continued

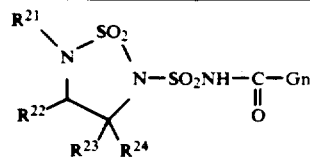

| $R^{21}$ | $R^{22}$ | $R^{23}$ | $R^{24}$ | Gn |
|---|---|---|---|---|
| CH(CH₃)CH₂Cl | H | H | CH₂COEt | Ga |
| CH(CH₃)CH₂Br | H | H | H | Ga |
| CH(CH₃)CH₂Br | H | H | Me | Gb |
| CH(CH₃)CH₂Br | Me | H | H | Ga |
| CH(CH₃)CH₂Br | Me | H | Me | Gb |
| CH(CH₃)CH₂Br | H | Me | Me | Ga |
| CH(CH₃)CH₂Br | H | H | CF₃ | Ga |
| CH(CH₃)CH₂Br | H | H | CH₂F | Ga |
| CH(CH₃)CH₂Br | H | H | CH₂Cl | Ga |
| CH(CH₃)CH₂Br | H | H | CH₂Br | Gb |
| CH(CH₃)CH₂Br | H | H | CH₂I | Gb |
| CH(CH₃)CH₂Br | H | H | CH₂OMe | Ga |
| CH(CH₃)CH₂Br | H | H | CH₂OCH₂CH=CH₂ | Ga |
| CH(CH₃)CH₂Br | H | H | CH₂OCH₂C≡CH | Ga |
| CH(CH₃)CH₂Br | H | H | CH₂OCHF₂ | Ga |
| CH(CH₃)CH₂Br | H | H | CH₂OCF₃ | Ga |
| CH(CH₃)CH₂Br | H | H | CH₂SMe | Ga |
| CH(CH₃)CH₂Br | H | H | CH₂SO₂Me | Ga |
| CH(CH₃)CH₂Br | H | H | CH₂CF₃ | Ga |
| CH(CH₃)CH₂Br | H | H | CH₂CN | Ga |
| CH(CH₃)CH₂Br | H | H | CO₂Me | Ga |
| CH(CH₃)CH₂Br | H | H | CH₂CO₂Me | Ga |
| CH(CH₃)CH₂Br | H | H | COMe | Ga |
| CH(CH₃)CH₂Br | H | H | CH₂COMe | Ga |
| CH(CH₃)CH₂I | H | H | H | Ga |
| CH(CH₃)CH₂I | H | H | Me | Gb |
| CH(CH₃)CH₂I | Me | H | H | Ga |
| CH(CH₃)CH₂I | Me | H | Me | Gb |
| CH(CH₃)CH₂I | H | Me | Me | Ga |
| CH(CH₃)CH₂I | H | H | CF₃ | Ga |
| CH(CH₃)CH₂I | H | H | CH₂F | Ga |
| CH(CH₃)CH₂I | H | H | CH₂Cl | Ga |
| CH(CH₃)CH₂I | H | H | CH₂Br | Gb |
| CH(CH₃)CH₂I | H | H | CH₂I | Gb |
| CH(CH₃)CH₂I | H | H | CH₂OMe | Ga |
| CH(CH₃)CH₂I | H | H | CH₂OCH₂CH=CH₂ | Ga |
| CH(CH₃)CH₂I | H | H | CH₂OCH₂C≡CH | Ga |
| CH(CH₃)CH₂I | H | H | CH₂OCHF₂ | Ga |
| CH(CH₃)CH₂I | H | H | CH₂OCF₃ | Ga |
| CH(CH₃)CH₂I | H | H | CH₂SMe | Ga |
| CH(CH₃)CH₂I | H | H | CH₂SO₂Me | Ga |
| CH(CH₃)CH₂I | H | H | CH₂CF₃ | Ga |
| CH(CH₃)CH₂I | H | H | CH₂CN | Ga |
| CH(CH₃)CH₂I | H | H | CO₂Me | Ga |
| CH(CH₃)CH₂I | H | H | CH₂CO₂Me | Ga |
| CH(CH₃)CH₂I | H | H | COMe | Ga |
| CH(CH₃)CH₂I | H | H | CH₂COMe | Ga |
| CH₂CF₃ | H | H | H | Ga |
| CH₂CF₃ | H | H | Me | Gb |
| CH₂CF₃ | H | H | Et | Gb |
| CH₂CF₃ | H | H | Pr-n | Gb |
| CH₂CF₃ | H | H | Pr-i | Gb |
| CH₂CF₃ | H | H | Bu-n | Gc |
| CH₂CF₃ | Me | H | H | Ga |
| CH₂CF₃ | Et | H | H | Gb |
| CH₂CF₃ | Me | H | Me | Gb |
| CH₂CF₃ | Me | H | Et | Gb |
| CH₂CF₃ | H | Me | Me | Ga |
| CH₂CF₃ | H | Me | Et | Gb |
| CH₂CF₃ | H | H | F | Ga |
| CH₂CF₃ | H | H | Cl | Ga |
| CH₂CF₃ | H | H | Br | Gb |
| CH₂CF₃ | H | H | I | Gb |
| CH₂CF₃ | H | H | CF₃ | Ga |
| CH₂CF₃ | H | H | CH₂F | Ga |
| CH₂CF₃ | H | H | CH₂Cl | Ga |
| CH₂CF₃ | H | H | CH₂Br | Gb |
| CH₂CF₃ | H | H | CH₂I | Gb |
| CH₂CF₃ | H | H | CH₂CH₂F | Ga |
| CH₂CF₃ | H | H | CH₂CH₂Cl | Ga |
| CH₂CF₃ | H | H | CH₂CH₂Br | Gb |
| CH₂CF₃ | H | H | CH₂CH₂I | Gb |

TABLE 7-continued

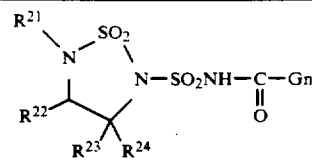

| $R^{21}$ | $R^{22}$ | $R^{23}$ | $R^{24}$ | Gn |
|---|---|---|---|---|
| CH₂CF₃ | H | H | CH(CH₃)CH₂F | Ga |
| CH₂CF₃ | H | H | CH(CH₃)CH₂Cl | Ga |
| CH₂CF₃ | H | H | CH(CH₃)CH₂Br | Gb |
| CH₂CF₃ | H | H | CH(CH₃)CH₂I | Gb |
| CH₂CF₃ | H | H | CH₂OMe | Ga |
| CH₂CF₃ | H | H | CH₂OEt | Ga |
| CH₂CF₃ | H | H | CH₂CH₂OMe | Ga |
| CH₂CF₃ | H | H | CH₂CH₂OEt | Ga |
| CH₂CF₃ | H | H | CH(CH₃)CH₂OMe | Gb |
| CH₂CF₃ | H | H | CH(CH₃)CH₂OEt | Gb |
| CH₂CF₃ | H | H | CH₂OCH₂CH=CH₂ | Ga |
| CH₂CF₃ | H | H | CH₂OCH₂C≡CH | Ga |
| CH₂CF₃ | H | H | CH₂OCHF₂ | Ga |
| CH₂CF₃ | H | H | CH₂OCF₃ | Ga |
| CH₂CF₃ | H | H | CH₂SMe | Ga |
| CH₂CF₃ | H | H | CH₂SEt | Ga |
| CH₂CF₃ | H | H | CH₂SO₂Me | Ga |
| CH₂CF₃ | H | H | CH₂SO₂Et | Ga |
| CH₂CF₃ | H | H | CH₂CF₃ | Ga |
| CH₂CF₃ | H | H | CH₂CN | Ga |
| CH₂CF₃ | H | H | CO₂Me | Ga |
| CH₂CF₃ | H | H | CO₂Et | Ga |
| CH₂CF₃ | H | H | CO₂Pr-n | Gb |
| CH₂CF₃ | H | H | CH₂CO₂Me | Ga |
| CH₂CF₃ | H | H | CH₂CO₂Et | Ga |
| CH₂CF₃ | H | H | CH₂CO₂Pr-n | Gb |
| CH₂CF₃ | H | H | COMe | Ga |
| CH₂CF₃ | H | H | COEt | Ga |
| CH₂CF₃ | H | H | COPr-n | Gb |
| CH₂CF₃ | H | H | CH₂COMe | Ga |
| CH₂CF₃ | H | H | CH₂COEt | Ga |
| CH₂CN | H | H | H | Ga |
| CH₂CN | H | H | Me | Gb |
| CH₂CN | H | H | Et | Gb |
| CH₂CN | H | H | Pr-n | Gb |
| CH₂CN | H | H | Pr-i | Gb |
| CH₂CN | H | H | Bu-n | Gc |
| CH₂CN | Me | H | H | Ga |
| CH₂CN | Et | H | H | Gb |
| CH₂CN | Me | H | Me | Gb |
| CH₂CN | Me | H | Et | Gb |
| CH₂CN | H | Me | Me | Ga |
| CH₂CN | H | Me | Et | Gb |
| CH₂CN | H | H | F | Ga |
| CH₂CN | H | H | Cl | Ga |
| CH₂CN | H | H | Br | Gb |
| CH₂CN | H | H | I | Gb |
| CH₂CN | H | H | CF₃ | Ga |
| CH₂CN | H | H | CH₂F | Ga |
| CH₂CN | H | H | CH₂Cl | Ga |
| CH₂CN | H | H | CH₂Br | Gb |
| CH₂CN | H | H | CH₂I | Gb |
| CH₂CN | H | H | CH₂CH₂F | Ga |
| CH₂CN | H | H | CH₂CH₂Cl | Ga |
| CH₂CN | H | H | CH₂CH₂Br | Gb |
| CH₂CN | H | H | CH₂CH₂I | Gb |
| CH₂CN | H | H | CH(CH₃)CH₂F | Ga |
| CH₂CN | H | H | CH(CH₃)CH₂Cl | Ga |
| CH₂CN | H | H | CH(CH₃)CH₂Br | Gb |
| CH₂CN | H | H | CH(CH₃)CH₂I | Gb |
| CH₂CN | H | H | CH₂OMe | Ga |
| CH₂CN | H | H | CH₂OEt | Ga |
| CH₂CN | H | H | CH₂CH₂OMe | Ga |
| CH₂CN | H | H | CH₂CH₂OEt | Ga |
| CH₂CN | H | H | CH(CH₃)CH₂OMe | Gb |
| CH₂CN | H | H | CH(CH₃)CH₂OEt | Gb |
| CH₂CN | H | H | CH₂OCH₂CH=CH₂ | Ga |
| CH₂CN | H | H | CH₂OCH₂C≡CH | Ga |
| CH₂CN | H | H | CH₂OCHF₂ | Ga |
| CH₂CN | H | H | CH₂OCF₃ | Ga |
| CH₂CN | H | H | CH₂SMe | Ga |
| CH₂CN | H | H | CH₂SEt | Ga |

TABLE 7-continued

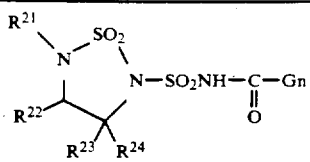

| R21 | R22 | R23 | R24 | Gn |
|---|---|---|---|---|
| CH2CN | H | H | CH2SO2Me | Ga |
| CH2CN | H | H | CH2SO2Et | Ga |
| CH2CN | H | H | CH2CF3 | Ga |
| CH2CN | H | H | CH2CN | Ga |
| CH2CN | H | H | CO2Me | Ga |
| CH2CN | H | H | CO2Et | Ga |
| CH2CN | H | H | CO2Pr-n | Gb |
| CH2CN | H | H | CH2CO2Me | Ga |
| CH2CN | H | H | CH2CO2Et | Ga |
| CH2CN | H | H | CH2CO2Pr-n | Gb |
| CH2CN | H | H | COMe | Ga |
| CH2CN | H | H | COEt | Ga |
| CH2CN | H | H | COPr-n | Gb |
| CH2CN | H | H | CH2COMe | Ga |
| CH2CN | H | H | CH2COEt | Ga |
| CH2CO2Me | H | H | H | Ga |
| CH2CO2Me | H | H | Me | Gb |
| CH2CO2Me | H | H | Et | Gb |
| CH2CO2Me | H | H | Pr-n | Gb |
| CH2CO2Me | H | H | Pr-i | Gb |
| CH2CO2Me | H | H | Bu-n | Gc |
| CH2CO2Me | Me | H | H | Ga |
| CH2CO2Me | Et | H | H | Gb |
| CH2CO2Me | Me | H | Me | Gb |
| CH2CO2Me | Me | H | Et | Gb |
| CH2CO2Me | H | Me | Me | Ga |
| CH2CO2Me | H | Me | Et | Gb |
| CH2CO2Me | H | H | F | Ga |
| CH2CO2Me | H | H | Cl | Ga |
| CH2CO2Me | H | H | Br | Gb |
| CH2CO2Me | H | H | I | Gb |
| CH2CO2Me | H | H | CF3 | Ga |
| CH2CO2Me | H | H | CH2F | Ga |
| CH2CO2Me | H | H | CH2Cl | Ga |
| CH2CO2Me | H | H | CH2Br | Gb |
| CH2CO2Me | H | H | CH2I | Gb |
| CH2CO2Me | H | H | CH2CH2F | Ga |
| CH2CO2Me | H | H | CH2CH2Cl | Ga |
| CH2CO2Me | H | H | CH2CH2Br | Gb |
| CH2CO2Me | H | H | CH2CH2I | Gb |
| CH2CO2Me | H | H | CH(CH3)CH2F | Ga |
| CH2CO2Me | H | H | CH(CH3)CH2Cl | Ga |
| CH2CO2Me | H | H | CH(CH3)CH2Br | Gb |
| CH2CO2Me | H | H | CH(CH3)CH2I | Gb |
| CH2CO2Me | H | H | CH2OMe | Ga |
| CH2CO2Me | H | H | CH2OEt | Ga |
| CH2CO2Me | H | H | CH2CH2OMe | Ga |
| CH2CO2Me | H | H | CH2CH2OEt | Ga |
| CH2CO2Me | H | H | CH(CH3)CH2OMe | Gb |
| CH2CO2Me | H | H | CH(CH3)CH2OEt | Gb |
| CH2CO2Me | H | H | CH2OCH2CH=CH2 | Ga |
| CH2CO2Me | H | H | CH2OCH2C≡CH | Ga |
| CH2CO2Me | H | H | CH2OCHF2 | Ga |
| CH2CO2Me | H | H | CH2OCF3 | Ga |
| CH2CO2Me | H | H | CH2SMe | Ga |
| CH2CO2Me | H | H | CH2SEt | Ga |
| CH2CO2Me | H | H | CH2SO2Me | Ga |
| CH2CO2Me | H | H | CH2SO2Et | Ga |
| CH2CO2Me | H | H | CH2CF3 | Ga |
| CH2CO2Me | H | H | CH2CN | Ga |
| CH2CO2Me | H | H | CO2Me | Ga |
| CH2CO2Me | H | H | CO2Et | Ga |
| CH2CO2Me | H | H | CO2Pr-n | Gb |
| CH2CO2Me | H | H | CH2CO2Me | Ga |
| CH2CO2Me | H | H | CH2CO2Et | Ga |
| CH2CO2Me | H | H | CH2CO2Pr-n | Gb |
| CH2CO2Me | H | H | COMe | Ga |
| CH2CO2Me | H | H | COEt | Ga |
| CH2CO2Me | H | H | COPr-n | Gb |
| CH2CO2Me | H | H | CH2COMe | Ga |
| CH2CO2Me | H | H | CH2COEt | Gb |
| CH2CO2Et | H | H | H | Ga |

TABLE 7-continued

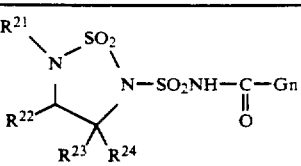

| R21 | R22 | R23 | R24 | Gn |
|---|---|---|---|---|
| CH2CO2Et | H | H | Me | Gb |
| CH2CO2Et | H | H | Et | Gb |
| CH2CO2Et | Me | H | H | Ga |
| CH2CO2Et | Et | H | H | Gb |
| CH2CO2Et | Me | H | Me | Gb |
| CH2CO2Et | Me | H | Et | Gb |
| CH2CO2Et | H | Me | Me | Ga |
| CH2CO2Et | H | Me | Et | Gb |
| CH2CO2Et | H | H | CF3 | Ga |
| CH2CO2Et | H | H | CH2F | Ga |
| CH2CO2Et | H | H | CH2Cl | Ga |
| CH2CO2Et | H | H | CH2Br | Gb |
| CH2CO2Et | H | H | CH2I | Gb |
| CH2CO2Et | H | H | CH2OMe | Ga |
| CH2CO2Et | H | H | CH2OEt | Ga |
| CH2CO2Et | H | H | CH2OCH2CH=CH2 | Ga |
| CH2CO2Et | H | H | CH2OCH2C≡CH | Ga |
| CH2CO2Et | H | H | CH2OCHF2 | Ga |
| CH2CO2Et | H | H | CH2OCF3 | Ga |
| CH2CO2Et | H | H | CH2SMe | Ga |
| CH2CO2Et | H | H | CH2SEt | Ga |
| CH2CO2Et | H | H | CH2SO2Me | Ga |
| CH2CO2Et | H | H | CH2SO2Et | Ga |
| CH2CO2Et | H | H | CH2CF3 | Ga |
| CH2CO2Et | H | H | CH2CN | Ga |
| CH2CO2Et | H | H | CO2Me | Ga |
| CH2CO2Et | H | H | CO2Et | Ga |
| CH2CO2Et | H | H | CH2CO2Me | Ga |
| CH2CO2Et | H | H | CH2CO2Et | Ga |
| CH2CO2Et | H | H | COMe | Ga |
| CH2CO2Et | H | H | COEt | Ga |
| CH2CO2Et | H | H | CH2COMe | Ga |
| CH2CO2Et | H | H | CH2COEt | Ga |
| CH2CO2Pr-n | H | H | H | Ga |
| CH2CO2Pr-n | H | H | Me | Gb |
| CH2CO2Pr-n | Me | H | H | Ga |
| CH2CO2Pr-n | Me | H | Me | Gb |
| CH2CO2Pr-n | H | Me | Me | Ga |
| CH2CO2Pr-n | H | H | CF3 | Ga |
| CH2CO2Pr-n | H | H | CH2F | Ga |
| CH2CO2Pr-n | H | H | CH2Cl | Ga |
| CH2CO2Pr-n | H | H | CH2Br | Gb |
| CH2CO2Pr-n | H | H | CH2I | Gb |
| CH2CO2Pr-n | H | H | CH2OMe | Ga |
| CH2CO2Pr-n | H | H | CH2OCH2CH=CH2 | Ga |
| CH2CO2Pr-n | H | H | CH2OCH2C≡CH | Ga |
| CH2CO2Pr-n | H | H | CH2OCHF2 | Ga |
| CH2CO2Pr-n | H | H | CH2OCF3 | Ga |
| CH2CO2Pr-n | H | H | CH2SMe | Ga |
| CH2CO2Pr-n | H | H | CH2SO2Me | Ga |
| CH2CO2Pr-n | H | H | CH2CF3 | Ga |
| CH2CO2Pr-n | H | H | CH2CN | Ga |
| CH2CO2Pr-n | H | H | CO2Me | Ga |
| CH2CO2Pr-n | H | H | CH2CO2Me | Ga |
| CH2CO2Pr-n | H | H | COMe | Ga |
| CH2CO2Pr-n | H | H | CH2COMe | Ga |
| CH2COMe | H | H | H | Ga |
| CH2COMe | H | H | Me | Gb |
| CH2COMe | H | H | Et | Gb |
| CH2COMe | H | H | Pr-n | Gb |
| CH2COMe | H | H | Pr-i | Gb |
| CH2COMe | H | H | Bu-n | Gc |
| CH2COMe | Me | H | H | Ga |
| CH2COMe | Et | H | H | Gb |
| CH2COMe | Me | H | Me | Gb |
| CH2COMe | Me | H | Et | Gb |
| CH2COMe | H | Me | Me | Ga |
| CH2COMe | H | Me | Et | Gb |
| CH2COMe | H | H | F | Ga |
| CH2COMe | H | H | Cl | Ga |
| CH2COMe | H | H | Br | Gb |
| CH2COMe | H | H | I | Gb |

TABLE 7-continued

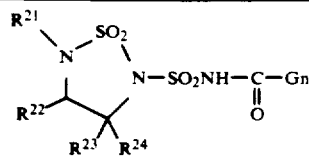

| R²¹ | R²² | R²³ | R²⁴ | Gn |
|---|---|---|---|---|
| CH₂COMe | H | H | CF₃ | Ga |
| CH₂COMe | H | H | CH₂F | Ga |
| CH₂COMe | H | H | CH₂Cl | Ga |
| CH₂COMe | H | H | CH₂Br | Gb |
| CH₂COMe | H | H | CH₂I | Gb |
| CH₂COMe | H | H | CH₂CH₂F | Ga |
| CH₂COMe | H | H | CH₂CH₂Cl | Ga |
| CH₂COMe | H | H | CH₂CH₂Br | Gb |
| CH₂COMe | H | H | CH₂CH₂I | Gb |
| CH₂COMe | H | H | CH(CH₃)CH₂F | Ga |
| CH₂COMe | H | H | CH(CH₃)CH₂Cl | Ga |
| CH₂COMe | H | H | CH(CH₃)CH₂Br | Gb |
| CH₂COMe | H | H | CH(CH₃)CH₂I | Gb |
| CH₂COMe | H | H | CH₂OMe | Ga |
| CH₂COMe | H | H | CH₂OEt | Ga |
| CH₂COMe | H | H | CH₂CH₂OMe | Ga |
| CH₂COMe | H | H | CH₂CH₂OEt | Ga |
| CH₂COMe | H | H | CH(CH₃)CH₂OMe | Gb |
| CH₂COMe | H | H | CH(CH₃)CH₂OEt | Gb |
| CH₂COMe | H | H | CH₂OCH₂CH=CH₂ | Ga |
| CH₂COMe | H | H | CH₂OCH₂C≡CH | Ga |
| CH₂COMe | H | H | CH₂OCHF₂ | Ga |
| CH₂COMe | H | H | CH₂OCF₃ | Ga |
| CH₂COMe | H | H | CH₂SMe | Ga |
| CH₂COMe | H | H | CH₂SEt | Ga |
| CH₂COMe | H | H | CH₂SO₂Me | Ga |
| CH₂COMe | H | H | CH₂SO₂Et | Ga |
| CH₂COMe | H | H | CH₂CF₃ | Ga |
| CH₂COMe | H | H | CH₂CN | Ga |
| CH₂COMe | H | H | CO₂Me | Ga |
| CH₂COMe | H | H | CO₂Et | Ga |
| CH₂COMe | H | H | CO₂Pr-n | Gb |
| CH₂COMe | H | H | CH₂CO₂Me | Ga |
| CH₂COMe | H | H | CH₂CO₂Et | Ga |
| CH₂COMe | H | H | CH₂CO₂Pr-n | Gb |
| CH₂COMe | H | H | COMe | Ga |
| CH₂COMe | H | H | COEt | Ga |
| CH₂COMe | H | H | COPr-n | Gb |
| CH₂COMe | H | H | CH₂COMe | Ga |
| CH₂COMe | H | H | CH₂COEt | Ga |
| CH₂COEt | H | H | H | Ga |
| CH₂COEt | H | H | Me | Gb |
| CH₂COEt | H | H | Et | Gb |
| CH₂COEt | Me | H | H | Ga |
| CH₂COEt | Et | H | H | Gb |
| CH₂COEt | Me | H | Me | Gb |
| CH₂COEt | Me | H | Et | Gb |
| CH₂COEt | H | Me | Me | Ga |
| CH₂COEt | H | Me | Et | Gb |
| CH₂COEt | H | H | CF₃ | Ga |
| CH₂COEt | H | H | CH₂F | Ga |
| CH₂COEt | H | H | CH₂Cl | Ga |
| CH₂COEt | H | H | CH₂Br | Gb |
| CH₂COEt | H | H | CH₂I | Gb |
| CH₂COEt | H | H | CH₂OMe | Ga |
| CH₂COEt | H | H | CH₂OEt | Ga |
| CH₂COEt | H | H | CH₂OCH₂CH=CH₂ | Ga |
| CH₂COEt | H | H | CH₂OCH₂C≡CH | Ga |
| CH₂COEt | H | H | CH₂OCHF₂ | Ga |
| CH₂COEt | H | H | CH₂OCF₃ | Ga |
| CH₂COEt | H | H | CH₂SMe | Ga |
| CH₂COEt | H | H | CH₂SEt | Ga |
| CH₂COEt | H | H | CH₂SO₂Me | Ga |
| CH₂COEt | H | H | CH₂SO₂Et | Ga |
| CH₂COEt | H | H | CH₂CF₃ | Ga |
| CH₂COEt | H | H | CH₂CN | Ga |
| CH₂COEt | H | H | CO₂Me | Ga |
| CH₂COEt | H | H | CO₂Et | Ga |
| CH₂COEt | H | H | CH₂CO₂Me | Ga |
| CH₂COEt | H | H | CH₂CO₂Et | Ga |
| CH₂COEt | H | H | COMe | Ga |
| CH₂COEt | H | H | COEt | Ga |
| CH₂COEt | H | H | CH₂COMe | Ga |
| CH₂COEt | H | H | CH₂COEt | Ga |
| Ph | H | H | H | Ga |
| Ph | H | H | Me | Ga |
| PhCH₂ | H | H | H | Gb |
| PhCH₂ | H | H | Me | Gb |
| Me | H | H | Ph | Ga |
| Me | H | H | PhCH₂ | Gb |
| Me | H | H | CH₂CH=CH₂ | Ga |
| Me | H | H | CH₂C≡CH | Ga |
| Bu-t | H | H | H | Gb |

TABLE 8

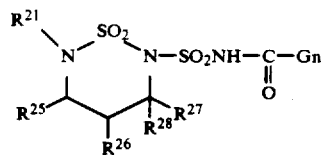

| R²¹ | R²⁵ | R²⁶ | R²⁷ | R²⁸ | Gn |
|---|---|---|---|---|---|
| H | H | H | H | H | Ga |
| H | H | H | H | Me | Ga |
| H | H | H | H | Et | Ga |
| H | H | H | H | Pr-n | Gb |
| H | Me | H | H | H | Ga |
| H | H | Me | H | H | Ga |
| H | Me | H | H | Me | Gb |
| H | Me | Me | H | Me | Gb |
| H | H | H | Me | Me | Gb |
| Me | H | H | H | H | Ga |
| Me | H | H | H | Me | Ga |
| Me | H | H | H | Et | Ga |
| Me | H | H | H | Pr-n | Gb |
| Me | Me | H | H | H | Ga |
| Me | H | Me | H | H | Ga |
| Me | Me | H | H | Me | Gb |
| Me | Me | Me | H | Me | Gb |

TABLE 8-continued

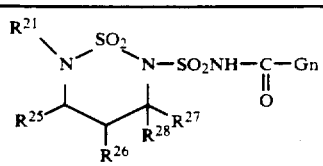

| R²¹ | R²⁵ | R²⁶ | R²⁷ | R²⁸ | Gn |
|---|---|---|---|---|---|
| Me | H | H | Me | Me | Gb |
| Me | H | H | H | CF₃ | Gb |
| Me | H | H | H | CH₂F | Gb |
| Me | H | H | H | CH₂Cl | Gb |
| Me | H | H | H | CH₂Br | Gb |
| Me | H | H | H | CH₂I | Gb |
| Me | H | H | H | CH₂OMe | Gb |
| Me | H | H | H | CH₂OEt | Gb |
| Me | H | H | H | CH₂OCH₂CH=CH₂ | Gb |
| Me | H | H | H | CH₂OCH₂C≡CH | Gb |
| Me | H | H | H | CH₂SMe | Gb |
| Me | H | H | H | CH₂SO₂Me | Gb |
| Me | H | H | H | CH₂CN | Gb |
| Me | H | H | H | CO₂Me | Gb |
| Me | H | H | H | CO₂Et | Gb |
| Me | H | H | H | COMe | Gb |
| Me | H | H | H | COEt | Gb |
| Me | H | H | H | CH₂CO₂Me | Gb |
| Me | H | H | H | CH₂CO₂Et | Gb |
| Me | H | H | H | CH₂COMe | Gb |
| Me | H | H | H | CH₂COEt | Gb |
| Et | H | H | H | H | Ga |
| Et | H | H | H | Me | Ga |
| Et | H | H | H | Et | Ga |
| Et | H | H | H | Pr-n | Gb |
| Et | Me | H | H | H | Ga |
| Et | H | Me | H | H | Ga |
| Et | Me | H | H | Me | Gb |
| Et | Me | Me | H | Me | Gb |
| Et | H | H | Me | Me | Gb |
| Et | H | H | H | CF₃ | Gb |
| Et | H | H | H | CH₂F | Gb |
| Et | H | H | H | CH₂Cl | Gb |
| Et | H | H | H | CH₂Br | Gb |
| Et | H | H | H | CH₂I | Gb |
| Et | H | H | H | CH₂OMe | Gb |
| Et | H | H | H | CH₂OEt | Gb |
| Et | H | H | H | CH₂CN | Gb |
| Et | H | H | H | COMe | Gb |
| Et | H | H | H | COEt | Gb |
| Et | H | H | H | CH₂CO₂Me | Gb |
| Et | H | H | H | CH₂CO₂Et | Gb |
| Et | H | H | H | CH₂COMe | Gb |
| Et | H | H | H | CH₂COEt | Gb |
| Pr-n | H | H | H | H | Ga |
| Pr-n | H | H | H | Me | Ga |
| Pr-n | H | H | H | Et | Ga |
| Pr-n | H | H | H | Pr-n | Gb |
| Pr-n | Me | H | H | H | Ga |
| Pr-n | H | Me | H | H | Ga |
| Pr-n | Me | H | H | Me | Gb |
| Pr-n | Me | Me | H | Me | Gb |
| Pr-n | H | H | Me | Me | Gb |
| Pr-n | H | H | H | CF₃ | Gb |
| Pr-n | H | H | H | CH₂F | Gb |
| Pr-n | H | H | H | CH₂Cl | Gb |
| Pr-n | H | H | H | CH₂Br | Gb |
| Pr-n | H | H | H | CH₂I | Gb |
| Pr-n | H | H | H | CH₂OMe | Gb |
| Pr-n | H | H | H | CH₂OEt | Gb |
| Pr-i | H | H | H | H | Ga |
| Pr-i | H | H | H | Me | Ga |
| Pr-i | H | H | H | Et | Ga |
| Pr-i | H | H | H | Pr-n | Gb |
| Pr-i | Me | H | H | H | Ga |
| Pr-i | H | Me | H | H | Ga |
| Pr-i | Me | H | H | Me | Gb |
| Pr-i | Me | Me | H | Me | Gb |
| Pr-i | H | H | Me | Me | Gb |
| Bu-n | H | H | H | H | Ga |
| Bu-n | H | H | H | Me | Ga |
| Bu-n | H | H | H | Et | Ga |

TABLE 8-continued $$\begin{array}{c} R^{21} \\ | \\ N-SO_2 \\ | \\ \end{array} \begin{array}{c} SO_2 \\ | \\ N-SO_2NH-C-Gn \\ || \\ O \end{array}$$

with $R^{25}$, $R^{26}$, $R^{27}$, $R^{28}$ on ring

| $R^{21}$ | $R^{25}$ | $R^{26}$ | $R^{27}$ | $R^{28}$ | Gn |
|---|---|---|---|---|---|
| Bu-n | H | H | H | Pr-n | Gb |
| CH₂CH=CH₂ | H | H | H | H | Ga |
| CH₂CH=CH₂ | H | H | H | Me | Ga |
| CH₂CH=CH₂ | H | H | H | Et | Ga |
| CH₂CH=CH₂ | H | H | H | Pr-n | Gb |
| CH₂CH=CH₂ | Me | H | H | H | Ga |
| CH₂CH=CH₂ | H | Me | H | H | Ga |
| CH₂CH=CH₂ | Me | H | H | Me | Gb |
| CH₂CH=CH₂ | Me | Me | H | Me | Gb |
| CH₂CH=CH₂ | H | H | Me | Me | Gb |
| CH₂C≡CH | H | H | H | H | Ga |
| CH₂C≡CH | H | H | H | Me | Ga |
| CH₂C≡CH | H | H | H | Et | Ga |
| CH₂C≡CH | H | H | H | Pr-n | Gb |
| CH₂C≡CH | Me | H | H | H | Ga |
| CH₂C≡CH | H | Me | H | H | Ga |
| CH₂C≡CH | Me | H | H | Me | Gb |
| CH₂C≡CH | Me | Me | H | Me | Gb |
| CH₂C≡CH | H | H | Me | Me | Gb |
| CH₂OMe | H | H | H | H | Ga |
| CH₂OMe | H | H | H | Me | Ga |
| CH₂OMe | H | H | H | Et | Ga |
| CH₂OMe | H | H | H | Pr-n | Gb |
| CH₂OMe | Me | H | H | H | Ga |
| CH₂OMe | H | Me | H | H | Ga |
| CH₂OMe | Me | H | H | Me | Gb |
| CH₂OMe | Me | Me | H | Me | Gb |
| CH₂OMe | H | H | Me | Me | Gb |
| CH₂OMe | H | H | H | CF₃ | Gb |
| CH₂OMe | H | H | H | CH₂F | Gb |
| CH₂OMe | H | H | H | CH₂Cl | Gb |
| CH₂OMe | H | H | H | CH₂Br | Gb |
| CH₂OMe | H | H | H | CH₂I | Gb |
| CH₂OMe | H | H | H | CH₂OMe | Gb |
| CH₂OMe | H | H | H | CH₂OEt | Gb |
| CH₂OMe | H | H | H | CH₂OCH₂CH=CH₂ | Gb |
| CH₂OMe | H | H | H | CH₂OCH₂C≡CH | Gb |
| CH₂OMe | H | H | H | CH₂SMe | Gb |
| CH₂OMe | H | H | H | CH₂SO₂Me | Gb |
| CH₂OMe | H | H | H | CH₂CN | Gb |
| CH₂OMe | H | H | H | CO₂Me | Gb |
| CH₂OMe | H | H | H | CO₂Et | Gb |
| CH₂OMe | H | H | H | COMe | Gb |
| CH₂OMe | H | H | H | COEt | Gb |
| CH₂OMe | H | H | H | CH₂CO₂Me | Gb |
| CH₂OMe | H | H | H | CH₂CO₂Et | Gb |
| CH₂OMe | H | H | H | CH₂COMe | Gb |
| CH₂OMe | H | H | H | CH₂COEt | Gb |
| CH₂OEt | H | H | H | H | Ga |
| CH₂OEt | H | H | H | Me | Ga |
| CH₂OEt | H | H | H | Et | Ga |
| CH₂OEt | H | H | H | Pr-n | Gb |
| CH₂OEt | Me | H | H | H | Ga |
| CH₂OEt | H | Me | H | H | Ga |
| CH₂OEt | Me | H | H | Me | Gb |
| CH₂OEt | Me | Me | H | Me | Gb |
| CH₂OEt | H | H | Me | Me | Gb |
| CH₂OEt | H | H | H | CF₃ | Gb |
| CH₂OEt | H | H | H | CH₂F | Gb |
| CH₂OEt | H | H | H | CH₂Cl | Gb |
| CH₂OEt | H | H | H | CH₂Br | Gb |
| CH₂OEt | H | H | H | CH₂I | Gb |
| CH₂OEt | H | H | H | CH₂OMe | Gb |
| CH₂OEt | H | H | H | CH₂OEt | Gb |
| CH₂OEt | H | H | H | CH₂CN | Gb |
| CH₂OEt | H | H | H | COMe | Gb |
| CH₂OEt | H | H | H | COEt | Gb |
| CH₂OEt | H | H | H | CH₂CO₂Me | Gb |
| CH₂OEt | H | H | H | CH₂CO₂Et | Gb |
| CH₂OEt | H | H | H | CH₂COMe | Gb |
| CH₂OEt | H | H | H | CH₂COEt | Gb |
| CH₂CH₂OMe | H | H | H | H | Ga |

TABLE 8-continued

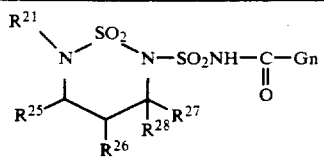

| R21 | R25 | R26 | R27 | R28 | Gn |
|---|---|---|---|---|---|
| CH2CH2OMe | H | H | H | Me | Ga |
| CH2CH2OMe | H | H | H | Et | Ga |
| CH2CH2OMe | H | H | H | Pr-n | Gb |
| CH2CH2OMe | Me | H | H | H | Ga |
| CH2CH2OMe | H | Me | H | H | Ga |
| CH2CH2OMe | Me | H | H | Me | Gb |
| CH2CH2OMe | Me | Me | H | Me | Gb |
| CH2CH2OMe | H | H | Me | Me | Gb |
| CH2CH2OMe | H | H | H | CF3 | Gb |
| CH2CH2OMe | H | H | H | CH2F | Gb |
| CH2CH2OMe | H | H | H | CH2Cl | Gb |
| CH2CH2OMe | H | H | H | CH2Br | Gb |
| CH2CH2OMe | H | H | H | CH2I | Gb |
| CH2CH2OMe | H | H | H | CH2OMe | Gb |
| CH2CH2OMe | H | H | H | CH2OEt | Gb |
| CH2CH2OMe | H | H | H | CH2CN | Gb |
| CH2CH2OMe | H | H | H | COMe | Gb |
| CH2CH2OMe | H | H | H | COEt | Gb |
| CH2CH2OMe | H | H | H | CH2CO2Me | Gb |
| CH2CH2OMe | H | H | H | CH2CO2Et | Gb |
| CH2CH2OMe | H | H | H | CH2COMe | Gb |
| CH2CH2OMe | H | H | H | CH2COEt | Gb |
| CH2CH2OEt | H | H | H | H | Ga |
| CH2CH2OEt | H | H | H | Me | Ga |
| CH2CH2OEt | H | H | H | Et | Ga |
| CH2CH2OEt | H | H | H | Pr-n | Gb |
| CH2CH2OEt | Me | H | H | H | Ga |
| CH2CH2OEt | H | Me | H | H | Ga |
| CH2CH2OEt | Me | H | H | Me | Gb |
| CH2CH2OEt | Me | Me | H | Me | Gb |
| CH2CH2OEt | H | H | Me | Me | Gb |
| CH2CH2OEt | H | H | H | CF3 | Gb |
| CH2CH2OEt | H | H | H | CH2F | Gb |
| CH2CH2OEt | H | H | H | CH2Cl | Gb |
| CH2CH2OEt | H | H | H | CH2Br | Gb |
| CH2CH2OEt | H | H | H | CH2I | Gb |
| CH2CH2OEt | H | H | H | CH2OMe | Gb |
| CH2CH2OEt | H | H | H | CH2OEt | Gb |
| CH(CH3)CH2OMe | H | H | H | H | Ga |
| CH(CH3)CH2OMe | H | H | H | Me | Ga |
| CH(CH3)CH2OMe | H | H | H | Et | Ga |
| CH(CH3)CH2OMe | H | H | H | Pr-n | Gb |
| CH(CH3)CH2OMe | Me | H | H | H | Ga |
| CH(CH3)CH2OMe | H | Me | H | H | Ga |
| CH(CH3)CH2OMe | Me | H | H | Me | Gb |
| CH(CH3)CH2OMe | Me | Me | H | Me | Gb |
| CH(CH3)CH2OMe | H | H | Me | Me | Gb |
| CH(CH3)CH2OMe | H | H | H | CF3 | Gb |
| CH(CH3)CH2OMe | H | H | H | CH2F | Gb |
| CH(CH3)CH2OMe | H | H | H | CH2Cl | Gb |
| CH(CH3)CH2OMe | H | H | H | CH2Br | Gb |
| CH(CH3)CH2OMe | H | H | H | CH2I | Gb |
| CH(CH3)CH2OMe | H | H | H | CH2OMe | Gb |
| CH(CH3)CH2OMe | H | H | H | CH2OEt | Gb |
| CH(CH3)CH2OEt | H | H | H | H | Ga |
| CH(CH3)CH2OEt | H | H | H | Me | Ga |
| CH(CH3)CH2OEt | H | H | H | Et | Ga |
| CH(CH3)CH2OEt | H | H | H | Pr-N | Gb |
| CH(CH3)CH2OEt | Me | H | H | H | Ga |
| CH(CH3)CH2OEt | H | Me | H | H | Ga |
| CH(CH3)CH2OEt | Me | H | H | Me | Gb |
| CH(CH3)CH2OEt | Me | Me | H | Me | Gb |
| CH(CH3)CH2OEt | H | H | Me | Me | Gb |
| CH2OCHF2 | H | H | H | H | Ga |
| CH2OCHF2 | H | H | H | Me | Ga |
| CH2OCHF2 | H | H | H | Et | Ga |
| CH2OCHF2 | H | H | H | Pr-n | Gb |
| CH2OCHF2 | Me | H | H | H | Ga |
| CH2OCHF2 | H | Me | H | H | Ga |
| CH2OCHF2 | Me | H | H | Me | Gb |
| CH2OCHF2 | Me | Me | H | Me | Gb |
| CH2OCHF2 | H | H | Me | Me | Gb |

TABLE 8-continued $$\underset{R^{25}}{\overset{R^{21}}{\underset{N}{\bigg|}}}\overset{SO_2}{\underset{R^{26}}{\bigg|}}N-SO_2NH-\underset{\overset{\|}{O}}{C}-Gn$$

| $R^{21}$ | $R^{25}$ | $R^{26}$ | $R^{27}$ | $R^{28}$ | Gn |
|---|---|---|---|---|---|
| CH₂SMe | H | H | H | H | Ga |
| CH₂SMe | H | H | H | Me | Ga |
| CH₂SMe | H | H | H | Et | Ga |
| CH₂SMe | H | H | H | Pr-n | Gb |
| CH₂SMe | Me | H | H | H | Ga |
| CH₂SMe | H | Me | H | H | Ga |
| CH₂SMe | Me | H | H | Me | Gb |
| CH₂SMe | Me | Me | H | Me | Gb |
| CH₂SMe | H | H | Me | Me | Gb |
| CH₂SMe | H | H | H | CF₃ | Gb |
| CH₂SMe | H | H | H | CH₂F | Gb |
| CH₂SMe | H | H | H | CH₂Cl | Gb |
| CH₂SMe | H | H | H | CH₂Br | Gb |
| CH₂SMe | H | H | H | CH₂I | Gb |
| CH₂SMe | H | H | H | CH₂OMe | Gb |
| CH₂SMe | H | H | H | CH₂OEt | Gb |
| CH₂SMe | H | H | H | CH₂OCH₂CH=CH₂ | Gb |
| CH₂SMe | H | H | H | CH₂OCH₂C≡CH | Gb |
| CH₂SMe | H | H | H | CH₂SMe | Gb |
| CH₂SMe | H | H | H | CH₂SO₂Me | Gb |
| CH₂SMe | H | H | H | CH₂CN | Gb |
| CH₂SMe | H | H | H | CO₂Me | Gb |
| CH₂SMe | H | H | H | CO₂Et | Gb |
| CH₂SMe | H | H | H | COMe | Gb |
| CH₂SMe | H | H | H | COEt | Gb |
| CH₂SMe | H | H | H | CH₂CO₂Me | Gb |
| CH₂SMe | H | H | H | CH₂CO₂Et | Gb |
| CH₂SMe | H | H | H | CH₂COMe | Gb |
| CH₂SMe | H | H | H | CH₂COEt | Gb |
| CH₂SEt | H | H | H | H | Ga |
| CH₂SEt | H | H | H | Me | Ga |
| CH₂SEt | H | H | H | Et | Ga |
| CH₂SEt | H | H | H | Pr-n | Gb |
| CH₂SEt | Me | H | H | H | Ga |
| CH₂SEt | H | Me | H | H | Ga |
| CH₂SEt | Me | H | H | Me | Gb |
| CH₂SEt | Me | Me | H | Me | Gb |
| CH₂SEt | H | H | Me | Me | Gb |
| CH₂SEt | H | H | H | CF₃ | Gb |
| CH₂SEt | H | H | H | CH₂F | Gb |
| CH₂SEt | H | H | H | CH₂Cl | Gb |
| CH₂SEt | H | H | H | CH₂Br | Gb |
| CH₂SEt | H | H | H | CH₂I | Gb |
| CH₂SEt | H | H | H | CH₂OMe | Gb |
| CH₂SEt | H | H | H | CH₂OEt | Gb |
| CH₂SO₂Me | H | H | H | H | Ga |
| CH₂SO₂Me | H | H | H | Me | Ga |
| CH₂SO₂Me | H | H | H | Et | Ga |
| CH₂SO₂Me | H | H | H | Pr-n | Gb |
| CH₂SO₂Me | Me | H | H | H | Ga |
| CH₂SO₂Me | H | Me | H | H | Ga |
| CH₂SO₂Me | Me | H | H | Me | Gb |
| CH₂SO₂Me | Me | Me | H | Me | Gb |
| CH₂SO₂Me | H | H | Me | Me | Gb |
| CH₂SO₂Me | H | H | H | CF₃ | Gb |
| CH₂SO₂Me | H | H | H | CH₂F | Gb |
| CH₂SO₂Me | H | H | H | CH₂Cl | Gb |
| CH₂SO₂Me | H | H | H | CH₂Br | Gb |
| CH₂SO₂Me | H | H | H | CH₂I | Gb |
| CH₂SO₂Me | H | H | H | CH₂OMe | Gb |
| CH₂SO₂Me | H | H | H | CH₂OEt | Gb |
| CH₂SO₂Et | H | H | H | H | Ga |
| CH₂SO₂Et | H | H | H | Me | Ga |
| CH₂SO₂Et | H | H | H | Et | Ga |
| CH₂SO₂Et | H | H | H | Pr-n | Gb |
| CH₂SO₂Et | Me | H | H | H | Ga |
| CH₂SO₂Et | H | Me | H | H | Ga |
| CH₂SO₂Et | Me | H | H | Me | Gb |
| CH₂SO₂Et | Me | Me | H | Me | Gb |
| CH₂SO₂Et | H | H | Me | Me | Gb |
| CH₂F | H | H | H | H | Ga |
| CH₂F | H | H | H | Me | Ga |

TABLE 8-continued

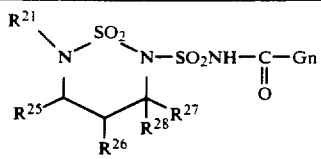

| R21 | R25 | R26 | R27 | R28 | Gn |
|---|---|---|---|---|---|
| CH2F | H | H | H | Et | Ga |
| CH2F | H | H | H | Pr-n | Gb |
| CH2F | Me | H | H | H | Ga |
| CH2F | H | Me | H | H | Ga |
| CH2F | Me | H | H | Me | Gb |
| CH2F | Me | Me | H | Me | Gb |
| CH2F | H | H | Me | Me | Gb |
| CH2F | H | H | H | CF3 | Gb |
| CH2F | H | H | H | CH2F | Gb |
| CH2F | H | H | H | CH2Cl | Gb |
| CH2F | H | H | H | CH2Br | Gb |
| CH2F | H | H | H | CH2I | Gb |
| CH2F | H | H | H | CH2OMe | Gb |
| CH2F | H | H | H | CH2OEt | Gb |
| CH2Cl | H | H | H | H | Ga |
| CH2Cl | H | H | H | Me | Ga |
| CH2Cl | H | H | H | Et | Ga |
| CH2Cl | H | H | H | Pr-n | Gb |
| CH2Cl | Me | H | H | H | Ga |
| CH2Cl | H | Me | H | H | Ga |
| CH2Cl | Me | H | H | Me | Gb |
| CH2Cl | Me | Me | H | Me | Gb |
| CH2Cl | H | H | Me | Me | Gb |
| CH2Cl | H | H | H | CF3 | Gb |
| CH2Cl | H | H | H | CH2F | Gb |
| CH2Cl | H | H | H | CH2Cl | Gb |
| CH2Cl | H | H | H | CH2Br | Gb |
| CH2Cl | H | H | H | CH2I | Gb |
| CH2Cl | H | H | H | CH2OMe | Gb |
| CH2Cl | H | H | H | CH2OEt | Gb |
| CH2Br | H | H | H | H | Ga |
| CH2Br | H | H | H | Me | Ga |
| CH2Br | H | H | H | Et | Ga |
| CH2Br | H | H | H | Pr-n | Gb |
| CH2Br | Me | H | H | H | Ga |
| CH2Br | H | Me | H | H | Ga |
| CH2Br | Me | H | H | Me | Gb |
| CH2Br | Me | Me | H | Me | Gb |
| CH2Br | H | H | Me | Me | Gb |
| CH2Br | H | H | H | CF3 | Gb |
| CH2Br | H | H | H | CH2F | Gb |
| CH2Br | H | H | H | CH2Cl | Gb |
| CH2Br | H | H | H | CH2Br | Gb |
| CH2Br | H | H | H | CH2I | Gb |
| CH2Br | H | H | H | CH2OMe | Gb |
| CH2Br | H | H | H | CH2OEt | Gb |
| CH2I | H | H | H | H | Ga |
| CH2I | H | H | H | Me | Ga |
| CH2I | H | H | H | Et | Ga |
| CH2I | H | H | H | Pr-n | Gb |
| CH2I | Me | H | H | H | Ga |
| CH2I | H | Me | H | H | Ga |
| CH2I | Me | H | H | Me | Gb |
| CH2I | Me | Me | H | Me | Gb |
| CH2I | H | H | Me | Me | Gb |
| CH2I | H | H | H | CF3 | Gb |
| CH2I | H | H | H | CH2F | Gb |
| CH2I | H | H | H | CH2Cl | Gb |
| CH2I | H | H | H | CH2Br | Gb |
| CH2I | H | H | H | CH2I | Gb |
| CH2I | H | H | H | CH2OMe | Gb |
| CH2I | H | H | H | CH2OEt | Gb |
| CH2CH2F | H | H | H | H | Ga |
| CH2CH2F | H | H | H | Me | Ga |
| CH2CH2F | H | H | H | Et | Ga |
| CH2CH2F | H | H | H | Pr-n | Gb |
| CH2CH2F | Me | H | H | H | Ga |
| CH2CH2F | H | Me | H | H | Ga |
| CH2CH2F | Me | H | H | Me | Gb |
| CH2CH2F | Me | Me | H | Me | Gb |
| CH2CH2F | H | H | Me | Me | Gb |
| CH2CH2Cl | H | H | H | H | Ga |

TABLE 8-continued

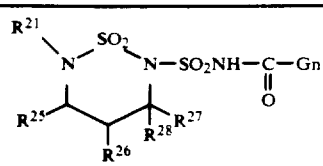

| R21 | R25 | R26 | R27 | R28 | Gn |
|---|---|---|---|---|---|
| CH2CH2Cl | H | H | H | Me | Ga |
| CH2CH2Cl | H | H | H | Et | Ga |
| CH2CH2Cl | H | H | H | Pr-n | Gb |
| CH2CH2Cl | Me | H | H | H | Ga |
| CH2CH2Cl | H | Me | H | H | Ga |
| CH2CH2Cl | Me | H | H | Me | Gb |
| CH2CH2Cl | Me | Me | H | Me | Gb |
| CH2CH2Cl | H | H | Me | Me | Gb |
| CH2CH2Br | H | H | H | H | Ga |
| CH2CH2Br | H | H | H | Me | Ga |
| CH2CH2Br | H | H | H | Et | Ga |
| CH2CH2Br | H | H | H | Pr-n | Gb |
| CH2CH2Br | Me | H | H | H | Ga |
| CH2CH2Br | H | Me | H | H | Ga |
| CH2CH2Br | Me | H | H | Me | Gb |
| CH2CH2Br | Me | Me | H | Me | Gb |
| CH2CH2Br | H | H | Me | Me | Gb |
| CH2CH2I | H | H | H | H | Ga |
| CH2CH2I | H | H | H | Me | Ga |
| CH2CH2I | H | H | H | Et | Ga |
| CH2CH2I | H | H | H | Pr-n | Gb |
| CH2CH2I | Me | H | H | H | Ga |
| CH2CH2I | H | Me | H | H | Ga |
| CH2CH2I | Me | H | H | Me | Gb |
| CH2CH2I | Me | Me | H | Me | Gb |
| CH2CH2I | H | H | Me | Me | Gb |
| CH(CH3)CH2F | H | H | H | H | Ga |
| CH(CH3)CH2F | H | H | H | Me | Ga |
| CH(CH3)CH2F | H | H | H | Et | Ga |
| CH(CH3)CH2F | H | H | H | Pr-n | Gb |
| CH(CH3)CH2F | Me | H | H | H | Ga |
| CH(CH3)CH2F | H | Me | H | H | Ga |
| CH(CH3)CH2F | Me | H | H | Me | Gb |
| CH(CH3)CH2F | Me | Me | H | Me | Gb |
| CH(CH3)CH2F | H | H | Me | Me | Gb |
| CH(CH3)CH2Cl | H | H | H | H | Ga |
| CH(CH3)CH2Cl | H | H | H | Me | Ga |
| CH(CH3)CH2Cl | H | H | H | Et | Ga |
| CH(CH3)CH2Cl | H | H | H | Pr-n | Gb |
| CH(CH3)CH2Cl | Me | H | H | H | Ga |
| CH(CH3)CH2Cl | H | Me | H | H | Ga |
| CH(CH3)CH2Cl | Me | H | H | Me | Gb |
| CH(CH3)CH2Cl | Me | Me | H | Me | Gb |
| CH(CH3)CH2Cl | H | H | Me | Me | Gb |
| CH(CH3)CH2Br | H | H | H | H | Ga |
| CH(CH3)CH2Br | H | H | H | Me | Ga |
| CH(CH3)CH2Br | H | H | H | Et | Ga |
| CH(CH3)CH2Br | H | H | H | Pr-n | Gb |
| CH(CH3)CH2Br | Me | H | H | H | Ga |
| CH(CH3)CH2Br | H | Me | H | H | Ga |
| CH(CH3)CH2Br | Me | H | H | Me | Gb |
| CH(CH3)CH2Br | Me | Me | H | Me | Gb |
| CH(CH3)CH2Br | H | H | Me | Me | Gb |
| CH(CH3)CH2I | H | H | H | H | Ga |
| CH(CH3)CH2I | H | H | H | Me | Ga |
| CH(CH3)CH2I | H | H | H | Et | Ga |
| CH(CH3)CH2I | H | H | H | Pr-n | Gb |
| CH(CH3)CH2I | Me | H | H | H | Ga |
| CH(CH3)CH2I | H | Me | H | H | Ga |
| CH(CH3)CH2I | Me | H | H | Me | Gb |
| CH(CH3)CH2I | Me | Me | H | Me | Gb |
| CH(CH3)CH2I | H | H | Me | Me | Gb |
| CH2CF3 | H | H | H | H | Ga |
| CH2CF3 | H | H | H | Me | Ga |
| CH2CF3 | H | H | H | Et | Ga |
| CH2CF3 | H | H | H | Pr-n | Gb |
| CH2CF3 | Me | H | H | H | Ga |
| CH2CF3 | H | Me | H | H | Ga |
| CH2CF3 | Me | H | H | Me | Gb |
| CH2CF3 | Me | Me | H | Me | Gb |
| CH2CF3 | H | H | Me | Me | Gb |
| CH2CF3 | H | H | H | CF3 | Gb |

TABLE 8-continued

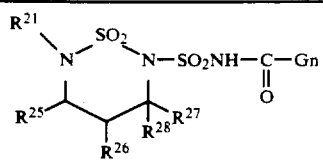

| R²¹ | R²⁵ | R²⁶ | R²⁷ | R²⁸ | Gn |
|---|---|---|---|---|---|
| CH₂CF₃ | H | H | H | CH₂F | Gb |
| CH₂CF₃ | H | H | H | CH₂Cl | Gb |
| CH₂CF₃ | H | H | H | CH₂Br | Gb |
| CH₂CF₃ | H | H | H | CH₂I | Gb |
| CH₂CF₃ | H | H | H | CH₂OMe | Gb |
| CH₂CF₃ | H | H | H | CH₂OEt | Gb |
| CH₂CN | H | H | H | H | Ga |
| CH₂CN | H | H | H | Me | Ga |
| CH₂CN | H | H | H | Et | Ga |
| CH₂CN | H | H | H | Pr-n | Gb |
| CH₂CN | Me | H | H | H | Ga |
| CH₂CN | H | Me | H | H | Ga |
| CH₂CN | Me | H | H | Me | Gb |
| CH₂CN | Me | Me | H | Me | Gb |
| CH₂CN | H | H | Me | Me | Gb |
| CH₂CN | H | H | H | CF₃ | Gb |
| CH₂CN | H | H | H | CH₂F | Gb |
| CH₂CN | H | H | H | CH₂Cl | Gb |
| CH₂CN | H | H | H | CH₂Br | Gb |
| CH₂CN | H | H | H | CH₂I | Gb |
| CH₂CN | H | H | H | CH₂OMe | Gb |
| CH₂CN | H | H | H | CH₂OEt | Gb |
| CH₂CO₂Me | H | H | H | H | Ga |
| CH₂CO₂Me | H | H | H | Me | Ga |
| CH₂CO₂Me | H | H | H | Et | Ga |
| CH₂CO₂Me | H | H | H | Pr-n | Gb |
| CH₂CO₂Me | Me | H | H | H | Ga |
| CH₂CO₂Me | H | Me | H | H | Ga |
| CH₂CO₂Me | Me | H | H | Me | Gb |
| CH₂CO₂Me | Me | Me | H | Me | Gb |
| CH₂CO₂Me | H | H | Me | Me | Gb |
| CH₂CO₂Me | H | H | H | CF₃ | Gb |
| CH₂CO₂Me | H | H | H | CH₂F | Gb |
| CH₂CO₂Me | H | H | H | CH₂Cl | Gb |
| CH₂CO₂Me | H | H | H | CH₂Br | Gb |
| CH₂CO₂Me | H | H | H | CH₂I | Gb |
| CH₂CO₂Me | H | H | H | CH₂OMe | Gb |
| CH₂CO₂Me | H | H | H | CH₂OEt | Gb |
| CH₂CO₂Et | H | H | H | H | Ga |
| CH₂CO₂Et | H | H | H | Me | Ga |
| CH₂CO₂Et | H | H | H | Et | Ga |
| CH₂CO₂Et | H | H | H | Pr-n | Gb |
| CH₂CO₂Et | Me | H | H | H | Ga |
| CH₂CO₂Et | H | Me | H | H | Ga |
| CH₂CO₂Et | Me | H | H | Me | Gb |
| CH₂CO₂Et | Me | Me | H | Me | Gb |
| CH₂CO₂Et | H | H | Me | Me | Gb |
| CH₂CO₂Pr-n | H | H | H | H | Ga |
| CH₂CO₂Pr-n | H | H | H | Me | Ga |
| CH₂CO₂Pr-n | H | H | H | Et | Ga |
| CH₂CO₂Pr-n | H | H | H | Pr-n | Gb |
| CH₂CO₂Pr-n | Me | H | H | H | Ga |
| CH₂CO₂Pr-n | H | Me | H | H | Ga |
| CH₂CO₂Pr-n | Me | H | H | Me | Gb |
| CH₂CO₂Pr-n | Me | Me | H | Me | Gb |
| CH₂CO₂Pr-n | H | H | Me | Me | Gb |
| CH₂COMe | H | H | H | H | Ga |
| CH₂COMe | H | H | H | Me | Ga |
| CH₂COMe | H | H | H | Et | Ga |
| CH₂COMe | H | H | H | Pr-n | Gb |
| CH₂COMe | Me | H | H | H | Ga |
| CH₂COMe | H | Me | H | H | Ga |
| CH₂COMe | Me | H | H | Me | Gb |
| CH₂COMe | Me | Me | H | Me | Gb |
| CH₂COMe | H | H | Me | Me | Gb |
| CH₂COMe | H | H | H | CF₃ | Gb |
| CH₂COMe | H | H | H | CH₂F | Gb |
| CH₂COMe | H | H | H | CH₂Cl | Gb |
| CH₂COMe | H | H | H | CH₂Br | Gb |
| CH₂COMe | H | H | H | CH₂I | Gb |
| CH₂COMe | H | H | H | CH₂OMe | Gb |
| CH₂COMe | H | H | H | CH₂OEt | Gb |

TABLE 8-continued

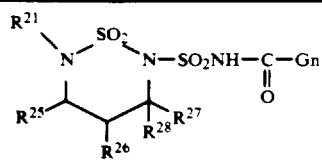

| R21 | R25 | R26 | R27 | R28 | Gn |
|---|---|---|---|---|---|
| $CH_2COEt$ | H | H | H | H | Ga |
| $CH_2COEt$ | H | H | H | Me | Ga |
| $CH_2COEt$ | H | H | H | Et | Ga |
| $CH_2COEt$ | H | H | H | Pr-n | Gb |
| $CH_2COEt$ | Me | H | H | H | Ga |
| $CH_2COEt$ | H | Me | H | H | Ga |
| $CH_2COEt$ | Me | H | H | Me | Gb |
| $CH_2COEt$ | Me | Me | H | Me | Gb |
| $CH_2COEt$ | H | H | Me | Me | Gb |
| $CH_2COEt$ | H | H | H | $CF_3$ | Gb |
| $CH_2COEt$ | H | H | H | $CH_2F$ | Gb |
| $CH_2COEt$ | H | H | H | $CH_2Cl$ | Gb |
| $CH_2COEt$ | H | H | H | $CH_2Br$ | Gb |
| $CH_2COEt$ | H | H | H | $CH_2I$ | Gb |
| $CH_2COEt$ | H | H | H | $CH_2OMe$ | Gb |
| $CH_2COEt$ | H | H | H | $CH_2OEt$ | Gb |
| Ph | H | H | H | H | Ga |
| $PhCH_2$ | H | H | H | H | Gb |
| Ph | H | H | H | Me | Ga |
| $PhCH_2$ | H | H | H | Me | Gb |
| Me | H | H | H | Ph | Ga |
| Me | H | H | H | $PhCH_2$ | Gb |
| Me | H | H | H | Cl | Gb |
| Me | H | H | H | $CH_2=CHCH_2$ | Ga |
| Me | H | H | H | $CH\equiv CCH_2$ | Ga |

TABLE 9

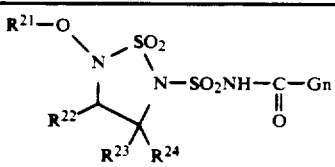

| R21 | R22 | R23 | R24 | Gn |
|---|---|---|---|---|
| Me | H | H | H | Ga |
| Me | H | H | Me | Ga |
| Me | H | H | Et | Gb |
| Me | H | H | Pr-n | Gb |
| Me | H | H | Pr-i | Gb |
| Me | H | H | Bu-n | Gc |
| Me | Me | H | H | Ga |
| Me | Et | H | H | Gb |
| Me | Me | H | Me | Gb |
| Me | Me | H | Et | Gb |
| Me | H | Me | Me | Ga |
| Me | H | Me | Et | Gb |
| Me | H | H | F | Ga |
| Me | H | H | Cl | Ga |
| Me | H | H | Br | Gb |
| Me | H | H | I | Gb |
| Me | H | H | $CF_3$ | Ga |
| Me | H | H | $CH_2F$ | Ga |
| Me | H | H | $CH_2Cl$ | Ga |
| Me | H | H | $CH_2Br$ | Gb |
| Me | H | H | $CH_2I$ | Gb |
| Me | H | H | $CH_2CH_2F$ | Ga |
| Me | H | H | $CH_2CH_2Cl$ | Ga |
| Me | H | H | $CH_2CH_2Br$ | Gb |
| Me | H | H | $CH_2CH_2I$ | Gb |
| Me | H | H | $CH(CH_3)CH_2F$ | Ga |
| Me | H | H | $CH(CH_3)CH_2Cl$ | Ga |
| Me | H | H | $CH(CH_3)CH_2Br$ | Gb |
| Me | H | H | $CH(CH_3)CH_2I$ | Gb |
| Me | H | H | $CH_2OMe$ | Ga |
| Me | H | H | $CH_2OEt$ | Ga |
| Me | H | H | $CH_2CH_2OMe$ | Ga |
| Me | H | H | $CH_2CH_2OEt$ | Ga |

TABLE 9-continued

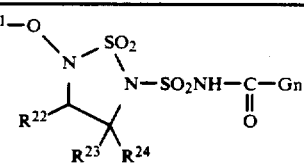

| R21 | R22 | R23 | R24 | Gn |
|---|---|---|---|---|
| Me | H | H | $CH(CH_3)CH_2OMe$ | Gb |
| Me | H | H | $CH(CH_3)CH_2OEt$ | Gb |
| Me | H | H | $CH_2OCH_2CH=CH_2$ | Ga |
| Me | H | H | $CH_2OCH_2C\equiv CH$ | Ga |
| Me | H | H | $CH_2OCHF_2$ | Ga |
| Me | H | H | $CH_2OCF_3$ | Ga |
| Me | H | H | $CH_2SMe$ | Ga |
| Me | H | H | $CH_2SEt$ | Ga |
| Me | H | H | $CH_2SO_2Me$ | Ga |
| Me | H | H | $CH_2SO_2Et$ | Ga |
| Me | H | H | $CH_2CF_3$ | Ga |
| Me | H | H | $CH_2CN$ | Ga |
| Me | H | H | $CO_2Me$ | Ga |
| Me | H | H | $CO_2Et$ | Ga |
| Me | H | H | $CO_2Pr-n$ | Gb |
| Me | H | H | $CH_2CO_2Me$ | Ga |
| Me | H | H | $CH_2CO_2Et$ | Ga |
| Me | H | H | $CH_2CO_2Pr-n$ | Gb |
| Me | H | H | COMe | Ga |
| Me | H | H | COEt | Ga |
| Me | H | H | COPr-n | Gb |
| Me | H | H | $CH_2COMe$ | Ga |
| Me | H | H | $CH_2COEt$ | Ga |
| Et | H | H | H | Ga |
| Et | H | H | Me | Ga |
| Et | H | H | Et | Gb |
| Et | H | H | Pr-n | Gb |
| Et | H | H | Pr-i | Gb |
| Et | H | H | Bu-n | Gc |
| Et | Me | H | H | Ga |
| Et | Et | H | H | Gb |
| Et | Me | H | Me | Gb |
| Et | Me | H | Et | Gb |

TABLE 9-continued

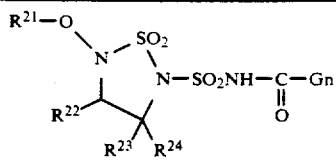

| R21 | R22 | R23 | R24 | Gn |
|---|---|---|---|---|
| Et | H | Me | Me | Ga |
| Et | H | Me | Et | Gb |
| Et | H | H | F | Ga |
| Et | H | H | Cl | Ga |
| Et | H | H | Br | Gb |
| Et | H | H | I | Gb |
| Et | H | H | CF$_3$ | Ga |
| Et | H | H | CH$_2$F | Ga |
| Et | H | H | CH$_2$Cl | Ga |
| Et | H | H | CH$_2$Br | Gb |
| Et | H | H | CH$_2$I | Gb |
| Et | H | H | CH$_2$CH$_2$F | Ga |
| Et | H | H | CH$_2$CH$_2$Cl | Ga |
| Et | H | H | CH$_2$CH$_2$Br | Gb |
| Et | H | H | CH$_2$CH$_2$I | Gb |
| Et | H | H | CH(CH$_3$)CH$_2$F | Ga |
| Et | H | H | CH(CH$_3$)CH$_2$Cl | Ga |
| Et | H | H | CH(CH$_3$)CH$_2$Br | Gb |
| Et | H | H | CH(CH$_3$)CH$_2$I | Gb |
| Et | H | H | CH$_2$OMe | Ga |
| Et | H | H | CH$_2$OEt | Ga |
| Et | H | H | CH$_2$CH$_2$OMe | Ga |
| Et | H | H | CH$_2$CH$_2$OEt | Ga |
| Et | H | H | CH(CH$_3$)CH$_2$OMe | Gb |
| Et | H | H | CH(CH$_3$)CH$_2$OEt | Gb |
| Et | H | H | CH$_2$OCH$_2$CH=CH$_2$ | Ga |
| Et | H | H | CH$_2$OCH$_2$C≡CH | Ga |
| Et | H | H | CH$_2$OCHF$_2$ | Ga |
| Et | H | H | CH$_2$OCF$_3$ | Ga |
| Et | H | H | CH$_2$SMe | Ga |
| Et | H | H | CH$_2$SEt | Ga |
| Et | H | H | CH$_2$SO$_2$Me | Ga |
| Et | H | H | CH$_2$SO$_2$Et | Ga |
| Et | H | H | CH$_2$CF$_3$ | Ga |
| Et | H | H | CH$_2$CN | Ga |
| Et | H | H | CO$_2$Me | Ga |
| Et | H | H | CO$_2$Et | Ga |
| Et | H | H | CO$_2$Pr-n | Gb |
| Et | H | H | CH$_2$CO$_2$Me | Ga |
| Et | H | H | CH$_2$CO$_2$Et | Ga |
| Et | H | H | CH$_2$CO$_2$Pr-n | Gb |
| Et | H | H | COMe | Ga |
| Et | H | H | COEt | Ga |
| Et | H | H | COPr-n | Gb |
| Et | H | H | CH$_2$COMe | Ga |
| Et | H | H | CH$_2$COEt | Ga |
| Pr-n | H | H | H | Ga |
| Pr-n | H | H | Me | Gb |
| Pr-n | H | H | Et | Gb |
| Pr-n | Me | H | H | Ga |
| Pr-n | Et | H | H | Gb |
| Pr-n | Me | H | Me | Gb |
| Pr-n | Me | H | Et | Gb |
| Pr-n | H | Me | Me | Ga |
| Pr-n | H | Me | Et | Gb |
| Pr-n | H | H | CF$_3$ | Ga |
| Pr-n | H | H | CH$_2$F | Ga |
| Pr-n | H | H | CH$_2$Cl | Ga |
| Pr-n | H | H | CH$_2$Br | Gb |
| Pr-n | H | H | CH$_2$I | Gb |
| Pr-n | H | H | CH$_2$OMe | Ga |
| Pr-n | H | H | CH$_2$OEt | Ga |
| Pr-n | H | H | CH$_2$OCH$_2$CH=CH$_2$ | Ga |
| Pr-n | H | H | CH$_2$OCH$_2$C≡CH | Ga |
| Pr-n | H | H | CH$_2$OCHF$_2$ | Ga |
| Pr-n | H | H | CH$_2$OCF$_3$ | Ga |
| Pr-n | H | H | CH$_2$SMe | Ga |
| Pr-n | H | H | CH$_2$SEt | Ga |
| Pr-n | H | H | CH$_2$SO$_2$Me | Ga |
| Pr-n | H | H | CH$_2$SO$_2$Et | Ga |
| Pr-n | H | H | CH$_2$CF$_3$ | Ga |
| Pr-n | H | H | CH$_2$CN | Ga |
| Pr-n | H | H | CO$_2$Me | Ga |
| Pr-n | H | H | CO$_2$Et | Ga |
| Pr-n | H | H | CH$_2$CO$_2$Me | Ga |
| Pr-n | H | H | CH$_2$CO$_2$Et | Ga |
| Pr-n | H | H | COMe | Ga |
| Pr-n | H | H | COEt | Ga |
| Pr-n | H | H | CH$_2$COMe | Ga |
| Pr-n | H | H | CH$_2$COEt | Ga |
| Pr-i | H | H | H | Ga |
| Pr-i | H | H | Me | Gb |
| Pr-i | H | H | Et | Gb |
| Pr-i | Me | H | H | Ga |
| Pr-i | Et | H | H | Gb |
| Pr-i | Me | H | Me | Gb |
| Pr-i | Me | H | Et | Gb |
| Pr-i | H | Me | Me | Ga |
| Pr-i | H | Me | Et | Gb |
| Pr-i | H | H | CF$_3$ | Ga |
| Pr-i | H | H | CH$_2$F | Ga |
| Pr-i | H | H | CH$_2$Cl | Ga |
| Pr-i | H | H | CH$_2$Br | Gb |
| Pr-i | H | H | CH$_2$I | Gb |
| Pr-i | H | H | CH$_2$OMe | Ga |
| Pr-i | H | H | CH$_2$OEt | Ga |
| Pr-i | H | H | CH$_2$OCH$_2$CH=CH$_2$ | Ga |
| Pr-i | H | H | CH$_2$OCH$_2$C≡CH | Ga |
| Pr-i | H | H | CH$_2$OCHF$_2$ | Ga |
| Pr-i | H | H | CH$_2$OCF$_3$ | Ga |
| Pr-i | H | H | CH$_2$SMe | Ga |
| Pr-i | H | H | CH$_2$SEt | Ga |
| Pr-i | H | H | CH$_2$SO$_2$Me | Ga |
| Pr-i | H | H | CH$_2$SO$_2$Et | Ga |
| Pr-i | H | H | CH$_2$CF$_3$ | Ga |
| Pr-i | H | H | CH$_2$CN | Ga |
| Pr-i | H | H | CO$_2$Me | Ga |
| Pr-i | H | H | CO$_2$Et | Ga |
| Pr-i | H | H | CH$_2$CO$_2$Me | Ga |
| Pr-i | H | H | CH$_2$CO$_2$Et | Ga |
| Pr-i | H | H | COMe | Ga |
| Pr-i | H | H | COEt | Ga |
| Pr-i | H | H | CH$_2$COMe | Ga |
| Pr-i | H | H | CH$_2$COEt | Ga |
| Bu-n | H | H | H | Ga |
| Bu-n | H | H | Me | Gb |
| Bu-n | Me | H | H | Ga |
| Bu-n | Me | H | Me | Gb |
| Bu-n | H | Me | Me | Ga |
| Bu-n | H | H | CF$_3$ | Ga |
| Bu-n | H | H | CH$_2$F | Ga |
| Bu-n | H | H | CH$_2$Cl | Ga |
| Bu-n | H | H | CH$_2$Br | Gb |
| Bu-n | H | H | CH$_2$I | Gb |
| Bu-n | H | H | CH$_2$OMe | Ga |
| Bu-n | H | H | CH$_2$OCH$_2$CH=CH$_2$ | Ga |
| Bu-n | H | H | CH$_2$OCH$_2$C≡CH | Ga |
| Bu-n | H | H | CH$_2$OCHF$_2$ | Ga |
| Bu-n | H | H | CH$_2$OCF$_3$ | Ga |
| Bu-n | H | H | CH$_2$SMe | Ga |
| Bu-n | H | H | CH$_2$SO$_2$Me | Ga |
| Bu-n | H | H | CH$_2$CF$_3$ | Ga |
| Bu-n | H | H | CH$_2$CN | Ga |
| Bu-n | H | H | CO$_2$Me | Ga |
| Bu-n | H | H | CH$_2$CO$_2$Me | Ga |
| Bu-n | H | H | COMe | Ga |
| Bu-n | H | H | CH$_2$COMe | Ga |
| CH$_2$CH=CH$_2$ | H | H | H | Ga |
| CH$_2$CH=CH$_2$ | H | H | Me | Gb |
| CH$_2$CH=CH$_2$ | H | H | Et | Gb |
| CH$_2$CH=CH$_2$ | Me | H | H | Ga |
| CH$_2$CH=CH$_2$ | Et | H | H | Gb |
| CH$_2$CH=CH$_2$ | Me | H | Me | Gb |
| CH$_2$CH=CH$_2$ | Me | H | Et | Gb |

TABLE 9-continued

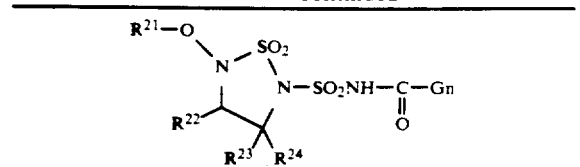

| $R^{21}$ | $R^{22}$ | $R^{23}$ | $R^{24}$ | Gn |
|---|---|---|---|---|
| CH₂CH=CH₂ | H | Me | Me | Ga |
| CH₂CH=CH₂ | H | Me | Et | Gb |
| CH₂CH=CH₂ | H | H | CF₃ | Ga |
| CH₂CH=CH₂ | H | H | CH₂F | Ga |
| CH₂CH=CH₂ | H | H | CH₂Cl | Ga |
| CH₂CH=CH₂ | H | H | CH₂Br | Gb |
| CH₂CH=CH₂ | H | H | CH₂I | Gb |
| CH₂CH=CH₂ | H | H | CH₂OMe | Ga |
| CH₂CH=CH₂ | H | H | CH₂OEt | Ga |
| CH₂CH=CH₂ | H | H | CH₂OCH₂CH=CH₂ | Ga |
| CH₂CH=CH₂ | H | H | CH₂OCH₂C≡CH | Ga |
| CH₂CH=CH₂ | H | H | CH₂OCHF₂ | Ga |
| CH₂CH=CH₂ | H | H | CH₂OCF₃ | Ga |
| CH₂CH=CH₂ | H | H | CH₂SMe | Ga |
| CH₂CH=CH₂ | H | H | CH₂SEt | Ga |
| CH₂CH=CH₂ | H | H | CH₂SO₂Me | Ga |
| CH₂CH=CH₂ | H | H | CH₂SO₂Et | Ga |
| CH₂CH=CH₂ | H | H | CH₂CF₃ | Ga |
| CH₂CH=CH₂ | H | H | CH₂CN | Ga |
| CH₂CH=CH₂ | H | H | CO₂Me | Ga |
| CH₂CH=CH₂ | H | H | CO₂Et | Ga |
| CH₂CH=CH₂ | H | H | CH₂CO₂Me | Ga |
| CH₂CH=CH₂ | H | H | CH₂CO₂Et | Ga |
| CH₂CH=CH₂ | H | H | COMe | Ga |
| CH₂CH=CH₂ | H | H | COEt | Ga |
| CH₂CH=CH₂ | H | H | CH₂COMe | Ga |
| CH₂CH=CH₂ | H | H | CH₂COEt | Ga |
| CH₂C≡CH | H | H | H | Ga |
| CH₂C≡CH | H | H | Me | Gb |
| CH₂C≡CH | H | H | Et | Gb |
| CH₂C≡CH | Me | H | H | Ga |
| CH₂C≡CH | Et | H | H | Gb |
| CH₂C≡CH | Me | H | Me | Gb |
| CH₂C≡CH | Me | H | Et | Gb |
| CH₂C≡CH | H | Me | Me | Ga |
| CH₂C≡CH | H | H | F | Ga |
| CH₂C≡CH | H | Me | Et | Gb |
| CH₂C≡CH | H | H | CF₃ | Ga |
| CH₂C≡CH | H | H | CH₂F | Ga |
| CH₂C≡CH | H | H | CH₂Cl | Ga |
| CH₂C≡CH | H | H | CH₂Br | Gb |
| CH₂C≡CH | H | H | CH₂I | Gb |
| CH₂C≡CH | H | H | CH₂OMe | Ga |
| CH₂C≡CH | H | H | CH₂OEt | Ga |
| CH₂C≡CH | H | H | CH₂OCH₂CH=CH₂ | Ga |
| CH₂C≡CH | H | H | CH₂OCH₂C≡CH | Ga |
| CH₂C≡CH | H | H | CH₂OCHF₂ | Ga |
| CH₂C≡CH | H | H | CH₂OCF₃ | Ga |
| CH₂C≡CH | H | H | CH₂SMe | Ga |
| CH₂C≡CH | H | H | CH₂SEt | Ga |
| CH₂C≡CH | H | H | CH₂SO₂Me | Ga |
| CH₂C≡CH | H | H | CH₂SO₂Et | Ga |
| CH₂C≡CH | H | H | CH₂CF₃ | Ga |
| CH₂C≡CH | H | H | CH₂CN | Ga |
| CH₂C≡CH | H | H | CO₂Me | Ga |
| CH₂C≡CH | H | H | CO₂Et | Ga |
| CH₂C≡CH | H | H | CH₂CO₂Me | Ga |
| CH₂C≡CH | H | H | CH₂CO₂Et | Ga |
| CH₂C≡CH | H | H | COMe | Ga |
| CH₂C≡CH | H | H | COEt | Ga |
| CH₂C≡CH | H | H | CH₂COMe | Ga |
| CH₂C≡CH | H | H | CH₂COEt | Ga |

TABLE 10

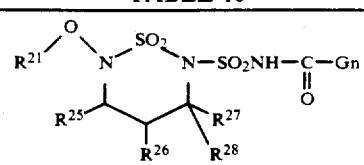

| $R^{21}$ | $R^{25}$ | $R^{26}$ | $R^{27}$ | $R^{28}$ | Gn |
|---|---|---|---|---|---|
| Me | H | H | H | H | Ga |
| Me | H | H | H | Me | Ga |
| Me | H | H | H | Et | Ga |
| Me | H | H | H | Pr-n | Gb |
| Me | Me | H | H | H | Ga |
| Me | H | Me | H | H | Ga |
| Me | Me | H | H | Me | Gb |
| Me | Me | Me | H | Me | Gb |
| Me | H | H | Me | Me | Gb |
| Me | H | H | H | CF₃ | Gb |
| Me | H | H | H | CH₂F | Gb |
| Me | H | H | H | CH₂Cl | Gb |
| Me | H | H | H | CH₂Br | Gb |
| Me | H | H | H | CH₂I | Gb |
| Me | H | H | H | CH₂OMe | Gb |
| Me | H | H | H | CH₂OEt | Gb |
| Me | H | H | H | CH₂OCH₂CH=CH₂ | Gb |
| Me | H | H | H | CH₂OCH₂C≡CH | Gb |
| Me | H | H | H | CH₂SMe | Gb |
| Me | H | H | H | CH₂SO₂Me | Gb |
| Me | H | H | H | CH₂CN | Gb |
| Me | H | H | H | CO₂Me | Gb |
| Me | H | H | H | CO₂Et | Gb |
| Me | H | H | H | COMe | Gb |
| Me | H | H | H | COEt | Gb |
| Me | H | H | H | CH₂CO₂Me | Gb |
| Me | H | H | H | CH₂CO₂Et | Gb |
| Me | H | H | H | CH₂COMe | Gb |
| Me | H | H | H | CH₂COEt | Gb |
| Et | H | H | H | H | Ga |
| Et | H | H | H | Me | Ga |
| Et | H | H | H | Et | Ga |
| Et | H | H | H | Pr-n | Gb |
| Et | Me | H | H | H | Ga |
| Et | H | Me | H | H | Ga |
| Et | Me | H | H | Me | Gb |
| Et | Me | Me | H | Me | Gb |
| Et | H | H | Me | Me | Gb |
| Et | H | H | H | CF₃ | Gb |
| Et | H | H | H | CH₂F | Gb |
| Et | H | H | H | CH₂Cl | Gb |
| Et | H | H | H | CH₂Br | Gb |
| Et | H | H | H | CH₂I | Gb |
| Et | H | H | H | CH₂OMe | Gb |
| Et | H | H | H | CH₂OEt | Gb |
| Et | H | H | H | CH₂CN | Gb |
| Et | H | H | H | COMe | Gb |
| Et | H | H | H | COEt | Gb |
| Et | H | H | H | CH₂CO₂Me | Gb |
| Et | H | H | H | CH₂CO₂Et | Gb |
| Et | H | H | H | CH₂COMe | Gb |
| Et | H | H | H | CH₂COEt | Gb |
| Pr-n | H | H | H | H | Ga |
| Pr-n | H | H | H | Me | Ga |
| Pr-n | H | H | H | Et | Ga |
| Pr-n | H | H | H | Pr-n | Gb |
| Pr-n | Me | H | H | H | Ga |
| Pr-n | H | Me | H | H | Ga |
| Pr-n | Me | H | H | Me | Gb |
| Pr-n | Me | Me | H | Me | Gb |
| Pr-n | H | H | Me | Me | Gb |
| Pr-n | H | H | H | CF₃ | Gb |
| Pr-n | H | H | H | CH₂F | Gb |
| Pr-n | H | H | H | CH₂Cl | Gb |
| Pr-n | H | H | H | CH₂Br | Gb |
| Pr-n | H | H | H | CH₂I | Gb |
| Pr-n | H | H | H | CH₂OMe | Gb |
| Pr-n | H | H | H | CH₂OEt | Gb |
| Pr-i | H | H | H | H | Ga |
| Pr-i | H | H | H | Me | Ga |
| Pr-i | H | H | H | Et | Ga |
| Pr-i | H | H | H | Pr-n | Gb |

TABLE 10-continued

Structure: $R^{21}$-O-N(SO$_2$)-N(SO$_2$NH-C(=O)-Gn) ring with $R^{25}$, $R^{26}$, $R^{27}$, $R^{28}$ substituents

| $R^{21}$ | $R^{25}$ | $R^{26}$ | $R^{27}$ | $R^{28}$ | Gn |
|---|---|---|---|---|---|
| Pr-i | Me | H | H | H | Ga |
| Pr-i | H | Me | H | H | Ga |
| Pr-i | Me | H | H | Me | Gb |
| Pr-i | Me | Me | H | Me | Gb |
| Pr-i | H | H | Me | Me | Gb |
| Bu-n | H | H | H | H | Ga |
| Bu-n | H | H | H | Me | Ga |
| Bu-n | H | H | H | Et | Ga |
| Bu-n | H | H | H | Pr-n | Gb |
| CH$_2$CH=CH$_2$ | H | H | H | H | Ga |
| CH$_2$CH=CH$_2$ | H | H | H | Me | Ga |
| CH$_2$CH=CH$_2$ | H | H | H | Et | Ga |
| CH$_2$CH=CH$_2$ | H | H | H | Pr-n | Gb |
| CH$_2$CH=CH$_2$ | Me | H | H | H | Ga |
| CH$_2$CH=CH$_2$ | H | Me | H | H | Ga |
| CH$_2$CH=CH$_2$ | Me | H | H | Me | Gb |
| CH$_2$CH=CH$_2$ | Me | Me | H | Me | Gb |
| CH$_2$CH=CH$_2$ | H | H | Me | Me | Gb |
| CH$_2$C≡CH | H | H | H | H | Ga |
| CH$_2$C≡CH | H | H | H | Me | Ga |
| CH$_2$C≡CH | H | H | H | Et | Ga |
| CH$_2$C≡CH | H | H | H | Pr-n | Gb |
| CH$_2$C≡CH | Me | H | H | H | Ga |
| CH$_2$C≡CH | H | Me | H | H | Ga |
| CH$_2$C≡CH | Me | H | H | Me | Gb |
| CH$_2$C≡CH | Me | Me | H | Me | Gb |
| CH$_2$C≡CH | H | H | Me | Me | Gb |

TABLE 11

Structure: $R^{21}$-N(SO$_2$)-N(SO$_2$NH-C(=S)-Gn) ring with $R^{22}$, $R^{23}$, $R^{24}$ substituents

| $R^{21}$ | $R^{22}$ | $R^{23}$ | $R^{24}$ | Gn |
|---|---|---|---|---|
| Me | H | H | H | Gc |
| Me | H | H | Me | Gc |
| Me | H | H | Et | Gc |
| Me | Me | H | H | Gc |
| Me | Et | H | H | Gc |
| Me | Me | H | Me | Gc |
| Me | H | Me | Me | Gc |
| Et | H | H | H | Gc |
| Et | H | H | Me | Gc |
| Et | H | H | Et | Gc |
| Et | Me | H | H | Gc |
| Et | H | Me | Me | Gc |

TABLE 12

Structure: $R^{21}$-N(SO$_2$)-N(SO$_2$NH-C(=S)-Gn) ring with $R^{25}$, $R^{26}$, $R^{27}$, $R^{28}$ substituents

| $R^{21}$ | $R^{25}$ | $R^{26}$ | $R^{27}$ | $R^{28}$ | Gn |
|---|---|---|---|---|---|
| Me | H | H | H | H | Gc |
| Me | H | H | H | Me | Gc |
| Me | H | H | H | Et | Gc |
| Me | Me | H | H | H | Gc |
| Me | H | Me | H | H | Gc |
| Me | H | H | Me | Me | Gc |

TABLE 12-continued

| $R^{21}$ | $R^{25}$ | $R^{26}$ | $R^{27}$ | $R^{28}$ | Gn |
|---|---|---|---|---|---|
| Me | Me | H | H | Me | Gc |
| Et | H | H | H | H | Gc |
| Et | H | H | Me | Me | Gc |
| Et | Me | H | H | H | Gc |
| Et | H | H | H | Me | Gc |

TABLE 13

Structure: $R^{21}$-O-N(SO$_2$)-N(SO$_2$NH-C(=O)-Gn) ring with $R^{22}$, $R^{23}$, $R^{24}$ substituents

| $R^{21}$ | $R^{22}$ | $R^{23}$ | $R^{24}$ | Gn |
|---|---|---|---|---|
| Me | H | H | H | Gc |
| Me | H | H | Me | Gc |
| Me | H | H | Et | Gc |
| Me | Me | H | H | Gc |
| Me | Et | H | H | Gc |
| Me | Me | H | Me | Gc |
| Me | H | Me | Me | Gc |
| Et | H | H | H | Gc |
| Et | H | H | Me | Gc |
| Et | H | H | Et | Gc |
| Et | Me | H | H | Gc |
| Et | H | Me | Me | Gc |

TABLE 14

Structure: $R^{21}$-O-N(SO$_2$)-N(SO$_2$NH-C(=S)-Gn) ring with $R^{25}$, $R^{26}$, $R^{27}$, $R^{28}$ substituents

| $R^{21}$ | $R^{25}$ | $R^{26}$ | $R^{27}$ | $R^{28}$ | Gn |
|---|---|---|---|---|---|
| Me | H | H | H | H | Gc |
| Me | H | H | H | Me | Gc |
| Me | H | H | H | Et | Gc |
| Me | Me | H | H | H | Gc |
| Me | H | Me | H | H | Gc |
| Me | H | H | Me | Me | Gc |
| Me | Me | H | H | Me | Gc |
| Et | H | H | H | H | Gc |
| Et | H | H | H | Me | Gc |
| Et | Me | H | H | H | Gc |
| Et | H | H | Me | Me | Gc |

TABLE 1A

Structure: $R^{11}$-N(SO$_2$N$R^{12}R^{13}$)(SO$_2$NH-C(=O)-Gn)

| $R^{11}$ | $R^{12}$ | $R^{13}$ | Gn |
|---|---|---|---|
| Me | Me | Me | G$_1$ |
| Me | Me | Me | G$_3$ |
| Me | Me | Me | G$_5$ |

TABLE 1A-continued

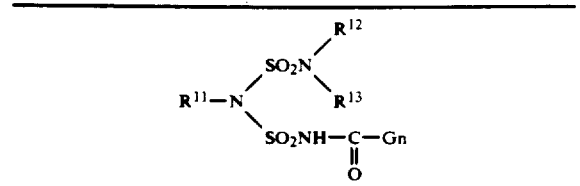

| $R^{11}$ | $R^{12}$ | $R^{13}$ | Gn |
|---|---|---|---|
| Me | Me | Me | $G_6$ |
| Me | Me | Me | $G_7$ |
| Me | Me | Me | $G_8$ |
| Me | Me | Me | $G_{11}$ |
| Me | Me | Me | $G_{12}$ |
| Me | Me | Me | $G_{13}$ |
| Me | Me | Me | $G_{14}$ |
| Me | Me | Me | $G_{15}$ |
| Me | Me | Me | $G_{16}$ |
| Me | Me | Me | $G_{19}$ |
| Me | Me | Me | $G_{20}$ |
| Me | Me | Me | $G_{23}$ |
| Me | Me | Me | $G_{25}$ |
| Me | Me | Me | $G_{26}$ |
| Me | Me | Me | $G_{27}$ |
| Me | Me | Me | $G_{29}$ |
| Me | Me | Me | $G_{31}$ |
| Me | Me | Me | $G_{34}$ |
| Me | Me | Me | $G_{36}$ |
| Me | Me | Me | $G_{39}$ |
| Me | Me | Me | $G_{41}$ |
| Me | Me | Me | $G_{42}$ |
| Me | Me | Me | $G_{44}$ |
| Me | Me | Me | $G_{99}$ |
| Me | Me | Me | $G_{100}$ |
| Me | Me | Me | $G_{103}$ |
| Me | Me | Me | $G_{116}$ |
| Me | Me | Me | $G_{117}$ |
| Me | Me | Me | $G_{120}$ |
| Me | Me | Me | $G_{121}$ |
| Me | Me | Me | $G_{122}$ |
| Me | Me | Me | $G_{123}$ |
| Me | Me | Me | $G_{124}$ |
| Me | Me | Me | $G_{125}$ |
| Me | Me | Me | $G_{126}$ |
| Me | Me | Me | $G_{129}$ |
| Me | Me | Me | $G_{132}$ |
| Me | Me | Me | $G_{144}$ |
| Me | Me | Me | $G_{180}$ |
| Me | Me | Me | $G_{181}$ |
| Me | Me | Me | $G_{189}$ |
| Me | Me | Me | $G_{190}$ |
| Me | Me | Me | $G_{192}$ |
| Me | Me | Me | $G_{193}$ |
| Me | Me | Me | $G_{194}$ |
| Me | Me | Me | $G_{196}$ |
| Me | Me | Me | $G_{197}$ |
| Me | Me | Me | $G_{198}$ |
| Me | Me | Me | $G_{209}$ |
| Me | Me | Me | $G_{213}$ |
| Me | Me | Me | $G_{214}$ |
| Me | Me | Me | $G_{215}$ |
| Me | Me | Me | $G_{219}$ |
| Me | Me | Me | $G_{220}$ |
| Me | Me | Me | $G_{221}$ |
| Me | Me | Me | $G_{222}$ |
| Me | Me | Me | $G_{224}$ |
| Me | Me | Me | $G_{226}$ |
| Me | Me | Me | $G_{229}$ |
| Me | Me | Me | $G_{232}$ |
| Me | Me | Me | $G_{235}$ |
| Me | Me | Me | $G_{236}$ |
| Me | Me | Me | $G_{238}$ |
| Me | Me | Me | $G_{248}$ |
| Me | Me | Me | $G_{250}$ |
| Me | Me | Me | $G_{259}$ |
| Me | Me | Me | $G_{262}$ |
| Me | Me | Me | $G_{265}$ |
| Me | Me | Me | $G_{267}$ |
| Me | Me | Me | $G_{268}$ |
| Me | Me | Me | $G_{269}$ |
| Me | Me | Me | $G_{270}$ |
| Me | Me | Me | $G_{271}$ |
| Me | Me | Me | $G_{272}$ |
| Me | Me | Me | $G_{273}$ |
| Me | Me | Me | $G_{274}$ |
| Me | Me | Me | $G_{275}$ |
| Me | Me | Me | $G_{276}$ |
| Me | Me | Me | $G_{277}$ |
| Me | Me | Me | $G_{278}$ |
| Me | Me | Me | $G_{280}$ |
| Me | Me | Me | $G_{283}$ |
| Me | Me | Me | $G_{286}$ |
| Me | Me | Me | $G_{289}$ |
| Me | Me | Me | $G_{292}$ |
| Me | Me | Me | $G_{295}$ |
| Me | Me | Me | $G_{296}$ |
| Me | Me | Me | $G_{298}$ |
| Me | Me | Me | $G_{299}$ |
| Me | Me | Me | $G_{301}$ |
| Me | Me | Me | $G_{302}$ |
| Me | Me | Me | $G_{304}$ |
| Me | Me | Me | $G_{305}$ |
| Me | Me | Me | $G_{309}$ |
| Me | Me | Me | $G_{310}$ |
| Me | Me | Me | $G_{311}$ |
| Me | Me | Me | $G_{316}$ |
| Me | Me | Me | $G_{317}$ |
| Me | Me | Me | $G_{319}$ |
| Me | Me | Me | $G_{320}$ |
| Me | Me | Me | $G_{328}$ |
| Me | Me | Me | $G_{329}$ |
| Me | Me | Me | $G_{334}$ |
| Me | Me | Me | $G_{335}$ |
| Me | Me | Me | $G_{343}$ |
| Me | Me | Me | $G_{344}$ |
| Me | Me | Me | $G_{346}$ |
| Me | Me | Me | $G_{347}$ |
| Me | Me | Me | $G_{349}$ |
| Me | Me | Me | $G_{350}$ |
| Me | Me | Me | $G_{352}$ |
| Me | Me | Me | $G_{353}$ |
| Me | Me | Me | $G_{355}$ |
| Me | Me | Me | $G_{356}$ |
| Me | Me | Me | $G_{358}$ |
| Me | Me | Me | $G_{359}$ |
| Me | Me | Me | $G_{364}$ |
| Me | Me | Me | $G_{367}$ |
| Me | Me | Me | $G_{370}$ |
| Me | Me | Me | $G_{373}$ |
| Me | Me | Me | $G_{376}$ |
| Me | Me | Me | $G_{377}$ |
| Me | Me | Me | $G_{382}$ |
| Me | Me | Me | $G_{383}$ |
| Me | Me | Me | $G_{385}$ |
| Me | Me | Me | $G_{386}$ |
| Me | Me | Me | $G_{394}$ |
| Me | Me | Me | $G_{395}$ |
| Me | Me | Me | $G_{403}$ |
| Me | Me | Me | $G_{406}$ |
| Me | Me | Me | $G_{409}$ |
| Me | Me | Me | $G_{415}$ |
| Me | Me | Me | $G_{421}$ |
| Me | Me | Me | $G_{427}$ |
| Me | Me | Me | $G_{430}$ |
| Me | Me | Me | $G_{439}$ |
| Me | Me | Me | $G_{448}$ |
| Me | Me | Me | $G_{451}$ |
| Me | Me | Me | $G_{454}$ |
| Me | Me | Me | $G_{455}$ |
| Me | Me | Me | $G_{457}$ |
| Me | Me | Me | $G_{458}$ |

TABLE 1A-continued

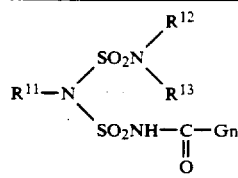

| R[11] | R[12] | R[13] | Gn |
|---|---|---|---|
| Me | Me | Me | G$_{463}$ |
| Me | Me | Me | G$_{464}$ |
| Me | Me | Me | G$_{469}$ |
| Me | Me | Me | G$_{472}$ |
| Me | Me | Me | G$_{475}$ |
| Me | Me | Me | G$_{478}$ |
| Me | Me | Me | G$_{484}$ |
| Me | Me | Me | G$_{498}$ |
| Me | Me | Me | G$_{499}$ |
| Me | Me | Me | G$_{500}$ |
| Me | Me | Me | G$_{501}$ |
| Me | Me | Me | G$_{503}$ |
| Me | Me | Me | G$_{504}$ |
| Me | Me | Me | G$_{505}$ |
| Me | Me | Me | G$_{506}$ |
| Me | Me | Me | G$_{507}$ |
| Me | Me | Me | G$_{508}$ |
| Me | Me | Me | G$_{509}$ |
| Me | Me | Me | G$_{510}$ |
| Me | Me | Me | G$_{511}$ |
| Me | Me | Me | G$_{512}$ |
| Me | Me | Me | G$_{513}$ |
| Me | Me | Me | G$_{514}$ |
| Me | Me | Me | G$_{515}$ |
| Me | Me | Me | G$_{537}$ |
| Me | Me | Me | G$_{538}$ |
| Me | Me | Me | G$_{539}$ |
| Me | Me | Me | G$_{543}$ |
| Me | Me | Me | G$_{544}$ |
| Me | Me | Me | G$_{545}$ |
| Me | Me | Me | G$_{549}$ |
| Me | Me | Me | G$_{550}$ |
| Me | Me | Me | G$_{551}$ |
| Me | Me | Me | G$_{555}$ |
| Me | Me | Me | G$_{556}$ |
| Me | Me | Me | G$_{557}$ |
| Me | Me | Me | G$_{561}$ |
| Me | Me | Me | G$_{562}$ |
| Me | Me | Me | G$_{563}$ |
| Me | Me | Me | G$_{567}$ |
| Me | Me | Me | G$_{568}$ |
| Me | Me | Me | G$_{569}$ |
| Me | Me | Me | G$_{573}$ |
| Me | Me | Me | G$_{574}$ |
| Me | Me | Me | G$_{575}$ |
| Me | Me | Me | G$_{579}$ |
| Me | Me | Me | G$_{580}$ |
| Me | Me | Me | G$_{581}$ |
| Me | Me | Me | G$_{585}$ |
| Me | Me | Me | G$_{586}$ |
| Me | Me | Me | G$_{587}$ |
| Me | Me | Me | G$_{593}$ |
| Me | Me | Me | G$_{598}$ |
| Me | Me | Me | G$_{599}$ |
| Me | Me | Me | G$_{601}$ |
| Me | Me | Me | G$_{606}$ |
| Me | Me | Me | G$_{608}$ |
| Me | Me | Me | G$_{610}$ |
| Me | Me | Me | G$_{611}$ |
| Me | Me | Me | G$_{612}$ |
| Me | Me | Me | G$_{613}$ |
| Me | Me | Me | G$_{614}$ |
| Me | Me | Me | G$_{615}$ |
| Me | Me | Me | G$_{617}$ |
| Me | Me | Me | G$_{618}$ |
| Me | Me | Me | G$_{620}$ |
| Me | Me | Me | G$_{621}$ |
| Me | Me | Me | G$_{622}$ |
| Me | Me | Me | G$_{626}$ |
| Me | Me | Me | G$_{627}$ |
| Me | Me | Me | G$_{628}$ |

TABLE 1A-continued

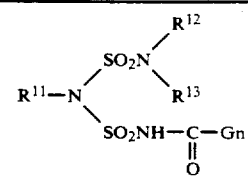

| R[11] | R[12] | R[13] | Gn |
|---|---|---|---|
| Me | Me | Me | G$_{632}$ |
| Me | Me | Me | G$_{633}$ |
| Me | Me | Me | G$_{634}$ |
| Me | Me | Me | G$_{638}$ |
| Me | Me | Me | G$_{639}$ |
| Me | Me | Me | G$_{640}$ |
| Me | Me | Me | G$_{643}$ |
| Me | Me | Et | G$_3$ |
| Me | Me | Et | G$_6$ |
| Me | Me | Et | G$_{268}$ |
| Me | Me | Et | G$_{269}$ |
| Me | Me | Et | G$_{271}$ |
| Me | Me | Et | G$_{272}$ |
| Me | Me | Et | G$_{274}$ |
| Me | Me | Et | G$_{275}$ |
| Me | Me | Et | G$_{277}$ |
| Me | Me | Et | G$_{278}$ |
| Me | Me | Et | G$_{355}$ |
| Me | Me | Ph | G$_3$ |
| Me | Me | Ph | G$_6$ |
| Me | Et | Et | G$_3$ |
| Me | Et | Et | G$_6$ |
| Me | —(CH$_2$)$_4$— | | G$_3$ |
| Me | —(CH$_2$)$_4$— | | G$_6$ |
| Me | —(CH$_2$)$_5$— | | G$_3$ |
| Me | —(CH$_2$)$_5$— | | G$_6$ |
| Et | Me | Me | G$_3$ |
| Et | Me | Me | G$_6$ |
| Et | Me | Me | G$_{268}$ |
| Et | Me | Me | G$_{269}$ |
| Et | Me | Me | G$_{271}$ |
| Et | Me | Me | G$_{272}$ |
| Et | Me | Me | G$_{274}$ |
| Et | Me | Me | G$_{275}$ |
| Et | Me | Me | G$_{277}$ |
| Et | Me | Me | G$_{278}$ |
| Et | Me | Me | G$_{355}$ |
| Et | Me | Et | G$_3$ |
| Et | Me | Et | G$_6$ |
| Et | Me | Ph | G$_3$ |
| Et | Me | Ph | G$_6$ |
| Et | Et | Et | G$_3$ |
| Et | Et | Et | G$_6$ |
| Et | —(CH$_2$)$_4$— | | G$_3$ |
| Et | —(CH$_2$)$_4$— | | G$_6$ |
| Et | —(CH$_2$)$_5$— | | G$_3$ |
| Et | —(CH$_2$)$_5$— | | G$_6$ |
| Pr-n | Me | Me | G$_3$ |
| Pr-n | Me | Me | G$_6$ |
| Pr-i | Me | Me | G$_3$ |
| Pr-i | Me | Me | G$_6$ |
| cyc-Pr | Me | Me | G$_3$ |
| cyc-Pr | Me | Me | G$_6$ |
| cyc-Pr | Me | Me | G$_{268}$ |
| cyc-Pr | Me | Me | G$_{269}$ |
| cyc-Pr | Me | Me | G$_{271}$ |
| cyc-Pr | Me | Me | G$_{272}$ |
| cyc-Pr | Me | Me | G$_{274}$ |
| cyc-Pr | Me | Me | G$_{275}$ |
| cyc-Pr | Me | Me | G$_{277}$ |
| cyc-Pr | Me | Me | G$_{278}$ |
| cyc-Pr | Me | Me | G$_{355}$ |
| cyc-Pr—CH$_2$ | Me | Me | G$_3$ |
| cyc-Pr—CH$_2$ | Me | Me | G$_6$ |
| Bu-n | Me | Me | G$_3$ |
| Bu-n | Me | Me | G$_6$ |
| Bu-sec | Me | Me | G$_3$ |
| Bu-sec | Me | Me | G$_6$ |
| Bu-i | Me | Me | G$_3$ |
| Bu-i | Me | Me | G$_6$ |
| cyc-Bu | Me | Me | G$_3$ |

TABLE 1A-continued $$R^{11}-N\begin{matrix}SO_2N\diagup R^{12}\\ \diagdown R^{13}\\ SO_2NH-\underset{\underset{O}{\|}}{C}-Gn\end{matrix}$$

| $R^{11}$ | $R^{12}$ | $R^{13}$ | Gn |
|---|---|---|---|
| cyc-Bu | Me | Me | $G_6$ |
| Bu-t | Me | Me | $G_3$ |
| Bu-t | Me | Me | $G_6$ |
| $CH_2\!=\!CHCH_2$ | Me | Me | $G_3$ |
| $CH_2\!=\!CHCH_2$ | Me | Me | $G_6$ |
| $CH\!\equiv\!CCH_2$ | Me | Me | $G_3$ |
| $CH\!\equiv\!CCH_2$ | Me | Me | $G_6$ |
| cyc-Pen | Me | Me | $G_3$ |
| cyc-Pen | Me | Me | $G_6$ |
| cyc-Hex | Me | Me | $G_3$ |
| cyc-Hex | Me | Me | $G_6$ |
| $MeOCH_2CH_2$ | Me | Me | $G_3$ |
| $MeOCH_2CH_2$ | Me | Me | $G_6$ |
| $MeOCH_2(CH_3)CH$ | Me | Me | $G_3$ |
| $MeOCH_2(CH_3)CH$ | Me | Me | $G_6$ |
| $CHF_2OCH_2$ | Me | Me | $G_3$ |
| $CHF_2OCH_2$ | Me | Me | $G_6$ |
| $FCH_2$ | Me | Me | $G_3$ |
| $FCH_2$ | Me | Me | $G_6$ |
| $FCH_2CH_2$ | Me | Me | $G_3$ |
| $FCH_2CH_2$ | Me | Me | $G_6$ |
| $ClCH_2CH_2$ | Me | Me | $G_3$ |
| $ClCH_2CH_2$ | Me | Me | $G_6$ |
| $CF_3CH_2$ | Me | Me | $G_3$ |
| $CF_3CH_2$ | Me | Me | $G_6$ |
| $NCCH_2$ | Me | Me | $G_3$ |
| $NCCH_2$ | Me | Me | $G_6$ |
| $MeO_2CCH_2$ | Me | Me | $G_3$ |
| $MeO_2CCH_2$ | Me | Me | $G_6$ |
| $MeO_2CCH_2$ | Me | Me | $G_{268}$ |
| $MeO_2CCH_2$ | Me | Me | $G_{269}$ |
| $MeO_2CCH_2$ | Me | Me | $G_{271}$ |
| $MeO_2CCH_2$ | Me | Me | $G_{272}$ |
| $MeO_2CCH_2$ | Me | Me | $G_{274}$ |
| $MeO_2CCH_2$ | Me | Me | $G_{275}$ |
| $MeO_2CCH_2$ | Me | Me | $G_{277}$ |
| $MeO_2CCH_2$ | Me | Me | $G_{278}$ |
| $MeO_2CCH_2$ | Me | Me | $G_{355}$ |
| $MeCOCH_2$ | Me | Me | $G_3$ |
| $MeCOCH_2$ | Me | Me | $G_6$ |
| $PhCH_2$ | Me | Me | $G_3$ |
| $PhCH_2$ | Me | Me | $G_6$ |
| Ph | Me | Me | $G_3$ |
| Ph | Me | Me | $G_6$ |
| Ph | Me | Me | $G_{268}$ |
| Ph | Me | Me | $G_{269}$ |
| Ph | Me | Me | $G_{271}$ |
| Ph | Me | Me | $G_{272}$ |
| Ph | Me | Me | $G_{274}$ |
| Ph | Me | Me | $G_{275}$ |
| Ph | Me | Me | $G_{277}$ |
| Ph | Me | Me | $G_{278}$ |
| Ph | Me | Me | $G_{355}$ |
| Ph-2-Me | Me | Me | $G_3$ |
| Ph-2-Me | Me | Me | $G_6$ |
| Ph-3-Me | Me | Me | $G_3$ |
| Ph-3-Me | Me | Me | $G_6$ |
| Ph-4-OMe | Me | Me | $G_3$ |
| Ph-4-OMe | Me | Me | $G_6$ |
| Ph-3-OMe | Me | Me | $G_3$ |
| Ph-3-OMe | Me | Me | $G_6$ |
| Ph-2-OMe | Me | Me | $G_3$ |
| Ph-2-OMe | Me | Me | $G_6$ |
| Ph-4-Cl | Me | Me | $G_3$ |
| Ph-4-Cl | Me | Me | $G_6$ |
| Ph-3-Cl | Me | Me | $G_3$ |
| Ph-3-Cl | Me | Me | $G_6$ |
| Ph-2-Cl | Me | Me | $G_3$ |
| Ph-2-Cl | Me | Me | $G_6$ |
| Ph-2,6-$Cl_2$ | Me | Me | $G_3$ |

TABLE 1A-continued $$R^{11}-N\begin{matrix}SO_2N\diagup R^{12}\\ \diagdown R^{13}\\ SO_2NH-\underset{\underset{O}{\|}}{C}-Gn\end{matrix}$$

| $R^{11}$ | $R^{12}$ | $R^{13}$ | Gn |
|---|---|---|---|
| Ph-2,6-$Cl_2$ | Me | Me | $G_6$ |

TABLE 2A $$R^{11}-O-N\begin{matrix}SO_2N\diagup R^{12}\\ \diagdown R^{13}\\ SO_2NH-\underset{\underset{O}{\|}}{C}-Gn\end{matrix}$$

| $R^{11}$ | $R^{12}$ | $R^{13}$ | Gn |
|---|---|---|---|
| Me | Me | Me | $G_3$ |
| Me | Me | Me | $G_6$ |
| Me | Me | Me | $G_{268}$ |
| Me | Me | Me | $G_{269}$ |
| Me | Me | Me | $G_{271}$ |
| Me | Me | Me | $G_{272}$ |
| Me | Me | Me | $G_{274}$ |
| Me | Me | Me | $G_{275}$ |
| Me | Me | Me | $G_{277}$ |
| Me | Me | Me | $G_{278}$ |
| Me | Me | Me | $G_{355}$ |
| Me | Me | Et | $G_3$ |
| Me | Me | Et | $G_6$ |
| Me | Me | Ph | $G_3$ |
| Me | Me | Ph | $G_6$ |
| Et | Me | Me | $G_3$ |
| Et | Me | Me | $G_6$ |
| Et | Me | Me | $G_{268}$ |
| Et | Me | Me | $G_{269}$ |
| Et | Me | Me | $G_{271}$ |
| Et | Me | Me | $G_{272}$ |
| Et | Me | Me | $G_{274}$ |
| Et | Me | Me | $G_{275}$ |
| Et | Me | Me | $G_{277}$ |
| Et | Me | Me | $G_{278}$ |
| Et | Me | Me | $G_{355}$ |
| Pr-n | Me | Me | $G_3$ |
| Pr-n | Me | Me | $G_6$ |
| Pr-i | Me | Me | $G_3$ |
| Pr-i | Me | Me | $G_6$ |
| $CH_2\!=\!CHCH_2$ | Me | Me | $G_3$ |
| $CH_2\!=\!CHCH_2$ | Me | Me | $G_6$ |
| $CH\!\equiv\!CCH_2$ | Me | Me | $G_3$ |
| $CH\!\equiv\!CCH_2$ | Me | Me | $G_6$ |
| $MeOCH_2$ | Me | Me | $G_3$ |
| $MeOCH_2$ | Me | Me | $G_6$ |
| $MeSCH_2$ | Me | Me | $G_3$ |
| $MeSCH_2$ | Me | Me | $G_6$ |
| $MeO_2CCH_2$ | Me | Me | $G_3$ |
| $MeO_2CCH_2$ | Me | Me | $G_6$ |
| Ph | Me | Me | $G_3$ |
| Ph | Me | Me | $G_6$ |
| $PhCH_2$ | Me | Me | $G_3$ |
| $PhCH_2$ | Me | Me | $G_6$ |

TABLE 3A

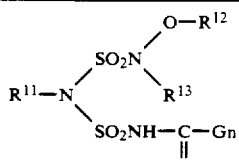

| $R^{11}$ | $R^{12}$ | $R^{13}$ | Gn |
|---|---|---|---|
| Me | Me | Me | $G_3$ |
| Me | Me | Me | $G_6$ |
| Me | Me | Me | $G_{268}$ |
| Me | Me | Me | $G_{269}$ |
| Me | Me | Me | $G_{271}$ |
| Me | Me | Me | $G_{272}$ |
| Me | Me | Me | $G_{274}$ |
| Me | Me | Me | $G_{275}$ |
| Me | Me | Me | $G_{277}$ |
| Me | Me | Me | $G_{278}$ |
| Me | Me | Me | $G_{355}$ |
| Et | Me | Me | $G_3$ |
| Et | Me | Me | $G_6$ |
| Pr-n | Me | Me | $G_3$ |
| Pr-n | Me | Me | $G_6$ |
| cyc-Pr | Me | Me | $G_3$ |
| cyc-Pr | Me | Me | $G_6$ |
| Me | Me | Et | $G_3$ |
| Me | Me | Et | $G_6$ |
| Me | Et | Me | $G_3$ |
| Me | Et | Me | $G_6$ |
| Me | —(CH$_2$)$_3$— | | $G_3$ |
| Me | —(CH$_2$)$_3$— | | $G_6$ |
| Me | —(CH$_2$)$_4$— | | $G_3$ |
| Me | —(CH$_2$)$_4$— | | $G_6$ |

TABLE 4A

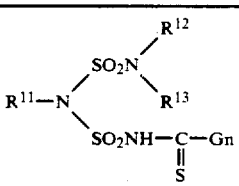

| $R^{11}$ | $R^{12}$ | $R^{13}$ | Gn |
|---|---|---|---|
| Me | Me | Me | $G_3$ |
| Me | Me | Me | $G_6$ |
| Me | Me | Et | $G_3$ |
| Me | Me | Et | $G_6$ |
| Et | Me | Me | $G_3$ |
| Et | Me | Me | $G_6$ |
| Pr-n | Me | Me | $G_3$ |
| Pr-n | Me | Me | $G_6$ |
| CH$_2$=CHCH$_2$ | Me | Me | $G_3$ |
| CH$_2$=CHCH$_2$ | Me | Me | $G_6$ |
| CH≡CCH$_2$ | Me | Me | $G_3$ |
| CH≡CCH$_2$ | Me | Me | $G_6$ |

TABLE 5A

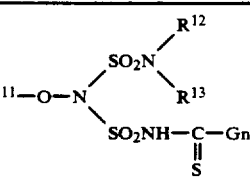

| $R^{11}$ | $R^{12}$ | $R^{13}$ | Gn |
|---|---|---|---|
| Me | Me | Me | $G_3$ |
| Me | Me | Me | $G_6$ |
| Me | Me | Et | $G_3$ |
| Me | Me | Et | $G_6$ |
| Et | Me | Me | $G_3$ |

TABLE 5A-continued

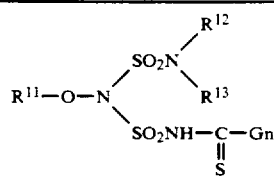

| $R^{11}$ | $R^{12}$ | $R^{13}$ | Gn |
|---|---|---|---|
| Et | Me | Me | $G_6$ |
| Pr-n | Me | Me | $G_3$ |
| Pr-n | Me | Me | $G_6$ |
| CH$_2$=CHCH$_2$ | Me | Me | $G_3$ |
| CH$_2$=CHCH$_2$ | Me | Me | $G_6$ |

TABLE 6A

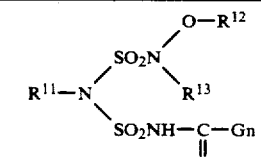

| $R^{11}$ | $R^{12}$ | $R^{13}$ | Gn |
|---|---|---|---|
| Me | Me | Me | $G_3$ |
| Me | Me | Me | $G_6$ |
| Et | Me | Me | $G_3$ |
| Et | Me | Me | $G_6$ |
| cyc-Pr | Me | Me | $G_3$ |
| cyc-Pr | Me | Me | $G_6$ |
| CH$_2$=CHCH$_2$ | Me | Me | $G_3$ |
| CH$_2$=CHCH$_2$ | Me | Me | $G_6$ |
| CH≡CCH$_2$ | Me | Me | $G_3$ |
| CH≡CCH$_2$ | Me | Me | $G_6$ |
| Me | Me | Et | $G_3$ |
| Me | Me | Et | $G_6$ |
| Me | Et | Me | $G_3$ |
| Me | Et | Me | $G_6$ |

TABLE 7A

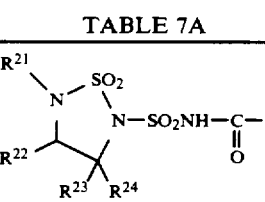

| $R^{21}$ | $R^{22}$ | $R^{23}$ | $R^{24}$ | Gn |
|---|---|---|---|---|
| H | H | H | H | $G_3$ |
| H | H | H | H | $G_6$ |
| Me | H | H | H | $G_3$ |
| Me | H | H | H | $G_6$ |
| Me | H | H | H | $G_{268}$ |
| Me | H | H | H | $G_{269}$ |
| Me | H | H | H | $G_{271}$ |
| Me | H | H | H | $G_{272}$ |
| Me | H | H | H | $G_{274}$ |
| Me | H | H | H | $G_{275}$ |
| Me | H | H | H | $G_{277}$ |
| Me | H | H | H | $G_{278}$ |
| Me | H | H | H | $G_{355}$ |
| Me | H | H | Me | $G_3$ |
| Me | H | H | Me | $G_6$ |
| Me | H | H | Me | $G_{268}$ |
| Me | H | H | Me | $G_{269}$ |
| Me | H | H | Me | $G_{271}$ |
| Me | H | H | Me | $G_{272}$ |
| Me | H | H | Me | $G_{274}$ |
| Me | H | H | Me | $G_{275}$ |
| Me | H | H | Me | $G_{277}$ |
| Me | H | H | Me | $G_{278}$ |

TABLE 7A-continued $$R^{21}-N(-SO_2-)N-SO_2NH-C(=O)-Gn$$
with $R^{22}$, $R^{23}$, $R^{24}$ substituents

| R²¹ | R²² | R²³ | R²⁴ | Gn |
|---|---|---|---|---|
| Me | H | H | Me | G₃₅₅ |
| Me | H | H | Et | G₃ |
| Me | H | H | Et | G₆ |
| Me | H | Me | Me | G₃ |
| Me | H | Me | Me | G₆ |
| Et | H | H | H | G₃ |
| Et | H | H | H | G₆ |
| Et | H | H | H | G₂₆₈ |
| Et | H | H | H | G₂₆₉ |
| Et | H | H | H | G₂₇₁ |
| Et | H | H | H | G₂₇₂ |
| Et | H | H | H | G₂₇₄ |
| Et | H | H | H | G₂₇₅ |
| Et | H | H | H | G₂₇₇ |
| Et | H | H | H | G₂₇₈ |
| Et | H | H | H | G₃₅₅ |
| Pr-n | H | H | H | G₃ |
| Pr-n | H | H | H | G₆ |
| Pr-i | H | H | H | G₃ |
| Pr-i | H | H | H | G₆ |
| Bu-n | H | H | H | G₃ |
| Bu-n | H | H | H | G₆ |
| Bu-t | H | H | H | G₃ |
| Bu-t | H | H | H | G₆ |
| CH₂=CHCH₂ | H | H | H | G₃ |
| CH₂=CHCH₂ | H | H | H | G₆ |
| CH≡CCH₂ | H | H | H | G₃ |
| CH≡CCH₂ | H | H | H | G₆ |
| MeOCH₂ | H | H | H | G₃ |
| MeOCH₂ | H | H | H | G₆ |
| MeO₂CCH₂ | H | H | H | G₃ |
| MeO₂CCH₂ | H | H | H | G₆ |

TABLE 8A $$R^{21}-N(-SO_2-)N-SO_2NH-C(=O)-Gn$$
with $R^{25}$, $R^{26}$, $R^{27}$, $R^{28}$ substituents

| R²¹ | R²⁵ | R²⁶ | R²⁷ | R²⁸ | Gn |
|---|---|---|---|---|---|
| Me | H | H | H | H | G₁ |
| Me | H | H | H | H | G₃ |
| Me | H | H | H | H | G₅ |
| Me | H | H | H | H | G₆ |
| Me | H | H | H | H | G₇ |
| Me | H | H | H | H | G₈ |
| Me | H | H | H | H | G₁₁ |
| Me | H | H | H | H | G₁₂ |
| Me | H | H | H | H | G₁₃ |
| Me | H | H | H | H | G₁₄ |
| Me | H | H | H | H | G₁₅ |
| Me | H | H | H | H | G₁₆ |
| Me | H | H | H | H | G₁₉ |
| Me | H | H | H | H | G₂₀ |
| Me | H | H | H | H | G₂₃ |
| Me | H | H | H | H | G₂₅ |
| Me | H | H | H | H | G₂₆ |
| Me | H | H | H | H | G₂₇ |
| Me | H | H | H | H | G₂₉ |
| Me | H | H | H | H | G₃₁ |
| Me | H | H | H | H | G₃₄ |
| Me | H | H | H | H | G₃₆ |
| Me | H | H | H | H | G₃₉ |
| Me | H | H | H | H | G₄₁ |
| Me | H | H | H | H | G₄₂ |
| Me | H | H | H | H | G₄₄ |

TABLE 8A-continued $$R^{21}-N(-SO_2-)N-SO_2NH-C(=O)-Gn$$
with $R^{25}$, $R^{26}$, $R^{27}$, $R^{28}$ substituents

| R²¹ | R²⁵ | R²⁶ | R²⁷ | R²⁸ | Gn |
|---|---|---|---|---|---|
| Me | H | H | H | H | G₉₉ |
| Me | H | H | H | H | G₁₀₀ |
| Me | H | H | H | H | G₁₀₃ |
| Me | H | H | H | H | G₁₁₆ |
| Me | H | H | H | H | G₁₁₇ |
| Me | H | H | H | H | G₁₂₀ |
| Me | H | H | H | H | G₁₂₁ |
| Me | H | H | H | H | G₁₂₂ |
| Me | H | H | H | H | G₁₂₃ |
| Me | H | H | H | H | G₁₂₄ |
| Me | H | H | H | H | G₁₂₅ |
| Me | H | H | H | H | G₁₂₆ |
| Me | H | H | H | H | G₁₂₉ |
| Me | H | H | H | H | G₁₃₂ |
| Me | H | H | H | H | G₁₄₄ |
| Me | H | H | H | H | G₁₈₀ |
| Me | H | H | H | H | G₁₈₁ |
| Me | H | H | H | H | G₁₈₉ |
| Me | H | H | H | H | G₁₉₀ |
| Me | H | H | H | H | G₁₉₂ |
| Me | H | H | H | H | G₁₉₃ |
| Me | H | H | H | H | G₁₉₄ |
| Me | H | H | H | H | G₁₉₆ |
| Me | H | H | H | H | G₁₉₇ |
| Me | H | H | H | H | G₁₉₈ |
| Me | H | H | H | H | G₂₀₉ |
| Me | H | H | H | H | G₂₁₃ |
| Me | H | H | H | H | G₂₁₄ |
| Me | H | H | H | H | G₂₁₅ |
| Me | H | H | H | H | G₂₁₉ |
| Me | H | H | H | H | G₂₂₀ |
| Me | H | H | H | H | G₂₂₁ |
| Me | H | H | H | H | G₂₂₂ |
| Me | H | H | H | H | G₂₂₄ |
| Me | H | H | H | H | G₂₂₆ |
| Me | H | H | H | H | G₂₂₉ |
| Me | H | H | H | H | G₂₃₂ |
| Me | H | H | H | H | G₂₃₅ |
| Me | H | H | H | H | G₂₃₆ |
| Me | H | H | H | H | G₂₃₈ |
| Me | H | H | H | H | G₂₄₈ |
| Me | H | H | H | H | G₂₅₀ |
| Me | H | H | H | H | G₂₅₉ |
| Me | H | H | H | H | G₂₆₂ |
| Me | H | H | H | H | G₂₆₅ |
| Me | H | H | H | H | G₂₆₇ |
| Me | H | H | H | H | G₂₆₈ |
| Me | H | H | H | H | G₂₆₉ |
| Me | H | H | H | H | G₂₇₀ |
| Me | H | H | H | H | G₂₇₁ |
| Me | H | H | H | H | G₂₇₂ |
| Me | H | H | H | H | G₂₇₃ |
| Me | H | H | H | H | G₂₇₄ |
| Me | H | H | H | H | G₂₇₅ |
| Me | H | H | H | H | G₂₇₆ |
| Me | H | H | H | H | G₂₇₇ |
| Me | H | H | H | H | G₂₇₈ |
| Me | H | H | H | H | G₂₈₀ |
| Me | H | H | H | H | G₂₈₃ |
| Me | H | H | H | H | G₂₈₆ |
| Me | H | H | H | H | G₂₈₉ |
| Me | H | H | H | H | G₂₉₂ |
| Me | H | H | H | H | G₂₉₅ |
| Me | H | H | H | H | G₂₉₆ |
| Me | H | H | H | H | G₂₉₈ |
| Me | H | H | H | H | G₂₉₉ |
| Me | H | H | H | H | G₃₀₁ |
| Me | H | H | H | H | G₃₀₂ |
| Me | H | H | H | H | G₃₀₄ |
| Me | H | H | H | H | G₃₀₅ |
| Me | H | H | H | H | G₃₀₉ |
| Me | H | H | H | H | G₃₁₀ |

TABLE 8A-continued

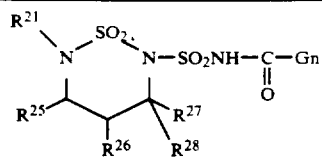

| R21 | R25 | R26 | R27 | R28 | Gn |
|---|---|---|---|---|---|
| Me | H | H | H | H | G311 |
| Me | H | H | H | H | G316 |
| Me | H | H | H | H | G317 |
| Me | H | H | H | H | G320 |
| Me | H | H | H | H | G328 |
| Me | H | H | H | H | G329 |
| Me | H | H | H | H | G334 |
| Me | H | H | H | H | G335 |
| Me | H | H | H | H | G343 |
| Me | H | H | H | H | G344 |
| Me | H | H | H | H | G346 |
| Me | H | H | H | H | G347 |
| Me | H | H | H | H | G349 |
| Me | H | H | H | H | G350 |
| Me | H | H | H | H | G352 |
| Me | H | H | H | H | G353 |
| Me | H | H | H | H | G355 |
| Me | H | H | H | H | G356 |
| Me | H | H | H | H | G358 |
| Me | H | H | H | H | G359 |
| Me | H | H | H | H | G364 |
| Me | H | H | H | H | G367 |
| Me | H | H | H | H | G370 |
| Me | H | H | H | H | G373 |
| Me | H | H | H | H | G376 |
| Me | H | H | H | H | G377 |
| Me | H | H | H | H | G382 |
| Me | H | H | H | H | G383 |
| Me | H | H | H | H | G385 |
| Me | H | H | H | H | G386 |
| Me | H | H | H | H | G394 |
| Me | H | H | H | H | G395 |
| Me | H | H | H | H | G403 |
| Me | H | H | H | H | G406 |
| Me | H | H | H | H | G409 |
| Me | H | H | H | H | G415 |
| Me | H | H | H | H | G421 |
| Me | H | H | H | H | G427 |
| Me | H | H | H | H | G430 |
| Me | H | H | H | H | G439 |
| Me | H | H | H | H | G448 |
| Me | H | H | H | H | G451 |
| Me | H | H | H | H | G454 |
| Me | H | H | H | H | G455 |
| Me | H | H | H | H | G457 |
| Me | H | H | H | H | G458 |
| Me | H | H | H | H | G463 |
| Me | H | H | H | H | G464 |
| Me | H | H | H | H | G469 |
| Me | H | H | H | H | G472 |
| Me | H | H | H | H | G475 |
| Me | H | H | H | H | G478 |
| Me | H | H | H | H | G484 |
| Me | H | H | H | H | G498 |
| Me | H | H | H | H | G499 |
| Me | H | H | H | H | G500 |
| Me | H | H | H | H | G501 |
| Me | H | H | H | H | G503 |
| Me | H | H | H | H | G504 |
| Me | H | H | H | H | G505 |
| Me | H | H | H | H | G506 |
| Me | H | H | H | H | G507 |
| Me | H | H | H | H | G508 |
| Me | H | H | H | H | G509 |
| Me | H | H | H | H | G510 |
| Me | H | H | H | H | G511 |
| Me | H | H | H | H | G512 |
| Me | H | H | H | H | G513 |
| Me | H | H | H | H | G514 |
| Me | H | H | H | H | G515 |
| Me | H | H | H | H | G537 |
| Me | H | H | H | H | G538 |

TABLE 8A-continued

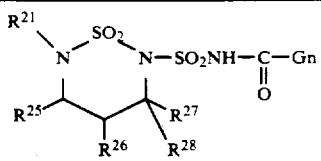

| R21 | R25 | R26 | R27 | R28 | Gn |
|---|---|---|---|---|---|
| Me | H | H | H | H | G539 |
| Me | H | H | H | H | G543 |
| Me | H | H | H | H | G544 |
| Me | H | H | H | H | G545 |
| Me | H | H | H | H | G549 |
| Me | H | H | H | H | G550 |
| Me | H | H | H | H | G551 |
| Me | H | H | H | H | G555 |
| Me | H | H | H | H | G556 |
| Me | H | H | H | H | G557 |
| Me | H | H | H | H | G561 |
| Me | H | H | H | H | G562 |
| Me | H | H | H | H | G563 |
| Me | H | H | H | H | G567 |
| Me | H | H | H | H | G568 |
| Me | H | H | H | H | G569 |
| Me | H | H | H | H | G573 |
| Me | H | H | H | H | G574 |
| Me | H | H | H | H | G575 |
| Me | H | H | H | H | G579 |
| Me | H | H | H | H | G580 |
| Me | H | H | H | H | G581 |
| Me | H | H | H | H | G585 |
| Me | H | H | H | H | G586 |
| Me | H | H | H | H | G587 |
| Me | H | H | H | H | G593 |
| Me | H | H | H | H | G598 |
| Me | H | H | H | H | G599 |
| Me | H | H | H | H | G601 |
| Me | H | H | H | H | G606 |
| Me | H | H | H | H | G608 |
| Me | H | H | H | H | G610 |
| Me | H | H | H | H | G611 |
| Me | H | H | H | H | G612 |
| Me | H | H | H | H | G613 |
| Me | H | H | H | H | G614 |
| Me | H | H | H | H | G615 |
| Me | H | H | H | H | G617 |
| Me | H | H | H | H | G618 |
| Me | H | H | H | H | G620 |
| Me | H | H | H | H | G621 |
| Me | H | H | H | H | G622 |
| Me | H | H | H | H | G626 |
| Me | H | H | H | H | G627 |
| Me | H | H | H | H | G628 |
| Me | H | H | H | H | G632 |
| Me | H | H | H | H | G633 |
| Me | H | H | H | H | G634 |
| Me | H | H | H | H | G638 |
| Me | H | H | H | H | G639 |
| Me | H | H | H | H | G640 |
| Me | H | H | H | H | G643 |
| Me | H | H | H | Me | G3 |
| Me | H | H | H | Me | G6 |
| Me | H | H | H | Me | G268 |
| Me | H | H | H | Me | G269 |
| Me | H | H | H | Me | G271 |
| Me | H | H | H | Me | G272 |
| Me | H | H | H | Me | G274 |
| Me | H | H | H | Me | G275 |
| Me | H | H | H | Me | G277 |
| Me | H | H | H | Me | G278 |
| Me | H | H | H | Me | G355 |
| Me | Me | H | H | H | G3 |
| Me | Me | H | H | H | G6 |
| Et | H | H | H | H | G3 |
| Et | H | H | H | H | G6 |
| Et | H | H | H | H | G268 |
| Et | H | H | H | H | G269 |
| Et | H | H | H | H | G271 |
| Et | H | H | H | H | G272 |
| Et | H | H | H | H | G274 |

TABLE 8A-continued

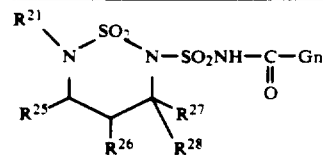

| R²¹ | R²⁵ | R²⁶ | R²⁷ | R²⁸ | Gn |
|---|---|---|---|---|---|
| Et | H | H | H | H | G₂₇₅ |
| Et | H | H | H | H | G₂₇₇ |
| Et | H | H | H | H | G₂₇₈ |
| Et | H | H | H | H | G₃₅₅ |
| Pr-n | H | H | H | H | G₃ |
| Pr-n | H | H | H | H | G₆ |
| CH₂=CHCH₂ | H | H | H | H | G₃ |
| CH₂=CHCH₂ | H | H | H | H | G₆ |
| CH≡CCH₂ | H | H | H | H | G₃ |
| CH≡CCH₂ | H | H | H | H | G₆ |

TABLE 9A

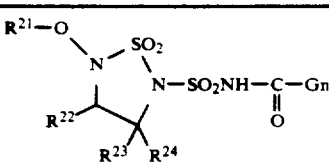

| R²¹ | R²² | R²³ | R²⁴ | Gn |
|---|---|---|---|---|
| Me | H | H | H | G₃ |
| Me | H | H | H | G₆ |
| Me | H | H | H | G₂₆₈ |
| Me | H | H | H | G₂₆₉ |
| Me | H | H | H | G₂₇₁ |
| Me | H | H | H | G₂₇₂ |
| Me | H | H | H | G₂₇₄ |
| Me | H | H | H | G₂₇₅ |
| Me | H | H | H | G₂₇₇ |
| Me | H | H | H | G₂₇₈ |
| Me | H | H | H | G₃₅₅ |
| Me | H | H | Me | G₃ |
| Me | H | H | Me | G₆ |
| Et | H | H | H | G₃ |
| Et | H | H | H | G₆ |
| CH₂=CHCH₂ | H | H | H | G₃ |
| CH₂=CHCH₂ | H | H | H | G₆ |
| CH≡CCH₂ | H | H | H | G₃ |
| CH≡CCH₂ | H | H | H | G₆ |

TABLE 10A

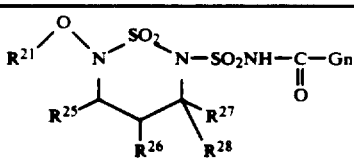

| R²¹ | R²⁵ | R²⁶ | R²⁷ | R²⁸ | Gn |
|---|---|---|---|---|---|
| Me | H | H | H | H | G₃ |
| Me | H | H | H | H | G₆ |
| Me | H | H | H | H | G₂₆₈ |
| Me | H | H | H | H | G₂₆₉ |
| Me | H | H | H | H | G₂₇₁ |
| Me | H | H | H | H | G₂₇₂ |
| Me | H | H | H | H | G₂₇₄ |
| Me | H | H | H | H | G₂₇₅ |
| Me | H | H | H | H | G₂₇₇ |
| Me | H | H | H | H | G₂₇₈ |
| Me | H | H | H | H | G₃₅₅ |
| Et | H | H | H | H | G₃ |
| Et | H | H | H | H | G₆ |
| CH₂=CHCH₂ | H | H | H | H | G₃ |
| CH₂=CHCH₂ | H | H | H | H | G₆ |

TABLE 10A-continued

| R²¹ | R²⁵ | R²⁶ | R²⁷ | R²⁸ | Gn |
|---|---|---|---|---|---|
| CH≡CCH₂ | H | H | H | H | G₃ |
| CH≡CCH₂ | H | H | H | H | G₆ |

TABLE 11A

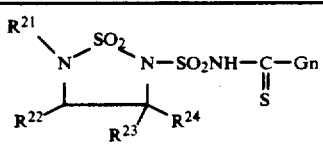

| R²¹ | R²² | R²³ | R²⁴ | Gn |
|---|---|---|---|---|
| Me | H | H | H | G₃ |
| Me | H | H | H | G₆ |
| Me | H | H | Me | G₃ |
| Me | H | H | Me | G₆ |

TABLE 12A

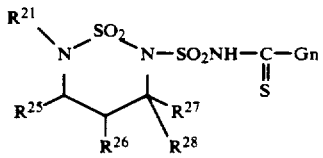

| R²¹ | R²⁵ | R²⁶ | R²⁷ | R²⁸ | Gn |
|---|---|---|---|---|---|
| Me | H | H | H | H | G₃ |
| Me | H | H | H | H | G₆ |
| Et | H | H | H | H | G₃ |
| Et | H | H | H | H | G₆ |

TABLE 13A

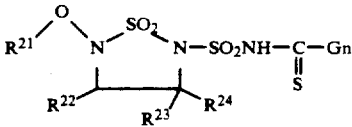

| R²¹ | R²² | R²³ | R²⁴ | Gn |
|---|---|---|---|---|
| Me | H | H | H | G₃ |
| Me | H | H | H | G₆ |
| Me | H | H | Me | G₃ |
| Me | H | H | Me | G₆ |

TABLE 14A

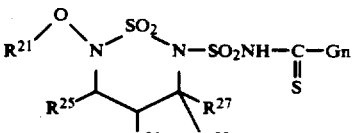

| R²¹ | R²⁵ | R²⁶ | R²⁷ | R²⁸ | Gn |
|---|---|---|---|---|---|
| Me | H | H | H | H | G₃ |
| Me | H | H | H | H | G₆ |
| Et | H | H | H | H | G₃ |

TABLE 14A-continued $$R^{21}-N\underset{R^{25}}{\overset{O}{\diagdown}}\underset{R^{26}}{\overset{SO_2}{\diagup}}N-SO_2NH-\underset{\underset{S}{\parallel}}{C}-Gn$$
$$R^{25}\quad R^{27}$$
$$R^{26}\quad R^{28}$$

| $R^{21}$ | $R^{25}$ | $R^{26}$ | $R^{27}$ | $R^{28}$ | Gn |
|---|---|---|---|---|---|
| Et | H | H | H | H | $G_6$ |

The compound of the present invention can be applied to control various weeds not only in the agricultural and horticultural fields such as upland fields, paddy fields or orchards, but also in non-agricultural fields such as play grounds, non-used vacant fields or railway sides.

The dose varies depending upon the application site, the season for application, the manner of application, the type of weeds to be controlled, the type of crop plants, etc. However, the dose is usually within a range of from 0.0001 to 10 kg per hectare, preferably from 0.005 to 5 kg per hectare, as the amount of the active ingredient.

Further, the compound of the present invention may be combined with other herbicides, various insecticides, fungicides, plant growth regulating agents and synergism agents at the time of the preparation of the formulations or at the time of the application, as the case requires.

Particularly, by the combined application with other herbicide, it can be expected to reduce the cost due to a decrease of the dose or to enlarge the herbicidal spectrum or obtain higher herbicidal effects due to a synergistic effect of the combined herbicides. In such a case, the compound of the present invention may be combined with a plurality of known herbicides. The herbicides of the type which can be used in combination with the compound of the present invention, may, for example, be compounds disclosed in Farm Chemicals Handbook (1990).

When the compound of the present invention is to be used as a herbicide, it is usually mixed with a suitable carrier, for instance, a solid carrier such as clay, talc, bentonite, diatomaceous earth or fine silica powder, or a liquid carrier such as water, an alcohol (such as isopropanol, butanol, benzyl alcohol or furfuryl alcohol), an aromatic hydrocarbon (such as toluene or xylene), an ether (such as anisole), a ketone (such as cyclohexanone or isophorone), an ester (such as butyl acetate), an acid amide (such as N-methylpyrrolidone), or a halogenated hydrocarbon (such as chlorobenzene). If desired, a surfactant, an emulsifier, a dispersing agent, a penetrating agent, a spreader, a thickener, an antifreezing agent, a coagulation preventing agent or a stabilizer may be added to prepare an optional formulation such as a liquid formulation, an emulsifiable concentrate, a wettable powder, a dry flowable, a flowable, a dust or a granule.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

| Wettable powder | |
|---|---|
| Compound of the present invention | 5-80 parts |
| Solid carrier | 10-85 parts |
| Surfactant | 1-10 parts |
| Other | 1-5 parts |

As other, a coagulation preventing agent may, for example, be mentioned.

| Emulsifiable concentrate | |
|---|---|
| Compound of the present invention | 1-30 parts |
| Liquid carrier | 30-95 parts |
| Surfactant | 5-15 parts |
| Flowable | |
| Compound of the present invention | 5-70 parts |
| Liquid carrier | 15-65 parts |
| Surfactant | 5-12 parts |
| Other | 5-30 parts |

As other, an antifreezing agent and a thickener may, for example, be mentioned.

| Granular wettable powder (dry flowable) | |
|---|---|
| Compound of the present invention | 20-90 parts |
| Solid carrier | 10-60 parts |
| Surfactant | 1-20 parts |
| Granule | |
| Compound of the present invention | 0.1-10 parts |
| Solid carrier | 90-99.99 parts |
| Other | 1-5 parts |

FORMULATION EXAMPLE 1

Wettable powder

| | |
|---|---|
| Compound No. 2 of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 2

Wettable powder

| | |
|---|---|
| Compound No. 3 of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 4 parts |

The above ingredients are homogeneously pulverized and mixed to form a wettable powder.

FORMULATION EXAMPLE 3

Emulsifiable concentrate

| | |
|---|---|
| Compound No. 5 of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE 4

Flowable

| | |
|---|---|
| Compound No. 6 of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE 5

Flowable

| | |
|---|---|
| Compound No. 11 of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE 6

Granular wettable powder (dry flowable)

| | |
|---|---|
| Compound No. 12 of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactant, manufactured by Sanyo Kokusaku Pulp Co., Ltd.) | 5 parts |
| Carplex #80 (tradename for fine silica powder, manufactured by Shionogi Pharmaceutical Co., Ltd.) | 10 parts |

The above ingredients are uniformly mixed and pulverized to form a dry flowable.

FORMULATION EXAMPLE 7

Granule

| | |
|---|---|
| Compound No. 13 of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

FORMULATION EXAMPLE 8

Wettable powder

| | |
|---|---|
| Compound No. 14 of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 9

Wettable powder

| | |
|---|---|
| Compound No. 15 of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 4 parts |

The above ingredients are homogeneously pulverized and mixed to form a wettable powder.

FORMULATION EXAMPLE 10

Emulsifiable concentrate

| | |
|---|---|
| Compound No. 31 of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate.

FORMULATION EXAMPLE 11

Flowable

| | |
|---|---|
| Compound No. 35 of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE 12

Flowable

| | |
|---|---|
| Compound No. 42 of the present invention | 40 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE 13

Granular wettable powder (dry flowable)

| | |
|---|---|
| Compound No. 47 of the present invention | 75 parts |
| Isoban No. 1 (tradename for an anionic surfactant, manufactured by Kuraray Isoprene Chemical Co., Ltd.) | 10 parts |
| Vanirex N (tradename for an anionic surfactnt, manufactured by Sanyo Kokusaku Pulp Co., Ltd.) | 5 parts |
| Carplex #80 (tradename for fine silica powder, manufactured by Shionogi Pharmaceutical Co., Ltd.) | 10 parts |

The above ingredients are uniformly mixed and pulverized to form a dry flowable.

FORMULATION EXAMPLE 14

Granule

| | |
|---|---|
| Compound No. 53 of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

In use, the above wettable powder, emulsifiable concentrate, flowable or granular wettable powder is diluted with water from 50 to 1,000 times and applied so that the active ingredient will be from 0.0001 to 10 kg per hectare.

Now, the herbicidal activities of the compounds of the present invention will be described in detail with reference to the following Test Examples.

TEST EXAMPLE 1

Test on the herbicidal effects in soil treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, oryza sativa, Zea mays, Triticum aestivum, Glycine max* and *Gossypium herbaceum* were sown, and the soil was covered thereon, and then a herbicide solution was applied by a small spray onto the surface of the soil uniformly so that the active ingredient was distributed at a predetermined concentration. The herbicide solution was prepared by diluting the formulation as described in the foregoing Formulation Examples with water and applied onto the entire soil surface. Three weeks after the application of the herbicidal solution, the herbicidal effects against each weed and the phytotoxicities against each crop plant were determined on the basis of the following standard ratings. The results are shown in Table 15.

Standard ratinqs:
5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left(1 - \frac{T}{N}\right) \times 100$$

where
T: Weight of the weed grown above the soil surface of the treated area
N: Weight of the weed grown above the soil surface of the non-treated area

TEST EXAMPLE 2

Test on the herbicidal effects in foliage treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, oryza sativa, Zea mays, Triticum aestivum, Glycine max, Gossypium herbaceum* and *Beta vulgaris* were spot-wisely sown. When the various weeds and crop plants grew to the 2 or 3 leaf stage, a herbicidal solution was uniformly sprayed on the foliages so that the active ingredient was applied in a predetermined concentration.

The herbicidal solution was prepared by diluting the formulation as described in the above Formulation Examples with water and applied onto the entire surface of the foliages of the weeds and the crop plants by a small spray. Three weeks after the application of the herbicide solution, the herbicidal effects against each weed and the phytotoxicities against each crop plant were determined on the basis of the standard ratings described in Test Example 1. The results are shown in Table 16.

In each Table, Compound Nos. correspond to Compound Nos. in the Examples, and symbols have the following meanings.

Dose: Dose of active ingredient (kg/ha)
N: *Echinochloa crus-galli* (barnyardgrass)
M: *Digitaria adscendens* (large crabgrass)
K: *Cyperus microiria* (annual sedge)
H: *Solanum nigrum* (black nightshade)
D: *Galinsoga ciliata* (hairy galinsoga)
I *Rorippa indica* (fieldcress)
R: *Oryza sativa* (rice)
T: *Zea mays* (corn)
S: *Glycine max (soybean)*
C: *Gossypium herbaceum* (cotton)
B: *Beta vulgaris* (sugar beet)

TABLE 15

| Comp. No. | Dose (kg/ha) | N | M | K | H | D | I | R | T | W | S | C |
|---|---|---|---|---|---|---|---|---|---|---|---|---|
| 1 | 0.16 | 1 | 2 | 2 | 4 | 5 | 5 | 0 | 0 | 0 | 3 | 2 |
|  | 0.32 | 2 | 3 | 3 | 5 | 5 | 5 | 0 | 0 | 0 | 4 | 3 |
|  | 0.63 | 3 | 4 | 4 | 5 | 5 | 5 | 2 | 1 | 1 | 5 | 4 |
| 2 | 0.16 | 2 | 3 | 3 | 5 | 5 | 5 | 3 | 0 | 0 | 2 | 3 |
|  | 0.32 | 4 | 4 | 4 | 5 | 5 | 5 | 4 | 1 | 1 | 3 | 4 |
|  | 0.63 | 5 | 5 | 5 | 5 | 5 | 5 | 5 | 2 | 4 | 4 | 5 |
| 3 | 0.16 | 2 | 2 | 2 | 5 | 5 | 5 | 0 | 0 | 0 | 2 | 2 |
|  | 0.32 | 3 | 4 | 4 | 5 | 5 | 5 | 1 | 0 | 1 | 3 | 3 |
|  | 0.63 | 4 | 5 | 5 | 5 | 5 | 5 | 3 | 1 | 3 | 4 | 4 |
| 4 | 0.16 | 1 | 1 | 1 | 4 | 5 | 5 | 1 | 0 | 0 | 1 | 1 |
|  | 0.32 | 2 | 2 | 2 | 5 | 5 | 5 | 2 | 0 | 0 | 2 | 2 |
|  | 0.63 | 3 | 3 | 3 | 5 | 5 | 5 | 4 | 1 | 1 | 3 | 4 |
| 5 | 0.16 | 3 | 3 | 3 | 5 | 5 | 5 | 0 | 0 | 0 | 2 | 2 |
|  | 0.32 | 4 | 3 | 4 | 5 | 5 | 5 | 1 | 1 | 1 | 3 | 3 |
|  | 0.63 | 5 | 4 | 5 | 5 | 5 | 5 | 2 | 3 | 3 | 4 | 4 |
| 6 | 0.16 | 2 | 2 | 1 | 5 | 5 | 5 | 3 | 0 | 0 | 2 | 3 |
|  | 0.32 | 4 | 4 | 2 | 5 | 5 | 5 | 4 | 0 | 1 | 3 | 4 |
|  | 0.63 | 5 | 5 | 3 | 5 | 5 | 5 | 5 | 2 | 4 | 4 | 5 |
| 7 | 0.63 | 3 | 4 | 4 | 5 | 5 | 5 | 3 | 0 | 0 | 2 | 2 |
| 8 | 0.16 | 1 | 2 | 2 | 4 | 5 | 5 | 3 | 0 | 0 | 2 | 2 |
|  | 0.32 | 2 | 2 | 2 | 5 | 5 | 5 | 4 | 0 | 0 | 3 | 3 |
|  | 0.63 | 3 | 3 | 3 | 5 | 5 | 5 | 5 | 1 | 2 | 3 | 4 |
| 9 | 0.16 | 0 | 0 | 0 | 3 | 5 | 5 | 0 | 0 | 0 | 0 | 0 |
|  | 0.32 | 1 | 1 | 1 | 4 | 5 | 5 | 0 | 0 | 0 | 1 | 1 |
|  | 0.63 | 2 | 2 | 3 | 5 | 5 | 5 | 0 | 0 | 0 | 2 | 2 |
| 10 | 0.16 | 0 | 1 | 0 | 3 | 5 | 5 | 0 | 0 | 0 | 1 | 0 |
|  | 0.32 | 1 | 2 | 1 | 4 | 5 | 5 | 1 | 0 | 0 | 2 | 1 |
|  | 0.63 | 2 | 3 | 2 | 5 | 5 | 5 | 2 | 0 | 0 | 3 | 3 |
| 11 | 0.16 | 4 | 4 | 4 | 5 | 5 | 5 | 0 | 0 | 0 | 3 | 3 |
|  | 0.32 | 5 | 5 | 4 | 5 | 5 | 5 | 1 | 0 | 0 | 4 | 3 |
|  | 0.63 | 5 | 5 | 5 | 5 | 5 | 5 | 4 | 0 | 1 | 4 | 4 |
| 14 | 0.04 | 1 | 2 | 1 | 5 | 5 | 5 | 2 | 0 | 0 | 0 | 0 |
|  | 0.08 | 2 | 4 | 2 | 5 | 5 | 5 | 3 | 0 | 0 | 1 | 1 |
|  | 0.16 | 3 | 5 | 4 | 5 | 5 | 5 | 3 | 1 | 2 | 4 | 2 |
| 15 | 0.04 | 1 | 2 | 1 | 4 | 5 | 5 | 0 | 0 | 0 | 1 | 0 |
|  | 0.08 | 2 | 3 | 2 | 5 | 5 | 5 | 0 | 0 | 0 | 2 | 1 |
|  | 0.16 | 3 | 4 | 3 | 5 | 5 | 5 | 0 | 0 | 0 | 2 | 3 |
| 16 | 0.63 | 1 | 3 | 3 | 4 | 5 | 5 | 1 | 0 | 0 | 1 | 0 |
| 17 | 0.63 | 3 | 4 | 3 | 5 | 5 | 5 | 0 | 0 | 0 | 4 | 2 |
| 19 | 0.16 | 0 | 1 | 1 | 5 | 4 | 5 | 0 | 0 | 0 | 0 | 0 |
|  | 0.32 | 1 | 1 | 2 | 5 | 5 | 5 | 0 | 0 | 0 | 1 | 1 |
|  | 0.63 | 2 | 3 | 3 | 5 | 5 | 5 | 0 | 0 | 0 | 2 | 2 |
| 20 | 0.16 | 2 | 1 | 1 | 5 | 4 | 5 | 0 | 0 | 0 | 2 | 1 |
|  | 0.32 | 3 | 1 | 2 | 5 | 5 | 5 | 0 | 0 | 0 | 3 | 2 |
|  | 0.63 | 4 | 2 | 3 | 5 | 5 | 5 | 2 | 0 | 0 | 4 | 4 |
| 21 | 0.16 | 3 | 3 | 4 | 5 | 5 | 5 | 2 | 0 | 1 | 2 | 2 |
|  | 0.32 | 4 | 4 | 5 | 5 | 5 | 5 | 3 | 0 | 2 | 3 | 3 |
|  | 0.63 | 5 | 5 | 5 | 5 | 5 | 5 | 4 | 1 | 3 | 4 | 4 |
| 22 | 0.16 | 2 | 3 | 4 | 5 | 5 | 5 | 4 | 0 | 4 | 0 | 2 |
|  | 0.32 | 4 | 4 | 5 | 5 | 5 | 5 | 5 | 1 | 5 | 1 | 3 |
|  | 0.63 | 5 | 5 | 5 | 5 | 5 | 5 | 5 | 2 | 5 | 3 | 4 |
| 23 | 0.63 | 1 | 2 | 3 | 5 | 5 | 5 | 0 | 0 | 0 | 0 | 2 |
| 27 | 0.63 | 2 | 3 | 2 | 5 | 5 | 5 | 3 | 0 | 3 | 4 | 3 |
| 28 | 0.63 | 2 | 3 | 3 | 5 | 5 | 5 | 2 | 0 | 4 | 4 | 4 |
| 32 | 0.63 | 1 | 2 | 1 | 5 | 5 | 5 | 0 | 0 | 1 | 2 | 1 |
| 33 | 0.16 | 1 | 1 | 0 | 5 | 5 | 4 | 0 | 0 | 0 | 3 | 0 |
|  | 0.32 | 3 | 4 | 1 | 5 | 5 | 5 | 2 | 0 | 0 | 4 | 1 |
|  | 0.63 | 5 | 5 | 3 | 5 | 5 | 5 | 4 | 1 | 3 | 5 | 2 |

TABLE 15-continued

| Comp. No. | Dose (kg/ha) | N | M | K | H | D | I | R | T | W | S | C |
|---|---|---|---|---|---|---|---|---|---|---|---|---|
| 34 | 0.63 | 1 | 2 | 2 | 4 | 5 | 5 | 3 | 0 | 1 | 4 | 4 |
| 35 | 0.63 | 1 | 2 | 1 | 4 | 5 | 5 | 0 | 1 | 0 | 3 | 3 |
| 42 | 0.63 | 3 | 4 | 3 | 5 | 5 | 5 | 5 | 3 | 3 | 4 | 3 |
| 43 | 0.16 | 2 | 3 | 3 | 4 | 5 | 5 | 3 | 0 | 0 | 1 | 2 |
|  | 0.32 | 3 | 4 | 3 | 5 | 5 | 5 | 4 | 1 | 0 | 2 | 3 |
|  | 0.63 | 4 | 4 | 4 | 5 | 5 | 5 | 4 | 2 | 0 | 4 | 4 |
| 47 | 0.63 | 4 | 5 | 3 | 4 | 5 | 4 | 4 | 1 | 1 | 0 | 0 |
| 48 | 0.16 | 0 | 1 | 2 | 4 | 4 | 5 | 0 | 0 | 0 | 1 | 1 |
|  | 0.32 | 1 | 2 | 3 | 5 | 5 | 5 | 0 | 0 | 0 | 2 | 2 |
|  | 0.63 | 2 | 4 | 4 | 5 | 5 | 5 | 1 | 0 | 0 | 3 | 2 |
| 49 | 0.16 | 2 | 4 | 1 | 4 | 5 | 5 | 3 | 0 | 2 | 2 | 3 |
|  | 0.32 | 3 | 5 | 2 | 5 | 5 | 5 | 4 | 0 | 3 | 3 | 3 |
|  | 0.63 | 4 | 5 | 3 | 5 | 5 | 5 | 5 | 1 | 4 | 4 | 4 |
| 52 | 0.16 | 2 | 3 | 2 | 5 | 5 | 5 | 4 | 0 | 2 | 4 | 4 |
|  | 0.32 | 3 | 4 | 3 | 5 | 5 | 5 | 5 | 1 | 3 | 5 | 5 |
|  | 0.63 | 3 | 4 | 3 | 5 | 5 | 5 | 5 | 2 | 3 | 5 | 5 |
| 53 | 0.16 | 2 | 4 | 2 | 5 | 5 | 5 | 5 | 0 | 4 | 5 | 4 |
|  | 0.32 | 4 | 5 | 3 | 5 | 5 | 5 | 5 | 1 | 5 | 5 | 5 |
|  | 0.63 | 5 | 5 | 4 | 5 | 5 | 5 | 5 | 3 | 5 | 5 | 5 |
| 55 | 0.16 | 1 | 1 | 2 | 4 | 5 | 5 | 2 | 0 | 0 | 0 | 0 |
|  | 0.32 | 2 | 3 | 3 | 5 | 5 | 5 | 3 | 0 | 1 | 1 | 1 |
|  | 0.63 | 4 | 5 | 4 | 5 | 5 | 5 | 4 | 0 | 3 | 4 | 3 |

TABLE 16

| Comp. No. | Dose (kg/ha) | N | M | K | H | D | I | R | T | W | S | C | B |
|---|---|---|---|---|---|---|---|---|---|---|---|---|---|
| 1 | 0.16 | 1 | 0 | 0 | 5 | 5 | 5 | 0 | 0 | 0 | 5 | 5 | 5 |
|  | 0.32 | 2 | 1 | 1 | 5 | 5 | 5 | 0 | 0 | 0 | 5 | 5 | 5 |
|  | 0.63 | 3 | 2 | 3 | 5 | 5 | 5 | 1 | 1 | 1 | 5 | 5 | 5 |
| 2 | 0.16 | 3 | 1 | 1 | 5 | 5 | 5 | 2 | 0 | 0 | 4 | 5 | 5 |
|  | 0.32 | 4 | 2 | 2 | 5 | 5 | 5 | 3 | 0 | 0 | 5 | 5 | 5 |
|  | 0.63 | 5 | 3 | 3 | 5 | 5 | 5 | 4 | 1 | 1 | 5 | 5 | 5 |
| 3 | 0.16 | 3 | 1 | 1 | 5 | 5 | 5 | 0 | 0 | 0 | 4 | 3 | 5 |
|  | 0.32 | 4 | 2 | 2 | 5 | 5 | 5 | 0 | 0 | 0 | 5 | 4 | 5 |
|  | 0.63 | 5 | 3 | 3 | 5 | 5 | 5 | 1 | 1 | 1 | 5 | 5 | 5 |
| 4 | 0.16 | 2 | 1 | 1 | 5 | 5 | 5 | 0 | 0 | 0 | 4 | 4 | 5 |
|  | 0.32 | 2 | 2 | 2 | 5 | 5 | 5 | 1 | 0 | 0 | 5 | 5 | 5 |
|  | 0.63 | 3 | 3 | 3 | 5 | 5 | 5 | 3 | 1 | 1 | 5 | 5 | 5 |
| 5 | 0.16 | 3 | 1 | 1 | 5 | 5 | 5 | 2 | 0 | 0 | 3 | 4 | 5 |
|  | 0.32 | 4 | 2 | 2 | 5 | 5 | 5 | 3 | 1 | 0 | 4 | 5 | 5 |
|  | 0.63 | 5 | 4 | 3 | 5 | 5 | 5 | 4 | 2 | 2 | 5 | 5 | 5 |
| 6 | 0.16 | 3 | 2 | 1 | 5 | 5 | 5 | 2 | 0 | 0 | 3 | 4 | 5 |
|  | 0.32 | 4 | 3 | 2 | 5 | 5 | 5 | 3 | 1 | 0 | 4 | 5 | 5 |
|  | 0.63 | 5 | 4 | 3 | 5 | 5 | 5 | 4 | 2 | 1 | 4 | 5 | 5 |
| 7 | 0.63 | 2 | 1 | 2 | 5 | 5 | 5 | 1 | 0 | 0 | 4 | 3 | 5 |
| 8 | 0.16 | 2 | 1 | 1 | 5 | 5 | 5 | 2 | 0 | 0 | 2 | 3 | 4 |
|  | 0.32 | 3 | 2 | 2 | 5 | 5 | 5 | 2 | 0 | 0 | 3 | 4 | 5 |
|  | 0.63 | 5 | 3 | 3 | 5 | 5 | 5 | 3 | 1 | 0 | 4 | 4 | 5 |
| 9 | 0.16 | 0 | 0 | 0 | 5 | 5 | 5 | 0 | 0 | 0 | 4 | 2 | 4 |
|  | 0.32 | 1 | 1 | 1 | 5 | 5 | 5 | 0 | 0 | 0 | 5 | 3 | 5 |
|  | 0.63 | 3 | 2 | 2 | 5 | 5 | 5 | 0 | 1 | 0 | 5 | 4 | 5 |
| 10 | 0.16 | 1 | 0 | 0 | 5 | 5 | 5 | 0 | 0 | 0 | 5 | 2 | 4 |
|  | 0.32 | 2 | 1 | 1 | 5 | 5 | 5 | 0 | 0 | 0 | 5 | 3 | 5 |
|  | 0.63 | 4 | 2 | 2 | 5 | 5 | 5 | 0 | 0 | 0 | 5 | 4 | 5 |
| 11 | 0.16 | 3 | 2 | 2 | 5 | 5 | 5 | 1 | 0 | 0 | 4 | 4 | 5 |
|  | 0.32 | 4 | 3 | 3 | 5 | 5 | 5 | 2 | 0 | 0 | 5 | 5 | 5 |
|  | 0.63 | 5 | 4 | 3 | 5 | 5 | 5 | 3 | 1 | 1 | 5 | 5 | 5 |
| 14 | 0.04 | 0 | 0 | 0 | 5 | 5 | 5 | 0 | 0 | 0 | 2 | 2 | 5 |
|  | 0.08 | 1 | 1 | 1 | 5 | 5 | 5 | 1 | 0 | 0 | 3 | 4 | 5 |
|  | 0.16 | 2 | 1 | 2 | 5 | 5 | 5 | 2 | 0 | 0 | 5 | 5 | 5 |
| 15 | 0.04 | 1 | 1 | 0 | 5 | 5 | 5 | 0 | 0 | 0 | 4 | 3 | 5 |
|  | 0.08 | 2 | 2 | 1 | 5 | 5 | 5 | 0 | 0 | 0 | 5 | 4 | 5 |
|  | 0.16 | 3 | 3 | 2 | 5 | 5 | 5 | 0 | 0 | 0 | 5 | 5 | 5 |
| 16 | 0.16 | 0 | 0 | 0 | 5 | 5 | 5 | 0 | 0 | 0 | 2 | 1 | 4 |
|  | 0.32 | 1 | 1 | 1 | 5 | 5 | 5 | 0 | 0 | 0 | 3 | 2 | 5 |
|  | 0.63 | 2 | 2 | 2 | 5 | 5 | 5 | 0 | 0 | 0 | 4 | 3 | 5 |
| 17 | 0.16 | 1 | 0 | 1 | 5 | 5 | 5 | 0 | 0 | 0 | 5 | 3 | 3 |
|  | 0.32 | 1 | 1 | 1 | 5 | 5 | 5 | 0 | 0 | 0 | 5 | 4 | 4 |
|  | 0.63 | 2 | 2 | 2 | 5 | 5 | 5 | 0 | 0 | 0 | 5 | 5 | 5 |
| 18 | 0.63 | 2 | 1 | 2 | 5 | 5 | 5 | 0 | 0 | 0 | 4 | 2 | 2 |
| 19 | 0.16 | 1 | 0 | 1 | 5 | 5 | 5 | 0 | 0 | 0 | 2 | 2 | 4 |
|  | 0.32 | 1 | 1 | 1 | 5 | 5 | 5 | 0 | 0 | 0 | 3 | 3 | 5 |
|  | 0.63 | 2 | 2 | 2 | 5 | 5 | 5 | 1 | 1 | 0 | 4 | 4 | 5 |
| 20 | 0.16 | 0 | 0 | 1 | 5 | 5 | 4 | 0 | 0 | 0 | 4 | 3 | 4 |
|  | 0.32 | 1 | 1 | 1 | 5 | 5 | 5 | 0 | 0 | 0 | 4 | 4 | 5 |
|  | 0.63 | 2 | 2 | 2 | 5 | 5 | 5 | 1 | 1 | 0 | 5 | 5 | 5 |

TABLE 16-continued

| Comp. No. | Dose (kg/ha) | N | M | K | H | D | I | R | T | W | S | C | B |
|---|---|---|---|---|---|---|---|---|---|---|---|---|---|
| 21 | 0.16 | 1 | 1 | 1 | 5 | 5 | 5 | 2 | 0 | 0 | 5 | 4 | 5 |
|  | 0.32 | 2 | 2 | 1 | 5 | 5 | 5 | 2 | 0 | 0 | 5 | 5 | 5 |
|  | 0.63 | 3 | 3 | 2 | 5 | 5 | 5 | 3 | 1 | 0 | 5 | 5 | 5 |
| 22 | 0.16 | 1 | 1 | 1 | 5 | 5 | 5 | 1 | 0 | 0 | 1 | 5 | 5 |
|  | 0.32 | 2 | 2 | 2 | 5 | 5 | 5 | 2 | 0 | 0 | 2 | 5 | 5 |
|  | 0.63 | 3 | 4 | 3 | 5 | 5 | 5 | 3 | 1 | 1 | 3 | 5 | 5 |
| 23 | 0.16 | 0 | 0 | 1 | 5 | 5 | 5 | 0 | 0 | 0 | 1 | 2 | 2 |
|  | 0.32 | 1 | 1 | 2 | 5 | 5 | 5 | 0 | 0 | 0 | 2 | 3 | 3 |
|  | 0.63 | 2 | 2 | 3 | 5 | 5 | 5 | 0 | 0 | 0 | 3 | 4 | 3 |
| 24 | 0.16 | 0 | 0 | 0 | 5 | 5 | 5 | 0 | 0 | 0 | 2 | 3 | 4 |
|  | 0.32 | 1 | 1 | 1 | 5 | 5 | 5 | 0 | 0 | 0 | 2 | 4 | 4 |
|  | 0.63 | 1 | 2 | 2 | 5 | 5 | 5 | 0 | 0 | 0 | 3 | 5 | 5 |
| 26 | 0.63 | 3 | 2 | 2 | 4 | 5 | 5 | 3 | 0 | 0 | 5 | 3 | 4 |
| 27 | 0.16 | 2 | 2 | 0 | 5 | 5 | 5 | 2 | 0 | 0 | 5 | 2 | 5 |
|  | 0.32 | 3 | 2 | 1 | 5 | 5 | 5 | 3 | 0 | 1 | 5 | 3 | 5 |
|  | 0.63 | 3 | 3 | 2 | 5 | 5 | 5 | 4 | 1 | 2 | 5 | 3 | 5 |
| 28 | 0.16 | 1 | 1 | 1 | 5 | 5 | 5 | 0 | 0 | 0 | 5 | 2 | 5 |
|  | 0.32 | 2 | 2 | 2 | 5 | 5 | 5 | 1 | 0 | 1 | 5 | 3 | 5 |
|  | 0.63 | 3 | 3 | 3 | 5 | 5 | 5 | 2 | 1 | 3 | 5 | 4 | 5 |
| 29 | 0.63 | 2 | 1 | 1 | 4 | 5 | 5 | 2 | 2 | 1 | 5 | 2 | 5 |
| 31 | 0.16 | 0 | 0 | 0 | 4 | 5 | 5 | 0 | 0 | 0 | 4 | 3 | 3 |
|  | 0.32 | 1 | 1 | 1 | 5 | 5 | 5 | 0 | 0 | 0 | 5 | 4 | 5 |
|  | 0.63 | 2 | 2 | 2 | 5 | 5 | 5 | 1 | 0 | 0 | 5 | 5 | 5 |
| 32 | 0.16 | 0 | 0 | 0 | 5 | 5 | 5 | 0 | 0 | 0 | 4 | 2 | 4 |
|  | 0.32 | 1 | 1 | 1 | 5 | 5 | 5 | 0 | 0 | 0 | 5 | 2 | 5 |
|  | 0.63 | 3 | 2 | 2 | 5 | 5 | 5 | 1 | 1 | 1 | 5 | 3 | 5 |
| 33 | 0.04 | 0 | 0 | 0 | 5 | 5 | 5 | 0 | 0 | 0 | 5 | 1 | 3 |
|  | 0.08 | 1 | 1 | 1 | 5 | 5 | 5 | 0 | 0 | 0 | 5 | 2 | 4 |
|  | 0.16 | 2 | 2 | 3 | 5 | 5 | 5 | 1 | 1 | 0 | 5 | 2 | 4 |
| 34 | 0.04 | 0 | 0 | 0 | 4 | 5 | 5 | 0 | 0 | 0 | 4 | 2 | 2 |
|  | 0.08 | 0 | 0 | 0 | 5 | 5 | 5 | 0 | 0 | 0 | 5 | 3 | 3 |
|  | 0.16 | 1 | 1 | 1 | 5 | 5 | 5 | 0 | 0 | 1 | 5 | 4 | 5 |
| 35 | 0.16 | 1 | 1 | 0 | 5 | 5 | 5 | 0 | 0 | 0 | 5 | 2 | 4 |
|  | 0.32 | 2 | 2 | 1 | 5 | 5 | 5 | 0 | 1 | 0 | 5 | 3 | 5 |
|  | 0.63 | 3 | 3 | 2 | 5 | 5 | 5 | 2 | 2 | 1 | 5 | 4 | 5 |
| 36 | 0.16 | 0 | 0 | 0 | 3 | 4 | 5 | 0 | 0 | 0 | 4 | 0 | 1 |
|  | 0.32 | 1 | 1 | 0 | 5 | 5 | 5 | 0 | 0 | 0 | 4 | 0 | 2 |
|  | 0.63 | 2 | 2 | 1 | 5 | 5 | 5 | 0 | 0 | 0 | 5 | 1 | 3 |
| 37 | 0.04 | 0 | 0 | 0 | 4 | 5 | 5 | 0 | 0 | 0 | 4 | 1 | 3 |
|  | 0.08 | 0 | 0 | 0 | 5 | 5 | 5 | 0 | 0 | 0 | 5 | 2 | 3 |
|  | 0.16 | 1 | 1 | 1 | 5 | 5 | 5 | 0 | 0 | 0 | 5 | 2 | 4 |
| 38 | 0.63 | 3 | 2 | 1 | 5 | 5 | 5 | 1 | 1 | 2 | 4 | 3 | 4 |
| 42 | 0.16 | 0 | 0 | 0 | 5 | 5 | 5 | 1 | 0 | 0 | 4 | 3 | 4 |
|  | 0.32 | 1 | 1 | 1 | 5 | 5 | 5 | 2 | 1 | 0 | 5 | 4 | 5 |
|  | 0.63 | 2 | 3 | 2 | 5 | 5 | 5 | 3 | 3 | 0 | 5 | 5 | 5 |
| 43 | 0.04 | 0 | 0 | 0 | 5 | 5 | 5 | 0 | 0 | 0 | 4 | 3 | 4 |
|  | 0.08 | 0 | 0 | 0 | 5 | 5 | 5 | 1 | 0 | 0 | 5 | 4 | 5 |
|  | 0.16 | 1 | 1 | 1 | 5 | 5 | 5 | 2 | 0 | 0 | 5 | 4 | 5 |
| 47 | 0.04 | 0 | 0 | 0 | 5 | 5 | 5 | 0 | 0 | 0 | 4 | 3 | 1 |
|  | 0.08 | 1 | 1 | 1 | 5 | 5 | 5 | 0 | 0 | 0 | 5 | 4 | 2 |
|  | 0.16 | 2 | 2 | 2 | 5 | 5 | 5 | 1 | 0 | 0 | 5 | 4 | 4 |
| 48 | 0.16 | 0 | 0 | 1 | 5 | 5 | 5 | 0 | 0 | 0 | 3 | 4 | 5 |
|  | 0.32 | 1 | 1 | 2 | 5 | 5 | 5 | 0 | 0 | 0 | 4 | 5 | 5 |
|  | 0.63 | 2 | 3 | 3 | 5 | 5 | 5 | 1 | 0 | 0 | 5 | 5 | 5 |
| 49 | 0.16 | 2 | 1 | 0 | 5 | 5 | 5 | 0 | 0 | 0 | 5 | 5 | 5 |
|  | 0.32 | 3 | 2 | 1 | 5 | 5 | 5 | 0 | 0 | 0 | 5 | 5 | 5 |
|  | 0.63 | 4 | 3 | 2 | 5 | 5 | 5 | 1 | 1 | 1 | 5 | 5 | 5 |
| 50 | 0.63 | 2 | 2 | 1 | 5 | 5 | 5 | 1 | 0 | 0 | 2 | 3 | 4 |
| 52 | 0.16 | 3 | 1 | 1 | 5 | 5 | 5 | 3 | 1 | 0 | 5 | 3 | 5 |
|  | 0.32 | 4 | 2 | 2 | 5 | 5 | 5 | 4 | 2 | 1 | 5 | 5 | 5 |
|  | 0.63 | 5 | 3 | 3 | 5 | 5 | 5 | 4 | 3 | 2 | 5 | 5 | 5 |
| 53 | 0.16 | 4 | 3 | 2 | 5 | 5 | 5 | 2 | 1 | 0 | 5 | 5 | 5 |
|  | 0.32 | 5 | 4 | 3 | 5 | 5 | 5 | 3 | 2 | 1 | 5 | 5 | 5 |
|  | 0.63 | 5 | 5 | 4 | 5 | 5 | 5 | 4 | 4 | 3 | 5 | 5 | 5 |
| 55 | 0.16 | 2 | 1 | 1 | 4 | 5 | 5 | 0 | 0 | 0 | 3 | 2 | 3 |
|  | 0.32 | 3 | 2 | 2 | 5 | 5 | 5 | 1 | 0 | 0 | 4 | 3 | 4 |
|  | 0.63 | 4 | 3 | 4 | 5 | 5 | 5 | 2 | 0 | 1 | 5 | 4 | 4 |

We claim:
1. A sulfamidosulfonamide derivative of the formula (1) and an agriculturally suitable salt thereof:

Wherein Q is

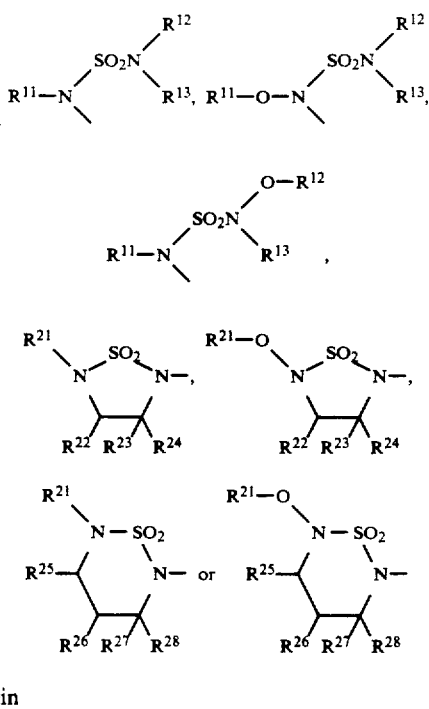

wherein
R[11] is a hydrogen atom, a $C_{1-6}$ alkyl group, a $C_{3-7}$ cycloalkyl group, a $C_{1-6}$ alkyl group substituted by a $C_{3-7}$ cycloalkyl group, a $C_{2-6}$ alkenyl group, a $C_{2-6}$ alkynyl group, a $C_{1-6}$ alkyl group substituted by a $C_{1-6}$ alkoxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ mono- or polyhalogenoalkyl group, a $C_{1-6}$ alkyl group substituted by a cyano group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a nitro group, a $C_{1-6}$ alkyl group, a $C_{1-6}$ alkoxy group and a $C_{1-6}$ alkoxycarbonyl group);

R[12] is a hydrogen atom, a $C_{1-6}$ alkyl group, a $C_{2-6}$ alkenyl group, a $C_{2-6}$ alkynyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group and a $C_{1-6}$ alkoxycarbonyl group);

R[13] is a hydrogen atom, a $C_{1-6}$ alkyl group, a $C_{2-6}$ alkenyl group, a $C_{2-6}$ alkynyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group); or, R[12] and R[13] form, together with the nitrogen atom to which they are bonded, a saturated 5-7-membered heterocyclic group;
or, $R^{12}$ and $R^{13}$ form, together With the oxygen atom and the nitrogen atom to which they are bonded, a saturated 5-7-membered heterocyclic group;
$R^{21}$; is a hydrogen atom, a $C_{1-6}$ alkyl group, a $C_{2-6}$ alkenyl group, a $C_{2-6}$ alkynyl group, a $C_{1-6}$ alkyl group substituted by a $C_{1-6}$ alkoxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ mono- or poly-halogenoalkyl group, a $C_{1-6}$ alkyl group Substituted by a cyano group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);
$R^{22}$ is a hydrogen atom or a $C_{1-6}$ alkyl group;
$R^{23}$ is a hydrogen atom or a $C_{1-6}$ alkyl group;
$R^{24}$ is a hydrogen atom, a $C_{1-6}$ alkyl group, a $C_{2-6}$ alkenyl group, a $C_{2-6}$ alkynyl group, a halogen atom, a $C_{1-6}$ mono- or poly-halogenoalkyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a $C_{1-6}$ mono- or poly-halogenoalkoxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkyl group substituted by a cyano group, a $C_{1-6}$ alkoxycarbonyl group, a $C_{1-6}$ alkyl group substituted by a $C_{1-6}$ alkoxycarbonyl group, a $C_{1-6}$ alkylcarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);
$R^{25}$ is a hydrogen atom or a $C_{1-6}$ alkyl group;
$R^{26}$ is a hydrogen atom or a $C_{1-6}$ alkyl group;
$R^{27}$ is a hydrogen atom or a $C_{1-6}$ alkyl group;
$R^{28}$ is a hydrogen atom, a halogen atom, a $C_{1-6}$ alkyl group, a $C_{2-6}$ alkenyl group, a $C_{2-6}$ alkynyl group, a $C_{1-6}$ mono- or poly-halogenoalkyl group, a $C_{1-6}$ alkyl group substituted by a $C_{1-6}$ alkoxy group, a $C_{1-6}$ alkyl group substituted by a $C_{2-6}$ alkenyloxy group, a $C_{1-6}$ alkyl group substituted by a $C_{2-6}$ alkynyloxy group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkyl group substituted by a cyano group, a $C_{1-6}$ alkoxycarbonyl group, a $C_{1-6}$ alkylcarbonyl group, a $C_{1-6}$ alkyl group substituted by a $C_{1-6}$ alkoxycarbonyl group, a $C_{1-6}$ alkyl group substituted by a $C_{1-6}$ alkylcarbonyl group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group);

X is an oxygen atom or a sulfur atom;
G is

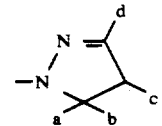

wherein each of a, b, c and d, which are independent from one another, is a hydrogen atom, a $C_{1-6}$ alkyl group, a $C_{2-6}$ alkenyl group, a $C_{2-6}$ alkynyl group, a $C_{1-6}$ alkyl group mono- or poly-substituted by a halogen atom, a $C_{1-6}$ alkoxy group, a $C_{1-6}$ alkyl group substituted by a $C_{1-6}$ alkoxy group, a $C_{1-6}$ alkoxycarbonyl group, a $C_{1-6}$ alkyl group substituted by a $C_{1-6}$ alkylthio group, a $C_{1-6}$ alkyl group substituted by a $C_{1-6}$ alkylsulfonyl group, a $C_{1-6}$ alkylthio group, a $C_{1-6}$ alkylcarbonyl group, a $C_{3-7}$ cycloalkyl group, a $C_{3-7}$ cycloalkenyl group, a cyano group, a nitro group, a phenyl group or a benzyl group (provided that such a phenyl group or a benzyl group may be substituted by one or more substituents selected from the group consisting of a halogen atom, a trifluoromethyl group, a $C_{1-6}$ alkyl group, a $C_{1-6}$ alkoxy group, a $C_{1-6}$ alkoxycarbonyl group and a nitro group), a 5- or 6-membered heterocyclic group (provided that such a heterocyclic group contains from 1 to 3 hetero atoms selected from the group consisting of nitrogen atoms, oxygen atoms and sulfur atoms in the ring, or contains a sulfonyl group, and such a heterocyclic group may be substituted by one or more substituents selected from the group consisting of a $C_{1-6}$ alkyl group, a $C_{1-6}$ alkoxy group, a halogen atom, a trifluoromethyl group, a nitro group and a $C_{1-6}$ alkoxycarbonyl group), a naphthyl group, a benzene-condensed heterocyclic group (provided that such a benzene-condensed heterocyclic group contains 1 or 2 hetero atoms selected from the group consisting of nitrogen atoms, oxygen atoms and sulfur atoms, and such a benzene-condensed heterocyclic group may be substituted by one or more substituents selected from the group consisting of a $C_{1-6}$ alkyl group, a $C_{1-6}$ alkoxy group, a halogen atom, a trifluoromethyl group, a nitro group and a $C_{1-6}$ alkoxycarbonyl group).

2. A selective herbicide containing one or more compounds defined in claim 1 as active ingredients.

3. A herbicidal composition comprising a herbicidally effective amount of one or more compounds defined in claim 1 and an agricultural adjuvant.

4. A herbicidal composition comprising a herbicidally effective amount of one or more compounds of formula I

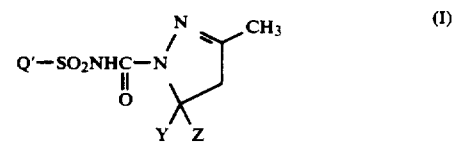

wherein Y is a member selected from the group consisting of phenyl, substituted phenyl which may be substituted with F, Cl, or OCH₃, and thienyl, Z is hydrogen or methyl, Q' is

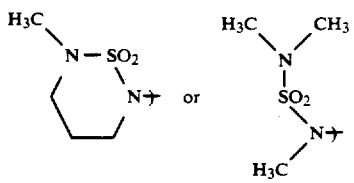

and an agricultural adjuvant

5. A herbicidal composition comprising a herbicidally effective amount of one or more compounds of formula I as defined in claim 4, wherein Q' is

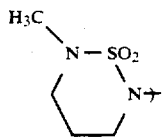

and an agricultural adjuvant.

6. A herbicidal composition comprising a herbicidally effective amount of one or more compounds of formula I as defined in claim 4, wherein Q' is

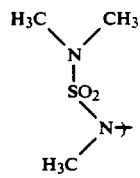

and an agricultural adjuvant.

7. A herbicidal composition comprising a herbicidally effective amount of a compound of formula I as defined in claim 5, wherein Y is phenyl, Z is methyl, and an agricultural adjuvant.

* * * * *

UNITED STATES PATENT AND TRADEMARK OFFICE
CERTIFICATE OF CORRECTION

PATENT NO. : 5,152,824
DATED : October 5, 1992
INVENTOR(S) : Kenzi Makino. et al.

It is certified that error appears in the above-indentified patent and that said Letters Patent is hereby corrected as shown below:

Column 2, lines 36-37, "a $C_{1-6}$ alkynyl group" should read --a $C_{2-6}$ alkynyl group--.

line 62, "a $C_{1-6}$ alkynyl group" should read --a $C_{2-6}$ alkynyl group--.

Column 4, line 25, "nitro group, a" should read --nitro group), a--.

Column 5, lines 56-57, "ester or thio)-carbonic" should read --ester or (thio)carbonic--.

Column 11, line 26, "Synthetic organic Chemistry," should read --Synthetic Organic Chemistry,--.

Column 58, line 31, figure G117,
"  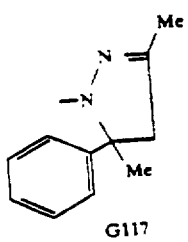  ", should read --  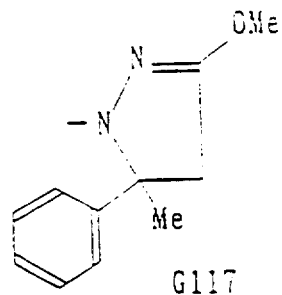  --.

UNITED STATES PATENT AND TRADEMARK OFFICE
CERTIFICATE OF CORRECTION

PATENT NO. : 5,152,824                                    Page 2 of 3
DATED      : October 5, 1992
INVENTOR(S) :

It is certified that error appears in the above-indentified patent and that said Letters Patent is hereby corrected as shown below:

Column 58, line 55, figure G122,
", should read --                                         --.

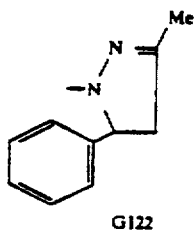   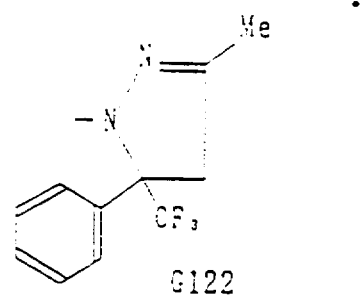

Column 60, line 35, figure G145,
", should read --                                         --.

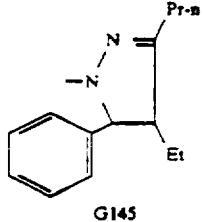   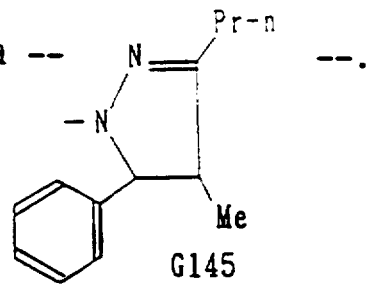

Column 191, line 29, Formulation Example 12,
    "Water              44.5 parts", should read
    --Water             29.5 parts--.

Column 196, line 40, "polyhalogenoalkyl", should read
    --poly-halogenoalkyl--.

Column 197, line 3, "together With the", should read
    --together with the--.

UNITED STATES PATENT AND TRADEMARK OFFICE
CERTIFICATE OF CORRECTION

PATENT NO. : 5,152,824
DATED : October 6, 1992
INVENTOR(S) : Kenzi Makino, et al.

It is certified that error appears in the above-indentified patent and that said Letters Patent is hereby corrected as shown below:

Column 197, line 14, "group Substituted by", should read --group substituted by--.

Signed and Sealed this

Eleventh Day of October, 1994

Attest:

BRUCE LEHMAN

Attesting Officer     Commissioner of Patents and Trademarks